United States Patent
Chen et al.

(10) Patent No.: US 12,365,732 B2
(45) Date of Patent: Jul. 22, 2025

(54) ANTI-CD96 ANTIBODIES AND METHODS OF USE THEREOF

(71) Applicant: 23andMe, Inc., Sunnyvale, CA (US)

(72) Inventors: Yu Chen, Foster City, CA (US); Chingwei Vivian Lee, Foster City, CA (US); Germaine Fuh-Kelly, Pacifica, CA (US); Zuoan Yi, Mountain View, CA (US); Yao-Ming Huang, San Mateo, CA (US); Valentine Yeung, Belmont, CA (US); Krista Maureen McCutcheon, Burlingame, CA (US); Samuel Nalle, Pacifica, CA (US); Augusta Eleanor Broughton, Fresno, CA (US); Louise Scharf, Redwood City, CA (US); Navneet Singh, San Francisco, CA (US); Tina Thai, San Mateo, CA (US); Shouhua Xiao, Foster City, CA (US)

(73) Assignee: 23andMe, Inc., San Francisco, CA (US)

( * ) Notice: Subject to any disclaimer, the term of this patent is extended or adjusted under 35 U.S.C. 154(b) by 431 days.

(21) Appl. No.: 18/057,152

(22) Filed: Nov. 18, 2022

(65) Prior Publication Data

US 2023/0183343 A1 Jun. 15, 2023

Related U.S. Application Data

(62) Division of application No. 16/719,108, filed on Dec. 18, 2019, now Pat. No. 11,555,073.

(60) Provisional application No. 62/783,118, filed on Dec. 20, 2018.

(51) Int. Cl.
*C07K 16/28* (2006.01)
*A61P 35/00* (2006.01)
*A61K 39/00* (2006.01)

(52) U.S. Cl.
CPC .......... *C07K 16/2803* (2013.01); *A61P 35/00* (2018.01); *C07K 16/2896* (2013.01); *A61K 2039/505* (2013.01); *C07K 2317/24* (2013.01); *C07K 2317/31* (2013.01); *C07K 2317/33* (2013.01); *C07K 2317/55* (2013.01); *C07K 2317/92* (2013.01)

(58) Field of Classification Search
CPC ............ C07K 16/2803; C07K 16/2896; C07K 2317/24; C07K 2317/31; C07K 2317/33; C07K 2317/55; C07K 2317/92; C07K 16/2818; C07K 2317/30; C07K 2317/70; C07K 2317/76; A61P 35/00; A61K 2039/505; A61K 2039/507; A61K 2039/86
See application file for complete search history.

(56) References Cited

U.S. PATENT DOCUMENTS

| | | |
|---|---|---|
| 6,737,056 B1 | 5/2004 | Presta |
| 7,332,581 B2 | 2/2008 | Presta |
| 7,658,921 B2 | 2/2010 | Dall Acqua |
| 7,767,410 B2 | 8/2010 | Weissman |
| 8,232,071 B2 | 7/2012 | Weissman |
| 8,333,953 B2 | 12/2012 | Lu |
| 8,673,321 B2 | 3/2014 | Brodsky |
| 9,182,385 B2 | 11/2015 | Fantl |
| 2004/0005559 A1 | 1/2004 | Loring |
| 2004/0121370 A1 | 6/2004 | Baldwin |
| 2004/0170982 A1 | 9/2004 | Morris |
| 2006/0013822 A1 | 1/2006 | Tittle |
| 2007/0048301 A1 | 3/2007 | Bodary-Winter |
| 2007/0134657 A1 | 6/2007 | Poznansky |
| 2010/0291112 A1 | 11/2010 | Kellner |
| 2011/0117578 A1 | 5/2011 | Acres |
| 2011/0183924 A1 | 7/2011 | Mintz |
| 2012/0070450 A1 | 3/2012 | Ishikawa |
| 2012/0142001 A1 | 6/2012 | Skog |
| 2013/0251720 A1 | 9/2013 | Clark |
| 2014/0010861 A1 | 1/2014 | Bancel |
| 2014/0056890 A1 | 2/2014 | Gurney |
| 2014/0186380 A1 | 7/2014 | Gurney |
| 2014/0242077 A1 | 8/2014 | Choi |
| 2014/0369924 A1 | 12/2014 | Weissman |
| 2015/0153356 A1 | 6/2015 | Meng |

(Continued)

FOREIGN PATENT DOCUMENTS

CN 102240901 11/2011
WO 2008073316 6/2008
(Continued)

OTHER PUBLICATIONS

Blake et al. teach (Cancer Discovery, Apr. 2016, pp. 446-459).*

(Continued)

*Primary Examiner* — Nelson B Moseley, II
(74) *Attorney, Agent, or Firm* — FisherBroyles, LLP; Adam K. Whiting

(57) ABSTRACT

The present disclosure provides binding proteins, such as antibodies and antigen-binding fragments, which specifically bind to human CD96 receptor protein (hu-CD96) and are capable of decreasing, inhibiting, and/or fully-blocking immune regulatory effects mediated by hu-CD96. The present disclosure also provides methods of using the antibodies (and compositions thereof) to treat diseases and conditions responsive to decreasing, inhibiting and/or blocking immune regulatory function or activity mediated by CD96 binding to CD155, including effects arising from CD96 interactions with CD226 and/or TIGIT.

24 Claims, 12 Drawing Sheets

Specification includes a Sequence Listing.

(56) References Cited

U.S. PATENT DOCUMENTS

| | | |
|---|---|---|
| 2015/0216970 A1 | 8/2015 | Grogan |
| 2015/0241427 A1 | 8/2015 | Fantl |
| 2015/0252431 A1 | 9/2015 | Yao |
| 2015/0361396 A1 | 12/2015 | Regev |
| 2016/0007893 A1 | 1/2016 | Roberts |
| 2016/0200800 A1 | 7/2016 | Ahmed |
| 2016/0200814 A1 | 7/2016 | Smythe |
| 2017/0029504 A1 | 2/2017 | White |
| 2017/0088607 A1 | 3/2017 | White |

FOREIGN PATENT DOCUMENTS

| | | |
|---|---|---|
| WO | 2008077546 | 7/2008 |
| WO | 2015024042 | 2/2015 |
| WO | 2015024060 | 2/2015 |
| WO | 2015066640 | 5/2015 |
| WO | 2015121454 | 8/2015 |
| WO | 2015138600 | 9/2015 |
| WO | 2015170108 | 11/2015 |
| WO | 2016005548 | 1/2016 |
| WO | 2019030377 | 2/2019 |

OTHER PUBLICATIONS

Nodehi, Sahar Mohseni, Improved antibody-dependent cell-mediated cytotoxicity (ADCC) of affinity maturated and Fc-Engineered antibodies directed against the AML stem cell antigen CD96, Dissertation in Fulfillment of the Requirements for a Degree of Doctor of Philosophy—Submitted to the Faculty of Mathematics and Natural Sciences—Christian Albrechts University of Kiel, 2010, 138 pages.

Seth, et al., The murine pan T cell marker CD96 is an adhesion receptor for CD155 and nectin-1,Biochem. and Biophys. Res. Communications, 2007, 364:959-965.

Shibuya, et al., CD226 (DNAM-1) is involved in lymphocyte function-associated antigen 1 costimulatory signal for naive T cell differentiation and proliferation, J. Exp. Med., 2003, 198(12):1829-1839.

Shields, et al., High resolution mapping of the binding site on human IgG1 for Fc gamma RI, Fc gamma RII, Fc gamma RIII, and FcRn and design of IgG1 variants with improved binding to the Fc gamma R., J Biol Chem., 2001, 276(9):6591-604.

Smyth, Mark J., NK cells in carcinogenesis and metastasis, Abstract, (Heidelberg Germany Natural Killer Cell Symposium 2012), 2012, 5 pages.

Souza-Fonseca-Guimaraes, et al., Abstract #S-24, Checkpoints and interferons in tumor control , J. Cyto., 2014, 70:21-27.

Stanietsky, et al., Mouse TIGIT inhibits NK-cell cytotoxicity upon interaction with PVR , Eur. J. Immunol., 2013, 43(8):2138-2150.

Stanietsky, et al., Paired NK cell receptors controlling NK cytotoxicity, Febs Letters, 2010, 584:4895-4900.

Stanietsky, et al., The interaction of TIGIT with PVR and PVRL2 inhibits human NK cell cytotoxicity, PNAS, 2009, 106(42):17858-17863.

Stengel, et al., Structure of TIGIT immunoreceptor bound to poliovirus receptor reveals a cell-cell adhesion and signaling mechanism that requires cis-trans receptor clustering, PNAS, 2012, 109(14):5399-5404.

Tahara-Hanaoka, et al., Functional characterization of DNAM-1 (CD226) interaction with its ligands PVR (CD155) and nectin-2 (PRR-2/CD112), Int. Immunol., 2004, 16(4):533-538.

Tahara-Hanaoka, et al., Tumor rejection by the poliovirus receptor family ligands of the DNAM-1 (CD226) receptor, Blood, 2006, 107:1491-1496.

The International Search Report and the Written Opinion of the International Search Authority in PCT Application PCT/US2019/067123 (dated Apr. 21, 2020).

Toutirais, et al., DNAX accessory molecule-1 (CD226) promotes human hepatocellular carcinoma cell lysis by Vγ9Vδ2 T cells, Eur. J. Immunol., 2009, 39:1361-1368.

Wang et al., Identification and molecular cloning of tactile. A novel human T cell activation antigen that is a member of the Ig gene superfamily, J. Immunol., 1992, 148:2600-2608.

Xu, et al., A novel interface consisting of homologous immunoglobulin superfamily members with multiple functions, Cellular & Molecular Immunol., 2010, 7:11-19.

Yu, et al., The surface protein TIGIT suppresses T cell activation by promoting the generation of mature immunoregulatory dendritic cells, Nature Reviews | Immunology, 2009, 10(1):48-57.

Zeng, et al., Human CD96 gene cloning, expression and identification, J. South Med. Univ., 2011, 31(7):1232-1235.

Zhu, et al., Identification of CD112R as a novel checkpoint for human T cells, JEM, 2016, 213(2):167-176.

Zhu, Shensheng, Expressions and Functions of Human CD96 Molecule, Ph.D. Dissertation, Fourth Military University, Apr. 2008, Classification No. R392, Abstract, 3 pages.

Barth, et al., Targeted indocyanine-green-loaded calcium phosphosilicate nanoparticles for In Vivo photodynamic therapy of leukemia, ACS nano.org, 2011, 5(7):15325-5337.

Bellora, et al., The interaction of human natural killer cells with either unpolarized or polarized macrophages results in different functional outcomes, PNAS, 2010, 107(50):121659-21664.

Bernhardt, Gunter, Tactile becomes tangible: CD96 discloses its inhibitory peculiarities, Nat. Immunol., 2014, 15(5):406-408.

Blake et al., "Suppression of Metastases Using a New Lymphocyte Checkpoint Target for Cancer Immunotherapy", Cancer Discovery, US, (Apr. 1, 2016), vol. 6, No. 4, doi:10.1158/2159-8290.CD-15-0944, ISSN 2159-8274, pp. 446-459, XP055344484.

Blake, et al., Molecular Pathways: Targeting CD96 and TIGIT for Cancer Immunotherapy, Clin. Cancer Res., 2016, 22:5183-5188.

Bottino, et al., Identification of PVR (CD155) and Nectin-2 (CD112) as cell surface ligands for the Human DNAM-1 (CD226) activating molecule, J. Exp. Med., 2003, 198(4):557-567.

Brenner, et al., Encoded combinatorial chemistry, Proc. Natl. Acad. Sci. USA, 1992, 89:5381-5583.

Bryceson, et al., Synergy among receptors on resting NK cells for the activation of natural cytotoxicity and cytokine secretion, Blood, 2005, 107(1):159-166.

Carsten, et al., DNAX accessory molecule-1 mediated recognition of freshly isolated ovarian carcinoma by resting natural killer cells, Cancer Res., 2007, 67(3):1317-1325.

Chan, Christopher James, Ph.D. Thesis, Monash University, (Advisors Andrews & Smyth), Mechanisms of NK cell-mediated regulation of inflammation and cancer, Ph.D. Thesis, 2012, 1-304.

Chan, et al., DNAM-1/CD155 Interactions Promote Cytokine and NK Cell-Mediated Suppression of Poorly Immunogenic Melanoma Metastases, J. Immunol., 2009, 184:902-911.

Chan, et al., Molecular mechanisms of natural killer cell activation in response to cellular stress, Cell Death and Differentiation, 2014, 21:5-14.

Chan, et al., Receptors that interact with nectin and nectin-like proteins in the immunosurveillance and immunotherapy of cancer, Current Opinion in Immunology, 2012, 24:246-251.

Chan, et al., The receptors CD96 and CD226 oppose each other in the regulation of natural killer cell functions, Nat. Immunol., 2014, 15(5):431-438.

Chen, et al., Molecular mechanisms of T cell co-stimulation and co-inhibition, Nature Reviews Immunology, 2013, 13:227-242.

Diken, et al., CIMT 2014: Next waves in cancer immunotherapy—Report on the 12th annual meeting of the Association for Cancer Immunotherapy, Human Vaccines & Immunotherapeutics, 2014, 10(10:3090-3100.

Dougall, et al., TIGIT and CD96: new checkpoint receptor targets for cancer immunotherapy, Immunological Reviews, 2017, 276:112-120.

El-Sherbiny, et al., The requirement for DNAM-1, NKG2D, and NKp46 in the natural killer cell-mediated killing of Myeloma cells, Can. Res., 2007, 67(18):8444-8449.

(56) References Cited

OTHER PUBLICATIONS

Eriksson, et al., Differential Expression of CD96 Surface Molecule Represents CD8+ T Cells with Dissimilar Effector Function during HIV-1 Infection, PLOS One, 2012, 7:e51696.

Ferrari De Andrade, et al., DNAM-1 control of natural killer cells functions through nectin and nectin-like proteins, Immunol. and Cell Biol., 2013, 92:237-244.

Fuchs, et al., Cutting edge: CD96 (tactile) promotes NK cell-target cell adhesion by interacting with the poliovirus receptor (CD155), J. Immunol., 2004, 172:3994-3998.

Fuchs, et al., The role of NK cell recognition of nectin and nectin-like proteins in tumor immunosurveillance, Seminars in Cancer Biology, 2006, 16:359-366.

Gilfillan, et al., DNAM-1 promotes activation of cytotoxic lymphocytes by nonprofessional antigen-presenting cells and tumors, J. Exp. Med., 2008, 205:2965-2973.

Gong, et al., Establishment of an enzyme-linked immunosorbent assay system for determining soluble CD96 and its application in the measurement of sCD96 in patients with viral hepatitis B and hepatic cirrhosis, Clin. Exp. Immunol., 2008, 155:207-215.

Gramatzki, et al., Antibodies TC-12 (unique) and TH-111 (CD96) characterize T-cell acute lymphoblastic leukemia and subgroup of acute myeloid leukemia, Exp. Hematol., 1998, 26:209-1214.

Gramatzki, et al., Abstract #274, "CD96 Antibody TH-111 Eradicates AML-LSC from Autografts and the Fc-Engineered Variant MSH-TH111e May be Used In Vivo", Biol Blood Marrow Transplant, 2016, 22:S200.

Guillerey, et al., Targeting natural killer cells in cancer immunotherapy, Nat. Immunol., 2016, 17(9):1025-1036.

Harjunpaa, et al., Abstract #3258, "The effects of targeting both PD-1 and CD96 on tumour immunity, autoimmunity and immune homeostasis", Eur. J. Immunol., 2016, 46(Suppl. 1):37.

Hosen, et al., CD96 is a leukemic stem cell-specific marker in human acute myeloid leukemia, Proc Natl Acad Sci, 2017, 104(26):11008-11013.

Hotzel, et al., A strategy for risk mitigation of antibodies with fast clearance, MABS, 2012, 4(6):753-760.

Iguchi-Manaka, et al., Accelerated tumor growth in mice deficient in DNAM-1 receptor, J. Exp. Med., 2008, 205(13):2959-2964.

Koenig, et al., Deep Sequencing-guided Design of a High Affinity Dual Specificity Antibody to Target Two Angiogenic Factors in Neovascular Age-related Macular Degeneration., J Biol Chem., 2015, 290:(36)21773-21786.

Krasnova, et al., Bench to bedside: NK cells and control of metastasis, Clin. Immunol., 2015, 1-10, http://dx.doi.org/10.1016/j.clim.2015.10.001.

Kunkel, et al., Rapid and efficient site-specific mutagenesis without phenotypic selection, Methods Enzymol., 1987, 154:367-382.

Lakshmikanth, et al., NCRs and DNAM-1 mediate NK cell recognition and lysis of human and mouse melanoma cell lines in vitro and in vivo, J. Clin. Invest., 2009, 119(5):1251-1263.

Larsen, et al., Nonviral transfection of leukemic primary cells and cells lines by siRNA—a direct comparison between Nucleofection and Accell delivery, Exp. Hematol., 2011, 39:1081-1089.

Lin et al. (African Journal of Biotechnology, 10(79):18294-18302, 2011).

Lozano, et al., The TIGIT/CD226 axis regulates human T cell function, J. Immunol., 2012, 188:3869-3875.

Mahoney, et al., Combination cancer immunotherapy and new immunomodulatory targets, Nature Reviews Drug Discovery, 2015, 14:561-584.

Maier, et al., The adhesion receptor CD155 determines the magnitude of humoral immune responses against orally ingested antigens, Eur. J. Immunol., 2007, 37:2214-2225.

Majeti, R., Monoclonal antibody therapy directed against human acute myeloid leukemia stem cells, Oncogene, 2010, 30:1009-1019.

Mariuzza (Annu. Rev. Biophys. Biophys. Chem., 16: 139-159, 1987).

Martinet, et al., Balancing natural killer cell activation through paired receptors, Nature Reviews Immunology, 2015, 15:243-254.

Martinet, et al., DNAM-1 Expression Marks an Alternative Program of NK Cell Maturation, Cell Reports, 2015, 11:85-97.

Martinet, et al., Regulation of Immune Cell Functions through Nectin and Nectin-like Receptors, Encyclopedia of Immunobiology, 2016, 2:404-414.

McCarthy et al. (J. Immunol. Methods, 251(1-2): 137-149, 2001).

Melero, et al., Evolving synergistic combinations of targeted immunotherapies to combat cancer, Nature Reviews Cancer, 2015, 15:457-472.

Meyer, et al., CD96 interaction with CD155 via its first Ig-like domain is modulated by alternative splicing or mutations in distal Ig-like domains, J. of Biol. Chem., 2008, 284(4):2235-2244.

Morimoto, et al., Interaction of cancer cells with platelets mediated by Necl-5/poliovirus receptor enhances cancer cell metastasis to the lungs, Oncogene, 2007, 27:264-273.

Nodehi, et al., Enhanced ADCC activity of affinity matured and Fc-Engineered Mini-Antibodies directed against the AML stem cell antigen CD96, PLOS One, 2012, 7:e42426.

\* cited by examiner

FIG. 1

Humanization of 12F8

VL domain sequence

```
12F8       1  DIVMTQSQKFMSTSVGDRVSVTCKASQNVGTAIVWYQKKPGQSPKTLIYSASTRYTGVPD  60
IGKV1-9*01 1  ..QL..PS.L.A......TI..R..GISSYLA....Q..KA.L..A...LQS...S     60
mAb1       1  ..QL..PSSL.A......TI............Q..KA.V..........S           60

12F8      61  RFTGSGSGTDFTLTISNVQSEDLAEYFCQQYSSSP  95
IGKV1-9*01 61 ..S.......E......SL.P..F.T.Y...LN.Y.  95
mAb1      61  ..S...............SL.P..F.T.Y.......  95
```

VH domain sequence

```
12F8        1  QVQLQQPGAELVTPGASVKLSCKASGFTFTNNWMHWVKQRPGQGLEWIGMIHPNSGITNI  60
IGHV1-46*01 1  ....V.S...VKK........V.......SYY....R.A......M.I.N.SG.S.SY   60
mAb1        1  ....V.S...VKK........V..........................V........   60
mAb1.v1     1  ....V.S...VKK........V.......R..............................  60
mAb1.v2     1  ....V.S...VKK........V.......R..............................  60
mAb1.v3     1  ....V.S...VKK........V.....................V..............   60
mAb1.v4     1  ....V.S...VKK........V.......R.A.............................  60
mAb1.v5     1  ....V.S...VKK........V.......R.A.............................  60
mAb1.v7     1  E...V.S...VKK........V.......R.A.............................  60

12F8       61  NEKFKNKATVTVDKSSSTVYIQLSSLTSEDSAVYYCRS       AR  98
IGHV1-46*01 61 AQ..QGRV.M.R.T.T......ME....R....T......      AR  96
mAb1       61  ......RV.M.T.T.T..A.ME.R....R.D.T......         96
mAb1.v1    61  .........R........T.............T......         98
mAb1.v2    61  ......RV.M......T...ME.R....R.D.T......         98
mAb1.v3    61  ......RV.M.......T..ME.R....R.D.T......         98
mAb1.v4    61  ......RV.M.T.T.T..A.ME.R....R.D.T......         98
mAb1.v5    61  ......RV.M......T...ME.R....R.D.T......      AR  96
mAb1.v7    61  ......RV.M.T.T.T..A.ME.R....R.D.T......         98
```

FIG. 2

Humanization of 10G1

VH domain sequence

```
IGHV7-4-1*02   1  QVQLVQSGSELKKPGASVKVSCKASGYTFTSYAMNWVRQAPGQGLEWMGWINTNTGNPTY  60
h10G1          1  EI................P.......P..T.G.S...........DS.V...        60
10G1           1  .I.......P......ET.I......P..T.G.S....K..K...DS.V...         60

IGHV7-4-1*02  61  AQGFTGRFVFSLDTSVSTAYLQISSLKAEDTAVYYCAR   98
h10G1         61  .DD.K.............................F...   98
10G1          61  .DD.K...A...E..AN.....N..N..A.T.F....   98
```

VL domain sequence

```
IGKV6D-21*02   1  EIVLTQSPDFQSVTPKEKVTITCRASQSIGSSLHWYQQKPDQSPKLLIKYASQSISGVPS  60
h10G1          1  ...M..........................D.YRN........T.....H..D.....I..  60
10G1           1  D.LM....TTL.....G.T.SLS.....D.YRN......SQGT.R.....H..D.....I..  60

IGKV6D-21*02  61  RFSGSGSGTDFTLTINSLEAEDAAAYYCHQSSSLP   95
h10G1         61  ..............................L.GY.M.    95
10G1          61  ..T.........S....VKP.EGI...L.GY.M.    95
```

ANTI-CD96 ANTIBODIES AND METHODS OF USE THEREOF

CROSS REFERENCE TO RELATED APPLICATIONS

This application is a divisional under 35 U.S.C. § 121 of U.S. patent application Ser. No. 16/719,108, filed Dec. 18, 2019, which claims the benefit under 35 U.S.C. § 119(e) to U.S. Provisional Patent Application Ser. No. 62/783,118, filed on Dec. 20, 2018, the entireties of which are incorporated herein by reference.

FIELD OF THE INVENTION

The present disclosure relates generally to binding proteins, such as antibodies and antigen-binding fragments, which bind to the CD96 receptor protein and methods of using such binding proteins.

REFERENCE TO SEQUENCE LISTING

The official copy of the Sequence Listing is submitted concurrently with the specification via USPTO Patent Center as an WIPO Standard ST.26 formatted XML file with file name "09402-003WO1_SeqList_ST26.xml", a creation date of Nov. 18, 2022, and a size of 663,685 bytes. This Sequence Listing filed via USPTO Patent Center is part of the specification and is incorporated in its entirety by reference herein. This ST.26 formatted version of the Sequence Listing replaces the ST.25 formatted version of the Sequence Listing with a file name of "09402-003WO1_SeqList_ST25.txt", a creation date of Dec. 16, 2019, and a size of 398,046 bytes, that was filed concurrently with parent application on Dec. 18, 2019, and adds no new matter to that original sequence listing.

BACKGROUND OF THE INVENTION

CD96 (also known as "TACTILE") is a receptor expressed on the surface of T cells and natural killer (NK) cells. (See e.g., Blake S J, et al., (2016) "Molecular Pathways: Targeting CD96 and TIGIT for Cancer Immunotherapy," Clin Cancer Res 22(21): 5183-8.) CD96 is a member of the Ig superfamily and is further categorized as a member of the nectin/NECL family. CD96 has been found to be expressed in humans on the surface of T cells ($\alpha\beta$ and $\gamma\delta$), NK cells, a subpopulation of B cells, and in mice on T cells, NK cells and NKT cells. CD96 is known to function in concert with CD155, CD226 (also known as "DNAM"), and TIGIT, and is believed to play an important role in inhibiting immune function. The main ligand for CD96 is CD155 to which it binds with a stronger affinity than CD226 binding to CD155, but weaker than TIGIT binding to CD155. Human CD96 exists as two splice variants that exhibit different binding affinities to CD155. (See e.g., Meyer D, et al., (2009) "CD96 interaction with CD155 via its first Ig-like domain is modulated by alternative splicing or mutations in distal Ig-like domains," J Biol Chem 284: 2235-44.) It has been observed that Cd96−/− mice exhibit a hypersensitive NK-cell response to stimulation by LPS, ID 2, or ID 8, as well as strong resistance to experimental lung metastases and MCA-induced fibrosarcomas. (See e.g., Chan C J, et al., (2014) "The receptors CD96 and CD226 oppose each other in regulation of natural killer cell functions," Nat Immunol 15:431-8.) Anti-CD96 mAbs have been shown to reduce the B16F10 and E0771 lung metastases in mouse models. (See e.g., Blake S J, et al., (2016) "Suppression of metastases using a new lymphocyte checkpoint target for cancer immunotherapy," Cancer Discover 6; 446-59.)

WO2015/024042A1 (published Feb. 26, 2015) suggests a method of reducing or relieving immune inhibition in a mammal that includes the step of at least partly inhibiting or reducing CD96 activity in one or more cells of the mammal. The suggested method includes a step of administering to the mammal a CD96 inhibitory agent, such as an anti-CD96 antibody, but no anti-CD96 antibodies are described in the disclosure.

WO2015/024060A1 (published Feb. 26, 2015) also suggests a method of reducing or relieving immune inhibition in a mammal that includes the step of at least partly inhibiting or reducing CD96 activity in one or more cells of the mammal. The disclosure suggests that a commercially available anti-human CD96 antibody "NK92.39" can be effective in increasing IFNγ production in human NK cells, but does not disclose any specific anti-CD96 antibodies that are capable of reducing CD96 activity or tumor growth.

SUMMARY OF THE INVENTION

The present disclosure provides antibodies that specifically bind human CD96 with high affinity. The antibodies are capable of decreasing, inhibiting, and/or fully-blocking immune regulatory effects mediated by CD96. Additionally, the antibodies are capable of decreasing, inhibiting, and/or fully-blocking immune regulatory function or activity mediated by CD96 binding to CD155. The present disclosure also provides compositions for and methods of treating diseases and conditions responsive to decreasing, inhibiting and/or blocking immune regulatory function or activity mediated by CD96, CD155, CD226, and/or TIGIT.

In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises an amino acid sequence selected from KASQNVGTAIV (SEQ ID NO: 13), KSSQSLL-DSDGKTYLN (SEQ ID NO: 17), RVSQDISFWLS (SEQ ID NO: 21), RASSNVKYMY (SEQ ID NO: 25), KASQSVTFADTGLMH (SEQ ID NO: 29), RSST-GAVTTSNYAN (SEQ ID NO: 33), RASQDIYRNLH (SEQ ID NO: 37), or RASQXIXXNXH (SEQ ID NO: 308), wherein X at position 5 is D, A, E, G, H, K, N, P, Q, S, or T; X at position 7 is Y, or F; X at position 8 is R, K, or Q; X at position 10 is L, I, M, or V;

(b) HVR-L2 comprises an amino acid sequence selected from SASTRYT (SEQ ID NO: 14), LVSKLDS (SEQ ID NO: 18), KASNLHT (SEQ ID NO: 22), YTSNLAS (SEQ ID NO: 26), RASNLEV (SEQ ID NO: 30), GTNNRAP (SEQ ID NO: 34), HASDSIS (SEQ ID NO: 38), or HAXXXXS (SEQ ID NO: 325), wherein X at position 3 is S, or E; X at position 4 is D, E, K, or Q; X at position 5 is S, H, L, R, or V; X at position 6 is I, or V;

(c) HVR-L3 comprises an amino acid sequence selected from QQYSSSPLT (SEQ ID NO: 15), LQATHSPQT (SEQ ID NO: 19), LQSQSYPYT (SEQ ID NO: 23), QQFTSSPLT (SEQ ID NO: 27), QQSREYPWT (SEQ ID NO: 31), SLWYGSHWV (SEQ ID NO: 35), LQGYSMPYT (SEQ ID NO: 39), or XQGYXMPXT (SEQ ID NO: 335), wherein X at position 1 is L, G, M, or Q; X at position 5 is S, A, E, Q, or V; X at position 8 is Y, or F;

(d) HVR-H1 comprises an amino acid sequence selected from TNNWMH (SEQ ID NO: 41), TGYGVT (SEQ ID NO: 45), TDYYIN (SEQ ID NO: 49), NDYYIN (SEQ ID NO: 53), SDYYMY (SEQ ID NO: 57), TNYGIH (SEQ ID NO: 61), TTYGMS (SEQ ID NO: 65), XNXXXH (SEQ ID NO: 72), wherein X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W, or XXXGXS (SEQ ID NO: 344), wherein X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V;

(e) HVR-H2 comprises an amino acid sequence selected from MIHPNSGITNINE (SEQ ID NO: 42), EIYPGTVITYYNA (SEQ ID NO: 46), WIFPGTEGIYYNE (SEQ ID NO: 50), WIFPGRIITYYNE (SEQ ID NO: 54), AISDDGTYTYYPD (SEQ ID NO: 58), IIWAGGSTNYNS (SEQ ID NO: 62), WINTDSGVPTYAD (SEQ ID NO: 66), XXHXXXXXXXXXNX (SEQ ID NO: 107), wherein X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y, or WINTXXGVPTYAD (SEQ ID NO: 369), wherein X at position 5 is D, or E; X at position 6 is S, or T;

(f) HVR-H3 comprises an amino acid sequence selected from RSDGTYEGYFDY (SEQ ID NO: 43), ARGLGRAMDY (SEQ ID NO: 47), AREGDYRYYSPLGY (SEQ ID NO: 51), ARGVGEGFDY (SEQ ID NO: 55), AKAGSYDYFDV (SEQ ID NO: 59), ARVSMMGFAY (SEQ ID NO: 63), ARNIYYGWGNFDY (SEQ ID NO: 67), RXDXXXXXYFDY (SEQ ID NO: 203), wherein X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T, or ARXIYYGWGXFDY (SEQ ID NO: 372), wherein X at position 3 is N, or M; X at position 10 is N, F, H, or Y.

In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises the amino acid sequence of SEQ ID NO: 13;
(b) HVR-L2 comprises the amino acid sequence of SEQ ID NO: 14;
(c) HVR-L3 comprises the amino acid sequence of SEQ ID NO: 15;
(d) HVR-H1 comprises an amino acid sequence selected from SEQ ID NOs: 41, 73-106;
(e) HVR-H2 comprises an amino acid sequence selected from SEQ ID NOs: 42, 108-202;
(f) HVR-H3 comprises an amino acid sequence selected from SEQ ID NOs: 43, 204-249.

In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises the amino acid sequence of SEQ ID NO: 13;
(b) HVR-L2 comprises the amino acid sequence of SEQ ID NO: 14;
(c) HVR-L3 comprises the amino acid sequence of SEQ ID NO: 15;
(d) HVR-H1 comprises an amino acid sequence selected from SEQ ID NOs: 41, 83, 91, 92, 94, 95, 102;
(e) HVR-H2 comprises an amino acid sequence selected from SEQ ID NOs: 42, 108, 112, 113, 116, 118, 122, 125, 138, 178, 181, 190, 197;
(f) HVR-H3 comprises an amino acid sequence selected from SEQ ID NOs: 43, 208, 219, 221, 223, 227.

In some embodiments, the present disclosure provides an anti-CD96 antibody comprising (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3), wherein:

(a) HVR-L1 comprises an amino acid sequence selected from SEQ ID NOs: 37, 309-324;
(b) HVR-L2 comprises an amino acid sequence selected from SEQ ID NOs: 38, 326-334;
(c) HVR-L3 comprises an amino acid sequence selected from SEQ ID NOs: 39, 336-343;
(d) HVR-H1 comprises an amino acid sequence selected from SEQ ID NOs: 65, 345-368;
(e) HVR-H2 comprises an amino acid sequence selected from SEQ ID NOs: 66, 370-371;
(f) HVR-H3 comprises an amino acid sequence selected from SEQ ID NOs: 67, 373-376.

In some embodiments, the anti-CD96 antibody of the present disclosure comprises a light chain variable domain ($V_L$) amino acid sequence having at least 90% identity to a sequence selected from SEQ ID NO: 12, 16, 20, 24, 28, 32, or 36; and/or a heavy chain variable domain ($V_H$) amino acid sequence having at least 90% identity to a sequence selected from SEQ ID NO: 40, 44, 48, 52, 56, 60, or 64.

In some embodiments, the present disclosure provides an anti-CD96 antibody wherein the antibody comprises a light chain variable domain ($V_L$) amino acid sequence having at least 90% identity to a sequence of SEQ ID NO: 68, and/or a heavy chain variable domain ($V_H$) amino acid sequence having at least 90% identity to a sequence selected from SEQ ID NOs: 69, 250, 251, 252, 253, 254, 255, 256, 257, 258, 259, 260, 261, 262, 263, 264, 265, 266, 267, 268, 269, 270, 271, 272, 273, 274, 275, 460, 461, 462, 463, or 464.

In some embodiments, the present disclosure provides an anti-CD96 antibody wherein the antibody comprises a light chain variable domain ($V_L$) amino acid sequence having at least 90% identity to a sequence selected from SEQ ID NO: 70, and 377-409; and/or a heavy chain variable domain ($V_H$) amino acid sequence having at least 90% identity to a sequence selected from SEQ ID NO: 71, and 410-439.

In some embodiments, the present disclosure provides an anti-CD96 antibody wherein the antibody comprises:
(a) a light chain variable domain ($V_L$) amino acid sequence having at least 90% identity to SEQ ID NO: 12, and/or a heavy chain variable domain ($V_H$) amino acid sequence having at least 90% identity to SEQ ID NO: 40;
(b) a light chain variable domain ($V_L$) amino acid sequence having at least 90% identity to SEQ ID NO: 36, and/or a heavy chain variable domain ($V_H$) amino acid sequence having at least 90% identity to SEQ ID NO: 64;
(c) a light chain variable domain ($V_L$) amino acid sequence having at least 90% identity to SEQ ID NO: 68, and/or a heavy chain variable domain ($V_H$) amino acid sequence having at least 90% identity to a sequence selected from SEQ ID NOs: 69, 250, 251, 252, 253, 254, 255, 256, 257, 258, 259, 260, 261, 262, 263, 264, 265, 266, 267, 268, 269, 270, 271, 272, 273, 274, 275, 460, 461, 462, 463, or 464; or
(d) a light chain variable domain ($V_L$) amino acid sequence having at least 90% identity to SEQ ID NO: 70, and/or a heavy chain variable domain ($V_H$) amino acid sequence having at least 90% identity to SEQ ID NO: 71.

In some embodiments, the present disclosure provides an anti-CD96 antibody wherein the antibody comprises:
(a) a light chain (LC) amino acid sequence having at least 90% identity to a sequence selected from SEQ ID NO: 440, 441, 442, 443, 444, 445, or 446; and/or a heavy chain (HC) amino acid sequence having at least 90% identity to a sequence selected from SEQ ID NO: 447, 448, 449, 450, 451, 452, 453, 484, 485, 486, 487, 488, 489, or 490;
(b) a light chain (LC) amino acid sequence having at least 90% identity to SEQ ID NO: 440; and/or a heavy chain (HC) amino acid sequence having at least 90% identity to SEQ ID NO: 447 or 484;
(c) a light chain (LC) amino acid sequence having at least 90% identity to SEQ ID NO: 446; and/or a heavy chain (HC) amino acid sequence having at least 90% identity to SEQ ID NO: 453 or 490;
(d) comprises a light chain (LC) amino acid sequence having at least 90% identity to SEQ ID NO: 454, and/or a heavy chain (HC) amino acid sequence having at least 90% identity to a sequence selected from SEQ ID NO: 455, 456, 457, 458, 459, 465, 466, 467, 468, 469, 491, 492, 493, 494, or 495; or
(e) a light chain (LC) amino acid sequence having at least 90% identity to SEQ ID NO: 470; and/or a heavy chain (HC) amino acid sequence having at least 90% identity to SEQ ID NO: 471 or 501.

In some embodiments, the present disclosure provides an anti-CD96 antibody comprising:
(a) a first light chain hypervariable region (HVR-L1) of SEQ ID NO: 13, a second light chain hypervariable region (HVR-L2) of SEQ ID NO: 14, and a third light chain hypervariable region (HVR-L3) of SEQ ID NO: 15; and/or a first heavy chain hypervariable region (HVR-H1) of SEQ ID NO: 72, a second heavy chain hypervariable region (HVR-H2) of SEQ ID NO: 107, and a third heavy chain hypervariable region (HVR-H3) of SEQ ID NO: 203; or
(b) a first light chain hypervariable region (HVR-L1) of SEQ ID NO: 308, a second light chain hypervariable region (HVR-L2) of SEQ ID NO: 325, a third light chain hypervariable region (HVR-L3) of SEQ ID NO: 335, and/or a first heavy chain hypervariable region (HVR-H1) of SEQ ID NO: 344, a second heavy chain hypervariable region (HVR-H2) of SEQ ID NO: 369, and a third heavy chain hypervariable region (HVR-H3) of SEQ ID NO: 372.

In some embodiments, the present disclosure provides an anti-CD96 antibody comprising:
(a) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 43;
(b) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 42, and a third heavy chain hypervariable region (HVR-H3) of SEQ ID NO: 43;
(c) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 108, and a third heavy chain hypervariable region (HVR-H3) of SEQ ID NO: 43;
(d) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 112, and a third heavy chain hypervariable region (HVR-H3) of SEQ ID NO: 43;
(e) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 190, and a third heavy chain hypervariable region (HVR-H3) of SEQ ID NO: 43;
(f) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 197, and a third heavy chain hypervariable region (HVR-H3) of SEQ ID NO: 43;

(g) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 221;

(h) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 227;

(i) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 221;

(j) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 227;

(k) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 221;

(l) a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 227; or (m) a first light chain hypervariable region (HVR-L1) of SEQ ID NO: 37, a second light chain hypervariable region (HVR-L2) of SEQ ID NO: 38, a third light chain hypervariable region (HVR-L3) of SEQ ID NO: 39; and/or a first heavy chain hypervariable region (HVR-H1) of SEQ ID NO: 65, a second heavy chain hypervariable region (HVR-H2) of SEQ ID NO: 66, and a third heavy chain hypervariable region (HVR-H3) of SEQ ID NO: 67.

In some embodiments, the present disclosure provides an anti-CD96 antibody comprising:

(a) a light chain variable domain ($V_L$) amino acid sequence of SEQ ID NO: 68; and/or a heavy chain variable domain ($V_H$) amino acid sequence of SEQ ID NO: 69;

(b) a light chain variable domain ($V_L$) amino acid sequence of SEQ ID NO: 68; and/or a heavy chain variable domain ($V_H$) amino acid sequence of SEQ ID NO: 250;

(c) a light chain variable domain ($V_L$) amino acid sequence of SEQ ID NO: 68; and/or a heavy chain variable domain ($V_H$) amino acid sequence of SEQ ID NO: 251;

(d) a light chain variable domain ($V_L$) amino acid sequence of SEQ ID NO: 68; and/or a heavy chain variable domain ($V_H$) amino acid sequence of SEQ ID NO: 252;

(e) a light chain variable domain ($V_L$) amino acid sequence of SEQ ID NO: 68; and/or a heavy chain variable domain ($V_H$) amino acid sequence of SEQ ID NO: 253;

(f) a light chain variable domain ($V_L$) amino acid sequence of SEQ ID NO: 68; and/or a heavy chain variable domain ($V_H$) amino acid sequence of SEQ ID NO: 254;

(g) a light chain variable domain ($V_L$) amino acid sequence of SEQ ID NO: 68; and/or a heavy chain variable domain ($V_H$) amino acid sequence of SEQ ID NO: 255;

(h) a light chain variable domain ($V_L$) amino acid sequence of SEQ ID NO: 68; and/or a heavy chain variable domain ($V_H$) amino acid sequence of SEQ ID NO: 256;

(i) a light chain variable domain ($V_L$) amino acid sequence of SEQ ID NO: 68; and/or a heavy chain variable domain ($V_H$) amino acid sequence of SEQ ID NO: 257;

(j) a light chain variable domain ($V_L$) amino acid sequence of SEQ ID NO: 68; and/or a heavy chain variable domain ($V_H$) amino acid sequence of SEQ ID NO: 258;

(k) a light chain variable domain ($V_L$) amino acid sequence of SEQ ID NO: 68; and/or a heavy chain variable domain ($V_H$) amino acid sequence of SEQ ID NO: 259;

(l) a light chain variable domain ($V_L$) amino acid sequence of SEQ ID NO: 68; and/or a heavy chain variable domain ($V_H$) amino acid sequence of SEQ ID NO: 260;

(m) a light chain variable domain ($V_L$) amino acid sequence of SEQ ID NO: 68; and/or a heavy chain variable domain ($V_H$) amino acid sequence of SEQ ID NO: 261;

(n) a light chain variable domain ($V_L$) amino acid sequence of SEQ ID NO: 68; and/or a heavy chain variable domain ($V_H$) amino acid sequence of SEQ ID NO: 262;

(o) a light chain variable domain ($V_L$) amino acid sequence of SEQ ID NO: 68; and/or a heavy chain variable domain ($V_H$) amino acid sequence of SEQ ID NO: 263;

(p) a light chain variable domain ($V_L$) amino acid sequence of SEQ ID NO: 68; and/or a heavy chain variable domain ($V_H$) amino acid sequence of SEQ ID NO: 264;

(q) a light chain variable domain (V_L) amino acid sequence of SEQ ID NO: 68; and/or a heavy chain variable domain (V_H) amino acid sequence of SEQ ID NO: 265;
(r) a light chain variable domain (V_L) amino acid sequence of SEQ ID NO: 68; and/or a heavy chain variable domain (V_H) amino acid sequence of SEQ ID NO: 266;
(s) a light chain variable domain (V_L) amino acid sequence of SEQ ID NO: 68; and/or a heavy chain variable domain (V_H) amino acid sequence of SEQ ID NO: 267;
(t) a light chain variable domain (V_L) amino acid sequence of SEQ ID NO: 68; and/or a heavy chain variable domain (V_H) amino acid sequence of SEQ ID NO: 268;
(u) a light chain variable domain (V_L) amino acid sequence of SEQ ID NO: 68; and/or a heavy chain variable domain (V_H) amino acid sequence of SEQ ID NO: 269;
(v) a light chain variable domain (V_L) amino acid sequence of SEQ ID NO: 68; and/or a heavy chain variable domain (V_H) amino acid sequence of SEQ ID NO: 270;
(w) a light chain variable domain (V_L) amino acid sequence of SEQ ID NO: 68; and/or a heavy chain variable domain (V_H) amino acid sequence of SEQ ID NO: 271;
(x) a light chain variable domain (V_L) amino acid sequence of SEQ ID NO: 68; and/or a heavy chain variable domain (V_H) amino acid sequence of SEQ ID NO: 272;
(y) a light chain variable domain (V_L) amino acid sequence of SEQ ID NO: 68; and/or a heavy chain variable domain (V_H) amino acid sequence of SEQ ID NO: 273;
(z) a light chain variable domain (V_L) amino acid sequence of SEQ ID NO: 68; and/or a heavy chain variable domain (V_H) amino acid sequence of SEQ ID NO: 274;
(aa) a light chain variable domain (V_L) amino acid sequence of SEQ ID NO: 68; and/or a heavy chain variable domain (V_H) amino acid sequence of SEQ ID NO: 275; or
(bb) a light chain variable domain (V_L) amino acid sequence of SEQ ID NO: 70; and/or a heavy chain variable domain (V_H) amino acid sequence of SEQ ID NO: 71.

In some embodiments, the present disclosure provides an anti-CD96 antibody wherein the antibody comprises:
(a) a light chain (LC) amino acid sequence of SEQ ID NO: 440, and a heavy chain (HC) amino acid sequence of SEQ ID NO: 447;
(b) a light chain (LC) amino acid sequence of SEQ ID NO: 441, and a heavy chain (HC) amino acid sequence of SEQ ID NO: 448;
(c) a light chain (LC) amino acid sequence of SEQ ID NO: 442, and a heavy chain (HC) amino acid sequence of SEQ ID NO: 449;
(d) a light chain (LC) amino acid sequence of SEQ ID NO: 443, and a heavy chain (HC) amino acid sequence of SEQ ID NO: 450;
(e) a light chain (LC) amino acid sequence of SEQ ID NO: 444, and a heavy chain (HC) amino acid sequence of SEQ ID NO: 451;
(f) a light chain (LC) amino acid sequence of SEQ ID NO: 445; and a heavy chain (HC) amino acid sequence of SEQ ID NO: 452;
(g) a light chain (LC) amino acid sequence of SEQ ID NO: 446, and a heavy chain (HC) amino acid sequence of SEQ ID NO: 453;
(h) a light chain (LC) amino acid sequence of SEQ ID NO: 454, and a heavy chain (HC) amino acid sequence of SEQ ID NO: 455;
(i) a light chain (LC) amino acid sequence of SEQ ID NO: 454, and a heavy chain (HC) amino acid sequence of SEQ ID NO: 456;
(j) a light chain (LC) amino acid sequence of SEQ ID NO: 454, and a heavy chain (HC) amino acid sequence of SEQ ID NO: 457;
(k) a light chain (LC) amino acid sequence of SEQ ID NO: 454, and a heavy chain (HC) amino acid sequence of SEQ ID NO: 458;
(l) a light chain (LC) amino acid sequence of SEQ ID NO: 454, and a heavy chain (HC) amino acid sequence of SEQ ID NO: 459;
(m) a light chain (LC) amino acid sequence of SEQ ID NO: 470, and a heavy chain (HC) amino acid sequence of SEQ ID NO: 471;
(n) a light chain (LC) amino acid sequence of SEQ ID NO: 440, and a heavy chain (HC) amino acid sequence of SEQ ID NO: 484;
(o) a light chain (LC) amino acid sequence of SEQ ID NO: 441, and a heavy chain (HC) amino acid sequence of SEQ ID NO: 485;
(p) a light chain (LC) amino acid sequence of SEQ ID NO: 442, and a heavy chain (HC) amino acid sequence of SEQ ID NO: 486;
(q) a light chain (LC) amino acid sequence of SEQ ID NO: 443, and a heavy chain (HC) amino acid sequence of SEQ ID NO: 487;
(r) a light chain (LC) amino acid sequence of SEQ ID NO: 444, and a heavy chain (HC) amino acid sequence of SEQ ID NO: 488;
(s) a light chain (LC) amino acid sequence of SEQ ID NO: 445; and a heavy chain (HC) amino acid sequence of SEQ ID NO: 489;
(t) a light chain (LC) amino acid sequence of SEQ ID NO: 446, and a heavy chain (HC) amino acid sequence of SEQ ID NO: 490;
(u) a light chain (LC) amino acid sequence of SEQ ID NO: 454, and a heavy chain (HC) amino acid sequence of SEQ ID NO: 491;
(v) a light chain (LC) amino acid sequence of SEQ ID NO: 454, and a heavy chain (HC) amino acid sequence of SEQ ID NO: 492;
(w) a light chain (LC) amino acid sequence of SEQ ID NO: 454, and a heavy chain (HC) amino acid sequence of SEQ ID NO: 493;
(x) a light chain (LC) amino acid sequence of SEQ ID NO: 454, and a heavy chain (HC) amino acid sequence of SEQ ID NO: 494;
(y) a light chain (LC) amino acid sequence of SEQ ID NO: 454, and a heavy chain (HC) amino acid sequence of SEQ ID NO: 495; or
(z) a light chain (LC) amino acid sequence of SEQ ID NO: 470, and a heavy chain (HC) amino acid sequence of SEQ ID NO: 501.

In various embodiments of the anti-CD96 antibody provided by the present disclosure, the antibody is characterized by one or more of the following properties:

(a) binds to human CD96 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD96 polypeptide of SEQ ID NO: 4;
(b) binds to cynomolgus monkey CD96 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a cy-CD96 polypeptide of SEQ ID NO: 7;
(c) binds to human CD96 and to cynomolgus monkey CD96 with a binding affinity of $1\times10^{-8}$ M or less, $1\times10^{-9}$ M or less, $1\times10^{-10}$ M or less, or $1\times10^{-11}$ M or less; optionally, wherein the binding affinity is measured by equilibrium dissociation constant ($K_D$) to a hu-CD96 polypeptide of SEQ ID NO: 4 and a cy-CD96 polypeptide of SEQ ID NO: 7;
(d) binds to human CD96 isoform 1 expressed on a cell with an antibody $EC_{50}$ concentration of 5 nM or less, 1 nM or less, or 0.1 nM or less; optionally, wherein the cell is a HEK293T cell;
(e) binds to human CD96 isoform 2 expressed on a cell with an antibody $EC_{50}$ concentration of 5 nM or less, 1 nM or less, or 0.1 nM or less; optionally, wherein the cell is a CHO cell;
(f) binds to human PBMCs with an antibody $EC_{50}$ concentration of 5 nM or less, 1 nM or less, or 0.1 nM or less;
(g) binds to cynomolgus monkey PBMCs with an antibody $EC_{50}$ concentration of 5 nM or less, 1 nM or less, or 0.1 nM or less;
(h) decreases binding of human CD155 to human CD96 expressed on CHO cells by at least 90%, at least 95%, at least 99%, or 100%; optionally, wherein at a human CD155 concentration of 10 nM the antibody has an $IC_{50}$ of 5 nM or less, 1 nM or less, or 0.1 nM or less;
(i) increases IFNγ secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less;
(j) increases IL-2 secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less;
(k) specifically binds to one or more amino acid residues within domain 1 of hu-CD96, wherein domain 1 comprises the amino acid sequence of SEQ ID NO: 5; optionally, wherein the one or more amino acid residues within domain 1 of hu-CD96 comprise residues T49 and V50 of SEQ ID NO:2, which correspond to residues T28 and V29 of SEQ ID NO: 5.
(l) does not bind to amino acid residues within domain 2 and/or domain 3 of human CD96;
(m) binds to human and/or cynomolgus monkey CD226 expressed on cells, optionally HEK293 cells, with an antibody $EC_{50}$ concentration of 500 nM or less, 300 nM or less, 250 nM or less, 200 nM or less, 150 nM or less, 100 nM or less, or 50 nM or less;
(n) binds to human CD226 with a binding affinity of 1 μM or less, 900 nM or less, 800 nM or less, 700 nM or less, from 1 μM to 50 nM, or from 800 nM to 200 nM; optionally, wherein the binding affinity is measured by equilibrium dissociation constant ($K_D$) to a huCD226 polypeptide of SEQ ID NO:482; and/or
(o) binds to cynomolgus monkey CD226 with a binding affinity of 1 μM or less, 800 nM or less, 500 nM or less, 300 nM or less, 100 nM or less, from 1 μM to 50 nM, from 500 nM to 60 nM, or from 300 nM to 70 nM; optionally, wherein the binding affinity is measured by equilibrium dissociation constant ($K_D$) to a cyCD226 polypeptide of SEQ ID NO:483.

The present disclosure also provides embodiments of the anti-CD96 antibody, wherein: (i) the antibody is a monoclonal antibody; (ii) the antibody is a human, humanized, or chimeric antibody; (iii) the antibody is a full length antibody of class IgG, optionally, wherein the class IgG antibody has an isotype selected from IgG1, IgG2, IgG3, and IgG4; (iv) the antibody is an Fc region variant, optionally an Fc region variant that alters effector function (e.g., a variant resulting in an effectorless antibody), or an Fc region variant that alters antibody half-life, or an Fc region variant that alters both effector function and antibody half-life, including in all instances where the Fc region may or may not contain a c-terminal lysine; (v) the antibody is an antibody fragment, optionally selected from the group consisting of F(ab')$_2$, Fab', Fab, Fv, single domain antibody (VHH), and scFv; (vi) the antibody is an immunoconjugate, optionally, wherein the immunoconjugate comprises a therapeutic agent for treatment of a CD96-mediated disease or condition; (vii) the antibody is a multi-specific antibody, optionally a bispecific antibody; and (viii) the antibody is a synthetic antibody, wherein the HVRs are grafted onto a scaffold or framework other than an immunoglobulin scaffold or framework; optionally, a scaffold selected from an alternative protein scaffold and an artificial polymer scaffold.

In some embodiments, the present disclosure provides an anti-CD96 antibody wherein the antibody is a multispecific antibody, optionally a bispecific antibody. In some embodiments, the present disclosure provides an anti-CD96 antibody wherein the antibody is a bispecific antibody comprising a specificity for an antigen that is an immune checkpoint molecule; optionally, wherein the immune checkpoint molecule is selected from PD1, TIGIT, LAG3, PVRIG, KIR, TIM-3, CRTAM, CTLA-4, BTLA, CD244, CD160, LIGHT, GITR, 4-1 BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA; optionally, wherein the antigen is selected from PD1, TIGIT, LAG3, PVRIG, KIR, TIM-3, and CRTAM.

In some embodiments, the present disclosure provides an anti-CD96 antibody that specifically binds CD96 and has a secondary affinity for CD226. In some embodiments, the present disclosure provides an anti-CD96 antibody that specifically binds human and/or cynomolgus monkey CD96 and has a secondary affinity for human and/or cynomolgus monkey CD226. Such secondary affinity may vary and may range from micromolar to nanomolar affinity and may be, e.g., a binding affinity of 1 μM or less, 900 nM or less, 800 nM or less, 700 nM or less, 600 nM or less, 500 nM or less, 400 nM or less, 300 nM or less, 200 nM or less, 100 nM or less, or 90 nM or less; optionally, wherein the binding affinity is measured by equilibrium dissociation constant ($K_D$) to a human CD226 polypeptide and/or a cynomolgus monkey CD226 polypeptide. In some embodiments, the secondary affinity of the anti-CD96 antibody for CD226 may be at least at least 50 nM, at least 60 nM, at least 70 nM, at least 80 nM, at least 90 nM, at least 100 nM, at least 200 nM, at least 300 nM, at least 400 nM, at least 500 nM, or at least 600 nM; optionally, wherein the binding affinity is measured by $K_D$ to a human CD226 polypeptide and/or a cynomolgus monkey CD226 polypeptide. In some embodiments, the secondary affinity of the anti-CD96 antibody for CD226 may range from 1 µM or less to 50 nM or more, 900 nM or less to 60 nM or more, 800 nM or less to 70 nM or more, or 700 nM or less to 80 nM or more; optionally, wherein the binding affinity is measured by $K_D$ to a human CD226 polypeptide and/or a cynomolgus monkey CD226 polypeptide. In some embodiments, the anti-CD96 antibody may bind CD226 with less than half the affinity with which the antibody binds CD96, including e.g., where the antibody binds CD96 with at least twice the affinity, at least 3× the affinity, at least 5× the affinity, or at least 10× the affinity, or at least 100× the affinity with which the antibody binds CD226.

In some embodiments, an anti-CD96 antibody of the present disclosure may bind to CD226 through a secondary affinity for CD226. In some embodiments, an anti-CD96 antibody of the present disclosure does not bind CD226 and is not characterized by having affinity for, e.g., a secondary affinity for, CD226. By "secondary affinity", as used herein, is meant an affinity for a secondary antigen that is substantially weaker than the affinity of the antibody for the primary antigen, i.e., CD96. By "substantially weaker", as used in this context, is generally meant that the primary affinity is at least twice the secondary affinity, at least 3× the secondary affinity, at least 5× the secondary affinity, at least 10× the secondary affinity, at least 100× the secondary affinity, etc. Accordingly, where the primary affinity, measured as $K_D$, may be in the nanomolar or subnanomolar range, the secondary affinity will generally be greater than 10 nM, including e.g., 25 nM or greater, 50 nM or greater, 75 nM or greater, 100 nM or greater, 250 nM or greater, 500 nM or greater, or 750 nM or greater.

Any binding due to secondary affinity may not result in a direct agonistic effect and/or a direct antagonistic effect on CD226 or any function thereof. By "not result in a direct agonistic effect on CD226", as used herein, is generally meant that administration of the active agent does not alone result in pharmacologically significant immune activation through CD226, such as immune cell proliferation and/or cytokine production, e.g., as compared to an appropriate control. By "not result in a direct antagonistic effect on CD226", as used herein, is generally meant that administration of the active agent does not alone result in pharmacologically significant inhibition of immune activation through CD226, such as inhibition of immune cell proliferation and/or cytokine production, e.g., as compared to an appropriate control. In some instances, direct binding to CD226 by an anti-CD96 antibody of the present disclosure may result in an enhancement of CD226-triggered cellular activity. In some instances, the anti-CD96 antibody is not an agonist and/or antagonist of CD226.

In other embodiments, the present disclosure provides isolated nucleic acids encoding the anti-CD96 antibodies disclosed herein.

In some embodiments, the present disclosure also provides a host cell comprising a nucleic acid encoding an anti-CD96 antibody as disclosed herein.

The disclosure also provides a method of producing an anti-CD96 antibody, wherein the method comprises culturing a host cell comprising a nucleic acid (or vector) encoding an anti-CD96 antibody so that an antibody is produced.

In some embodiments, the disclosure provides a pharmaceutical composition comprising an anti-CD96 antibody as disclosed herein and a pharmaceutically acceptable carrier. In some embodiments, the pharmaceutical composition further comprises a therapeutic agent for treatment of a CD96-mediated disease or condition. In some embodiments, the anti-CD96 antibody is the sole active agent of the pharmaceutical composition. In some embodiments, the pharmaceutical composition comprises the anti-CD96 antibody and an additional active agent, such as but not limited to e.g., a checkpoint inhibitor such as e.g., a second antibody comprising a specificity for an antigen that is an immune checkpoint molecule; optionally, wherein the immune checkpoint molecule is selected from PD1, TIGIT, LAG3, PVRIG, KIR, TIM-3, CRTAM, CTLA-4, BTLA, CD244, CD160, LIGHT, GITR, 4-1 BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA; optionally, wherein the antigen is selected from PD1, TIGIT, LAG3, PVRIG, KIR, TIM-3, and CRTAM.

In some embodiments, the present disclosure provides a method of treating a CD96-mediated disease in a subject, comprising administering to the subject a therapeutically effective amount of an anti-CD96 antibody as disclosed herein, or a therapeutically effective amount of a pharmaceutical formulation of an anti-CD96 antibody as disclosed herein. In some embodiments, the anti-CD96 antibody is the sole active agent administered to the subject to treat the subject for the CD96-mediated condition. In some embodiments, the subject is administered more than one active agents, including e.g., 2 or more, 3 or more, 4 or more, or 5 or more active agents effective to treat the subject for the CD96-mediated condition, including e.g., where the more than one active agents include the anti-CD96 antibody and at least one additional active agent, such as but not limited to e.g., a checkpoint inhibitor such as e.g., one or more antibodies comprising a specificity for an antigen that is an immune checkpoint molecule.

In some embodiments, the present disclosure provides a method of treating a disease mediated by binding to CD155 expressed on cells in a subject, comprising administering to the subject a therapeutically effective amount of an anti-CD96 antibody as disclosed herein, or a therapeutically effective amount of a pharmaceutical formulation of an anti-CD96 antibody as disclosed herein. In some embodiments, the anti-CD96 antibody is the sole active agent administered to the subject to treat the subject for the disease mediated by binding to CD155 expressed on cells in the subject. In some embodiments, the subject is administered a plurality of active agents effective to treat the subject for the disease mediated by binding to CD155 expressed on cells in the subject, including e.g., where the plurality of active agents include the anti-CD96 antibody and an additional active agent, such as but not limited to e.g., a checkpoint inhibitor such as e.g., a second antibody comprising a specificity for an antigen that is an immune checkpoint molecule.

In some embodiments, the present disclosure provides a method of treating a disease mediated by CD226 and/or TIGIT in a subject, comprising administering to the subject a therapeutically effective amount of an anti-CD96 antibody as disclosed herein, or a therapeutically effective amount of a pharmaceutical formulation of an anti-CD96 antibody as disclosed herein. In some embodiments, the anti-CD96 antibody is the sole active agent administered to the subject to treat the subject for the disease mediated by CD226 and/or TIGIT in the subject. In some embodiments, the subject is administered a plurality of active agents effective to treat the subject for the disease mediated by CD226 and/or TIGIT in the subject, including e.g., where the plurality of active agents include the anti-CD96 antibody and an additional active agent, such as but not limited to e.g., a checkpoint inhibitor such as e.g., a second antibody comprising a specificity for an antigen that is an immune checkpoint molecule.

In some embodiments of the uses and methods of treatment disclosed herein, the CD96-mediated diseases and conditions, or the diseases mediated by CD155, CD226, and/or TIGIT, that can be treated with the anti-CD96 antibodies of the present disclosure, or pharmaceutical compositions thereof, include cancer and viral infections. In some embodiments, the cancer is selected from adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer. In some embodiments, the cancer is selected from lung cancer, skin cancer (e.g., melanoma), pancreatic cancer, endometrial cancer, prostate cancer, colorectal cancer, ovarian cancer, and bladder cancer. In some embodiments, the viral infection is selected from Cytomegalovirus (CMV), Epstein Barr Virus (EBV), Herpes Simplex Virus (HSV), Human Immunodeficiency Virus (HIV), Human Papilloma Virus (HPV), and Varicella Zoster Virus (VSV).

BRIEF DESCRIPTION OF THE FIGURES

FIG. 1 depicts the amino acid sequence alignment of the closest human germline kappa light chain $V_L$ region (Gene ID—V gene: IGKV1-9*01, J gene: IGKJ2*01) and heavy chain $V_H$ region (Gene ID—V gene: IGHV1-46*01, J gene: IGHJ4*03) against the $V_L$ and $V_H$ regions of the hybridoma-derived murine anti-hu-CD96 antibody, 12F8, and the humanized version of this antibody, mAb1, as well as six $V_H$ region variants mAb1.v1, mAb1.v2, mAb1.v3, mAb1.v4, mAb1.v5, and mAb1.v7.

FIG. 2 depicts the amino acid sequence alignment of the closest human germline kappa light chain $V_L$ region (Gene ID—V gene: IGKV6D-21*02, J gene: IGKJ4*02) and heavy chain $V_H$ region (Gene ID—V gene: IGHV7-4-1*02, J gene: IGHJ4*03) against the $V_L$ and $V_H$ regions of the hybridoma-derived murine anti-hu-CD96 antibody, 10G1, and the humanized version of this antibody, h10G1.

FIG. 4A shows upregulation of surface expression levels of CD96; CD226, and CD155 in response to FHA and IL-2 treatment; FIG. 4B shows IL-2 secretion levels in response to incubation with anti-CD-96 antibodies in comparison to control ("IgG1 iso").

FIG. 5A shows surface expression levels of CD96; FIG. 5B shows surface expression levels of CD226; FIG. 5C shows surface expression levels of CD155.

FIG. 10A depicts changes in IL-2 levels and FIG. 10B depicts changes in IFNγ levels.

FIG. 11A depicts changes in IFNγ levels and FIG. 11B depicts changes in IL-2 levels.

FIG. 12A depicts binding to purified human CD226 ectodomain protein and FIG. 12B depicts binding to expressed purified cynomolgus monkey CD226 ectodomain protein.

DETAILED DESCRIPTION

Figure 3:
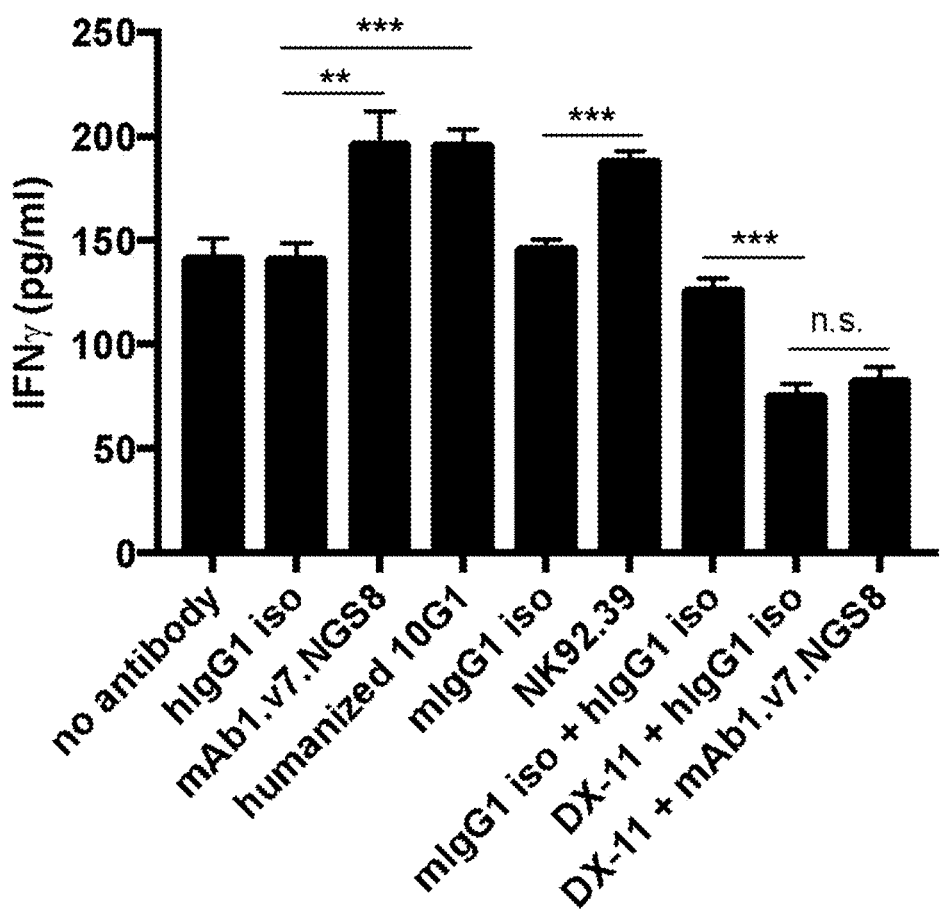
FIG. 3 depicts plots of IFNγ secretion triggered by the anti-CD96 antibodies mAb1.v7.NGS8 (or "NGS8"), humanized 10G1 ("h10G1"), NK92.39, and the control antibodies humanized IgG1+N297G mutation ("hIgG1 N297G iso", indicated as "hIgG iso" in the figure), mouse IgG1 ("mIgG1 iso"), alone, and also triggered by NGS8 or the control antibodies in the presence of the anti-CD226 antibody DX-11. Each condition was tested in 5 biological replicates. Student T-test was used to compare indicated groups. , p<0.005; *, p<0.001; NS, not significant.

The present disclosure provides antibodies, including humanized antibodies, that specifically bind CD96 with high affinity and thereby inhibit, decrease, and/or fully block the function of CD96 as a cell surface receptor involved in immune regulation, particularly the function of CD96 as an inhibitor of lymphocyte (e.g., T cell and NK cell) activation. Accordingly, it is contemplated that any of the compositions or formulations comprising an anti-CD96 antibody of the present disclosure can be used as therapeutics for treatment of diseases mediated by the function of CD96 or its target antigen, CD155, such as cancers and viral infections. Further, it is contemplated that the anti-CD96 antibody of the present disclosure can be used as a therapeutic in combination with other therapeutics, such as antibodies that target immune checkpoint molecules including, but not limited to, PD1, TIGIT, LAG3, PVRIG, KIR, TIM-3, and CRTAM. Among the therapeutics contemplated by the present disclosure is a bispecific antibody comprising the anti-CD96 binding specificity of an antibody of the present disclosure and another binding specificity of an antibody to an immune checkpoint molecule such as PD1, TIGIT, LAG3, PVRIG, KIR, TIM-3, and CRTAM.

Overview of Terminology and Techniques

For the descriptions herein and the appended claims, the singular forms "a", and "an" include plural referents unless the context clearly indicates otherwise. Thus, for example, reference to "a protein" includes more than one protein, and reference to "a compound" refers to more than one compound. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

Generally, the nomenclature used herein and the techniques and procedures described herein include those that are well understood and commonly employed by those of ordinary skill in the art, such as the common techniques and methodologies described in Sambrook et al., Molecular Cloning-A Laboratory Manual (2nd Ed.), Vols. 1-3, Cold Spring Harbor Laboratory, Cold Spring Harbor, N.Y., 1989 (hereinafter "Sambrook"); Current Protocols in Molecular Biology, F. M. Ausubel et al., eds., Current Protocols, a joint venture between Greene Publishing Associates, Inc. and John Wiley & Sons, Inc. (supplemented through 2011) (hereinafter "Ausubel"); Antibody Engineering, Vols. 1 and 2, R. Kontermann and S. Dubel, eds., Springer-Verlag, Berlin and Heidelberg (2010); Monoclonal Antibodies: Methods and Protocols, V. Ossipow and N. Fischer, eds., 2nd Ed., Humana Press (2014); Therapeutic Antibodies: From Bench to Clinic, Z. An, ed., J. Wiley & Sons, Hoboken, N.J. (2009); and Phage Display, Tim Clackson and Henry B. Lowman, eds., Oxford University Press, United Kingdom (2004).

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

Unless defined otherwise, all technical and scientific terms used herein have the same meaning as commonly understood by one of ordinary skill in the art to which the present invention pertains. It is to be understood that the terminology used herein is for the purpose of describing particular embodiments only and is not intended to be limiting. For purposes of interpreting this disclosure, the following description of terms will apply and, where appropriate, a term used in the singular form will also include the plural form and vice versa.

"CD96," as used herein, refers to a transmembrane glycoprotein of the Ig superfamily that that is encoded by the cluster of differentiation 96 gene in humans, however "CD96" as used herein encompasses the CD96 proteins of human, cynomolgus monkey, rhesus monkey, and their various isoforms. CD96 is expressed on the surface of T cells and NK cells and is also commonly referred to in the art as "TACTILE." Amino acid sequences of various exemplary CD96 proteins are known in the art and are provided in Table 1 below and the attached Sequence Listing.

"CD96 mediated condition" or "CD96 mediated disease," as used herein, encompasses any medical condition associated with the specific binding of CD96 to an antigen (e.g., CD155). For example, specific binding of CD96 to the cell surface receptor CD155 can affect the binding of CD155 to the immune regulatory molecules CD226 and/or TIGIT, which alters activation of lymphocytes (e.g., T cells and NK cells). Accordingly, CD96 mediated diseases can include, but are not limited to, any disease or condition mediated by and/or responsive to antagonists or inhibitors of CD155, CD226, and/or TIGIT, and/or any disease or condition responsive to inhibition of immune checkpoint inhibitors, including but not limited to cancers and viral infections. Specific exemplary cancers and viral infections are provided elsewhere herein.

"CD226," as used herein, refers to a transmembrane glycoprotein of the Ig superfamily that that is encoded by the cluster of differentiation 226 gene in humans, however "CD226" as used herein encompasses the CD226 proteins of human, cynomolgus monkey, rhesus monkey, mouse, and their various isoforms. CD226 is expressed on the surface of NK cells, platelets, monocytes, and a subset of T cells, and is also commonly referred to in the art as "DNAM-1." Amino acid sequences of exemplary CD226 proteins are known in the art and provided elsewhere herein.

"CD155," as used herein, refers to a transmembrane glycoprotein of the Ig superfamily that is encoded by the cluster of differentiation 155 gene in humans, however "CD155" as used herein encompasses the CD155 proteins of human, cynomolgus monkey, rhesus monkey, mouse, and their various isoforms that may exist. CD155 is expressed on the surface of many cancer cell lines and primary tumors and is also commonly referred to as "PVR" or "Necl5." Amino acid sequences of exemplary CD155 proteins are known in the art and are provided in Table 1 below and the attached Sequence Listing.

"TIGIT," as used herein, refers to a transmembrane glycoprotein of the Ig superfamily that that is expressed on the surface of T cells and NK cells. TIGIT is also referred to in the art as "T cell immunoreceptor with Ig and ITIM domains." Amino acid sequences of exemplary TIGIT proteins are known in the art.

"Immune checkpoint molecule," as used herein, refers to a molecule that functions to regulate an immune system pathway and thereby prevent it from attacking cells unnecessarily. Many immune checkpoint molecules, both inhibitory and co-stimulatory, are targets for immunotherapy (e.g., with blocking antibodies to block immune inhibition or with agonists to promote immune stimulation) in the treatment of cancer and viral infections. Exemplary immune checkpoint molecules targeted for cancer immunotherapy include, but are not limited to, PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA.

"Antibody," as used herein, refers to a molecule comprising one or more polypeptide chains that specifically binds to, or is immunologically reactive with, a particular antigen. Exemplary antibodies of the present disclosure include monoclonal antibodies, polyclonal antibodies, chimeric antibodies, humanized antibodies, human antibodies, multispecific (or heteroconjugate) antibodies (e.g., bispecific antibodies), monovalent antibodies (e.g., single-arm antibodies), multivalent antibodies, antigen-binding fragments (e.g., Fab', F(ab')$_2$, Fab, Fv, rIgG, and scFv fragments), antibody fusions, and synthetic antibodies (or antibody mimetics).

"Anti-CD96 antibody" or "antibody that binds CD96" refers to an antibody that binds CD96 with sufficient affinity such that the antibody is useful as a diagnostic and/or therapeutic agent in targeting CD96. In some embodiments, the extent of binding of an anti-CD96 specific antibody to an unrelated, non-CD96 antigen is less than about 20%, less than about 15%, less than about 10%, or less than about 5% of the binding of the antibody to CD96 as measured, e.g., by a radioimmunoassay (RIA) or surface plasmon resonance (SPR). In some embodiments, an antibody that binds to CD96 has a dissociation constant ($K_D$) of <1 µM, <100 nM, <10 nM, <1 nM, <0.1 nM, <0.01 nM, or <1 µM (e.g., $10^{-8}$ M or less, e.g., from $10^{-8}$ M to $10^{-13}$ M, e.g., from $10^{-9}$ M to $10^{-13}$ M).

"Full-length antibody," "intact antibody," or "whole antibody" are used herein interchangeably to refer to an antibody having a structure substantially similar to a native antibody structure or having heavy chains that contain an Fc region as defined herein.

"Antibody fragment" refers to a portion of a full-length antibody which is capable of binding the same antigen as the full-length antibody. Examples of antibody fragments include, but are not limited to, Fv, Fab, Fab', Fab'-SH, F(ab')$_2$; diabodies; linear antibodies; monovalent, or single-armed antibodies; single-chain antibody molecules (e.g., scFv); and multispecific antibodies formed from antibody fragments.

"Class" of an antibody refers to the type of constant domain or constant region possessed by its heavy chain. There are five major classes of antibodies: IgA, IgD, IgE, IgG, and IgM, and several of these are further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and µ, respectively.

"Variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs) (see, e.g., Kindt et al., Kuby Immunology, 6$^{th}$ ed., W.H. Freeman and Co., page 91). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (see, e.g., Portolano et al., J. Immunol. 150: 880-887 (1993); Clarkson et al., Nature 352:624-628 (1991)).

"Hypervariable region" or "HVR," as used herein, refers to each of the regions of an antibody variable domain which are hypervariable in sequence and/or form structurally defined loops ("hypervariable loops"). Generally, native antibodies comprise four chains with six HVRs; three in the heavy chain variable domain, $V_H$ (HVR-H1, HVR-H2, HVR-H3), and three in the light chain variable domain, $V_L$ (HVR-L1, HVR-L2, HVR-L3). The HVRs generally comprise amino acid residues from the hypervariable loops and/or from the "complementarity determining regions" (CDRs). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted in the table below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B[1] | H26-H35B[1] | H26-H32[1] | H30-H35B[1] |
|    | H31-H35[2] | H26-H35[2] | H26-H32[2] | H30-H35[2] |
| H2 | H50-H65 | H50-H58 | H53-H55 | H47-H58 |
| H3 | H95-H102 | H95-H102 | H96-H101 | H93-H101 |

[1]Kabat numbering
[2]Chothia numbering

Unless otherwise indicated, HVR residues and other residues in the variable domain (e.g., FR residues) are numbered herein according to Kabat et al., supra.

Hypervariable regions, as used herein, may include extended or alternative hypervariable regions as follows: 24-36 or 24-34 (L1), 46-56 or 50-56 (L2) and 89-97 or 89-96 (L3) in the $V_L$ domain and 26-35 or 30-35 (H1), 50-61, 50-65 or 49-65 (H2) and 93-102, 94-102, or 95-102 (H3) in the $V_H$ domain. The variable domain residues are numbered according to Kabat et al., supra, for each of these definitions.

"Complementarity determining region," or "CDR," as used herein, refers to the regions within the HVRs of the variable domain which have the highest sequence variability and/or are involved in antigen recognition. Generally, native antibodies comprise four chains with six CDRs; three in the heavy chain variable domains, $V_H$ (H1, H2, H3), and three in the light chain variable domains, $V_L$ (L1, L2, L3). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35 of H1, 50-61 of H2, and 95-102 of H3. (Numbering according to Kabat et al., supra).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in $V_H$ (or $V_L$): FR1-H1(L1)-FR2-H2(L2)-FR3-H3(L3)-FR4.

"Native antibody" refers to a naturally occurring immunoglobulin molecule. For example, native IgG antibodies are heterotetrameric glycoproteins of about 150,000 Daltons, composed of two identical light chains and two identical heavy chains that are disulfide-bonded. From N- to C-terminus, each heavy chain has a variable region ($V_H$), also called a variable heavy domain or a heavy chain variable domain, followed by three constant domains (CH1, CH2, and CH3). Similarly, from N- to C-terminus, each light chain has a variable region ($V_L$), also called a variable light domain or a light chain variable domain, followed by a constant light (CL) domain. The light chain of an antibody may be assigned to one of two types, called kappa (κ) and lambda (λ), based on the amino acid sequence of its constant domain.

"Monoclonal antibody" as used herein refers to an antibody obtained from a substantially homogeneous population of antibodies, i.e., the individual antibodies comprising the population are identical and/or bind the same epitope, except for possible variant antibodies (e.g., variant antibodies contain mutations that occur naturally or arise during production of a monoclonal antibody, and generally are present in minor amounts). In contrast to polyclonal antibody preparations, which typically include different antibodies directed against different determinants (epitopes), each monoclonal antibody of a monoclonal antibody preparation is directed against a single determinant on an antigen. Thus, the term "monoclonal" indicates the character of the antibody as being obtained from a substantially homogeneous population of antibodies and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Chimeric antibody" refers to an antibody in which a portion of the heavy and/or light chain is derived from a particular source or species, while the remainder of the heavy and/or light chain is derived from a different source or species.

"Humanized antibody" refers to a chimeric antibody comprising amino acid sequences from non-human HVRs and amino acid sequences from human FRs. In certain embodiments, a humanized antibody will comprise substantially all of at least one, and typically two, variable domains, in which all or substantially all of the HVRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

"Human antibody" refers to an antibody which possesses an amino acid sequence corresponding to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Human consensus framework" is a framework which represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the $V_L$, the subgroup is subgroup kappa I as in Kabat et al., supra. In one embodiment, for the $V_H$, the subgroup is subgroup III as in Kabat et al., supra.

"Acceptor human framework" as used herein is a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the $V_L$ acceptor human framework is identical in sequence to the $V_L$ human immunoglobulin framework sequence or human consensus framework sequence.

"Fc region," refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain.

"Fc receptor" or "FcR," refers to a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see, e.g., Daeron, Annu. Rev. Immunol. 15:203-234 (1997)). FcR, as used herein, also includes the neonatal receptor, FcRn, which is responsible for the transfer of maternal IgGs to the fetus (Guyer et al, J. Immunol. 1 17:587 (1976) and Kim et al, J. Immunol. 24:249 (1994)) and regulation of homeostasis of immunoglobulins. FcRs are reviewed, for example, in Ravetch and Kinet, Annu. Rev. Immunol 9:457-92 (1991); Capel et al, Immunomethods 4:25-34 (1994); and de Haas et al, J. Lab. Clin. Med. 126:330-41 (1995).

"Multivalent antibody," as used herein, is an antibody comprising three or more antigen binding sites. The multivalent antibody is preferably engineered to have the three or more antigen binding sites and is generally not a native sequence IgM or IgA antibody.

"Multispecific antibody" is an antibody having at least two different binding sites, each site with a different binding specificity. A multispecific antibody can be a full length antibody or an antibody fragment, and the different binding sites may bind each to a different antigen or the different binding sites may bind to two different epitopes of the same antigen.

"Fv fragment" refers to an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

"Fab fragment" refers to an antibody fragment that contains a variable and constant domain of the light chain and a variable domain and the first constant domain (CH1) of the heavy chain. "F(ab')$_2$ fragments" comprise a pair of Fab fragments which are generally covalently linked near their carboxy termini by hinge cysteines between them. Other chemical couplings of antibody fragments also are known in the art.

"Antigen binding arm," as used herein, refers to a component of an antibody that has an ability to specifically bind a target molecule of interest. Typically the antigen binding arm is a complex of immunoglobulin polypeptide sequences, e.g., HVR and/or variable domain sequences of an immunoglobulin light and heavy chain.

"Single-chain Fv" or "scFv" refer to antibody fragments comprising the $V_H$ and $V_L$ domains of an antibody, wherein these domains are present in a single polypeptide chain. Generally, an Fv polypeptide further comprises a polypeptide linker between the $V_H$ and $V_L$ domains which enables the scFv to form the desired antigen binding structure.

"Diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites.

"Linear antibodies" refers to the antibodies described in Zapata et al., Protein Eng., 8(10): 1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

"Naked antibody" refers to an antibody that is not conjugated to a heterologous moiety (e.g., a cytotoxic moiety) or radiolabel.

"Affinity" refers to the strength of the sum total of noncovalent interactions between a single binding site of a molecule (e.g., an antibody) and its binding partner (e.g., an antigen). "Binding affinity" refers to intrinsic binding affinity which reflects a 1:1 interaction between members of a binding pair (e.g., antibody and antigen). The affinity of a molecule X for its partner Y can generally be represented by the equilibrium dissociation constant ($K_D$). Affinity can be measured by common methods known in the art, including those described herein. Specific illustrative and exemplary embodiments for measuring binding affinity are described in the following.

"Binds specifically" or "specific binding" refers to binding of an antibody to an antigen with an affinity value of no more than about $1 \times 10^{-7}$ M. In some embodiments, an antibody may have a secondary affinity for an antigen other than the antigen to which it binds specifically, where "secondary affinity" will generally refer to binding of an antibody to a secondary antigen with an affinity value of more than about 10 nM as described elsewhere herein. Where an antibody may have a secondary affinity for a secondary antigen, such an antibody will nevertheless bind specifically to the primary antigen.

"Affinity matured" antibody refers to an antibody with one or more alterations in one or more HVRs, compared to a parent antibody which does not possess such alterations, such alterations resulting in an improvement in the affinity of the antibody for antigen.

"Functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen.

"Isolated antibody" refers to an antibody which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic methods (e.g., ion exchange or reverse phase HPLC). For review of methods for assessment of antibody purity, see, e.g., Flatman et al., J. Chromatogr. B 848:79-87.

"Substantially similar" or "substantially the same," as used herein, refers to a sufficiently high degree of similarity between two numeric values (for example, one associated with a test antibody and the other associated with a reference antibody), such that one of skill in the art would consider the difference between the two values to be of little or no biological and/or statistical significance within the context of the biological characteristic measured by said values (e.g., $K_D$ values).

"Substantially different," as used herein, refers to a sufficiently high degree of difference between two numeric values (generally one associated with a molecule and the other associated with a reference molecule) such that one of skill in the art would consider the difference between the two values to be of statistical significance within the context of the biological characteristic measured by said values (e.g., $K_D$ values).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

"Immunoconjugate" refers to an antibody conjugated to one or more heterologous molecule(s), including but not limited to a cytotoxic agent.

"Treatment," "treat" or "treating" refers to clinical intervention in an attempt to alter the natural course of a disorder in the individual being treated, and can be performed either for prophylaxis or during the course of clinical pathology. Desired results of treatment can include, but are not limited to, preventing occurrence or recurrence of the disorder, alleviation of symptoms, diminishment of any direct or indirect pathological consequences of the disorder, preventing metastasis, decreasing the rate of progression, amelioration or palliation of a disease state, and remission or improved prognosis. For example, treatment can include administration of a therapeutically effective amount of pharmaceutical formulation comprising an anti-CD96 antibody to a subject to delay development or slow progression of a disease or condition mediated by CD96 or disease or condition in which CD96 may play a role in the pathogenesis and/or progression.

"Pharmaceutical formulation" refers to a preparation in a form that allows the biological activity of the active ingredient(s) to be effective, and which contain no additional components which are toxic to the subjects to which the formulation is administered. A pharmaceutical formulation may include one or more active agents. For example, a pharmaceutical formulation may include an anti-CD96 antibody as the sole active agent of the formulation or may include an anti-CD96 antibody and one or more additional active agents, such as e.g., an immune checkpoint inhibitor.

By "sole active agent", as used herein, is meant that the agent referred to is the only agent present in the formulation, or used in the therapy, that provides, or would be expected to provide, the relevant pharmacological effect to treat the subject for the condition, consistent with the description of "treatment" as provided herein. A pharmaceutical formulation comprising a sole active agent does not exclude the presence of one or more non-active agents, such as e.g., a pharmaceutically acceptable carrier, in the formulation. A "non-active agent" is an agent that would not be expected to provide, or otherwise significantly contribute to, the relevant pharmacological effect intended to treat the subject for the condition.

"Pharmaceutically acceptable carrier" refers to an ingredient in a pharmaceutical formulation, other than an active ingredient, which is nontoxic to the subject to whom it is administered. A pharmaceutically acceptable carrier includes, but is not limited to, a buffer, excipient, stabilizer, or preservative.

"Therapeutically effective amount" refers to the amount of an active ingredient or agent (e.g., a pharmaceutical formulation) to achieve a desired therapeutic or prophylactic result, e.g., to treat or prevent a disease, disorder, or condition in a subject. In the case of a CD96 mediated disease or condition, the therapeutically effective amount of the therapeutic agent is an amount that reduces, prevents, inhibits, and/or relieves to some extent one or more of the symptoms associated with the disease, disorder, or condition. For cancer therapy, efficacy in vivo can, for example, be measured by assessing the growth of a primary tumor, occurrence and/or growth of secondary tumor(s), occurrence and/or number of metastases, duration, severity, and/or recurrence of symptoms, the response rate (RR), duration of response, and/or quality of life.

"Concurrently," as used herein, refers to administration of two or more therapeutic agents, where at least part of the administration overlaps in time. Accordingly, concurrent administration includes a dosing regimen when the administration of one or more agent(s) continues after discontinuing the administration of one or more other agent(s).

"Individual" or "subject" refers to a mammal, including but not limited to, domesticated animals (e.g., cows, sheep, cats, dogs, and horses), primates (e.g., humans and non-human primates such as monkeys), rabbits, and rodents (e.g., mice and rats).

Detailed Description of Various Embodiments

I. CD96

CD96 is a transmembrane glycoprotein of the Ig superfamily that is expressed on the surface of cells, notable T cells and NK cells. The sequence and annotation of human CD96 (also referred to herein as "hu-CD96") can be found at UniProt entry P40200. The sequence of the full-length 585 amino acid hu-CD96 precursor protein (UniProt P40200) is set forth herein as SEQ ID NO: 1. A shorter isoform of hu-CD96, referred to as "isoform 2," is believed to be the predominant in vivo form of hu-CD96 (Meyer et al., (2009)). The sequence of the 569 amino acid isoform 2 of hu-CD96 precursor protein (UniProt P40200-2) is set forth herein as SEQ ID NO: 2. The 16-amino add sequence at positions 183-198 of the full-length hu-CD96 isoform 1 (SEQ ID NO: 1) is missing in isoform 2 (SEQ ID NO: 2). An exemplary 1710 nucleotide sequence encoding isoform 2 hu-CD96 (GenBank M88282.1) is set forth herein as SEQ ID NO: 3.

The amino acid sequence of hu-CD96 comprises in consecutive order a signal peptide, extracellular domain, transmembrane domain, and cytoplasmic domain. The signal sequence of hu-CD96 comprises amino acids 1-21, the extracellular domain comprises amino acids 22-519, the transmembrane domain comprises amino acid 520-540, and the cytoplasmic domain comprises amino acids 541-585 (position numbering based on SEQ ID NO: 1). The extracellular domain of hu-CD96 further comprises three distinct Ig-like domains: "D1" comprises amino acids 38-125; "D2" comprises amino acids 156-238; and "D3" comprises amino acids 269-375 (position numbering based on SEQ ID NO: 1).

Recombinant polypeptide constructs corresponding to the extracellular portions of the isoform 2 hu-CD96 protein can be used as antigens to elicit anti-CD96 antibodies capable of binding the CD96 target antigen with high affinity, and preventing binding of CD96 to CD155. Polypeptide constructs corresponding to the extracellular portions of isoform 2, hu-CD96 protein useful as antigens include the polypeptides of amino acid sequences of SEQ ID NO: 4, 5, and 6. These polypeptides comprise the extracellular domain of isoform 2, hu-CD96 (positions V22-K516) (SEQ ID NO: 4), the D1 extracellular domain (positions V22-Q137) (SEQ ID NO: 5), and the combined domains D1, D2, and D3 (or "D1D3") (positions V22-T375) (SEQ ID NO: 6). Additionally, recombinant polypeptide constructs corresponding to the complete extracellular domain and D1D3 domains of the cynomolgus monkey CD96 protein ("cy-CD96") (SEQ ID NO: 7 and 8), and the D1 D3 domains of the rhesus monkey CD96 protein (rh-CD96) (SEQ ID NO: 9) are useful in as antigens in generating anti-CD96 antibodies capable of cross reacting with human CD96 and these primate species CD96 proteins. Recombinant polypeptide constructs corresponding to the extracellular portions of the CD96 target antigen human CD155 protein (SEQ ID NO: 10), and the corresponding mouse CD155 protein (SEQ ID NO: 11), are useful in developing the anti-CD96 antibodies with high affinity and cross-reactivity.

Recombinant polypeptide constructs corresponding to the extracellular portions of the human CD226 protein (SEQ ID NO: 482), and the corresponding cynomolgus CD226 protein (SEQ ID NO: 483), are useful in determining secondary binding properties of the anti-CD96 antibodies with CD226.

Table 1 below provides a summary description of the sequences of the various CD96 proteins, and the recombinant CD96, CD155, and CD226 polypeptide constructs of the present disclosure, and their sequence identifiers. The sequences also are included in the accompanying Sequence Listing.

TABLE 1

CD96 and CD155 Sequences

| Name | Sequence | SEQ ID NO: |
|---|---|---|
| hu-CD96 isoform 1 (UniProt 40200) | MEKKWKYCAVYYIIQIHFVKGVWEKTVNTEENVYATLGSDVNLTCQTQTVGFFV QMQWSKVTNKIDLIAVYHPQYGFYCAYGRPCESLVTFTETPENGSKWTLHLRNM SCSVSGRYECMLVLYPEGIQTKIYNLLIQTHVTADEWNSNHTIEIEINQTLEIP CFQNSSSKISSEFTYAWSVENSSTDSWVLLSKGIKEDNGTQETLISQNHLISNS TLLKDRVKLGTDYRLHLSPVQIFDDGRKFSCHIRVGPNKILRSSTTVKVFAKPE IPVIVENNSTDVLVERRFTCLLKNVFPKANITWFIDGSFLHDEKEGIYITNEER KGKDGFLELKSVLTRVHSNKPAQSDNLTIWCMALSPVPGNKVWNISSEKITFLL GSEISSTDPPLSVTESTLDTQPSPASSVSPARYPATSSVTLVDVSALRPNTTPQ PSNSSMTTRGFNYPWTSSGTDTKKSVSRIPSETYSSSPSGAGSTLHDNVFTSTA RAFSEVPTTANGSTKTNHVHITGIVVNKPKDGMSWPVIVAALLFCCMILFGLGV RKWCQYQKEIMERPPPFKPPPPPIKYTCIQEPNESDLPYHEMETL | 1 |
| hu-CD96 isoform 2 (UniProt 40200-2) | MEKKWKYCAVYYIIQIHFVKGVWEKTVNTEENVYATLGSDVNLTCQTQTVGFFV QMQWSKVTNKIDLIAVYHPQYGFYCAYGRPCESLVTFTETPENGSKWTLHLRNM SCSVSGRYECMLVLYPEGIQTKIYNLLIQTHVTADEWNSNHTIEIEINQTLEIP CFQNSSSKISSEFTYAWSVEDNGTQETLISQNHLISNSTLLKDRVKLGTDYRLH LSPVQIFDDGRKFSCHIRVGPNKILRSSTTVKVFAKPEIPVIVENNSTDVLVER RFTCLLKNVFPKANITWFIDGSFLHDEKEGIYITNEERKGKDGFLELKSVLTRV HSNKPAQSDNLTIWCMALSPVPGNKVWNISSEKITFLLGSEISSTDPPLSVTES TLDTQPSPASSVSPARYPATSSVTLVDVSALRPNTTPQPSNSSMTTRGFNYPWT SSGTDTKKSVSRIPSETYSSSPSGAGSTLHDNVFTSTARAFSEVPTTANGSTKT NHVHITGIVVNKPKDGMSWPVIVAALLFCCMILFGLGVRKWCQYQKEIMERPPP FKPPPPPIKYTCIQEPNESDLPYHEMETL | 2 |
| hu-CD96 isoform 2 (GenBank M88282.1) | ATGGAGAAAAAATGGAAATACTGTGCTGTCTATTAGATCATCCAGATACATTTTG TCAAGGGAGTTTGGGAAAAAACAGTCAACACAGAAGAAAATGTTTATGCTACACT TGGCTCTGATGTCAACCTGACCTGCCAAACACAGACAGTAGGCTTCTTCGTGCAG ATGCAATGGTCCAAGGTCACCAATAAGATAGACCTGATTGCTGTCTATCATCCCC AATACGGCTTCTACTGTGCCTATGGGAGACCCTGTGAGTCACTTGTGACTTTCAC AGAAACTCCTGAGAATGGGTCAAAATGGACTCTGCACTTAAGGAATATGTCTTGT TCAGTCAGTGGAAGGTACGAGTGTATGCTTGTTCTGTATCCAGAGGGCATTCAGA CTAAAATCTACAACCTTCTCATTCAGACACACGTTACAGCAGATGAATGGAACAG CAACCATACGATAGAAATAGAGATAAATCAGACTCTGGAAATACCATGCTTTCAA AATAGCTCCTCAAAAATTTCATCTGAGTTCACCTATGCATGGTCGGTGGAGGATA ATGGAACTCAGGGAAACACTTATCTCCCAAAATCACCTCATCAGCAATTCCACATT ACTTAAAGATAGAGTCAAGCTTGGTACAGACTACAGACTCCACCTCTCTCCAGTC CAAATCTTCGATGATGGGCGGAAGTTCTCTTGCCACATTAGAGTCGGTCCTAACA AAATCTTGAGGAGCTCCACCACAGTCAAGGTTTTTGCTAAACCAGAAATCCCTGT GATTGTGGAAAATAACTCCACGGATGTCTTGGTAGAGAGAAGATTTACCTGCTTA CTAAAGAATGTATTTCCCAAAGCAAATATCACATGGTTTATAGATGGAAGTTTTC TTCATGATGAAAAGAAGGAATATATATTACTAATGAAGAGAGAAAAGGCAAAGA TGGATTTTTGGAACTGAAGTCTGTTTTAACAAGGGTACATAGTAATAAACCAGCC CAATCAGACAACTTGACCATTTGGTGTATGGCTCTGTCTCCAGTCCCAGGAAATA AAGTGTGGAACATCTCATCAGAAAAGATCACTTTTCTCTTAGGTTCTGAAATTTC CTCAACAGACCCTCCACTGAGTGTTACAGAATCTACCCTTGACACCCAACCTTCT CCAGCCAGCAGTGTATCTCCTGCAAGATATCCAGCTACATCTTCAGTGACCCTTG TAGATGTGAGTGCCTTGAGGCCAAACACCACTCCTCAACCCAGCAATTCCAGTAT GACTACCCGAGGCTTCAACTATCCCTGGACCTCCAGTGGGACAGATACCAAAAAA TCAGTTTCACGGATACCTAGTGAAACATACAGTTCATCCCCCTCAGGTGCAGGCT CAACACTTCATGACAATGTCTTTACCAGCACAGCCAGAGCATTTTCAGAAGTCCC CACAACTGCCAATGGATCTACGAAAACTAATCACGTCCATATCACTGGTATTGTG GTCAATAAGCCCAAAGATGGAATGTCCTGGCCAGTGATTGTAGCAGCTTTACTCT TTTGCTGCATGATATTGTTTGGTCTTGGAGTGAGAAAATGGTGTCAGTACCAAAA AGAAATAATGGAAAGACCTCCACCTTTCAAGCCACCACCACCTCCCATCAAGTAC ACTTGCATTCAAGAGCCCAACGAAAGTGATCTGCCTTATCATGAGATGGAGACCC TCTAG | 3 |
| hu-CD96 isoform 2 extracellular domain V22-K516 | VWEKTVNTEENVYATLGSDVNLTCQTQTVGFFVQMQWSKVTNKIDLIAVYHPQY GFYCAYGRPCESLVTFTETPENGSKWTLHLRNMSCSVSGRYECMLVLYPEGIQT KIYNLLIQTHVTADEWNSNHTIEIEINQTLEIPCFQNSSSKISSEFTYAWSVED NGTQETLISQNHLISNSTLLKDRVKLGTDYRLHLSPVQIFDDGRKFSCHIRVGP NKILRSSTTVKVFAKPEIPVIVENNSTDVLVERRFTCLLKNVFPKANITWFIDG SFLHDEKEGIYITNEERKGKDGFLELKSVLTRVHSNKPAQSDNLTIWCMALSPV PGNKVWNISSEKITFLLGSEISSTDPPLSVTESTLDTQPSPASSVSPARYPATS SVTLVDVSALRPNTTPQPSNSSMTTRGFNYPWTSSGTDTKKSVSRIPSETYSSS PSGAGSTLHDNVFTSTARAFSEVPTTANGSTKTNHVHITGIVVNKPK | 4 |

TABLE 1-continued

CD96 and CD155 Sequences

| Name | Sequence | SEQ ID NO: |
|---|---|---|
| hu-CD96 isoform 2 domain D1 V22-Q137 | VWEKTVNTEENVYATLGSDVNLTCQTQTVGFFVQMQWSKVTNKIDLIAVYHPQY GFYCAYGRPCESLVTFTETPENGSKWTLHLRNMSCSVSGRYECMLVLYPEGIQT KIYNLLIQ | 5 |
| hu-CD96 isoform 2 domains D1-D3 V22-T375 | VWEKTVNTEENVYATLGSDVNLTCQTQTVGFFVQMQWSKVTNKIDLIAVYHPQY GFYCAYGRPCESLVTFTETPENGSKWTLHLRNMSCSVSGRYECMLVLYPEGIQT KIYNLLIQTHVTADEWNSNHTIEIEINQTLEIPCFQNSSSKISSEFTYAWSVED NGTQETLISQNHLISNSTLLKDRVKLGTDYRLHLSPVQIFDDGRKFSCHIRVGP NKILRSSTTVKVFAKPEIPVIVENNSTDVLVERRFTCLLKNVFPKANITWFIDG SFLHDEKEGIYITNEERKGKDGFLELKSVLTRVHSNKPAQSDNLTIWCMALSPV PGNKVWNISSEKIT | 6 |
| cy-CD96 isoform 2 extracellular domains V22-K516 | VWGKPFNTEENIYATLGSDVNLTCQTQAKGFLVQMQWSKVTDKADLIALYHPQY GFHCAYGSPCESLVTFTQTPENGSKWTLHLRNMSSSVSGRYECMLTLYPEGMQT KIYNLLIQTHVTPDEWKSNHTIEIEINQTLEIPCFQNSSSEISSEFTYAWLVED NGTQQTLISQDHLISSSTLLKDRVKVGIDYRLHLSPVQIFDDGRKFSCHIRVGP DKILRSSTTIKVFAKPEIPMIVENNSTDVLVERTFTCLLKNVFPKANIIWFIDG SFLHDEKEGIYITNEERKGKDGFLELKSVLTRVHSDKPAQSDNLTIWCMALSPV PGNKVWNISSEKITFLLGSEMSTTDLPPSVTESTLDTQPSPASSVSPTRYPATS SVTLADVSALRPNTTPQSSSSSVTTQDFNYPWTSSGTDAKKSFSQIPSETYSSS PSGAGSTLHDNVFTSTTRALSEVPTTANGSTKTNHVHITGIVVSKPK | 7 |
| cy-CD96 domains D1D3 V22-T375 | VWGKPFNTEENIYATLGSDVNLTCQTQAKGFLVQMQWSKVTDKADLIALYHPQY GFHCAYGSPCESLVTFTQTPENGSKWTLHLRNMSSSVSGRYECMLTLYPEGMQT KIYNLLIQTHVTPDEWKSNHTIEIEINQTLEIPCFQNSSSEISSEFTYAWLVED NGTQQTLISQDHLISSSTLLKDRVKVGIDYRLHLSPVQIFDDGRKFSCHIRVGP DKILRSSTTIKVFAKPEIPMIVENNSTDVLVERTFTCLLKNVFPKANIIWFIDG SFLHDEKEGIYITNEERKGKDGFLELKSVLTRVHSDKPAQSDNLTIWCMALSPV PGNKVWNISSEKIT | 8 |
| rh-CD96 domains D1D3 V22-T375 | VWGKPLNTEENIYATLGSDVNLTCQTQAKGFLVQMQWSKVTDKADLIALYHPQY GFHCAYGSPCESLVTFTQTPENGSKWTLHLRNMSSSVSGRYECMLTLYPEGMQT KIYNLLIQTHVTPDEWKSNHTIEIEINQTLEIPCFQNSSSEISSEFTYAWLVED NGTQQTLISQDHLISSSTLLKDRVKVGTDYRLHLSPVQIFDDGRKFSCHIRVGP DKILRSSTTIKVFAKPEIPMIVENNSTDVLVERIFTCLLTNVFPKANIIWFIDG SFLHDEKEGIYITNEERKGKDGFLELKSVLTRVHSDKPAQSDNLTIWCMALSPV PGNKVWNISSEKIT | 9 |
| hu-CD155 extracellular domains W20-N343 | WPPPGTGDVVVQAPTQVPGFLGDSVTLPCYLQVPNMEVTHVSQLTWARHGESGS MAVFHQTQGPSYSESKRLEFVAARLGAELRNASLRMFGLRVEDEGNYTCLFVTF PQGSRSVDIWLRVLAKPQNTAEVQKVQLTGEPVPMARCVSTGGRPPAQITWHSD LGGGMPNTSQVPGFLSGTVTVTSLWILVPSSQVDGKNVTCKVEHESFEKPQLLTV NLTVYYPPEVSISGYDNNWYLGQNEATLTCDARSNPEPTGYNWSTTMGPLPPFA VAQGAQLLIRPVDKPINTTLICNVTNALGARQAELTVQVKEGPPSEHSGMSRN | 10 |
| mo-CD155-extracellular domains D29-R345 | DIRVLVPYNSTGVLGGSTTLHCSLTSNENVTITQITWMKKDSGGSHALVAVFHP KKGPNIKEPERVKFLAAQQDLRNASLAISNLSVEDEGIYECQIATFPRGSRSTN AWLKVQARPKNTAEALEPSPTLILQDVAKCISANGHPPGRISWPSNVNGSHREM KEPGSQPGTTTVTSYLSMVPSRQADGKNITCTVEHESLQELDQLLVTLSQPYPP ENVSISGYDNGNWYVGLTNLTLTCEAHSKPAPDMAGYNWSTTTGDFPNSVKRQGN MLLISTVEDGLNNTVIVCEVTNALGSGQGQVHIIVKEKPENMQQNTR | 11 |
| hu-CD226 | MDYPTLLLALLHVYRALCEEVLWHTSVPFAENMSLECVYPSMGILTQVEWFKIG TQQDSIAIFSPTHGMVIRKPYAERVYFLNSTMASNNMTLFFRNASEDDVGYYSC SLYTYPQGTWQKVIQVVQSDSFEAAVPSNSHIVSEPGKNVTLTCQPMTWPVQA VRWEKIQPRQIDLLTYCNLVHGRNFTSKFPRQIVSNCSHGRWSVIVIPDVTVSD SGLYRCYLQASAGENETFVMRLTVAEGKTDNQYTLFVAGGTVLLLLFVISITTI IVIFLNRRRRRERRDLFTESWDTQKAPNNYRSPISTSQPTNQSMDDTREDIYVN YPTFSRRPKTRVDYKDDDDK | 482 |
| cy-CD226 | MDYPTLLLALLHVYRALCEEVLWHTSVPFAENMSLECVYPSVGILTQVEWFKIG TEKDSIAIFSPTHGMVIRKPYAERVYFLNSTMASNNMTLFFRNASEDDVGYYSC SLYTYPQGTWQKVIQVVQSDGFEAAVPPNSHIVSEPGKNITLTCQPMTWPVQE VRWEKVQPHQIDLLTYCDLVHGRNFTSKFPRQIVSNCSHGSWSFIVVPDVTASD SGLYRCHLQASAGENETFVMRLTVAEGTDNQYTRFVTGGTVLLLLFVISITTI IVIFLNRRRRRERNDLYTESWDTQKAPKNYRSPISANQPTNQSMDDTREDIYVN YPTFSRRPKTRVDYKDDDDK | 483 |

II. Anti-CD96 Antibodies in some embodiments, the present disclosure provides structures of anti-CD96 antibodies in terms of the amino acid and encoding nucleotide sequences of the various well-known immunoglobulin features (e.g., HVRs, FRs, $V_H$, $V_L$ domains, and full-length heavy and light chains). Table 2 below provides a summary description of anti-CD96 antibody sequences of the present disclosure, and their sequence identifiers. The sequences are included in the accompanying Sequence Listing.

TABLE 2

Anti-CD96 antibody sequences

| Description | Sequence | SEQ ID NO: |
|---|---|---|
| 12F8 (mAb1)-VL | DIVMTQSQKFMSTSVGDRVSVTCKASQNVGTAIVWYQKKPGQSPKTLIYSASTRYTGVPDRFTGSGSGTDFTLTISNVQSEDLAEYFCQQYSSSPLTFGSGTKLEIK | 12 |
| 12F8-HVR-L1 (VL positions 24-34) | KASQNVGTAIV | 13 |
| 12F8-HVR-L2 (VL positions 50-56) | SASTRYT | 14 |
| 12F8-HVR-L3 (VL positions 89-97) | QQYSSSPLT | 15 |
| 10H5-VL | DVVMTQTPLTLSVTLGHPASISCKSSQSLLDSDGKTYLNWLLQRPGESPKLLIYLVSKLDSGVPDRFTGSGSGTDFTLKISRVEAEDLGVYYCLQATHSPQTFGGGTKLEIK | 16 |
| 10H5-HVR-L1 (VL positions 24-34) | KSSQSLLDSDGKTYLN | 17 |
| 10H5-HVR-L2 (VL positions 50-56) | LVSKLDS | 18 |
| 10H5-HVR-L3 (VL positions 89-97) | LQATHSPQT | 19 |
| 1G8-VL | DIQMNQSPSSLSASLGDTITITCRVSQDISFWLSWYQQKPGNIPKLLIYKASNLHTGVPPRFSGSGSGTDFTLTISSLQPEDIAAYYCLQSQSYPYTFGGGTKLEIK | 20 |
| 1G8-HVR-L1 (VL positions 24-34) | RVSQDISFWLS | 21 |
| 1G8-HVR-L2 (VL positions 50-56) | KASNLHT | 22 |
| 1G8-HVR-L3 (VL positions 89-97) | LQSQSYPYT | 23 |
| 16D9-VL | ENVLTQSPAIMSATLGEKVTMNCRASSNVKYMYWYQQKSGVSPKLWIYYTSNLASGVPTRFSGSGSGTSYSLTISSVEAEDAATYYCQQFTSSPLTFGAGTKLELK | 24 |
| 16D9-HVR-L1 (VL positions 24-34) | RASSNVKYMY | 25 |
| 16D9-HVR-L2 (VL positions 50-56) | YTSNLAS | 26 |
| 16D9-HVR-L3 (VL positions 89-97) | QQFTSSPLT | 27 |
| 9H4-VL | DIVLTQSPASLAVSLGQRAIISCKASQSVTFADTGLMHWYQQKPGQQPKLLIYRASNLEVGVPTRFSGSGSGTDFTLNIHPVEEEDVATYYCQQSREYPWTFGGGTKLEIK | 28 |
| 9H4-HVR-L1 (VL positions 24-34) | KASQSVTFADTGLMH | 29 |
| 9H4-HVR-L2 (VL positions 50-56) | RASNLEV | 30 |
| 9H4-HVR-L3 (VL positions 89-97) | QQSREYPWT | 31 |

TABLE 2-continued

Anti-CD96 antibody sequences

| Description | Sequence | SEQ ID NO: |
|---|---|---|
| 7E5-VL | QAVVTQESALTTSPGETVTLTCRSSTGAVTTSNYANWVQEKPDHLFTGLI GGTNNRAPGVPARFSGSLIGDKAALTITGAQTEDEAIYFCSLWYGSHWVF GGGTKLTVL | 32 |
| 7E5-HVR-L1 (VL positions 24-34) | RSSTGAVTTSNYAN | 33 |
| 7E5-HVR-L2 (VL positions 50-56) | GTNNRAP | 34 |
| 7E5-HVR-L3 (VL positions 89-97) | SLWYGSHWV | 35 |
| 10G1-VL | DILMTQSPTTLSVTPGETVSLSCRASQDIYRNLHWYQQKSQGTPRLLIKH ASDSISGIPSRFTGSGSGTDFTLSINSVKPEDEGIYYCLQGYSMPYTFGG GTKLEIK | 36 |
| 10G1-HVR-L1 (VL positions 24-34) | RASQDIYRNLH | 37 |
| 10G1-HVR-L2 (VL positions 50-56) | HASDSIS | 38 |
| 10G1-HVR-L3 (VL positions 89-97) | LQGYSMPYT | 39 |
| 12F8-VH | QVQLQQPGAELVTPGASVKLSCKASGFTFTNNWMHWVKQRPGQGLEWIGM IHPNSGITNINEKFKNKATVTVDKSSSTVYIQLSSLTSEDSAVYYCRSDG TYEGYFDYWGQGTPLTVSS | 40 |
| 12F8-HVR-H1 (VH positions 30-35) | TNNWMH | 41 |
| 12F8-HVR-H2 (VH positions 50-61) | MIHPNSGITNINE | 42 |
| 12F8-HVR-H3 (VH positions 93-102) | RSDGTYEGYFDY | 43 |
| 10H5-VH | QVQLQQSGADLARPGASIKLSCKASGYTFTGYGVTWVKQSTGQGLDWIGE IYPGTVITYYNAKFKGKATLTADKSSSTAYMELRSLTSEDSAVYFCARGL GRAMDYWGQGTSVTVSS | 44 |
| 10H5-HVR-H1 (VH positions 30-35) | TGYGVT | 45 |
| 10H5-HVR-H2 (VH positions 50-61) | EIYPGTVITYYNA | 46 |
| 10H5-HVR-H3 (VH positions 93-102) | ARGLGRAMDY | 47 |
| 1G8-VH | QVQLQQSGPELLKPGASVKISCKASGYTFTDYYINWVKQRPGQGLEWIGW IFPGTEGIYYNEKFKGKATLTVDKSSTTAYMLLSSLTSEDSAVYFCAREG DYRYYSPLGYWGQGTLVTVSA | 48 |
| 1G8-HVR-H1 (VH positions 30-35) | TDYYIN | 49 |
| 1G8-HVR-H2 (VH positions 50-61) | WIFPGTEGIYYNE | 50 |
| 1G8-HVR-H3 (VH positions 93-102) | AREGDYRYYSPLGY | 51 |
| 16D9-VH | QVQLQQSGPELVKPGASVKISCKASGYNFNDYYINWVQRPGQGLEWIGW IFPGRIITYYNEKFKGKATLTVDTSSNTAYMLLSSLTSEDSAVYFCARGV GEGFDYWGQGTTLTVSS | 52 |
| 16D9-HVR-H1 (VH positions 30-35) | NDYYIN | 53 |

TABLE 2-continued

Anti-CD96 antibody sequences

| Description | Sequence | SEQ ID NO: |
| --- | --- | --- |
| 16D9-HVR-H2 (VH positions 50-61) | WIFPGRIITYYNE | 54 |
| 16D9-HVR-H3 (VH positions 93-102) | ARGVGEGFDY | 55 |
| 9H4-VH | EVQLLETGGGLVKSGGSLKLSCAASGFTFSDYYMYWVRQTPEKRLEWVAA ISDDGTYTYYPDSVKGRFTISRDNANNYLYLQMSSLKSEDTAIYYCAKAG SYDYFDVWGAGTTVTVSS | 56 |
| 9H4-HVR-H1 (VH positions 30-35) | SDYYMY | 57 |
| 9H4-HVR-H2 (VH positions 50-61) | AISDDGTYTYYPD | 58 |
| 9H4-HVR-H3 (VH positions 93-102) | AKAGSYDYFDV | 59 |
| 7E5-VH | QVQLKESGPGLVAPSQSLSIICTVSGFSLTNYGIHWIRQPPGKGLEWLGI IWAGGSTNYNSALMSRLTISKDNSKSQVFLKMNSLQTNDTAIYYCARVSM MGFAYWGQGTLVTVSA | 60 |
| 7E5-HVR-H1 (VH positions 30-35) | TNYGIH | 61 |
| 7E5-HVR-H2 (VH positions 50-61) | IIWAGGSTNYNS | 62 |
| 7E5-HVR-H3 (VH positions 93-102) | ARVSMMGFAY | 63 |
| 10G1-VH | QIQLVQSGPELKKPGETVKISCKASGYPFTTYGMSWVKQAPGKGLKWMGW INTDSGVPTYADDFKGRFAFSLETSANTAYLQINSLKNEDAATYFCARNI YYGWGNFDYWGQGTILTVSS | 64 |
| 10G1-HVR-H1 (VH positions 30-35) | TTYGMS | 65 |
| 10G1-HVR-H2 (VH positions 50-61) | WINTDSGVPTYAD | 66 |
| 10G1-HVR-H3 (VH positions 93-102) | ARNIYYGWGNFDY | 67 |
| mAb1v7-VL (humanized 12F8) | DIQLTQSPSSLSASVGDRVTITCKASQNVGTAIVWYQQKPGKAPKVLIYS ASTRYTGVPSRFSGSGSGTDFTLTISSLQPEDFATYYCQQYSSSPLTFGQ GTKVEIK | 68 |
| mAb1v7-VH (humanized 12F8) | EVQLVQSGAEVKKPGASVKVSCKASGFTFTNNWMHWVRQAPGQGLEWIGM IHPNSGITNINEKFKNRVTMTTDTSTSTAYMELRSLRSEDTAVYYCRSDG TYEGYFDYWGQGTLVTVSS | 69 |
| h10G1-VL (humanized 10G1) | EIVMTQSPDFQSVTPKEKVTITCRASQDIYRNLHWYQQKPDQTPKLLIKH ASDSISGIPSRFSGSGSGTDFTLTINSLEAEDAAAYYCLQGYSMPYTFGG GTKVEIK | 70 |
| h10G1-VH (humanized 10G1) | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGNFDYWGQGTLVTVSS | 71 |
| mAb1v7-HVR-H1-generic formula | XNXXXH<br>X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W | 72 |
| mAb1v7-HVR-H1-T30A | ANNWMH | 73 |
| mAb1v7-HVR-H1-T30D | DNNWMH | 74 |

TABLE 2-continued

Anti-CD96 antibody sequences

| Description | Sequence | SEQ ID NO: |
|---|---|---|
| mAb1v7-HVR-H1-T30E | ENNWMH | 75 |
| mAb1v7-HVR-H1-T30G | GNNWMH | 76 |
| mAb1v7-HVR-H1-T30H | HNNWMH | 77 |
| mAb1v7-HVR-H1-T30K | KNNWMH | 78 |
| mAb1v7-HVR-H1-T30N | NNNWMH | 79 |
| mAb1v7-HVR-H1-T30Q | QNNWMH | 80 |
| mAb1v7-HVR-H1-T30R | RNNWMH | 81 |
| mAb1v7-HVR-H1-T30S | SNNWMH | 82 |
| mAb1v7-HVR-H1-T30V | VNNWMH | 83 |
| mAb1v7-HVR-H1-T30W | WNNWMH | 84 |
| mAb1v7-HVR-H1-T30Y | YNNWMH | 85 |
| mAb1v7-HVR-H1-N32A | TNAWMH | 86 |
| mAb1v7-HVR-H1-N32F | TNFWMH | 87 |
| mAb1v7-HVR-H1-N32G | TNGWMH | 88 |
| mAb1v7-HVR-H1-N32H | TNHWMH | 89 |
| mAb1v7-HVR-H1-N32M | TNMWMH | 90 |
| mAb1v7-HVR-H1-N32R | TNRWMH | 91 |
| mAb1v7-HVR-H1-N32S | TNSWMH | 92 |
| mAb1v7-HVR-H1-N32V | TNVWMH | 93 |
| mAb1v7-HVR-H1-N32Y | TNYWMH | 94 |
| mAb1v7-HVR-H1-W33F | TNNFMH | 95 |
| mAb1v7-HVR-H1-M34A | TNNWAH | 96 |
| mAb1v7-HVR-H1-M34D | TNNWDH | 472 |
| mAb1v7-HVR-H1-M34E | TNNWEH | 97 |

TABLE 2-continued

Anti-CD96 antibody sequences

| Description | Sequence | SEQ ID NO: |
|---|---|---|
| mAb1v7-HVR-H1-M34F | TNNWFH | 98 |
| mAb1v7-HVR-H1-M34G | TNNWGH | 473 |
| mAb1v7-HVR-H1-M34L | TNNWLH | 99 |
| mAb1v7-HVR-H1-M34N | TNNWNH | 100 |
| mAb1v7-HVR-H1-M34Q | TNNWQH | 101 |
| mAb1v7-HVR-H1-M34R | TNNWRH | 102 |
| mAb1v7-HVR-H1-M34S | TNNWSH | 103 |
| mAb1v7-HVR-H1-M34T | TNNWTH | 104 |
| mAb1v7-HVR-H1-M34V | TNNWVH | 105 |
| mAb1v7-HVR-H1-M34W | TNNWWH | 106 |
| mAb1v7-HVR-H2-generic formula | XXHXXXXXXXXNX<br>X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y | 107 |
| mAb1v7-HVR-H2-M50F | FIHPNSGITNINE | 108 |
| mAb1v7-HVR-H2-I51L | MLHPNSGITNINE | 109 |
| mAb1v7-HVR-H2-I51M | MMHPNSGITNINE | 110 |
| mAb1v7-HVR-H2-I51V | MVHPNSGITNINE | 111 |
| mAb1v7-HVR-H2-P52aA | MIHANSGITNINE | 112 |
| mAb1v7-HVR-H2-M50F/P52aA | FIHANSGITNINE | 113 |
| mAb1v7-HVR-H2-P52aD | MIHDNSGITNINE | 114 |
| mAb1v7-HVR-H2-P52aE | MIHENSGITNINE | 115 |
| mAb1v7-HVR-H2-P52aF | MIHFNSGITNINE | 116 |
| mAb1v7-HVR-H2-P52aG | MIHGNSGITNINE | 117 |

TABLE 2-continued

Anti-CD96 antibody sequences

| Description | Sequence | SEQ ID NO: |
| --- | --- | --- |
| mAb1v7-HVR-H2-P52aH | MIHHNSGITNINE | 118 |
| mAb1v7-HVR-H2-P52aI | MIHINSGITNINE | 119 |
| mAb1v7-HVR-H2-P52aK | MIHKNSGITNINE | 120 |
| mAb1v7-HVR-H2-P52aL | MIHLNSGITNINE | 121 |
| mAb1v7-HVR-H2-P52aM | MIHMNSGITNINE | 122 |
| mAb1v7-HVR-H2-P52aN | MIHNNSGITNINE | 123 |
| mAb1v7-HVR-H2-P52aQ | MIHQNSGITNINE | 124 |
| mAb1v7-HVR-H2-P52aR | MIHRNSGITNINE | 125 |
| mAb1v7-HVR-H2-P52aS | MIHSNSGITNINE | 126 |
| mAb1v7-HVR-H2-P52aT | MIHTNSGITNINE | 127 |
| mAb1v7-HVR-H2-P52aV | MIHVNSGITNINE | 128 |
| mAb1v7-HVR-H2-P52aW | MIHWNSGITNINE | 129 |
| mAb1v7-HVR-H2-N53A | MIHPASGITNINE | 130 |
| mAb1v7-HVR-H2-N53D | MIHPDSGITNINE | 131 |
| mAb1v7-HVR-H2-N53E | MIHPESGITNINE | 132 |
| mAb1v7-HVR-H2-N53F | MIHPFSGITNINE | 133 |
| mAb1v7-HVR-H2-N53G | MIHPGSGITNINE | 134 |
| mAb1v7-HVR-H2-N53H | MIHPHSGITNINE | 135 |
| mAb1v7-HVR-H2-N53I | MIHPISGITNINE | 136 |
| mAb1v7-HVR-H2-N53K | MIHPKSGITNINE | 137 |
| mAb1v7-HVR-H2-N53L | MIHPLSGITNINE | 138 |
| mAb1v7-HVR-H2-N53M | MIHPMSGITNINE | 139 |
| mAb1v7-HVR-H2-N53Q | MIHPQSGITNINE | 140 |
| mAb1v7-HVR-H2-N53R | MIHPRSGITNINE | 141 |

TABLE 2-continued

Anti-CD96 antibody sequences

| Description | Sequence | SEQ ID NO: |
|---|---|---|
| mAb1v7-HVR-H2-N53S | MIHPSSGITNINE | 142 |
| mAb1v7-HVR-H2-N53T | MIHPTSGITNINE | 143 |
| mAb1v7-HVR-H2-N53V | MIHPVSGITNINE | 144 |
| mAb1v7-HVR-H2-N53W | MIHPWSGITNINE | 145 |
| mAb1v7-HVR-H2-N53Y | MIHPYSGITNINE | 146 |
| mAb1v7-HVR-H2-S54A | MIHPNAGITNINE | 147 |
| mAb1v7-HVR-H2-S54G | MIHPNGGITNINE | 148 |
| mAb1v7-HVR-H2-S54T | MIHPNTGITNINE | 149 |
| mAb1v7-HVR-H2-S54V | MIHPNVGITNINE | 150 |
| mAb1v7-HVR-H2-G55A | MIHPNSAITNINE | 151 |
| mAb1v7-HVR-H2-G55S | MIHPNSSITNINE | 152 |
| mAb1v7-HVR-H2-I56A | MIHPNSGATNINE | 153 |
| mAb1v7-HVR-H2-I56V | MIHPNSGVTNINE | 154 |
| mAb1v7-HVR-H2-T57A | MIHPNSGIANINE | 155 |
| mAb1v7-HVR-H2-T57D | MIHPNSGIDNINE | 156 |
| mAb1v7-HVR-H2-T57E | MIHPNSGIENINE | 157 |
| mAb1v7-HVR-H2-T57G | MIHPNSGIGNINE | 158 |
| mAb1v7-HVR-H2-T57H | MIHPNSGIHNINE | 159 |
| mAb1v7-HVR-H2-T57I | MIHPNSGIININE | 160 |
| mAb1v7-HVR-H2-T57K | MIHPNSGIKNINE | 161 |
| mAb1v7-HVR-H2-T57L | MIHPNSGILNINE | 162 |
| mAb1v7-HVR-H2-T57M | MIHPNSGIMNINE | 163 |
| mAb1v7-HVR-H2-T57N | MIHPNSGINNINE | 164 |
| mAb1v7-HVR-H2-T57Q | MIHPNSGIQNINE | 165 |

TABLE 2-continued

Anti-CD96 antibody sequences

| Description | Sequence | SEQ ID NO: |
|---|---|---|
| mAb1v7-HVR-H2-T57R | MIHPNSGIRNINE | 166 |
| mAb1v7-HVR-H2-T57S | MIHPNSGISNINE | 167 |
| mAb1v7-HVR-H2-T57V | MIHPNSGIVNINE | 168 |
| mAb1v7-HVR-H2-T57W | MIHPNSGIWNINE | 169 |
| mAb1v7-HVR-H2-T57Y | MIHPNSGIYNINE | 170 |
| mAb1v7-HVR-H2-N58A | MIHPNSGITAINE | 474 |
| mAb1v7-HVR-H2-N58M | MIHPNSGITMINE | 171 |
| mAb1v7-HVR-H2-N58S | MIHPNSGITSINE | 172 |
| mAb1v7-HVR-H2-I59F | MIHPNSGITNFNE | 173 |
| mAb1v7-HVR-H2-I59G | MIHPNSGITNGNE | 174 |
| mAb1v7-HVR-H2-I59H | MIHPNSGITNHNE | 175 |
| mAb1v7-HVR-H2-I59K | MIHPNSGITNKNE | 176 |
| mAb1v7-HVR-H2-I59L | MIHPNSGITNLNE | 177 |
| mAb1v7-HVR-H2-I59M | MIHPNSGITNMNE | 178 |
| mAb1v7-HVR-H2-I59N | MIHPNSGITNNNE | 179 |
| mAb1v7-HVR-H2-I59Q | MIHPNSGITNQNE | 180 |
| mAb1v7-HVR-H2-I59R | MIHPNSGITNRNE | 181 |
| mAb1v7-HVR-H2-I59S | MIHPNSGITNSNE | 182 |
| mAb1v7-HVR-H2-I59T | MIHPNSGITNTNE | 183 |
| mAb1v7-HVR-H2-I59V | MIHPNSGITNVNE | 184 |
| mAb1v7-HVR-H2-I59W | MIHPNSGITNWNE | 185 |
| mAb1v7-HVR-H2-I59Y | MIHPNSGITNYNE | 186 |
| mAb1v7-HVR-H2-E61A | MIHPNSGITNINA | 187 |
| mAb1v7-HVR-H2-E61D | MIHPNSGITNIND | 188 |

TABLE 2-continued

Anti-CD96 antibody sequences

| Description | Sequence | SEQ ID NO: |
|---|---|---|
| mAb1v7-HVR-H2-E61G | MIHPNSGITNING | 189 |
| mAb1v7-HVR-H2-E61H | MIHPNSGITNINH | 190 |
| mAb1v7-HVR-H2-E61K | MIHPNSGITNINK | 191 |
| mAb1v7-HVR-H2-E61L | MIHPNSGITNINL | 192 |
| mAb1v7-HVR-H2-E61M | MIHPNSGITNINM | 193 |
| mAb1v7-HVR-H2-E61N | MIHPNSGITNINN | 194 |
| mAb1v7-HVR-H2-E61P | MIHPNSGITNINP | 195 |
| mAb1v7-HVR-H2-E61Q | MIHPNSGITNINQ | 196 |
| mAb1v7-HVR-H2-E61R | MIHPNSGITNINR | 197 |
| mAb1v7-HVR-H2-E61S | MIHPNSGITNINS | 198 |
| mAb1v7-HVR-H2-E61T | MIHPNSGITNINT | 199 |
| mAb1v7-HVR-H2-E61V | MIHPNSGITNINV | 200 |
| mAb1v7-HVR-H2-E61W | MIHPNSGITNINW | 201 |
| mAb1v7-HVR-H2-E61Y | MIHPNSGITNINY | 202 |
| mAb1v7-HVR-H3-generic formula | RXDXXXXYFDY<br>X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T | 203 |
| mAb1v7-HVR-H3-S94A | RADGTYEGYFDY | 204 |
| mAb1v7-HVR-H3-S94F | RFDGTYEGYFDY | 205 |
| mAb1v7-HVR-H3-S94G | RGDGTYEGYFDY | 206 |
| mAb1v7-HVR-H3-S94I | RIDGTYEGYFDY | 207 |
| mAb1v7-HVR-H3-S94L | RLDGTYEGYFDY | 208 |
| mAb1v7-HVR-H3-S94M | RMDGTYEGYFDY | 209 |
| mAb1v7-HVR-H3-S94N | RNDGTYEGYFDY | 210 |
| mAb1v7-HVR-H3-S94R | RRDGTYEGYFDY | 211 |

TABLE 2-continued

Anti-CD96 antibody sequences

| Description | Sequence | SEQ ID NO: |
|---|---|---|
| mAb1v7-HVR-H3-S94T | RTDGTYEGYFDY | 212 |
| mAb1v7-HVR-H3-S94V | RVDGTYEGYFDY | 213 |
| mAb1v7-HVR-H3-S94W | RWDGTYEGYFDY | 214 |
| mAb1v7-HVR-H3-S94Y | RYDGTYEGYFDY | 215 |
| mAb1v7-HVR-H3-G96W | RSDWTYEGYFDY | 216 |
| mAb1v7-HVR-H3-T97D | RSDGDYEGYFDY | 217 |
| mAb1v7-HVR-H3-T97E | RSDGEYEGYFDY | 218 |
| mAb1v7-HVR-H3-T97F | RSDGFYEGYFDY | 219 |
| mAb1v7-HVR-H3-T97H | RSDGHYEGYFDY | 220 |
| mAb1v7-HVR-H3-T97I | RSDGIYEGYFDY | 221 |
| mAb1v7-HVR-H3-T97K | RSDGKYEGYFDY | 222 |
| mAb1v7-HVR-H3-T97L | RSDGLYEGYFDY | 223 |
| mAb1v7-HVR-H3-T97M | RSDGMYEGYFDY | 224 |
| mAb1v7-HVR-H3-T97N | RSDGNYEGYFDY | 225 |
| mAb1v7-HVR-H3-T97Q | RSDGQYEGYFDY | 226 |
| mAb1v7-HVR-H3-T97V | RSDGVYEGYFDY | 227 |
| mAb1v7-HVR-H3-T97W | RSDGWYEGYFDY | 228 |
| mAb1v7-HVR-H3-T97Y | RSDGYYEGYFDY | 229 |
| mAb1v7-HVR-H3-Y98D | RSDGTDEGYFDY | 230 |
| mAb1v7-HVR-H3-Y98F | RSDGTFEGYFDY | 231 |
| mAb1v7-HVR-H3-Y98H | RSDGTHEGYFDY | 232 |
| mAb1v7-HVR-H3-Y98N | RSDGTNEGYFDY | 233 |
| mAb1v7-HVR-H3-Y98R | RSDGTREGYFDY | 234 |
| mAb1v7-HVR-H3-Y98W | RSDGTWEGYFDY | 235 |

TABLE 2-continued

Anti-CD96 antibody sequences

| Description | Sequence | SEQ ID NO: |
|---|---|---|
| mAb1v7-HVR-H3-E99D | RSDGTYDGYFDY | 236 |
| mAb1v7-HVR-H3-E99G | RSDGTYGGYFDY | 237 |
| mAb1v7-HVR-H3-E99H | RSDGTYHGYFDY | 238 |
| mAb1v7-HVR-H3-E99K | RSDGTYKGYFDY | 239 |
| mAb1v7-HVR-H3-E99M | RSDGTYMGYFDY | 240 |
| mAb1v7-HVR-H3-E99N | RSDGTYNGYFDY | 241 |
| mAb1v7-HVR-H3-E99Q | RSDGTYQGYFDY | 242 |
| mAb1v7-HVR-H3-E99R | RSDGTYRGYFDY | 243 |
| mAb1v7-HVR-H3-E99V | RSDGTYVGYFDY | 244 |
| mAb1v7-HVR-H3-E99Y | RSDGTYYGYFDY | 245 |
| mAb1v7-HVR-H3-G100K | RSDGTYEKYFDY | 246 |
| mAb1v7-HVR-H3-G100R | RSDGTYERYFDY | 247 |
| mAb1v7-HVR-H3-G100S | RSDGTYESYFDY | 248 |
| mAb1v7-HVR-H3-G100T | RSDGTYETYFDY | 249 |
| mAb1v7-VH-M34R/P52aF/T97V (mAb1v7.2) | EVQLVQSGAEVKKPGASVKVSCKASGFTFTNNWRHWVRQAPGQGLEWIGM IHFNSGITNINEKFKNRVTMTTDTSTSTAYMELRSLRSEDTAVYYCRSDG VYEGYFDYWGQGTLVTVSS | 250 |
| mAb1v7-VH-N32R/P52aV/T97L (mAb1v7.6) | EVQLVQSGAEVKKPGASVKVSCKASGFTFTNRWMHWVRQAPGQGLEWIGM IHVNSGITNINEKFKNRVTMTTDTSTSTAYMELRSLRSEDTAVYYCRSDG LYEGYFDYWGQGTLVTVSS | 251 |
| mAb1v7-VH-M34D/N53L/T97V (mAb1v7.8) | EVQLVQSGAEVKKPGASVKVSCKASGFTFTNNWDHWVRQAPGQGLEWIGM IHPLSGITNINEKFKNRVTMTTDTSTSTAYMELRSLRSEDTAVYYCRSDG VYEGYFDYWGQGTLVTVSS | 252 |
| mAb1v7-VH-M34R/P52aM/T97V (mAb1v7.9) | EVQLVQSGAEVKKPGASVKVSCKASGFTFTNNWRHWVRQAPGQGLEWIGM IHMNSGITNINEKFKNRVTMTTDTSTSTAYMELRSLRSEDTAVYYCRSDG VYEGYFDYWGQGTLVTVSS | 253 |
| mAb1v7-VH-M34R/N53L/T97V (mAb1v7.10) | EVQLVQSGAEVKKPGASVKVSCKASGFTFTNNWRHWVRQAPGQGLEWIGM IHPLSGITNINEKFKNRVTMTTDTSTSTAYMELRSLRSEDTAVYYCRSDG VYEGYFDYWGQGTLVTVSS | 254 |
| mAb1v7-VH-T30V/I59T/T97I (mAb1v7.14) | EVQLVQSGAEVKKPGASVKVSCKASGFTFVNNWMHWVRQAPGQGLEWIGM IHPNSGITNTNEKFKNRVTMTTDTSTSTAYMELRSLRSEDTAVYYCRSDG IYEGYFDYWGQGTLVTVSS | 255 |
| mAb1v7-VH-M34D/N53M/T97F (mAb1v7.15) | EVQLVQSGAEVKKPGASVKVSCKASGFTFTNNWDHWVRQAPGQGLEWIGM IHPMSGITNINEKFKNRVTMTTDTSTSTAYMELRSLRSEDTAVYYCRSDG FYEGYFDYWGQGTLVTVSS | 256 |
| mAb1v7-VH-M34R/T97V (mAb1v7.16) | EVQLVQSGAEVKKPGASVKVSCKASGFTFTNNWRHWVRQAPGQGLEWIGM IHPNSGITNINEKFKNRVTMTTDTSTSTAYMELRSLRSEDTAVYYCRSDG VYEGYFDYWGQGTLVTVSS | 257 |

TABLE 2-continued

Anti-CD96 antibody sequences

| Description | Sequence | SEQ ID NO: |
|---|---|---|
| mAb1v7-VH-N32S/I59R/T97I (mAb1v7.19) | EVQLVQSGAEVKKPGASVKVSCKASGFTFTNSWMHWVRQAPGQGLEWIGM IHPNSGITNRNEKFKNRVTMTTDTSTSTAYMELRSLRSEDTAVYYCRSDG IYEGYFDYWGQGTLVTVSS | 258 |
| mAb1v7-VH-N32Y/I59M/T97V (mAb1v7.21) | EVQLVQSGAEVKKPGASVKVSCKASGFTFTNYWMHWVRQAPGQGLEWIGM IHPNSGITNMNEKFKNRVTMTTDTSTSTAYMELRSLRSEDTAVYYCRSDG VYEGYFDYWGQGTLVTVSS | 259 |
| mAb1v7-VH-M34G/P52aR/T97 (mAb1v7.24) | EVQLVQSGAEVKKPGASVKVSCKASGFTFTNNWGHWVRQAPGQGLEWIGM IHRNSGITNINEKFKNRVTMTTDTSTSTAYMELRSLRSEDTAVYYCRSDG IYEGYFDYWGQGTLVTVSS | 260 |
| mAb1v7-VH-N32R/P52aH/T97V (mAb1v7.48) | EVQLVQSGAEVKKPGASVKVSCKASGFTFTNRWMHWVRQAPGQGLEWIGM IHHNSGITNINEKFKNRVTMTTDTSTSTAYMELRSLRSEDTAVYYCRSDG VYEGYFDYWGQGTLVTVSS | 261 |
| mAb1v7-VH-M34S/P52aR/T97V (mAb1v7.50) | EVQLVQSGAEVKKPGASVKVSCKASGFTFTNNWSHWVRQAPGQGLEWIGM IHRNSGITNINEKFKNRVTMTTDTSTSTAYMELRSLRSEDTAVYYCRSDG VYEGYFDYWGQGTLVTVSS | 262 |
| mAb1v7-VH-M34N//N58A/S94L (mAb1v7.59) | EVQLVQSGAEVKKPGASVKVSCKASGFTFTNNWNHWVRQAPGQGLEWIGM IHPNSGITAINEKFKNRVTMTTDTSTSTAYMELRSLRSEDTAVYYCRLDG TYEGYFDYWGQGTLVTVSS | 263 |
| mAb1v7-VH-N32R/P52aA/T97V (mAb1v7.70) | EVQLVQSGAEVKKPGASVKVSCKASGFTFTNRWMHWVRQAPGQGLEWIGM IHANSGITNINEKFKNRVTMTTDTSTSTAYMELRSLRSEDTAVYYCRSDG VYEGYFDYWGQGTLVTVSS | 264 |
| mAb1v7-VH-W33F (mAb1v7.NGS1) | EVQLVQSGAEVKKPGASVKVSCKASGFTFTNNFMHWVRQAPGQGLEWIGM IHPNSGITNINEKFKNRVTMTTDTSTSTAYMELRSLRSEDTAVYYCRSDG TYEGYFDYWGQGTLVTVSS | 265 |
| mAb1v7-VH-M50F (mAb1v7.NGS2) | EVQLVQSGAEVKKPGASVKVSCKASGFTFTNNWMHWVRQAPGQGLEWIGF IHPNSGITNINEKFKNRVTMTTDTSTSTAYMELRSLRSEDTAVYYCRSDG TYEGYFDYWGQGTLVTVSS | 266 |
| mAb1v7-VH-P52aA (mAb1v7.NGS3) | EVQLVQSGAEVKKPGASVKVSCKASGFTFTNNWMHWVRQAPGQGLEWIGM IHANSGITNINEKFKNRVTMTTDTSTSTAYMELRSLRSEDTAVYYCRSDG TYEGYFDYWGQGTLVTVSS | 267 |
| mAb1v7-VH-E61H (mAb1v7.NGS4) | EVQLVQSGAEVKKPGASVKVSCKASGFTFTNNWMHWVRQAPGQGLEWIGM IHPNSGITNINHKFKNRVTMTTDTSTSTAYMELRSLRSEDTAVYYCRSDG TYEGYFDYWGQGTLVTVSS | 268 |
| mAb1v7-VH-E61R (mAb1v7.NGS5) | EVQLVQSGAEVKKPGASVKVSCKASGFTFTNNWMHWVRQAPGQGLEWIGM IHPNSGITNINRKFKNRVTMTTDTSTSTAYMELRSLRSEDTAVYYCRSDG TYEGYFDYWGQGTLVTVSS | 269 |
| mAb1v7-VH-T97I (mAb1v7.NGS6) | EVQLVQSGAEVKKPGASVKVSCKASGFTFTNNWMHWVRQAPGQGLEWIGM IHPNSGITNINEKFKNRVTMTTDTSTSTAYMELRSLRSEDTAVYYCRSDG TYEGYFDYWGQGTLVTVSS | 270 |
| mAb1v7-VH-T97V (mAb1v7.NGS7) | EVQLVQSGAEVKKPGASVKVSCKASGFTFTNNWMHWVRQAPGQGLEWIGM IHPNSGITNINEKFKNRVTMTTDTSTSTAYMELRSLRSEDTAVYYCRSDG VYEGYFDYWGQGTLVTVSS | 271 |
| mAb1v7-VH-W33F/P52aA/T97I (mAb1v7.NGS8) | EVQLVQSGAEVKKPGASVKVSCKASGFTFTNNFMHWVRQAPGQGLEWIGM IHANSGITNINEKFKNRVTMTTDTSTSTAYMELRSLRSEDTAVYYCRSDG TYEGYFDYWGQGTLVTVSS | 272 |
| mAb1v7-VH-W33F/P52aA/T97V (mAb1v7.NGS9) | EVQLVQSGAEVKKPGASVKVSCKASGFTFTNNFMHWVRQAPGQGLEWIGM IHANSGITNINEKFKNRVTMTTDTSTSTAYMELRSLRSEDTAVYYCRSDG VYEGYFDYWGQGTLVTVSS | 273 |
| mAb1v7-VH-W33F/M50F/P52aA/T97I (mAb1v7.NGS10) | EVQLVQSGAEVKKPGASVKVSCKASGFTFTNNFMHWVRQAPGQGLEWIGF IHANSGITNINEKFKNRVTMTTDTSTSTAYMELRSLRSEDTAVYYCRSDG TYEGYFDYWGQGTLVTVSS | 274 |
| mAb1v7-VH-W33F/M50F/P52aA/T97V (mAb1v7.NGS11) | EVQLVQSGAEVKKPGASVKVSCKASGFTFTNNFMHWVRQAPGQGLEWIGF IHANSGITNINEKFKNRVTMTTDTSTSTAYMELRSLRSEDTAVYYCRSDG VYEGYFDYWGQGTLVTVSS | 275 |

TABLE 2-continued

Anti-CD96 antibody sequences

| Description | Sequence | SEQ ID NO: |
|---|---|---|
| 12F8-FR-L1 | DIVMTQSQKFMSTSVGDRVSVTC | 276 |
| 12F8-FR-L2 | WYQKKPGQSPKTLIY | 277 |
| 12F8-FR-L3 | GVPDRFTGSGSGTDFTLTISNVQSEDLAEYFC | 278 |
| 12F8-FR-L4 | FGSGTKLEIK | 279 |
| mAb1v7-FR-L1 | DIQLTQSPSSLSASVGDRVTITC | 280 |
| mAb1v7-FR-L2 | WYQQKPGKAPKVLIY | 281 |
| mAb1v7-FR-L3 | GVPSRFSGSGSGTDFTLTISSLQPEDFATYYC | 282 |
| mAb1v7-FR-L4 | FGQGTKVEIK | 283 |
| 10G1-FR-L1 | DILMTQSPTTLSVTPGETVSLSC | 284 |
| 10G1-FR-L2 | WYQQKSQGTPRLLIK | 285 |
| 10G1-FR-L3 | GIPSRFTGSGSGTDFTLSINSVKPEDEGIYYC | 286 |
| 10G1-FR-L4 | FGGGTKLEIK | 287 |
| h10G1-FR-L1 | EIVMTQSPDFQSVTPKEKVTITC | 288 |
| h10G1-FR-L2 | WYQQKPDQTPKLLIK | 289 |
| h10G1-FR-L3 | GIPSRFSGSGSGTDFTLTINSLEAEDAAAYYC | 290 |
| h10G1-FR-L4 | FGGGTKVEIK | 291 |
| 12F8-FR-H1 | QVQLQQPGAELVTPGASVKLSCKASGFTF | 292 |
| 12F8-FR-H2 | WVKQRPGQGLEWIG | 293 |
| 12F8-FR-H3 | KFKNKATVTVDKSSSTVYIQLSSLTSEDSAVYYC | 294 |
| 12F8-FR-H4 | WGQGTPLTVSS | 295 |
| 10G1-FR-H1 | QIQLVQSGPELKKPGETVKISCKASGYPF | 296 |
| 10G1-FR-H2 | WVKQAPGKGLKWMG | 297 |
| 10G1-FR-H3 | DFKGRFAFSLETSANTAYLQINSLKNEDAATYFC | 298 |
| 10G1-FR-H4 | WGQGTILTVSS | 299 |
| mAb1v7-FR-H1 | EVQLVQSGAEVKKPGASVKVSCKASGFTF | 300 |
| mAb1v7-FR-H2 | WVRQAPGQGLEWIG | 301 |
| mAb1v7-FR-H3 | KFKNRVTMTTDTSTSTAYMELRSLRSEDTAVYYC | 302 |
| mAb1v7-FR-H4 | WGQGTLVTVSS | 303 |
| h10G1-FR-H1 | EIQLVQSGSELKKPGASVKVSCKASGYPF | 304 |
| h10G1-FR-H2 | WVRQAPGQGLEWMG | 305 |
| h10G1-FR-H3 | DFKGRFVFSLDTSVSTAYLQISSLKAEDTAVYFC | 306 |
| h10G1-FR-H4 | WGQGTLVTVSS | 307 |
| h10G1-HVR-L1-generic formula | RASQXIXXNXH X at position 5 is D, A, E, G, H, K, N, P, Q, S, or T; X at position 7 is Y, or F; X at position 8 is R, K, or Q; X at position 10 is L, I, M, or V. | 308 |
| h10G1-HVR-L1-D28A | RASQAIYRNLH | 309 |

TABLE 2-continued

Anti-CD96 antibody sequences

| Description | Sequence | SEQ ID NO: |
|---|---|---|
| h10G1-HVR-L1-D28E | RASQEIYRNLH | 310 |
| h10G1-HVR-L1-D28G | RASQGIYRNLH | 311 |
| h10G1-HVR-L1-D28H | RASQHIYRNLH | 312 |
| h10G1-HVR-L1-D28K | RASQKIYRNLH | 313 |
| h10G1-HVR-L1-D28N | RASQNIYRNLH | 314 |
| h10G1-HVR-L1-D28P | RASQPIYRNLH | 315 |
| h10G1-HVR-L1-D28Q | RASQQIYRNLH | 316 |
| h10G1-HVR-L1-D28S | RASQSIYRNLH | 317 |
| h10G1-HVR-L1-D28T | RASQTIYRNLH | 318 |
| h10G1-HVR-L1-Y30F | RASQDIFRNLH | 319 |
| h10G1-HVR-L1-R31K | RASQDIYKNLH | 320 |
| h10G1-HVR-L1-R31Q | RASQDIYQNLH | 321 |
| h10G1-HVR-L1-L33I | RASQDIYRNIH | 322 |
| h10G1-HVR-L1-L33M | RASQDIYRNMH | 323 |
| h10G1-HVR-L1-L33V | RASQDIYRNVH | 324 |
| h10G1-HVR-L2-generic formula | HAXXXXS<br>X at position 3 is S, or E; X at position 4 is D, E, K, or Q; X at position 5 is S, H, L, R, or V; X at position 6 is I, or V. | 325 |
| h10G1-HVR-L2-S52E | HAEDSIS | 326 |
| h10G1-HVR-L2-D53E | HASESIS | 327 |
| h10G1-HVR-L2-D53K | HASKSIS | 328 |
| h10G1-HVR-L2-D53Q | HASQSIS | 329 |
| h10G1-HVR-L2-S54H | HASDHIS | 330 |
| h10G1-HVR-L2-S54L | HASDLIS | 331 |
| h10G1-HVR-L2-S54R | HASDRIS | 332 |
| h10G1-HVR-L2-S54V | HASDVIS | 333 |

TABLE 2-continued

Anti-CD96 antibody sequences

| Description | Sequence | SEQ ID NO: |
|---|---|---|
| h10G1-HVR-L2-I55V | HASDSVS | 334 |
| h10G1-HVR-L3-generic formula | XQGYXMPXT<br>X at position 1 is L, G, M, or Q; X at position 5 is S, A, E, Q, or V; X at position 8 is Y, or F. | 335 |
| h10G1-HVR-L3-L89G | GQGYSMPYT | 336 |
| h10G1-HVR-L3-L89M | MQGYSMPYT | 337 |
| h10G1-HVR-L3-L89Q | QQGYSMPYT | 338 |
| h10G1-HVR-L3-S93A | LQGYAMPYT | 339 |
| h10G1-HVR-L3-S93E | LQGYEMPYT | 340 |
| h10G1-HVR-L3-S93Q | LQGYQMPYT | 341 |
| h10G1-HVR-L3-S93V | LQGYVMPYT | 342 |
| h10G1-HVR-L3-Y96F | LQGYSMPFT | 343 |
| h10G1-HVR-H1-generic formula | XXXGXS<br>X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V. | 344 |
| h10G1-HVR-H1-T30A | ATYGMS | 345 |
| h10G1-HVR-H1-T30D | DTYGMS | 346 |
| h10G1-HVR-H1-T30E | ETYGMS | 347 |
| h10G1-HVR-H1-T30G | GTYGMS | 348 |
| h10G1-HVR-H1-T30H | HTYGMS | 349 |
| h10G1-HVR-H1-T30K | KTYGMS | 350 |
| h10G1-HVR-H1-T30M | MTYGMS | 351 |
| h10G1-HVR-H1-T30N | NTYGMS | 352 |
| h10G1-HVR-H1-T30Q | QTYGMS | 353 |
| h10G1-HVR-H1-T30R | RTYGMS | 354 |
| h10G1-HVR-H1-T30S | STYGMS | 355 |
| h10G1-HVR-H1-T31D | TDYGMS | 356 |

TABLE 2-continued

Anti-CD96 antibody sequences

| Description | Sequence | SEQ ID NO: |
|---|---|---|
| h10G1-HVR-H1-T31E | TEYGMS | 357 |
| h10G1-HVR-H1-T31G | TGYGMS | 358 |
| h10G1-HVR-H1-T31H | THYGMS | 359 |
| h10G1-HVR-H1-T31N | TNYGMS | 360 |
| h10G1-HVR-H1-T31Q | TQYGMS | 361 |
| h10G1-HVR-H1-T31S | TSYGMS | 362 |
| h10G1-HVR-H1-Y32F | TTFGMS | 363 |
| h10G1-HVR-H1-Y32M | TTMGMS | 364 |
| h10G1-HVR-H1-Y32Q | TTQGMS | 365 |
| h10G1-HVR-H1-M34I | TTYGIS | 366 |
| h10G1-HVR-H1-M34L | TTYGLS | 367 |
| h10G1-HVR-H1-M34V | TTYGVS | 368 |
| h10G1-HVR-H2-generic formula | WINTXXGVPTYAD<br>X at position 5 is D, or E; X at position 6 is S, or T. | 369 |
| h10G1-HVR-H2-D53E | WINTESGVPTYAD | 370 |
| h10G1-HVR-H2-S54T | WINTDTGVPTYAD | 371 |
| h10G1-HVR-H3-generic formula | ARXIYYGWGXFDY<br>X at position 3 is N, or M; X at position 10 is N, F, H, or Y. | 372 |
| h10G1-HVR-H3-N95M | ARMIYYGWGNFDY | 373 |
| h10G1-HVR-H3-N100bF | ARNIYYGWGFFDY | 374 |
| h10G1-HVR-H3-N100bH | ARNIYYGWGHFDY | 375 |
| h10G1-HVR-H3-N100bY | ARNIYYGWGYFDY | 376 |
| h10G1-VL-D28A | EIVMTQSPDFQSVTPKEKVTITCRASQAIYRNLHWYQQKPDQTPKLLIKH<br>ASDSISGIPSRFSGSGSGTDFTLTINSLEAEDAAAYYCLQGYSMPYTFGG<br>GTKVEIK | 377 |
| h10G1-VL-D28E | EIVMTQSPDFQSVTPKEKVTITCRASQEIYRNLHWYQQKPDQTPKLLIKH<br>ASDSISGIPSRFSGSGSGTDFTLTINSLEAEDAAAYYCLQGYSMPYTFGG<br>GTKVEIK | 378 |
| h10G1-VL-D28G | EIVMTQSPDFQSVTPKEKVTITCRASQGIYRNLHWYQQKPDQTPKLLIKH<br>ASDSISGIPSRFSGSGSGTDFTLTINSLEAEDAAAYYCLQGYSMPYTFGG<br>GTKVEIK | 379 |

TABLE 2-continued

Anti-CD96 antibody sequences

| Description | Sequence | SEQ ID NO: |
| --- | --- | --- |
| h10G1-VL-D28H | EIVMTQSPDFQSVTPKEKVTITCRASQHIYRNLHWYQQKPDQTPKLLIKH<br>ASDSISGIPSRFSGSGSGTDFTLTINSLEAEDAAAYYCLQGYSMPYTFGG<br>GTKVEIK | 380 |
| h10G1-VL-D28K | EIVMTQSPDFQSVTPKEKVTITCRASQKIYRNLHWYQQKPDQTPKLLIKH<br>ASDSISGIPSRFSGSGSGTDFTLTINSLEAEDAAAYYCLQGYSMPYTFGG<br>GTKVEIK | 381 |
| h10G1-VL-D28N | EIVMTQSPDFQSVTPKEKVTITCRASQNIYRNLHWYQQKPDQTPKLLIKH<br>ASDSISGIPSRFSGSGSGTDFTLTINSLEAEDAAAYYCLQGYSMPYTFGG<br>GTKVEIK | 382 |
| h10G1-VL-D28P | EIVMTQSPDFQSVTPKEKVTITCRASQPIYRNLHWYQQKPDQTPKLLIKH<br>ASDSISGIPSRFSGSGSGTDFTLTINSLEAEDAAAYYCLQGYSMPYTFGG<br>GTKVEIK | 383 |
| h10G1-VL-D28Q | EIVMTQSPDFQSVTPKEKVTITCRASQQIYRNLHWYQQKPDQTPKLLIKH<br>ASDSISGIPSRFSGSGSGTDFTLTINSLEAEDAAAYYCLQGYSMPYTFGG<br>GTKVEIK | 384 |
| h10G1-VL-D28S | EIVMTQSPDFQSVTPKEKVTITCRASQSIYRNLHWYQQKPDQTPKLLIKH<br>ASDSISGIPSRFSGSGSGTDFTLTINSLEAEDAAAYYCLQGYSMPYTFGG<br>GTKVEIK | 385 |
| h10G1-VL-D28T | EIVMTQSPDFQSVTPKEKVTITCRASQTIYRNLHWYQQKPDQTPKLLIKH<br>ASDSISGIPSRFSGSGSGTDFTLTINSLEAEDAAAYYCLQGYSMPYTFGG<br>GTKVEIK | 386 |
| h10G1-VL-Y30F | EIVMTQSPDFQSVTPKEKVTITCRASQDIFRNLHWYQQKPDQTPKLLIKH<br>ASDSISGIPSRFSGSGSGTDFTLTINSLEAEDAAAYYCLQGYSMPYTFGG<br>GTKVEIK | 387 |
| h10G1-VL-R31K | EIVMTQSPDFQSVTPKEKVTITCRASQDIYKNLHWYQQKPDQTPKLLIKH<br>ASDSISGIPSRFSGSGSGTDFTLTINSLEAEDAAAYYCLQGYSMPYTFGG<br>GTKVEIK | 388 |
| h10G1-VL-R31Q | EIVMTQSPDFQSVTPKEKVTITCRASQDIYQNLHWYQQKPDQTPKLLIKH<br>ASDSISGIPSRFSGSGSGTDFTLTINSLEAEDAAAYYCLQGYSMPYTFGG<br>GTKVEIK | 389 |
| h10G1-VL-L33I | EIVMTQSPDFQSVTPKEKVTITCRASQDIYRNIHWYQQKPDQTPKLLIKH<br>ASDSISGIPSRFSGSGSGTDFTLTINSLEAEDAAAYYCLQGYSMPYTFGG<br>GTKVEIK | 390 |
| h10G1-VL-L33M | EIVMTQSPDFQSVTPKEKVTITCRASQDIYRNMHWYQQKPDQTPKLLIKH<br>ASDSISGIPSRFSGSGSGTDFTLTINSLEAEDAAAYYCLQGYSMPYTFGG<br>GTKVEIK | 391 |
| h10G1-VL-L33V | EIVMTQSPDFQSVTPKEKVTITCRASQDIYRNVHWYQQKPDQTPKLLIKH<br>ASDSISGIPSRFSGSGSGTDFTLTINSLEAEDAAAYYCLQGYSMPYTFGG<br>GTKVEIK | 392 |
| h10G1-VL-S52E | EIVMTQSPDFQSVTPKEKVTITCRASQDIYRNLHWYQQKPDQTPKLLIKH<br>AEDSISGIPSRFSGSGSGTDFTLTINSLEAEDAAAYYCLQGYSMPYTFGG<br>GTKVEIK | 393 |
| h10G1-VL-D53E | EIVMTQSPDFQSVTPKEKVTITCRASQDIYRNLHWYQQKPDQTPKLLIKH<br>ASESISGIPSRFSGSGSGTDFTLTINSLEAEDAAAYYCLQGYSMPYTFGG<br>GTKVEIK | 394 |
| h10G1-VL-D53K | EIVMTQSPDFQSVTPKEKVTITCRASQDIYRNLHWYQQKPDQTPKLLIKH<br>ASKSISGIPSRFSGSGSGTDFTLTINSLEAEDAAAYYCLQGYSMPYTFGG<br>GTKVEIK | 395 |
| h10G1-VL-D53Q | EIVMTQSPDFQSVTPKEKVTITCRASQDIYRNLHWYQQKPDQTPKLLIKH<br>ASQSISGIPSRFSGSGSGTDFTLTINSLEAEDAAAYYCLQGYSMPYTFGG<br>GTKVEIK | 396 |
| h10G1-VL-S54H | EIVMTQSPDFQSVTPKEKVTITCRASQDIYRNLHWYQQKPDQTPKLLIKH<br>ASDHISGIPSRFSGSGSGTDFTLTINSLEAEDAAAYYCLQGYSMPYTFGG<br>GTKVEIK | 397 |

TABLE 2-continued

Anti-CD96 antibody sequences

| Description | Sequence | SEQ ID NO: |
|---|---|---|
| h10G1-VL-S54L | EIVMTQSPDFQSVTPKEKVTITCRASQDIYRNLHWYQQKPDQTPKLLIKH ASDLISGIPSRFSGSGSGTDFTLTINSLEAEDAAAYYCLQGYSMPYTFGG GTKVEIK | 398 |
| h10G1-VL-S54R | EIVMTQSPDFQSVTPKEKVTITCRASQDIYRNLHWYQQKPDQTPKLLIKH ASDRISGIPSRFSGSGSGTDFTLTINSLEAEDAAAYYCLQGYSMPYTFGG GTKVEIK | 399 |
| h10G1-VL-S54V | EIVMTQSPDFQSVTPKEKVTITCRASQDIYRNLHWYQQKPDQTPKLLIKH ASDVISGIPSRFSGSGSGTDFTLTINSLEAEDAAAYYCLQGYSMPYTFGG GTKVEIK | 400 |
| h10G1-VL-I55V | EIVMTQSPDFQSVTPKEKVTITCRASQDIYRNLHWYQQKPDQTPKLLIKH ASDSVSGIPSRFSGSGSGTDFTLTINSLEAEDAAAYYCLQGYSMPYTFGG GTKVEIK | 401 |
| h10G1-VL-L89G | EIVMTQSPDFQSVTPKEKVTITCRASQDIYRNLHWYQQKPDQTPKLLIKH ASDSISGIPSRFSGSGSGTDFTLTINSLEAEDAAAYYCGQGYSMPYTFGG GTKVEIK | 402 |
| h10G1-VL-L89M | EIVMTQSPDFQSVTPKEKVTITCRASQDIYRNLHWYQQKPDQTPKLLIKH ASDSISGIPSRFSGSGSGTDFTLTINSLEAEDAAAYYCMQGYSMPYTFGG GTKVEIK | 403 |
| h10G1-VL-L89Q | EIVMTQSPDFQSVTPKEKVTITCRASQDIYRNLHWYQQKPDQTPKLLIKH ASDSISGIPSRFSGSGSGTDFTLTINSLEAEDAAAYYCQQGYSMPYTFGG GTKVEIK | 404 |
| h10G1-VL-S93A | EIVMTQSPDFQSVTPKEKVTITCRASQDIYRNLHWYQQKPDQTPKLLIKH ASDSISGIPSRFSGSGSGTDFTLTINSLEAEDAAAYYCLQGYAMPYTFGG GTKVEIK | 405 |
| h10G1-VL-S93E | EIVMTQSPDFQSVTPKEKVTITCRASQDIYRNLHWYQQKPDQTPKLLIKH ASDSISGIPSRFSGSGSGTDFTLTINSLEAEDAAAYYCLQGYEMPYTFGG GTKVEIK | 406 |
| h10G1-VL-S93Q | EIVMTQSPDFQSVTPKEKVTITCRASQDIYRNLHWYQQKPDQTPKLLIKH ASDSISGIPSRFSGSGSGTDFTLTINSLEAEDAAAYYCLQGYQMPYTFGG GTKVEIK | 407 |
| h10G1-VL-S93V | EIVMTQSPDFQSVTPKEKVTITCRASQDIYRNLHWYQQKPDQTPKLLIKH ASDSISGIPSRFSGSGSGTDFTLTINSLEAEDAAAYYCLQGYVMPYTFGG GTKVEIK | 408 |
| h10G1-VL-Y96F | EIVMTQSPDFQSVTPKEKVTITCRASQDIYRNLHWYQQKPDQTPKLLIKH ASDSISGIPSRFSGSGSGTDFTLTINSLEAEDAAAYYCLQGYSMPFTFGG GTKVEIK | 409 |
| h10G1-VH-T30A | EIQLVQSGSELKKPGASVKVSCKASGYPFATYGMSWVRQAPGQGLEWMGW INTDSGVPTYADDFKGRFVFSLDTSVSTAYLQISSLKAEDTAVYFCARNI YYGWGNFDYWGQGTLVTVSS | 410 |
| h10G1-VH-T30D | EIQLVQSGSELKKPGASVKVSCKASGYPFDTYGMSWVRQAPGQGLEWMGW INTDSGVPTYADDFKGRFVFSLDTSVSTAYLQISSLKAEDTAVYFCARNI YYGWGNFDYWGQGTLVTVSS | 411 |
| h10G1-VH-T30E | EIQLVQSGSELKKPGASVKVSCKASGYPFETYGMSWVRQAPGQGLEWMGW INTDSGVPTYADDFKGRFVFSLDTSVSTAYLQISSLKAEDTAVYFCARNI YYGWGNFDYWGQGTLVTVSS | 412 |
| h10G1-VH-T30G | EIQLVQSGSELKKPGASVKVSCKASGYPFGTYGMSWVRQAPGQGLEWMGW INTDSGVPTYADDFKGRFVFSLDTSVSTAYLQISSLKAEDTAVYFCARNI YYGWGNFDYWGQGTLVTVSS | 413 |
| h10G1-VH-T30H | EIQLVQSGSELKKPGASVKVSCKASGYPFHTYGMSWVRQAPGQGLEWMGW INTDSGVPTYADDFKGRFVFSLDTSVSTAYLQISSLKAEDTAVYFCARNI YYGWGNFDYWGQGTLVTVSS | 414 |
| h10G1-VH-T30K | EIQLVQSGSELKKPGASVKVSCKASGYPFKTYGMSWVRQAPGQGLEWMGW INTDSGVPTYADDFKGRFVFSLDTSVSTAYLQISSLKAEDTAVYFCARNI YYGWGNFDYWGQGTLVTVSS | 415 |

TABLE 2-continued

Anti-CD96 antibody sequences

| Description | Sequence | SEQ ID NO: |
|---|---|---|
| h10G1-VH-T30M | EIQLVQSGSELKKPGASVKVSCKASGYPFMTYGMSWVRQAPGQGLEWMGW INTDSGVPTYADDFKGRFVFSLDTSVSTAYLQISSLKAEDTAVYFCARNI YYGWGNFDYWGQGTLVTVSS | 416 |
| h10G1-VH-T30N | EIQLVQSGSELKKPGASVKVSCKASGYPFNTYGMSWVRQAPGQGLEWMGW INTDSGVPTYADDFKGRFVFSLDTSVSTAYLQISSLKAEDTAVYFCARNI YYGWGNFDYWGQGTLVTVSS | 417 |
| h10G1-VH-T30Q | EIQLVQSGSELKKPGASVKVSCKASGYPFQTYGMSWVRQAPGQGLEWMGW INTDSGVPTYADDFKGRFVFSLDTSVSTAYLQISSLKAEDTAVYFCARNI YYGWGNFDYWGQGTLVTVSS | 418 |
| h10G1-VH-T30R | EIQLVQSGSELKKPGASVKVSCKASGYPFRTYGMSWVRQAPGQGLEWMGW INTDSGVPTYADDFKGRFVFSLDTSVSTAYLQISSLKAEDTAVYFCARNI YYGWGNFDYWGQGTLVTVSS | 419 |
| h10G1-VH-T30S | EIQLVQSGSELKKPGASVKVSCKASGYPFSTYGMSWVRQAPGQGLEWMGW INTDSGVPTYADDFKGRFVFSLDTSVSTAYLQISSLKAEDTAVYFCARNI YYGWGNFDYWGQGTLVTVSS | 420 |
| h10G1-VH-T31D | EIQLVQSGSELKKPGASVKVSCKASGYPFTDYGMSWVRQAPGQGLEWMGW INTDSGVPTYADDFKGRFVFSLDTSVSTAYLQISSLKAEDTAVYFCARNI YYGWGNFDYWGQGTLVTVSS | 421 |
| h10G1-VH-T31E | EIQLVQSGSELKKPGASVKVSCKASGYPFTEYGMSWVRQAPGQGLEWMGW INTDSGVPTYADDFKGRFVFSLDTSVSTAYLQISSLKAEDTAVYFCARNI YYGWGNFDYWGQGTLVTVSS | 422 |
| h10G1-VH-T31G | EIQLVQSGSELKKPGASVKVSCKASGYPFTGYGMSWVRQAPGQGLEWMGW INTDSGVPTYADDFKGRFVFSLDTSVSTAYLQISSLKAEDTAVYFCARNI YYGWGNFDYWGQGTLVTVSS | 423 |
| h10G1-VH-T31H | EIQLVQSGSELKKPGASVKVSCKASGYPFTHYGMSWVRQAPGQGLEWMGW INTDSGVPTYADDFKGRFVFSLDTSVSTAYLQISSLKAEDTAVYFCARNI YYGWGNFDYWGQGTLVTVSS | 424 |
| h10G1-VH-T31N | EIQLVQSGSELKKPGASVKVSCKASGYPFTNYGMSWVRQAPGQGLEWMGW INTDSGVPTYADDFKGRFVFSLDTSVSTAYLQISSLKAEDTAVYFCARNI YYGWGNFDYWGQGTLVTVSS | 425 |
| h10G1-VH-T31Q | EIQLVQSGSELKKPGASVKVSCKASGYPFTQYGMSWVRQAPGQGLEWMGW INTDSGVPTYADDFKGRFVFSLDTSVSTAYLQISSLKAEDTAVYFCARNI YYGWGNFDYWGQGTLVTVSS | 426 |
| h10G1-VH-T31S | EIQLVQSGSELKKPGASVKVSCKASGYPFTSYGMSWVRQAPGQGLEWMGW INTDSGVPTYADDFKGRFVFSLDTSVSTAYLQISSLKAEDTAVYFCARNI YYGWGNFDYWGQGTLVTVSS | 427 |
| h10G1-VH-Y32F | EIQLVQSGSELKKPGASVKVSCKASGYPFTTFGMSWVRQAPGQGLEWMGW INTDSGVPTYADDFKGRFVFSLDTSVSTAYLQISSLKAEDTAVYFCARNI YYGWGNFDYWGQGTLVTVSS | 428 |
| h10G1-VH-Y32M | EIQLVQSGSELKKPGASVKVSCKASGYPFTTMGMSWVRQAPGQGLEWMGW INTDSGVPTYADDFKGRFVFSLDTSVSTAYLQISSLKAEDTAVYFCARNI YYGWGNFDYWGQGTLVTVSS | 429 |
| h10G1-VH-Y32Q | EIQLVQSGSELKKPGASVKVSCKASGYPFTTQGMSWVRQAPGQGLEWMGW INTDSGVPTYADDFKGRFVFSLDTSVSTAYLQISSLKAEDTAVYFCARNI YYGWGNFDYWGQGTLVTVSS | 430 |
| h10G1-VH-M34I | EIQLVQSGSELKKPGASVKVSCKASGYPFTTYGISWVRQAPGQGLEWMGW INTDSGVPTYADDFKGRFVFSLDTSVSTAYLQISSLKAEDTAVYFCARNI YYGWGNFDYWGQGTLVTVSS | 431 |
| h10G1-VH-M34L | EIQLVQSGSELKKPGASVKVSCKASGYPFTTYGLSWVRQAPGQGLEWMGW INTDSGVPTYADDFKGRFVFSLDTSVSTAYLQISSLKAEDTAVYFCARNI YYGWGNFDYWGQGTLVTVSS | 432 |
| h10G1-VH-M34V | EIQLVQSGSELKKPGASVKVSCKASGYPFTTYGVSWVRQAPGQGLEWMGW INTDSGVPTYADDFKGRFVFSLDTSVSTAYLQISSLKAEDTAVYFCARNI YYGWGNFDYWGQGTLVTVSS | 433 |

TABLE 2-continued

Anti-CD96 antibody sequences

| Description | Sequence | SEQ ID NO: |
|---|---|---|
| h10G1-VH-D53E | EIQLVQSGSELKKPGASVKVSCKASGYPFTTYGMSWVRQAPGQGLEWMGW INTESGVPTYADDFKGRFVFSLDTSVSTAYLQISSLKAEDTAVYFCARNI YYGWGNFDYWGQGTLVTVSS | 434 |
| h10G1-VH-S54T | EIQLVQSGSELKKPGASVKVSCKASGYPFTTYGMSWVRQAPGQGLEWMGW INTDTGVPTYADDFKGRFVFSLDTSVSTAYLQISSLKAEDTAVYFCARNI YYGWGNFDYWGQGTLVTVSS | 435 |
| h10G1-VH-N95M | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARMI YYGWGNFDYWGQGTLVTVSS | 436 |
| h10G1-VH-N100bF | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGFFDYWGQGTLVTVSS | 437 |
| h10G1-VH-N100bH | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGHFDYWGQGTLVTVSS | 438 |
| h10G1-VH-N100bY | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGYFDYWGQGTLVTVSS | 439 |
| 12F8-LC Full length | DIVMTQSQKFMSTSVGDRVSVTCKASQNVGTAIVWYQKKPGQSPKTLIYS ASTRYTGVPDRFTGSGSGTDFTLTISNVQSEDLAEYFCQQYSSSPLTFGS GTKLEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 440 |
| 10H5-LC Full length | DVVMTQTPLTLSVTLGHPASISCKSSQSLLDSDGKTYLNWLLQRPGESPK LLIYLVSKLDSGVPDRFTGSGSGTDFTLKISRVEAEDLGVYYCLQATHSP QTFGGGTKLEIKGQPKAAPSVTLFPPSSEELQANKATLVCLISDFYPGAV TVAWKADSSPVKAGVETTTPSKQSNNKYAASSYLSLTPEQWKSHKSYSCQ VTHEGSTVEKTVAPTECS | 441 |
| 1G8-LC Full length | DIQMNQSPSSLSASLGDTITITCRVSQDISFWLSWYQQKPGNIPKLLIYK ASNLHTGVPPRFSGSGSGTDFTLTISSLQPEDIAAYYCLQSQSYPYTFGG GTKLEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 442 |
| 16D9-LC Full length | ENVLTQSPAIMSATLGEKVTMNCRASSNVKYMYWYQQKSGVSPKLWIYYT SNLASGVPTRFSGSGSGTSYSLTISSVEAEDAATYYCQQFTSSPLTFGAG TKLELKGQPKAAPSVTLFPPSSEELQANKATLVCLISDFYPGAVTVAWKA DSSPVKAGVETTTPSKQSNNKYAASSYLSLTPEQWKSHKSYSCQVTHEGS TVEKTVAPTECS | 443 |
| 9H4-LC Full length | DIVLTQSPASLAVSLGQRAIISCKASQSVTFADTGLMHWYQKPGQQPKL LIYRASNLEVGVPTRFSGSGSGTDFTLNIHPVEEEDVATYYCQQSREYPW TFGGGTKLEIKGQPKAAPSVTLFPPSSEELQANKATLVCLISDFYPGAVT VAWKADSSPVKAGVETTTPSKQSNNKYAASSYLSLTPEQWKSHKSYSCQV THEGSTVEKTVAPTECS | 444 |
| 7E5-LC Full length | QAVVTQESALTTSPGETVTLTCRSSTGAVTTSNYANWVQEKPDHLFTGLI GGTNNRAPGVPARFSGSLIGDKAALTITGAQTEDEAIYFCSLWYGSHWVF GGGTKLTVLGQPKAAPSVTLFPPSSEELQANKATLVCLISDFYPGAVTVA WKADSSPVKAGVETTTPSKQSNNKYAASSYLSLTPEQWKSHKSYSCQVTH EGSTVEKTVAPTECS | 445 |
| 10G1-LC Full length | DILMTQSPTTLSVTPGETVSLSCRASQDIYRNLHWYQQKSQGTPRLLIKH ASDSISGIPSRFTGSGSGTDFTLSINSVKPEDEGIYYCLQGYSMPYTFGG GTKLEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 446 |
| 12F8-HC Full length hIgG1.N297G | QVQLQQPGAELVTPGASVKLSCKASGFTFTNNWMHWVKQRPGQGLEWIGM IHPNSGITNINEKFKNKATVTVDKSSSTVYIQLSSLTSEDSAVYYCRSDG TYEGYFDYWGQGTPLTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV | 447 |

TABLE 2-continued

Anti-CD96 antibody sequences

| Description | Sequence | SEQ ID NO: |
|---|---|---|
| | YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPG | |
| 10H5-HC<br>Full length<br>hIgG1.N297G | QVQLQQSGADLARPGASIKLSCKASGYTFTGYGVTWVKQSTGQGLDWIGE<br>IYPGTVITYYNAKFKGKATLTADKSSSTAYMELRSLTSEDSAVYFCARGL<br>GRAMDYWGQGTSVTVSSASTKGPSVFPLAPSSKSTSGGTAALGCLVKDYF<br>PEPVTVSWNSGALTSGVHTFPAVLQSSGLYSLSSVVTVPSSSLGTQTYIC<br>NVNHKPSNTKVDKKVEPKSCDKTHTCPPCPAPELLGGPSVFLFPPKPKDT<br>LMISRTPEVTCVVVDVSHEDPEVKFNWYVDGVEVHNAKTKPREEQYGSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 448 |
| 1G8-HC<br>Full length<br>hIgG1.N297G | QVQLQQSGPELLKPGASVKISCKASGYTFTDYYINWVKQRPGQGLEWIGW<br>IFPGTEGIYYNEKFKGKATLTVDKSSTTAYMLLSSLTSEDSAVYFCAREG<br>DYRYYSPLGYWGQGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPK<br>PKDTLMISRTPEVTCVVVDVSHEDPEVKFNWYVDGVEVHNAKTKPREEQY<br>GSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPP<br>VLDSDGSFFLYSKLTVDKSRWQQGNVFSCSVMHEALHNHYTQKSLSLSPG | 449 |
| 16D9-HC<br>Full length<br>hIgG1.N297G | QVQLQQSGPELVKPGASVKISCKASGYNFNDYYINWVNQRPGQGLEWIGW<br>IFPGRIITYYNEKFKGKATLTVDTSSNTAYMLLSSLTSEDSAVYFCARGV<br>GEGFDYWGQGTTLTVSSASTKGPSVFPLAPSSKSTSGGTAALGCLVKDYF<br>PEPVTVSWNSGALTSGVHTFPAVLQSSGLYSLSSVVTVPSSSLGTQTYIC<br>NVNHKPSNTKVDKKVEPKSCDKTHTCPPCPAPELLGGPSVFLFPPKPKDT<br>LMISRTPEVTCVVVDVSHEDPEVKFNWYVDGVEVHNAKTKPREEQYGSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPG | 450 |
| 9H4-HC<br>Full length<br>hIgG1.N297G | EVQLLETGGGLVKSGGSLKLSCAASGFTFSDYYMYWVRQTPEKRLEWVAA<br>ISDDGTYTYYPDSVKGRFTISRDNANNYLYLQMSSLKSEDTAIYYCAKAG<br>SYDYFDVWGAGTTVTVSSASTKGPSVFPLAPSSKSTSGGTAALGCLVKDY<br>FPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYGST<br>YRVVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPG | 451 |
| 7E5-HC<br>Full length<br>hIgG1.N297G | QVQLKESGPGLVAPSQSLSIICTVSGFSLTNYGIHWIRQPPGKGLEWLGI<br>IWAGGSTNYNSALMSRLTISKDNSKSQVFLKMNSLQTNDTAIYYCARVSM<br>MGFAYWGQGTLVTVSSASTKGPSVFPLAPSSKSTSGGTAALGCLVKDYFP<br>EPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQYGSTYR<br>VVSVLTVLHQDWLNGKEYKCKVSNKALPAPIEKTISKAKGQPREPQVYTL<br>PPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPG | 452 |
| 10G1-HC<br>Full length<br>hIgG1.N297G | QIQLVQSGPELKKPGETVKISCKASGYPFTTYGMSWVKQAPGKGLKWMGW<br>INTDSGVPTYADDFKGRFAFSLETSANTAYLQINSLKNEDAATYFCARNI<br>YYGWGNFDYWGQGTILTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYG<br>STYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPG | 453 |
| mAb1v7-LC<br>Full length | DIQLTQSPSSLSASVGDRVTITCKASQNVGTAIVWYQQKPGKAPKVLIYS<br>ASTRYTGVPSRFSGSGSGTDFTLTISSLQPEDFATYYCQQYSSSPLTFGQ<br>GTKVEIKGQPKAAPSVTLFPPSSEELQANKATLVCLISDFYPGAVTVAWK<br>ADSSPVKAGVETTTPSKQSNNKYAASSYLSLTPEQWKSHKSYSCQVTHEG<br>STVEKTVAPTECS | 454 |
| mAb1v7-HC<br>Full length<br>hIgG.N297G | EVQLVQSGAEVKKPGASVKVSCKASGFTFTNNWMHWVRQAPGQGLEWIGM<br>IHPNSGITNINEKFKNRVTMTTDTSTSTAYMELRSLRSEDTAVYYCRSDG<br>TYEGYFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK | 455 |

TABLE 2-continued

Anti-CD96 antibody sequences

| Description | Sequence | SEQ ID NO: |
|---|---|---|
| | DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | |
| mAb1v7-HC-W33F/P52aA/T97I (mAb1v7.NGS8) Full length hIgG1.N297G | EVQLVQSGAEVKKPGASVKVSCKASGFTF<u>TNNFMH</u>WVRQAPGQGLEWIGM <u>IHANSGITNINEKFKN</u>RVTMTTDTSTSTA<u>YMELRS</u>LRSEDTAVYYC<u>RSDG IYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 456 |
| mAb1v7-HC-W33F/P52aA/T97V (mAb1v7.NGS9) Full length hIgG1.N297G | EVQLVQSGAEVKKPGASVKVSCKASGFTF<u>TNNFMH</u>WVRQAPGQGLEWIGM <u>IHANSGITNINEKFKN</u>RVTMTTDTSTSTA<u>YMELRS</u>LRSEDTAVYYC<u>RSDG VYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 457 |
| mAb1v7-HC-W33F/M50F/P52aA/T97I (mAb1v7.NGS10) Full length hIgG1.N297G | EVQLVQSGAEVKKPGASVKVSCKASGFTF<u>TNNFMH</u>WVRQAPGQGLEWIG<u>F IHANSGITNINEKFKN</u>RVTMTTDTSTSTA<u>YMELRS</u>LRSEDTAVYYC<u>RSDG IYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 458 |
| mAb1v7-HC-W33F/M50F/P52aA/T97V (mAb1v7.NGS11) Full length hIgG1.N297G | EVQLVQSGAEVKKPGASVKVSCKASGFTF<u>TNNFMH</u>WVRQAPGQGLEWIG<u>F IHANSGITNINEKFKN</u>RVTMTTDTSTSTA<u>YMELRS</u>LRSEDTAVYYC<u>RSDG VYEGYFDY</u>WGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 459 |
| mAb1.v1-VH | QVQLVQSGAEVKKPGASVKVSCKASGFTFTNNWMHWVRQRPGQGLEWIGM IHPNSGITNINEKFKNRATVTVDKSSSTVYTELRSLRSEDTAVYYCRSDG TYEGYFDYWGQGTLVTVSS | 460 |
| mAb1.v2-VH | QVQLVQSGAEVKKPGASVKVSCKASGFTFTNNWMHWVRQRPGQGLEWIGM IHPNSGITNINEKFKNRATVTVDKSSSTVYIELRSLRSEDTAVYYCRSDG TYEGYFDYWGQGTLVTVSS | 461 |
| mAb1.v3-VH | QVQLVQSGAEVKKPGASVKVSCKASGFTFTNNWMHWVRQAPGQGLEWVGM IHPNSGITNINEKFKNRVTMTVDKSTSTVYMELRSLRSDDTAVYYCRSDG TYEGYFDYWGQGTLVTVSS | 462 |
| mAb1.v4-VH | QVQLVQSGAEVKKPGASVKVSCKASGFTFTNNWMHWVRQRPGQGLEWIGM IHPNSGITNINEKFKNRVTMTTDTSTSTAYMELRSLRSDDTAVYYCRSDG TYEGYFDYWGQGTLVTVSS | 463 |
| mAb1.v5-VH | QVQLVQSGAEVKKPGASVKVSCKASGFTFTNNWMHWVRQRPGQGLEWIGM IHPNSGITNINEKFKNRVTMTVDKSTSTVYMELRSLRSDDTAVYYCARDG TYEGYFDYWGQGTLVTVSS | 464 |
| mAb1.v1-HC Full length hIgG1.N297G | QVQLVQSGAEVKKPGASVKVSCKASGFTFTNNWMHWVRQRPGQGLEWIGM IHPNSGITNINEKFKNRATVTVDKSSSTVYIELRSLRSEDTAVYYCRSDG TYEGYFDYWGQGTLVTVSSASTKGPSVFPLAPSSKSTSGGTRALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 465 |

TABLE 2-continued

Anti-CD96 antibody sequences

| Description | Sequence | SEQ ID NO: |
|---|---|---|
| mAb1.v2-HC Full length hIgG1.N297G | QVQLVQSGAEVKKPGASVKVSCKASGFTFTNNWMHWVRQRPGQGLEWIGM IHPNSGITNINEKFKNRATVTVDKSSSTVYIELRSLRSEDTAVYYCRSDG TYEGYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 466 |
| mAb1.v3-HC Full length hIgG1.N297G | QVQLVQSGAEVKKPGASVKVSCKASGFTFTNNWMHWVRQRPGQGLEWVGM IHPNSGITNINEKFKNRVTMTVDKSTSTVYMELRSLRSDDTAVYYCRSDG TYEGYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPG | 467 |
| mAb1.v4-HC Full length hIgG1.N297G | QVQLVQSGAEVKKPGASVKVSCKASGFTFTNNWMHWVRQRPGQGLEWIGM IHPNSGITNINEKFKNRVTMTTDTSTSTAYMELRSLRSDDTAVYYCRSDG TYEGYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGEYPSDIAVEWESNGQPENNYKTTPPVI DSDGSFFLYSKLTVDKSRWQQGNVFSCSVMHEALHNHYTQKSLSLSPG | 468 |
| mAb1.v5-HC Full length hIgG1.N297G | QVQLVQSGAEVKKPGASVKVSCKASGFTFTNNWMHWVRQAPGQGLEWIGM IHPNSGITNINEKFKNRVTMTVDKSTSTVYMELRSLRSDDTAVYYCARDG TYEGYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPEMNYKTTPPVL DSDGSFFLYSKLTVDKSRWQQGNVFSCSVMHEALHNHYTQKSLSLSPG | 469 |
| h10G1-LC Full length | EIVMTQSPDFQSVTPKEKVTITCRASQDIYRNLHWYQQKPDQTPKLLIKH ASDSISGIPSRFSGSGSGTDFTLTINSLEAEDAAAYYCLQGYSMPYTFGG GTKVEIKGQPKAAPSVTLFPPSSEELQANKATLVCLISDFYPGAVTVAWK ADSSPVKAGVETTTPSKQSNNKYAASSYLSLTPEQWKSHKSYSCQVTHEG STVEKTVAPTECS | 470 |
| h10G1-HC Full length hIgG1.N297G | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGNFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYG STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPG | 471 |
| 12F8-HC Full length hIgG1.N297G + C-term Lys | QVQLQQPGAELVTPGASVKLSCKASGFTF<ins>TNNWMH</ins>WVKQRPGQGLEWIGM <ins>IHPNSGITNINEKFKN</ins>KATVTVDKSSSTVY<ins>IQLSSLTSEDSAVYYCRSDG</ins> <ins>TYEGYFDY</ins>WGQGPLTVSSASTKGPSVFPLAPSSKSTSGGTAALGC<ins>LVKD</ins> YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 484 |
| 10H5-HC Full length hIgG1.N297G + C-term Lys | QVQLQQSGADLARPGASIKLSCKASGYTF<ins>TGYGVT</ins>WVKQSTGQGLDWIGE <ins>IYPGTVITYYNAKF</ins>KGKATLTADKSSSTAYMELRS<ins>LTSEDSAVYYCARGL</ins> <ins>GRAMDY</ins>WGQGTSVTVSSASTKGPSVFPLAPSSKSTSGGTAALGCLV<ins>KDYF</ins> <ins>PEPVTVSWNSGALTSGVHTFPAVLQSSGLYSLSSVVTVPSSSLGTQTYIC</ins> NVNHKPSNTKVDKKVEPKSCDKTHTCPPCPAPELLGGPSVFLFPPKPKDT LMISRTPEVTCVVVDVSHEDPEVKFNWYVDGVEVHNAKTKPREEQYGSTY RVVSVLTVLHQDWLNGKEYKCKVSNKALPAPIEKTISKAKGQPREPQVYT | 485 |

TABLE 2-continued

Anti-CD96 antibody sequences

| Description | Sequence | SEQ ID NO: |
|---|---|---|
| | LPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPGK | |
| 1G8-HC<br>Full length<br>hIgG1.N297G + C-<br>term Lys | QVQLQQSGPELLKPGASVKISCKASGYTFTDYYINWVKQRPGQGLEWIGW<br>IFPGTEGIYYNEKFKGKATLTVDKSSTTAYMLLSSLTSEDSAVYFCAREG<br>DYRYYSPLGYWGQGTLVTVSAASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPK<br>PKDTLMISRTPEVTCVVVDVSHEDPEVKFNWYVDGVEVHNAKTKPREEQY<br>GSTYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPP<br>VLDSDGSFFLYSKLTVDKSRWQQGNVFSCSVMHEALHNHYTQKSLSLSPG<br>K | 486 |
| 16D9-HC<br>Full length<br>hIgG1.N297G + C-<br>term Lys | QVQLQQSGPELVKPGASVKISCKASGYNFDYYINWVNQRPGQGLEWIGW<br>IFPGRIITYYNEKFKGKATLTVDTSSNTAYMLLSSLTSEDSAVYFCARGV<br>GEGFDYWGQGTTLTVSSASTKGPSVFPLAPSSKSTSGGTAALGCLVKDYF<br>PEPVTVSWNSGALTSGVHTFPAVLQSSGLYSLSSVVTVPSSSLGTQTYIC<br>NVNHKPSNTKVDKKVEPKSCDKTHTCPPCPAPELLGGPSVFLFPPKPKDT<br>LMISRTPEVTCVVVDVSHEDPEVKFNWYVDGVEVHNAKTKPREEQYGSTY<br>RVVSVLTVLHQDWLNGKEYKCKVSNKALPAPIEKTISKAKGQPREPQVYT<br>LPPSRDELTKNQVSLTCLVKGFYPSDIAVEWESNGQPENNYKTTPPVLDS<br>DGSFFLYSKLTVDKSRWQQGNVFSCSVMHEALHNHYTQKSLSLSPGK | 487 |
| 9H4-HC<br>Full length<br>hIgG1.N297G + C-<br>term Lys | EVQLLETGGGLVKSGGSLKLSCAASGFTFSDYYMYWVRQTPEKRLEWVAA<br>ISDDGTYTYYPDSVKGRFTISRDNANNYLYLQMSSLKSEDTAIYYCAKAG<br>SYDYFDVWGAGTTVTVSSASTKGPSVFPLAPSSKSTSGGTAALGCLVKDY<br>FPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYGST<br>YRVVSVLTVLHQDWLNGKEYKCKVSNKALPAPIEKTISKAKGQPREPQVY<br>TLPPSRDELTKNQVSLTCLVKGFYPSDIAVEWESNGQPENNYKTTPPVLD<br>SDGSFFLYSKLTVDKSRWQQGNVFSCSVMHEALHNHYTQKSLSLSPGK | 488 |
| 7E5-HC<br>Full length<br>hIgG1.N297G + C-<br>term Lys | QVQLKESGPGLVAPSQSLSIICTVSGFSLTNYGIHWIRQPPGKGLEWLGI<br>IWAGGSTNYNSALMSRLTISKDNSKSQVFLKMNSLQTNDTAIYYCARVSM<br>MGFAYWGQGTLVTVSAASTKGPSVFPLAPSSKSTSGGTAALGCLVKDYFP<br>EPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTL<br>MISRTPEVTCVVVDVSHEDPEVKFNWYVDGVEVHNAKTKPREEQYGSTYR<br>VVSVLTVLHQDWLNGKEYKCKVSNKALPAPIEKTISKAKGQPREPQVYTL<br>PPSRDELTKNQVSLTCLVKGFYPSDIAVEWESNGQPENNYKTTPPVLDSD<br>GSFFLYSKLTVDKSRWQQGNVFSCSVMHEALHNHYTQKSLSLSPGK | 489 |
| 10G1-HC<br>Full length<br>hIgG1.N297G + C-<br>term Lys | QIQLVQSGPELKKPGETVKISCKASGYPFTTYGMSWVKQAPGKGLKWMGW<br>INTDSGVPTYADDFKGRFAFSLETSANTAYLQINSLKNEDAATYFCARNI<br>YYGWGNFDYWGQGTILTVSSASTKGPSVFPLAPSSKSTSGGTAALGCLVK<br>DYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKP<br>KDTLMISRTPEVTCVVVDVSHEDPEVKFNWYVDGVEVHNAKTKPREEQYG<br>STYRVVSVLTVLHQDWLNGKEYKCKVSNKALPAPIEKTISKAKGQPREPQ<br>VYTLPPSRDELTKNQVSLTCLVKGFYPSDIAVEWESNGQPENNYKTTPPV<br>LDSDGSFFLYSKLTVDKSRWQQGNVFSCSVMHEALHNHYTQKSLSLSPGK | 490 |
| mAb1v7-HC<br>Full length<br>hIgG.N297G + C-term<br>Lys | EVQLVQSGAEVKKPGASVKVSCKASGFTFTNNWMHWVRQAPGQGLEWIGM<br>IHPNSGITNINEKFKNRVTMTTDTSTSTAYMELRSLRSEDTAVYYCRSDG<br>TYEGYFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 491 |
| mAb1v7-HC-<br>W33F/P52aA/T97I<br>(mAb1v7.NGS8)<br>Full length<br>hIgG1.N297G + C-<br>term Lys | EVQLVQSGAEVKKPGASVKVSCKASGFTFTNNFMHWVRQAPGQGLEWIGM<br>IHANSGITNINEKFKNRVTMTTDTSTSTAYMELRSLRSEDTAVYYCRSDG<br>IYEGYFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 492 |

TABLE 2-continued

Anti-CD96 antibody sequences

| Description | Sequence | SEQ ID NO: |
|---|---|---|
| mAb1v7-HC-W33F/P52aA/T97V (mAb1v7.NGS9) Full length hIgG1.N297G + C-term Lys | EVQLVQSGAEVKKPGASVKVSCKASGFTF<u>TNNFMH</u>WVRQAPGQGLEWIGM<br><u>IHANSGI</u>TNINEKFKNRVTMTTDTSTSTAYMELRSLRSEDTAVYYC<u>RSDG</u><br><u>VYEGYFDY</u>WGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 493 |
| mAb1v7-HC-W33F/M50F/P52aA/T97I (mAb1v7.NGS10) Full length hIgG1.N297G + C-term Lys | EVQLVQSGAEVKKPGASVKVSCKASGFTF<u>TNNFMH</u>WVRQAPGQGLEWIG<u>F</u><br><u>IHANSGI</u>TNINEKFKNRVTMTTDTSTSTAYMELRSLRSEDTAVYYC<u>RSDG</u><br><u>IYEGYFDY</u>WGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 494 |
| mAb1v7-HC-W33F/M50F/P52aA/T97V (mAb1v7.NGS11) Full length hIgG1.N297G + C-term Lys | EVQLVQSGAEVKKPGASVKVSCKASGFTF<u>TNNFMH</u>WVRQAPGQGLEWIG<u>F</u><br><u>IHANSGI</u>TNINEKFKNRVTMTTDTSTSTAYMELRSLRSEDTAVYYC<u>RSDG</u><br><u>VYEGYFDY</u>WGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 495 |
| mAb1.v1-HC Full length hIgG1.N297G + C-term Lys | QVQLVQSGAEVKKPGASVKVSCKASGFTF<u>TNNWMH</u>WVRQRPGQGLEWIGM<br><u>IHPNSGI</u>TNINEKFKNRATVTVDKSSSTV<u>YIELRSL</u>RSEDTAVYYC<u>RSDG</u><br><u>TYEGYFDY</u>WGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSD1AVEWESNGQPENNYKTTPPVL<br>DSDGSEFLYSKLTVDKSRWQQGNVFSCSVMHEALHNHYTQKSLSLSPGK | 496 |
| mAb1.v2-HC Full length hIgG1.N297G + C-term Lys | QVQLVQSGAEVKKPGASVKVSCKASGFTFTNNWMHWVRQRPGQGLEWIGM<br>IHPNSGITNINEKFKNRATVTVDKSSSTVYIELRSLRSEDTAVYYCRSDG<br>TYEGYFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 497 |
| mAb1.v3-HC Full length hIgG1.N297G + C-term Lys | QVQLVQSGAEVKKPGASVKVSCKASGFTFTNNWMHWVRQAPGQGLEWVGM<br>IHPNSGITNINEKFKNRVTMTVDKSTSTVYMELRSLRSDDTAVYYCRSDG<br>TYEGYFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 498 |
| mAb1.v4-HC Full length hIgG1.N297G + C-term Lys | QVQLVQSGAEVKKPGASVKVSCKASGFTFTNNWMHWVRQAPGQGLEWIGM<br>IHPNSGITNINEKFKNRVTMTTDTSTSTAYMELRSLRSDDTAVYYCRSDG<br>TYEGYFDYWGQGTLVTVSSASTKGPSVFPLAPSSKSTSGGTAALGCLVKD<br>YFPEPVTVSWNSGALTSGVHTFPAVLQSSGLYSLSSVVTVPSSSLGTQTY<br>ICNVNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPREEQYGS<br>TYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVL<br>DSDGSFFLYSKLTVDKSRWQQGNVFSCSVMHEALHNHYTQKSLSLSPGK | 499 |

TABLE 2-continued

Anti-CD96 antibody sequences

| Description | Sequence | SEQ ID NO: |
|---|---|---|
| mAb1.v5-HC Full length hIgG1.N297G + C-term Lys | QVQLVQSGAEVKKPGASVKVSCKASGFTFTNNWMHWVRQAPGQGLEWIGM IHPNSGITNINEKFKNRVTMTVDKSTSTVYMELRSLRSDDTAVYYCARDG TYEGYFDYWGQGTLVTVSSASTKGPSVFPLAPSSKSTSGGTAALGCLVKD YFPEPVTVSWNSGALTSGVHTFPAVLQSSGLYSLSSVVTVPSSSLGTQTY ICNVNHKPSNTKVDKKVEPKSCDKTHTCPPCPAPELLGGPSVFLFPPKPK DTLMISRTPEVTCVVVDVSHEDPEVKFNWYVDGVEVHNAKTKPREEQYGS TYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK | 500 |
| h10G1-HC Full length hIgG1.N297G + C-term Lys | EIQLVQSGSELKKPGASVKVSCKASGYPFTTYGMSWVRQAPGQGLEWMGW INTDSGVPTYADDFKGRFVFSLDTSVSTAYLQISSLKAEDTAVYFCARNI YYGWGNFDYWGQGTLVTVSSASTKGPSVFPLAPSSKSTSGGTAALGCLVK DYFPEPVTVSWNSGALTSGVHTFPAVLQSSGLYSLSSVVTVPSSSLGTQT YICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQYG STYRVVSVLTVLHQDWLNGKEYKCKVSNKALPAPIEKTISKAKGQPREPQ VYTLPPSRDELTKNQVSLTCLVKGFYPSDIAVEWESNGQPENNYKTTPPV LDSDGSFFLYSKLTVDKSRWQQGNVFSCSVMHEALHNHYTQKSLSLSPGK | 501 |

1. Binding Affinity and Cell-Signaling Inhibition of Anti-CD96 Antibodies

In some embodiments, the anti-CD96 antibodies provided herein have an equilibrium dissociation constant ($K_D$) for binding to CD96 of <100 nM, <10 nM, <1 nM, <0.1 nM, <0.01 nM, or <0.001 nM (ag., $10^{-8}$ M or less, from $10^{-8}$ M to $10^{-13}$ M, ag., from $10^{-9}$ M to $10^{-13}$ M).

It is contemplated that the various anti-CD96 antibodies generated as disclosed herein include antibodies capable of high-affinity binding to hu-CD96, cy-CD96, and both hu-CD96 and cy-CD96. More specifically, in some embodiments, the anti-CD96 antibodies of the present disclosure bind to hu-CD96 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the hu-CD96 polypeptide of SEQ ID NO: 4. In some embodiments, the anti-CD96 antibodies of the present disclosure bind to cy-CD96 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the cy-CD96 polypeptide of SEQ ID NO: 7. In some embodiments, the anti-CD96 antibodies of the present disclosure bind to both hu-CD96 and cy-CD96 with a binding affinity of $1 \times 10^{-8}$ M or less, $1 \times 10^{-9}$ M or less, $1 \times 10^{-10}$ M or less, or $1 \times 10^{-11}$ M or less. In some embodiments, the binding affinity is measured as the equilibrium dissociation constant ($K_D$) for binding to the hu-CD96 polypeptide of SEQ ID NO: 4 and the cy-CD96 polypeptide of SEQ ID NO: 7.

Generally, binding affinity of a ligand to its receptor can be determined using any of a variety of assays and expressed in terms of a variety of quantitative values. Specific CD96 binding assays useful in determining affinity of the antibodies are disclosed in the Examples herein. Additionally, antigen binding assays are known in the art and can be used herein including without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in WO2005/012359), immunoprecipitation assays, fluorescent immunoassays, protein A immunoassays, flow cytometric and fluorescence activated cell sorting (FACS) assays, and the like.

Accordingly, in some embodiments, the binding affinity is expressed as $K_D$ values and reflects intrinsic binding affinity (e.g., with minimized avidity effects). The anti-CD96 antibodies of the present disclosure exhibit strong binding affinities for the hu-CD96 polypeptide of SEQ ID NO: 4, for example, exhibiting $K_D$ values of between 10 nM and 1 μM. Accordingly, Anti-CD96 antibodies of the present disclosure may compete with antibodies having lower affinity for the same or overlapping epitopes of CD96, including epitopes within the D1 domain of hu-CD96 or the D1 domain of cy-CD96. For example, in some embodiments, antibodies of the present disclosure, having a $K_D$ for binding to hu-CD96 of 10 nM or less, compete with NK92.39 for binding of hu-CD96, including where such antibodies compete with NK92.39 for binding of the D1 domain of hu-CD96, including where such binding affinity is determined by surface plasmon resonance (SPR) measurement.

In some embodiments, the anti-CD96 antibodies provided herein decrease, inhibit, and/or fully-block CD96 binding to CD155, and immune regulation and/or immune signaling mediated by CD96 binding to CD155, including the activation of T cells and NK cells mediated by CD226. The ability of the antibodies to inhibit these immune regulatory and immune signaling pathways mediated by CD96 binding to CD155 can be assayed in vitro using known cell-based assays including the primary cell-based assays described in the Examples of the present disclosure.

Accordingly, in some embodiments, the CD96 antibodies of the present disclosure are characterized by one or more of following functional properties based on the ability to decrease, inhibit, and/or fully-block intracellular signaling by CD96-mediated pathways.

In some embodiments the anti-CD96 antibody binds to human CD96 isoform 1 expressed on a cell, such as an HEK293T cell, with an antibody $EC_{50}$ concentration of 5 nM or less, 1 nM or less, or 0.1 nM or less.

In some embodiments the anti-CD96 antibody binds to human CD96 isoform 2 expressed on a cell, such as a CHO cell, with an antibody $EC_{50}$ concentration of 5 nM or less, 1 nM or less, or 0.1 nM or less.

In some embodiments the anti-CD96 antibody binds to human PBMCs with an antibody $EC_{50}$ concentration of 5 nM or less, 1 nM or less, or 0.1 nM or less.

In some embodiments the anti-CD96 antibody binds to cynomolgus monkey PBMCs with an antibody $EC_{50}$ concentration of 5 nM or less, 1 nM or less, or 0.1 nM or less.

In some embodiments the anti-CD96 antibody decreases binding of human CD155 to human CD96 expressed on cells, such as CHO cells, by at least 90%, at least 95%, at least 99%, or 100%. In some embodiments, at a human CD155 concentration of 10 nM, the anti-CD96 anti body has an $IC_{50}$ value for decreasing CD155 binding of 5 nM or less, 1 nM or less, or 0.1 nM or less.

In some embodiments the anti-CD96 antibody increases IFNγ secretion and/or IL-2 secretion from human PBMCs (e.g., NK cells, T-cells) by at least 1.8-fold, at least 1.9-fold, at least 2-fold, at least 2.1-fold, or at least 2.2-fold; and in a further embodiment, this increase in IFNγ secretion is observed where the anti-CD96 has an $EC_{50}$ concentration of 0.3 nM or less, 0.2 nM or less, or 0.1 nM or less.

2. Antibody Fragments

In some embodiments, the anti-CD96 antibody of the present disclosure can be an antibody fragment. Antibody fragments useful with the binding determinants the present disclosure include, but are not limited to, Fab, Fab', Fab'-SH, F(ab')$_2$, Fv, scFv fragments, monovalent, single domain antibody, one-armed or single-arm antibody, and other fragments described herein and known in the art. Accordingly, in some embodiments of the anti-CD96 antibodies of the present disclosure, the antibody is an antibody fragment selected from the group consisting of F(ab')$_2$, Fab', Fab, Fv, single domain antibody (VHH), single-arm antibody, and scFv.

For a review of various antibody fragments, see e.g., Hudson et al. Nat. Med. 9: 129-134 (2003). For a review of scFv fragments, see, e.g., Pluckthun, in The Pharmacology of Monoclonal Antibodies, vol, 113, Rosenburg and Moore eds., (Springer-Verlag, New York), pp, 269-315 (1994); see also WO93/16185; and U.S. Pat. Nos. 5,571,894 and 5,587,458. For a description of Fab and F(ab')$_2$ fragments comprising salvage receptor binding epitope residues and having increased in vivo halt-life, see U.S. Pat. No. 5,869,046. Other monovalent antibody forms are described in, e.g., WO2007/048037, WO2008/145137, WO2008/145138, and WO2007/059782. Monovalent, single-armed antibodies are described, e.g., in WO2005/063816. Diabodies are antibody fragments with two antigen-binding sites that may be bivalent or bispecific (see e.g., EP0404097; WO93/01161; Hudson et al., Nat. Med. 9: 129-134 (2003); and Hollinger et al., Proc. Natl. Acad. Sci. USA 90: 6444-6448 (1993)).

In some embodiments, the antibody fragments are single-domain antibodies which comprise all or a portion of the heavy chain variable domain or all or a portion of the light chain variable domain of an antibody. In some embodiments, a single-domain antibody is a human single-domain antibody (Domantis, Inc., Waltham, MA; see, e.g., U.S. Pat. No. 6,248,516).

Antibody fragments can be made by various techniques, including but not limited to proteolytic digestion of an intact antibody as well as production by recombinant host cells (e.g., E. coli or phage), as described herein.

3. Chimeric and Humanized Antibodies

In some embodiments, the anti-CD96 antibody of the present disclosure can be a chimeric antibody. (See e.g., chimeric antibodies as described in U.S. Pat. No. 4,816,567; and Morrison et al., Proc. Natl. Acad. Sci. USA, 81:6851-6855 (1984)). In one embodiment, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched: antibody in which the class or subclass has been changed from that of the parent antibody. It is contemplated that chimeric antibodies can include antigen-binding fragments thereof.

In some embodiments, the anti-CD96 antibody of the present disclosure is a humanized antibody. Typically, a non-human antibody is humanized to reduce immunogenicity to humans, while retaining the specificity and affinity of the parental non-human antibody. Generally, a humanized antibody comprises one or more variable domains in which HVRs, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived) to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., Nature 332:323-329 (1988); Queen et al., Proc. Nat'l Acad. Sci. USA 86: 10029-10033 (1989); U.S. Pat. Nos. 5,821,337, 7,527,791, 6,982,321, and 7,087,409; Kashmiri et al, Methods 36:25-34 (2005) (describing SDR (a-HVR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol, 151:2623 (1993)); human mature (somatically mutated) framework regions or human germline framework regions (see, e.g., Almagro and Fransson, Front. Biosci. 13: 1619-1633 (2008)); and framework regions derived from screening FR libraries (see, e.g., Baca et al., J. Biol. Chem. 272: 10678-10684 (1997) and Rosok et al., J. Biol. Chem. 271:2261 1-22618 (1996)).

4. Human Antibodies

In some embodiments, the anti-CD96 antibody of the present disclosure can be a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008). Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., XENOMOUSE™ technology in U.S. Pat. Nos. 6,075,181 and 6,150,584; HUMAB® technology in U.S. Pat. No. 5,770,429; K-M MOUSE® technology in U.S. Pat. No. 7,041,870; and VELOCIMOUSE® technology in U.S. Pat. Appl. Pub. No. US 2007/0061900). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. See, e.g., Kozbor J. Immunol, 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991). Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

In some embodiments, the anti-CD96 antibody of the present disclosure may be isolated by screening combinatorial libraries for antibodies with the desired activity or activities. For example, a variety of methods are known in the art for generating phage display libraries and screening such libraries for antibodies possessing the desired binding characteristics. The use of phage display for preparation of affinity matured variants of the humanized version of the anti-CD96 antibody of the present disclosure are described in the Examples disclosed herein. Other methods for producing such library-derived antibodies can be found in e.g; Hoogenboom et al., Methods in Molecular Biology 178: 1-37 (O'Brien et al., ed., Human Press, Totowa, NJ, 2001); McCafferty et al., Nature 348:552-554; Clackson et al., Nature 352: 624-628 (1991); Marks et al., J. Mol. Biol. 222: 581-597 (1992); Marks and Bradbury, m Methods in Molecular Biology 248: 161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 1 19-132(2004).

6. Multispecific Antibodies

In some embodiments, the anti-CD96 antibody of the present disclosure is a multispecific antibody, e.g., a bispecific antibody. In some embodiments, the multispecific antibody is a monoclonal antibody having at least two different binding sites, each with a binding specificity for a different antigen, at least one of which specifically binds CD96.

In some embodiments, the multispecific antibody is a bispecific antibody comprising a specificity for CD96 and a specificity for another antigen that mediates immune regulation, immune signaling, and/or is expressed on a cancer or tumor cell. In some embodiments of the bispecific antibody, the other specificity is for an antigen that is an immune checkpoint molecule selected from PD1, TIGIT, LAG3, PVRIG, KIR, TIM-3, CRTAM, CTLA-4, BTLA, CD244, CD160, LIGHT, GITR, 4-1 BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA. In some embodiments, the anti-CD96 bispecific antibody, the other antigen for which the antibody has specificity is selected from PD1, TIGIT, LAG3, PVRIG, KIR, TIM-3, and CRTAM.

In some embodiments, at least one of binding sites specifically binds a cytotoxic agent. In exemplary embodiments, an anti-CD96 antibody of the present disclosure is a bispecific antibody and can be used to localize a cytotoxic agent to cells which express CD96.

Techniques for making multispecific antibodies include, but are not limited to, recombinant co-expression of two immunoglobulin heavy chain-light chain pairs having different specificities (see e.g., Milstein and Cuello, Nature 305: 537 (1983), WO 93/08829, and Traunecker et al., EMBOJ. 10: 3655 (1991)). "Knob-in-hole" engineering can also be used to generate bispecific antibodies useful with the anti-CD96 antibodies of the present disclosure. Techniques for knob-in-hole engineering are known in the art and described in e.g., U.S. Pat. No. 5,731,168.

Multispecific antibodies can also be made by engineering "electrostatic steering" effects that favor formation of Fc-heterodimeric antibody molecules rather than homodimers (WO 2009/089004A1); cross-linking two or more antibodies or fragments (see, e.g., U.S. Pat. No. 4,676,980, and Brennan et al., Science, 229: 81 (1985)); using leucine zippers to produce bispecific antibodies (see, e.g., Kostelny et al., J. Immunol, 148(5): 1547-1553 (1992)); using "diabody" technology for making bispecific antibody fragments (see, e.g., Hollinger et al., Proc. Natl. Acad. Sci. USA, 90; 6444-6448 (1993)); using single-chain Fv (scFv) dimers (see, e.g. Gruber et al., J. Immunol, 152:5368 (1994)); or tri-specific antibodies (see e.g., Tutt et al., J. Immunol. 147:60 (1991).

7. Antibody Variants

In some embodiments, variants of the anti-CD96 antibody of the present disclosure are also contemplated. For example, antibodies with improved binding affinity and/or other biological properties of the antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristic of CD96 antigen binding.

A. Substitution, Insertion and Deletion Variants

In some embodiments, anti-CD96 antibody variants having one or more amino acid substitutions in addition to those described herein are provided. Sites for mutagenesis can include the HVRs and FRs. Typical "conservative" amino acid substitutions and/or substitutions based on common side-chain class or properties are well-known in the art and can be used in the embodiments of the present disclosure.

The present disclosure also contemplates variants based on non-conservative amino acid substitutions in which a member of one of amino acid side chain class is exchanged for an amino acid from another class.

Amino acid side chains are typically grouped according to the following classes or common properties: (1) hydrophobic: Met, Ala, Val, Leu, Ile, Norleucine; (2) neutral hydrophilic: Cys, Ser, Thr, Asn, Gln; (3) acidic: Asp, Glu; (4) basic: His, Lys, Arg; (5) chain orientation influencing: Gly, Pro; and (6) aromatic: Trp, Tyr, Phe.

Techniques are well-known in the art for amino acid substitution into an antibody and subsequent screening for desired function, e.g., retained/improved antigen binding, decreased immunogenicity, or improved ADCC or CDC.

Amino acid substitution variants can include substituting one or more hypervariable region residues of a parent antibody (e.g., a humanized or human antibody). Generally, the resulting variant(s) selected for further study will have modifications in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described in the Examples herein. Briefly, one or more HVR residues are mutated and the variant antibodies displayed on phage and screened for a particular biological activity (e.g., binding affinity).

A useful method for identifying residues or regions of an antibody that may be targeted for mutagenesis is "alanine scanning mutagenesis" (see e.g., Cunningham and Wells (1989) Science, 244: 1081-1085). In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen can be determined. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Substitutions can be made in HVRs to improve antibody affinity. Such alterations may be made in "hotspots," i.e., residues encoded by codons that undergo mutation at high frequency during the somatic maturation process (see, e.g., Chowdhury, Methods Mol. Biol. 207: 179-196 (2008)) with the resulting variant $V_H$ or $V_L$ being tested for binding affinity. In one embodiment, affinity maturation can be carried out by constructing and reselecting from secondary libraries (see e.g., in Hoogenboom et al., Methods in Molecular Biology 178: 1-37 (O'Brien et al., ed., Human Press, Totowa, NJ, (2001).) Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots." In some embodiments of the variant $V_H$ and $V_L$ sequences provided above, each HVR either is unaltered, or contains no more than one, two or three amino acid substitutions.

B. Glycosylation Variants

In some embodiments, the anti-CD96 antibody of the present disclosure is altered to increase or decrease the extent to which the antibody is glycosylated. Addition or deletion of glycosylation sites to an antibody can be carried out by altering the amino acid sequence such that one or more glycosylation sites is created or removed.

In embodiments where the antibody comprises an Fc region, the carbohydrate attached to the Fc region can be altered. Typically, native antibodies produced by mammalian cells comprise a branched, biantennary oligosaccharide attached by an N-linkage to the asparagine at about position 297 ("N297") of the CH2 domain of the Fc region (see, e.g., Wright et al, TIBTECH 15:26-32 (1997)). The oligosaccharide may include various carbohydrates, such as mannose, N-acetyl glucosamine (GlcNAc), galactose, and sialic acid, as well as, a fucose attached to a GlcNAc in the "stem" of the bi-antennary oligosaccharide structure. In some embodiments, the modifications of the oligosaccharide of an Fc region of an antibody can create a variant with certain improved properties.

In some embodiments, the anti-CD96 antibody of the present disclosure can be a variant of a parent antibody, wherein the variant comprises a carbohydrate structure that lacks fucose attached (directly or indirectly) to an Fc region. For example, the amount of fucose in such antibody may be from about 1% to about 80%, from about 1% to about 65%, from about 5% to about 65%, or from about 20% to about 40%. The amount of fucose can be determined by calculating the average amount of fucose within the sugar chain at N297, relative to the sum of all glyco-structures attached to Asn 297 (e.g., complex; hybrid and high mannose structures) as measured by MALDI-TOF mass spectrometry (see e.g., WO 2008/077546), N297 refers to the asparagine residue located at about position 297 in the Fc region (Eu numbering of Fc region residues); however, N297 may also be located about ±3 amino acids upstream or downstream of position 297, i.e., between positions 294 and 300, due to minor sequence variations in antibodies.

In some embodiments, the fucosylation variants can have improved ADCC function. See, e.g., US Patent Publication Nos. US 2003/0157108, or US 2004/0093621. Examples of "defucosylated" or "fucose-deficient" antibodies and associated methods for preparing them are disclosed in e.g., US2003/0157108; US2003/0115614; US2002/0164328; US2004/0093621; US2004/0132140; US2004/0110704; US2004/0110282; US2004/0109865; WO2000/61739; WO2001/29246; WO2003/085119; WO2003/084570; WO2005/035586; WO2005/035778; WO2005/053742;

WO2002/031140; Okazaki et al. J. Mol. Biol. 336: 1239-1249 (2004); Yamane-Ohnuki et al. Biotech. Bioeng. 87: 614 (2004).

Cell lines useful for producing defucosylated antibodies include Led 3 CHO cells deficient in protein fucosylation (see e.g., Ripka et al. Arch. Biochem. Biophys. 249:533-545 (1986); US200310157108, and WO2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

C. Fc Region Variants

In some embodiments, an anti-CD96 antibody of the present disclosure can comprise one or more amino acid modifications in the Fc region (i.e., an Fc region variant). The Fc region variant may comprise a human Fc region sequence (e.g., a human IgG1, IgG2, IgG3, or IgG4 Fc region) comprising an amino acid substitution at one or more amino acid residue positions. A wide range of Fc region variants known in the art that are useful with the anti-CD96 antibodies of the present disclosure are described below.

In some embodiments, the anti-CD96 antibody is an Fc region variant which has altered effector function. In some embodiments, the antibody with altered effector function possesses some (but not all of) the effector functions, decreased effector function, or none of the effector functions (e.g., effectorless) of the parent antibody. Effectorless Fc region variants are more desirable for certain applications where effector function (such as ADCC) is unnecessary or deleterious, and/or in vivo half-life of the antibody is important.

Fc region variant antibodies with reduced effector function, or which are effectorless, can include an amino acid substitution at one or more of the following Fc region positions: 238, 265, 269, 270, 297, 327 and 329. (see, e.g., U.S. Pat. No. 6,737,056). Such Fc region variants can include amino acid substitutions at two or more of positions 265, 269, 270, 297 and 327. Such Fc region variants can also include substitutions of both residues 265 and 297 to alanine (see e.g., U.S. Pat. No. 7,332,581). As disclosed in the Examples and elsewhere herein, in some embodiments, the anti-CD96 antibodies of the present disclosure are effectorless Fc region variants. In some embodiments, the effectorless Fc region variants of the anti-CD96 antibodies comprise the amino acid substitution N297G.

Fc region variants having improved or diminished binding to FcRs are disclosed in e.g., U.S. Pat. No. 6,737,056; WO 2004/056312; and Shields et al., J. Biol. Chem. 9(2): 6591-6604 (2001). Fc region variants having improved ADCC can comprise one or more amino acid substitutions at e.g., positions 298, 333, and/or 334 of the Fc region (based on EU numbering). Fc region variants having altered (i.e., either improved or diminished) C1q binding and/or Complement Dependent Cytotoxicity (CDC), as described in e.g., U.S. Pat. No. 6,194,551, WO99/51642, and Idusogie et al., J. Immunol. 164: 4178-4184 (2000). Fc region variants with increased half-lives and improved binding to the neonatal Fc receptor (FcRn) are disclosed in e.g., US2005/0014934A1 (Hinton et al.). Such Fc region variants comprise amino acid substitutions at one or more of positions: 238, 256, 265, 272, 286, 303, 305, 307, 311, 312, 317, 340, 356, 360, 362, 376, 378, 380, 382, 413, 424, and 434. Other Fc region variants with increased half-lives include the set of YTE mutations at positions 252, 254, and 256 (i.e., M252Y/S254T/T256E) described in e.g., U.S. Pat. No. 7,658,921B2 (Dall'Acqua et al.). Other examples of Fc region variants can be found in e.g., U.S. Pat. Nos. 5,648,260 and 5,624,821; and WO94/29351.

Generally, in vitro and/or in vivo cytotoxicity assays can be carried out to confirm the reduction/depletion of CDC and/or ADCC activities in an Fc region variant. For example, Fc receptor (FcR) binding assays can be conducted to ensure that the antibody lacks FcγR binding (hence likely lacking ADCC activity) but retains FcRn binding ability. The primary cells for mediating ADCC, NK cells express FcγRIII only, whereas monocytes express FcγRI, FcγRII, and FcγRIII. Non-limiting examples of in vitro assays to assess ADCC activity of a molecule of interest is described in U.S. Pat. No. 5,500,362 (see, e.g. Hellstrom, et al., Proc. Nat'l Acad. Sci. USA 83:7059-7063 (1986)) and Hellstrom, et al., Proc. Nat'l Acad. Sci. USA 82: 1499-1502 (1985); 5,821,337 (see Bruggemann, M. et al., J. Exp. Med. 166: 1351-1361 (1987)). Alternatively, non-radioactive assay methods may be employed (see, for example, ACTI nonradioactive cytotoxicity assay for flow cytometry (CellTechnology, Inc. Mountain View, CA; and CytoTox96® non-radioactive cytotoxicity assay (Promega, Madison, WI), Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity, See, e.g., C1q and C3c binding ELISA in WO2006/029879 and WO2005/100402. To assess complement activation, a CDC assay may be performed (see, e.g., Gazzano-Santoro et al., J. Immunol. Methods 202: 163 (1996); Cragg, M. S. et al., Blood 101: 1045-1052 (2003); and Cragg, M. S. and M. J. Glennie, SW 103:2738-2743 (2004)). FcRn binding and in vivo clearance/half-life determinations can be performed using methods known in the art (see, e.g., Petkova, et al., Intl. Immunol. 18(12): 1759-1769 (2006)).

D. Cysteine Engineered Antibody Variants

In some embodiments, it is contemplated that the anti-CD96 antibody described herein can be substituted at specific non-HVR positions with cysteine residues so as to create reactive thiol groups. Such engineered "thioMAbs" can be used to conjugate the antibody to e.g., drug moieties or linker-drug moieties and thereby create immunoconjugates, as described elsewhere herein. Cysteine engineered antibodies can be generated as described in e.g., U.S. Pat. No. 7,521,541. In some embodiments, any one or more of the following antibody residues can be substituted with cysteine: V205 (Kabat numbering) of the light chain; A118 (EU numbering) of the heavy chain; and 5400 (EU numbering) of the heavy chain Fc region.

E. Antibody Derivatives

In some embodiments, the anti-CD96 antibody of the present disclosure may be further modified (i.e., derivatized) with non-proteinaceous moieties. Non-proteinaceous moieties suitable for derivatization of the antibody include, but are not limited to, water soluble polymers, such as: polyethylene glycol (PEG), copolymers of ethylene glycol and propylene glycol, carboxy-methylcellulose, dextran, polyvinyl alcohol, polyvinyl pyrrolidone, poly-1, 3-dioxolane, poly-1, 3, 6-trioxane, ethylene/maleic anhydride copolymer, poly-amino acid homo-polymers or random co-polymers, and dextran or poly(n-vinyl pyrrolidone)polyethylene glycol, propropylene glycol homo-polymers, polypropylene oxide/ethylene oxide co-polymers, polyoxy-ethylated polyols (e.g., glycerol), polyvinyl alcohol, and mixtures thereof. In some embodiments, modification of the antibody can be carried out using methoxy-polyethylene glycol propionaldehyde. The polymers may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody, e.g., whether the antibody derivative will be used in a therapy under defined conditions.

8. Immunoconjugates

In some embodiments, the anti-CD96 antibody of the present disclosure can also be an immunoconjugate, wherein the immunoconjugate comprises an anti-CD96 antibody conjugated to one or more cytotoxic agents. Suitable cytotoxic agents contemplated by the present disclosure include chemotherapeutic agents, drugs, growth inhibitory agents, toxins (e.g., protein toxins, enzymatically active toxins of bacterial, fungal, plant, or animal origin, or fragments thereof), or radioactive isotopes.

In some embodiments, the immunoconjugate is an antibody-drug conjugate (ADC) in which an anti-CD96 antibody, as described herein, is conjugated to one or more drugs.

In some embodiments, an immunoconjugate of the present disclosure comprises an anti-CD96 antibody as described herein conjugated to a drug or therapeutic agent for the treatment of a CD96-mediated disease or condition.

In some embodiments, an anti-CD96 antibody as described herein can be conjugated to an enzymatically active toxin or a fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate of the present disclosure comprises an anti-CD96 antibody as described herein conjugated to a radioactive isotope (i.e., a radioconjugate). A variety of radioactive isotopes are available for the production of such radioconjugates. Examples include $^{211}At$, $^{131}I$, $^{125}I$, $^{90}Y$, $^{186}Re$, $^{188}Re$, $^{153}Sm$, $^{212}Bi$, $^{32}P$, $^{212}Pb$, and radioactive isotopes of Lu. In some embodiments, the immunoconjugate may comprise a radioisotope for scintigraphic detection, or a spin label for NMR detection or MR. Suitable radioisotopes or spin labels can include, as $^{123}I$, $^{131}I$, $^{111}In$, $^{13}C$, $^{19}F$, $^{15}N$, $^{17}O$, various isotopes of Gd, Mn, and Fe.

Immunoconjugates of an anti-CD96 antibody and a cytotoxic agent, can be made using a variety of well-known bifunctional reagents and chemistries suitable for conjugating to proteins. Such reagents include but are not limited to: N-succinimidyl-3-(2-pyridyldithio) propionate (SPDP), succinimidyl-4-(N-maleimidoethyl) cyclohexane-1-carboxylate (SMCC), iminothiolane (IT), bifunctional derivatives of imidoesters (e.g., dimethyl adipimidate HQ), active esters (e.g., disuccinimidyl suberate), aldehydes (e.g., glutaraldehyde), bis-azido compounds (e.g., bis-(p-azidobenzoyl)-hexanediamine), bis-diazonium derivatives (e.g., bis-(p-diazoniumbenzoyl)-ethylenediamine), diisocyanates (e.g., toluene-2,6-diisocyanate), and bis-active fluorine compounds (e.g., 1,5-difluoro-2,4-dinitrobenzene).

Reagents for preparing immunoconjugates of the present disclosure can also include commercially available "cross-linking" reagents such as: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) (see e.g., Pierce Biotechnology, Inc., Rockford, IL., U.S.A).

9. Synthetic Antibodies

In some embodiments, the anti-CD96 antibody of the present disclosure can be a synthetic antibody comprising a set of CDRs or HVRs from an anti-CD96 immunoglobulin (e.g., HVR-L1, etc.) grafted onto a scaffold or framework other than an immunoglobulin scaffold or framework, such as an alternative protein scaffold, or an artificial polymer scaffold.

Exemplary alternative protein scaffolds contemplated for preparation of synthetic antibodies of the present disclosure can include, but are not limited to: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain Src homology domain 3, PDL domains, TEM-1 beta-lactamase, thioredoxin, staphylococcal nuclease, PHD-fmger domains, CL-2, BPTI, APPI, HPSTI, ecotin, LACI-D1, LDTI, MTI-II, scorpion toxins, insect defensin-A peptide, EETI-II, Min-23, CBD, PBP, cytochrome b-562, Ldl receptor domains, gamma-crystallin, ubiquitin, transferrin, and/or C-type lectin-like domains.

Exemplary artificial polymer (non-protein) scaffolds useful for synthetic antibodies are described in e.g., Fiedler et al., (2014) "Non-Antibody Scaffolds as Alternative Therapeutic Agents," in Handbook of Therapeutic Antibodies (eds S. Dübel and J. M. Reichert), Wiley-VCH Verlag GmbH & Co.; Gebauer et al., Curr. ©pin. Chem. Biol, 13:245-255 (2009); Binz et al, Nat. Biotech., 23(10): 1257-1268 (2005).

IV. Recombinant Methods and Compositions

The anti-CD96 antibody of the present disclosure can be produced using recombinant methods and materials well-known in the art of antibody production. In some embodiments, the present disclosure provides an isolated nucleic acid encoding an anti-CD96 antibody. The nucleic acid can encode an amino acid sequence comprising the $V_L$ and/or an amino acid sequence comprising the $V_H$ of the antibody (e.g., the light and/or heavy chains of the antibody). In some embodiments, one or more vectors (e.g., expression vectors) comprising nucleic acid sequences encoding an anti-CD96 antibody of the present disclosure are provided. In some embodiments, a host cell comprising nucleic acid sequences encoding an anti-CD96 antibody of the present disclosure are provided. In one embodiment, the host cell has been transformed with a vector comprising a nucleic acid that encodes an amino acid sequence comprising the $V_L$ of the antibody and an amino acid sequence comprising the $V_H$ of the antibody. In another embodiment, the host cell has been transformed with a first vector comprising a nucleic acid that encodes an amino acid sequence comprising the $V_L$ of the antibody and a second vector comprising a nucleic acid that encodes an amino acid sequence comprising the $V_H$ of the antibody.

In some embodiments of the recombinant methods, the host cell used is a eukaryotic cell, such as a Chinese Hamster Ovary (CHO) cell, or a lymphoid cell (e.g., Y0, NS0, Sp20). In one embodiment, a method of making an anti-CD96 antibody is provided, wherein the method comprises culturing a host cell comprising a nucleic acid encoding the antibody, as provided above, under conditions suitable for expression of the antibody, and optionally recovering the antibody from the host cell (or host cell culture medium).

Briefly, recombinant production of an anti-CD96 antibody is carried out by isolating a nucleic acid encoding an antibody (e.g., as described herein) and inserting this nucleic acid into one or more vectors for further cloning and/or expression in a host cell. Such nucleic acids are readily isolated and sequenced using conventional procedures well-known in the art (e.g., by using oligonucleotide probes that are capable of binding specifically to genes encoding the heavy and light chains of the desired antibody). Suitable host cells and culturing methods for cloning or expressing the antibody-encoding vectors are well-known in the art and include prokaryotic or eukaryotic cells. Typically, after expression, the antibody may be isolated from cell paste in a soluble fraction and further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see e.g., Gerngross, Nat. Biotech. 22: 1409-1414 (2004), and Li et al., Nat. Biotech, 24:210-215 (2006)).

Suitable host cells for the expression of glycosylated anti-C©96 antibodies of the present disclosure can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (see, e.g., U.S. Pat. Nos. 5,959,177, 6,040,498, 6,420,548, and 7,125,978

Examples of mammalian host cell lines useful for the production of the anti-CD96 antibodies of the present disclosure include Chinese hamster ovary (CHO) cells, including DHFR-CHO cells (see e.g., Urlaub et al., Proc. Natl. Acad. Sci. USA 77:4216 (1980)); myeloma cell lines such as Y0, NS0 and Sp2/0; monkey kidney CVI line transformed by SV40 (COS-7); human embryonic kidney line (293 or 293 cells as described, e.g., in Graham et al., J. Gen Virol. 36:59 (1977)); baby hamster kidney cells (BHK); mouse Sertoli cells (TM4 cells as described, e.g., in Mather, Biol. Reprod. 23:243-251 (1980)); monkey kidney cells (CVI); African green monkey kidney cells (VERO-76); human cervical carcinoma cells (HFLA); canine kidney cells (MDCK; buffalo rat liver cells (BRL 3A); human lung cells (W138); human liver cells (Hep G2); mouse mammary tumor (MMT 060562); TR1 cells (see e.g., in Mather et al., Annals N Y. Acad. Sci. 383:44-68 (1982) and U.S. Pat. No. 6,235,498); Medical Research Council 5 (MRC 5) cells (such as e.g., those available from ATCC and also referred to as CCL-171); and Foreskin 4 (FS-4) cells (see e.g., in Vilcek et al. Ann. N. Y. Acad. Sci, 284:703-710 (1977), Gardner & Vilcek. J. Gen. Virol. 44:161-168 (1979), and Pang et al. Proc. Natl. Acad. Sci, U.S.A, 77:5341-5345 (1980)). For a general review of useful mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

V. Pharmaceutical Compositions and Formulations of Anti-CD96 Antibodies

The present disclosure also provides pharmaceutical compositions and pharmaceutical formulations comprising an anti-CD96 antibody. In some embodiments, the present disclosure provides a pharmaceutical formulation comprising an anti-CD96 antibody as described herein and a pharmaceutically acceptable carrier. In some embodiments, the anti-CD96 antibody is the sole active agent of the pharmaceutical composition. Such pharmaceutical formulations can be prepared by mixing an anti-CD96 antibody, having the desired degree of purity, with one or more pharmaceutically acceptable carriers. Typically, such antibody formulations can be prepared as an aqueous solution (see e.g., U.S. Pat. No. 6,171,586, and WO2006/044908) or as a lyophilized formulation (see e.g., U.S. Pat. No. 6,267,958).

Pharmaceutically acceptable carriers are generally non-toxic to recipients at the dosages and concentrations employed. A wide range of such pharmaceutically acceptable carriers are well-known in the art (see e.g., Remington's Pharmaceutical Sciences 16th edition, Osol, A, Ed. (1980)). Exemplary pharmaceutically acceptable carriers useful in the formulations of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Pharmaceutically acceptable carriers useful in the formulations of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

It is also contemplated that the formulations disclosed herein may contain active ingredients in addition to the anti-CD96, as necessary for the particular indication being treated in the subject to whom the formulation is administered. Preferably, any additional active ingredient has activity complementary to that of the anti-CD96 antibody activity and the activities do not adversely affect each other.

In some embodiments, the pharmaceutical composition comprises the anti-CD96 antibody and an additional active agent such as, but not limited to, a checkpoint inhibitor. Checkpoint inhibitors useful in such embodiments include, but are not limited to, a second antibody comprising a specificity for an antigen that is an immune checkpoint molecule. In some embodiments, the second antibody comprises a specificity for an immune checkpoint molecule selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA.

In at least one embodiment, the pharmaceutical composition comprises an anti-CD96 antibody and an additional active agent, wherein the additional active agent is an antibody comprising a specificity for an immune checkpoint molecule selected from PD1, TIGIT, LAG3, PVRIG, KIR, TIM-3, and CRTAM.

In at least one embodiment, the pharmaceutical composition comprising an anti-CD96 antibody and an additional active agent, wherein the additional active agent is an antibody comprising a specificity for the immune checkpoint molecule PD1. Exemplary antibodies comprising a specificity for PD1 that are useful in the pharmaceutical composition embodiments disclosed herein include, but are not limited to, dostarlimab, pembrolizumab, nivolumab, and pidilizumab.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, the formulation can be a sustained-release preparation of the antibody and/or other active ingredients. Suitable examples of sustained-release preparations include semipermeable matrices of solid hydrophobic polymers containing the antibody, which matrices are in the form of shaped articles, e.g. films, or microcapsules.

Typically, the formulations of the present disclosure to be administered to a subject are sterile. Sterile formulations may be readily prepared using well-known techniques, e.g., by filtration through sterile filtration membranes.

IV. Uses and Methods of Treatment

It is contemplated that any of the compositions or formulations comprising an anti-CD96 antibody of the present disclosure can be used for any methods or uses, such as in therapeutic methods that utilize their ability to specifically bind to CD96 and thereby inhibit, decrease, and/or fully block the function of CD96 as a cell surface receptor involved in immune regulation or signaling, particularly the function of CD96 in negatively regulating (or inhibiting) T cell or NK cell activation.

The cell surface receptor CD155 is the natural target antigen of CD96. Expression of CD155 on cells is understood to be induced by stress, and CD155 levels are affect the activation, by CD226, or the inhibition, by CD96 or TIGIT, of lymphocytes in mounting an immune response (e.g., activation of T cells and/or NK cells). Accordingly, it is contemplated that the anti-CD96 antibodies can be used in therapeutic methods that involve inhibiting, decreasing, and/or fully blocking the specific binding of CD96 to CD155.

CD226, another cell surface receptor in Ig superfamily which has a structure closely related to CD96, also binds CD155. CD226, however, functions to activate T cells or NK cells. Thus, without intending to be limited by any specific mechanism, the ability of the anti-CD96 antibodies of the present disclosure to block CD96 binding to CD155, may allow increased CD155 binding to CD226, which further results in increased CD226 activation of T cells and NK cells. In addition, without being bound by theory, a secondary affinity for CD226 of an anti-CD96 antibody may cause the antibody to act as an enhancer of CD226-triggered cellular activity, preventing CD226 from interacting with TIGIT, increase the effective local concentration of the antibody with respect to cells expressing both CD96 and CD226, or some combination thereof. Accordingly, it is further contemplated that the anti-CD96 antibodies of the present disclosure can be used in any therapeutic methods that utilize increased activation of T cells and NK cells.

There are a range of diseases, disorders, and conditions that can potentially be treated by inhibiting, decreasing, and/or fully blocking the immune regulatory and/or immune signaling activity of CD96, particularly, the immune inhibitory effect of CD96 on lymphocyte activation. The range of diseases, disorders, and conditions include, but are not limited to, cancers and viral infections.

For example, agents that block the immune inhibitory effects of certain proteins (e.g., PD1, TIGIT) are currently under development to treat a wide range of cancers including adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer. Accordingly, it is contemplated that any of the compositions or formulations comprising an anti-CD96 antibody of the present disclosure can be used for a method or use for the treatment of any of the above-listed cancers. In some embodiments, the cancer is selected from lung cancer, skin cancer (e.g., melanoma), pancreatic cancer, endometrial cancer, prostate cancer, colorectal cancer, ovarian cancer, and bladder cancer. In some embodiments, the present disclosure provides a method of treating cancer in a subject, the method comprising administering to the subject in need thereof a therapeutically effective amount of an anti-CD96 antibody of the present disclosure or administering to a subject a therapeutically effective amount of a pharmaceutical composition comprising an anti-CD96 antibody of the present disclosure and a pharmaceutically acceptable carrier.

Accordingly, in some embodiments, the present disclosure provides a method of treating a pathogenic infection in a subject, the method comprising administering to the subject in need thereof a therapeutically effective amount of an anti-CD96 antibody of the present disclosure or administering to a subject a therapeutically effective amount of a pharmaceutical composition comprising an anti-CD96 antibody of the present disclosure and a pharmaceutically acceptable carrier. It is contemplated that any of the compositions or formulations comprising an anti-CD96 antibody of the present disclosure can be used for such a method for the treatment of a pathogenic infection, including, but not limited to an infection by one or more of the following clinically relevant pathogens: *Acinetobacter baumannii, Acinetobacter lwoffii, Acinetobacter* spp. (incl. MDR), *Actinomycetes, Adenovirus, Aeromonas* spp., *Alcaligenes faecalis, Alcaligenes* spp./*Achromobacter* spp., *Alcaligenes xylosoxidans* (incl. ESBL/MRGN), Arbovirus, *Aspergillus* spp., *Astrovirus, Bacillus anthracis, Bacillus cereus, Bacillus subtilis, Bacteroides fragilis, Bartonella quintana, Bordetella pertussis, Borrelia burgdorferi, Borrelia recurrentis, Brevundimonas diminuta, Brevundimonas vesicularis, Brucella* spp., *Burkholderia cepacia* (incl. MDR), *Burkholderia mallei, Burkholderia pseudomallei, Campylobacter jejuni/coli, Candida albicans, Candida krusei, Candida parapsilosis,* Chikungunya virus (CHIKV), *Chlamydia pneumoniae, Chlamydia psittaci, Chlamydia trachomatis, Citrobacter* spp., *Clostridium botulinum, Clostridium difficile, Clostridium perfringens, Clostridium tetani,* Coronavirus (incl. SARS- and MERS-CoV), *Corynebacterium diphtheriae, Corynebacterium pseudotuberculosis, Corynebacterium* spp., *Corynebacterium ulcerans, Coxiella burnetii,* Coxsackievirus, Crimean-Congo haemorrhagic fever virus, *Cryptococcus neoformans, Cryptosporidium hominis, Cryptosporidium parvum, Cyclospora cayetanensis,* Cytomegalovirus (CMV), Dengue virus, Ebola virus, Echovirus, *Entamoeba histolytica, Enterobacter aerogenes, Enterobacter cloacae* (incl. ESBL/MRGN), *Enterococcus faecalis* (incl. VRE), *Enterococcus faecium* (incl. VRE), *Enterococcus hirae, Epidermophyton* spp., Epstein-Barr virus (EBV), *Escherichia coli* (incl. EHEC, EPEC, ETEC, EIEC, EAEC, ESBL/MRGN, DAEC), Foot-and-mouth disease virus (FMDV), *Francisella tularensis, Giardia lamblia, Haemophilus influenzae,* Hantavirus, *Helicobacter pylori,* Helminths (Worms), Hepatitis A virus (HAV), Hepatitis B virus (HBV), Hepatitis C virus (HCV), Hepatitis D virus, Hepatitis E virus, Herpes simplex virus (HSV), *Histoplasma capsulatum,* Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, *Klebsiella granulomatis, Klebsiella oxytoca* (incl. ESBL/MRGN), *Klebsiella pneumoniae* MDR (incl. ESBL/MRGN), Lassa virus, *Leclercia adecarboxylata, Legionella pneumophila, Leishmania* spp., *Leptospira interrogans, Leuconostoc pseudomesenteroides, Listeria monocytogenes,* Marburg virus, Measles virus, *Micrococcus luteus, Microsporum* spp., Molluscipoxvirus, *Morganella* spp., Mumps virus, *Mycobacterium chimaera* Myco, *Mycobacterium leprae* Myco, *Mycobacterium tuberculosis* (incl. MDR), *Mycoplasma genitalium, Mycoplasma pneumoniae, Neisseria meningitidis, Neisseria gonorrhoeae,* Norovirus, *Orientia tsutsugamushi, Pantoea agglomerans,* Parainfluenza virus, Parvovirus, *Pediculus humanus capitis, Pediculus humanus corporis, Plasmodium* spp., *Pneumocystis jiroveci,* Poliovirus, Polyomavirus, *Proteus mirabilis* (incl. ESBL/MRGN), *Proteus vulgaris, Providencia rettgeri, Providencia stuartii, Pseudomonas aeruginosa, Pseudomonas* spp., Rabies virus, *Ralstonia* spp., Respiratory syncytial virus (RSV), Rhinovirus, *Rickettsia prowazekii, Rickettsia typhi, Roseomonas gilardii,* Rotavirus, Rubella virus, *Salmonella enteritidis, Salmonella paratyphi, Salmonella* spp., *Salmonella typhimurium, Sarcoptes scabiei* (Itch mite), Sapovirus, *Serratia marcescens* (incl. ESBL/MRGN), *Shigella sonnei, Sphingomonas species, Staphylococcus aureus* (incl. MRSA, VRSA), *Staphylococcus capitis, Staphylococcus epidermidis* (incl. MRSE), *Staphylococcus haemolyticus, Staphylococcus hominis, Staphylococcus lugdunensis, Staphylococcus saprophyticus, Stenotrophomonas maltophilia, Streptococcus pneumoniae, Streptococcus pyogenes* (incl. PRSP), *Streptococcus* spp., TBE virus, *Toxoplasma gondii, Treponema pallidum, Trichinella spiralis, Trichomonas vaginalis, Trichophyton* spp., *Trichosporon* spp., *Trypanosoma brucei* gambiense, *Trypanosoma brucei rhodesiense, Trypanosoma cruzi,* Vaccinia virus, Varicella zoster virus (VSV), Variola virus, *Vibrio cholerae,* West Nile virus (WNV), Yellow fever virus, *Yersinia enterocolitica, Yersinia pestis, Yersinia pseudotuberculosis,* Zika virus, and the like.

In at least one embodiment, a composition or formulation comprising an anti-CD96 antibody of the present disclosure can be used for a method or use for the treatment of a viral infection, wherein the virus is selected from Adenovirus, Arbovirus, Astrovirus, Chikungunya virus (CHIKV), Coronavirus (incl. SARS- and MERS-CoV), Crimean-Congo haemorrhagic fever virus, Cytomegalovirus (CMV), Dengue virus, Ebola virus, Echovirus, Epstein-Barr virus (EBV), Foot-and-mouth disease virus (FMDV), Hantavirus, Hepatitis A virus (HAV), Hepatitis B virus (HBV), Hepatitis C virus (HCV), Hepatitis D virus, Hepatitis E virus, Herpes simplex virus (HSV), Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, Marburg virus, Measles virus, Mumps virus. Norovirus, Parainfluenza virus, Parvovirus, Poliovirus, Polyomavirus, Rabies virus, Respiratory syncytial virus (RSV), Rhinovirus, Rotavirus, Rubella virus, Sapovirus, TBE virus, Vaccinia virus, Varicella zoster virus (VSV), Variola virus, West Nile virus (WNV), Yellow fever virus, and Zika virus.

As disclosed herein, including in the Examples below, the anti-CD96 antibodies of the present disclosure have the ability to decrease, inhibit, and/or block CD96 binding to CD155, and thereby alter CD155 interaction with the immune signaling pathways mediated by CD226 and TIGIT. Accordingly, in some embodiments, the present disclosure provides a method of treating a CD96-mediated disease or condition in a subject, the method comprising administering to the subject a therapeutically effective amount of an anti-CD96 antibody of the present disclosure or administering to a subject in need thereof a therapeutically effective amount of a pharmaceutical composition comprising an anti-CD96 antibody of the present disclosure and a pharmaceutically acceptable carrier. Similarly, in some embodiments, the present disclosure provides a method of treating a disease mediated by binding to CD155 expressed on cells in a subject, the method comprising administering to the subject, the method comprising administering to the subject a therapeutically effective amount of an anti-CD96 antibody of the present disclosure or administering to a subject in need thereof a therapeutically effective amount of a pharmaceutical composition comprising an anti-CD96 antibody of the present disclosure and a pharmaceutically acceptable carrier.

Administration of the anti-CD96 antibody, composition, or pharmaceutical formulation in accordance with the method of treatment provides an antibody-induced therapeutic effect that protects the subject from and/or treats the progression of a CD96-mediated disease in a subject. In some embodiments, the method of treatment can further comprise administration of one or more additional therapeutic agents or treatments known to those of skill in the art to prevent and/or treat the CD96-mediated disease or condition. Such methods comprising administration of one or more additional agents can encompass combined administration (where two or more therapeutic agents are included in the same or separate formulations), and separate administration, in which case, administration of the antibody composition or formulation can occur prior to, simultaneously, and/or following, administration of the additional therapeutic agent.

In some embodiments of the methods of treatment of the present disclosure, the anti-CD96 antibody or pharmaceutical formulation comprising an anti-CD96 antibody is administered to a subject by any mode of administration that delivers the agent systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebro spinal, and intrasternal injection and infusion.

In some embodiments, a pharmaceutical formulation of the anti-CD96 antibody is formulated such that the antibody is protected from inactivation in the gut. Accordingly, the method of treatments can comprise oral administration of the formulation.

In some embodiments, use of the compositions or formulations comprising an anti-CD96 antibody of the present disclosure as a medicament are also provided. Additionally, in some embodiments, the present disclosure also provides for the use of a composition or a formulation comprising an anti-CD96 antibody in the manufacture or preparation of a medicament, particularly a medicament for treating, preventing or inhibiting a CD96-mediated disease. In a further embodiment, the medicament is for use in a method for treating, preventing or inhibiting a CD96-mediated disease comprising administering to an individual having a CD96-mediated disease an effective amount of the medicament. In certain embodiments, the medicament further comprises an effective amount of at least one additional therapeutic agent, or treatment. Exemplary additional therapeutic agents or treatments that can be used in such medicaments can include but are not limited to an antibody comprising a specificity for an immune checkpoint molecule such as PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA. In at least one embodiment, the additional therapeutic agent or treatment present in a medicament of the present disclosure is an antibody comprising a specificity for the immune checkpoint molecule PD1, including but not limited to an antibody selected from dostarlimab, pembrolizumab, nivolumab, and pidilizumab.

In a further embodiment, the medicament is for use in treating, inhibiting or preventing a CD96-mediated disease in a subject comprising administering to the subject an amount effective of the medicament to treat, inhibit or prevent the CD96-mediated disease.

For the prevention or treatment of a CD96-mediated disease or condition, the appropriate dosage of the anti-CD96 antibody contained in the compositions and formulations of the present disclosure (when used alone or in combination with one or more other additional therapeutic agents) will depend on the specific disease or condition being treated, the severity and course of the disease, whether the antibody is administered for preventive or therapeutic purposes, the previous therapy administered to the patient, the patient's clinical history and response to the antibody, and the discretion of the attending physician. The anti-CD96 antibody included in the compositions and formulations described herein, can be suitably administered to the patient at one time, or over a series of treatments. Various dosing schedules including but not limited to single or multiple administrations over various time-points, bolus administration, and pulse infusion are contemplated herein.

Depending on the type and severity of the disease, about 1 μg/kg to 15 mg/kg of anti-CD96 antibody in a formulation of the present disclosure is an initial candidate dosage for administration to a human subject, whether, for example, by one or more separate administrations, or by continuous infusion. Generally, the administered dosage of the antibody would be in the range from about 0.05 mg/kg to about 10 mg/kg. In some embodiments, one or more doses of about 0.5 mg/kg, 2.0 mg/kg, 4.0 mg/kg or 10 mg/kg (or any combination thereof) may be administered to a patient.

Dosage administration can be maintained over several days or longer, depending on the condition of the subject, for example, administration can continue until the CD96-mediated disease is sufficiently treated, as determined by methods known in the art. In some embodiments, an initial higher loading dose may be administered, followed by one or more lower doses. However, other dosage regimens may be useful. The progress of the therapeutic effect of dosage administration can be monitored by conventional techniques and assays.

Accordingly, in some embodiments of the methods of the present disclosure, the administration of the anti-CD96 antibody comprises a daily dosage from about 1 mg/kg to about 100 mg/kg. In some embodiments, the dosage of anti-CD96 antibody comprises a daily dosage of at least about 1 mg/kg, at least about 5 mg/kg, at least about 10 mg/kg, at least about 20 mg/kg, or at least about 30 mg/kg.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Generation of CD96 Polypeptides

This example illustrates the preparation of the various CD96 polypeptide constructs used as antigens in eliciting and screening the anti-CD96 antibodies of the present disclosure.

The extracellular domains of human (hu), cynomolgus monkey (cy) and rhesus monkey (rh) CD96 isoform 2 were produced recombinantly as full-length ECD or truncated (D1-D2-D3 Ig-like domains, referred to as D1 D3, and D1-Ig-like domain only, referred to as D1) forms. The isoform 2 (short form) of CD96 was reported to be the predominant form in vivo (Meyer et al, (2009)). The extracellular domain of human CD155 was also produced recombinantly. The amino acid sequence boundaries of the expression constructs are provided in Table 1. All constructs had the following C-terminal TEV-Fc-FLAG tag sequence for purification and detection purposes: GGGGSEN-LYFQGGGGS-[human IgG1 Fc]-DYKDDDDK (SEQ ID NO: 475).

CD96-Fc fusion proteins were expressed in ExpiCHO cells (Thermo Fisher Scientific, Waltham, MA, USA) according to the manufacturer's protocol. The CD155-Fc fusion protein was expressed in Expi293 cells (Thermo Fisher Scientific, Waltham, MA, USA) according to the manufacturer's protocol. After harvest the clarified supernatant was applied to MabSelectSuRe protein A columns (GE Healthcare, Chicago, IL, USA) equilibrated in TBS buffer (20 mM Tris pH 7.5, 150 mM NaCl, 0.02% NaN$_3$).

Proteins were eluted with a 10CV of elution buffer (20 mM Citrate pH 2.95, 150 mM NaCl). Protein containing fractions were pooled and loaded onto Superdex 200 Increase columns (GE Healthcare, Chicago, IL, USA) equilibrated in HBS (25 mM HEPES pH 7.5, 150 mM NaCl). Peak fractions containing monodisperse protein were pooled and stored in HBS.

For some applications, the Fc tag was removed from the CD96 fusion proteins by cleavage with TEV protease (ATUM) according to the manufacturer's protocol. The cleavage products were applied to MabSelectSuRe protein A and HisTrap FF crude columns (GE Healthcare, Chicago, IL, USA) equilibrated in TBS (20 mM Tris pH 7.5, 150 mM NaCl, 0.02% NaN3) to remove Fc and His-tagged TEV protease, respectively. The flow-through containing CD96 proteins was applied to Superdex 200 Increase columns equilibrated in HBS (25 mM HEPES pH 7.5, 150 mM NaCl). Peak fractions containing monodisperse protein were pooled and stored in HBS.

For some applications, recombinant hu-CD96 (M1-M503—polyHis) and CD155-Fc (M1-N343—hIgG1 Fc) were purchased from ThermoFisher Scientific (Waltham, MA, USA).

Example 2: Generation of Anti-Hu-CD96 Antibodies Using Hybridoma Methods, Screening and Characterization This example illustrates the methods using mouse hybridoma technology to generate anti-hu-CD96 antibodies, and methods to screen and select antibodies for further characterization.

Immunizations and fusions: Balb/c, Swiss Webster, and C57BL/6 mice were immunized with recombinant extracellular domains of human, cynomolgus monkey, or rhesus monkey CD96 produced in-house or purchased commercially as described in Example 1. The adjuvant Magic Mouse (Creative Diagnostics, Shirley, NY) was used for all immunizations. Titers were determined by ELISA as described below. Mice selected based on their titers were given a final pre-fusion boost without adjuvant. One day later, spleens were harvested and processed according to standard protocols. Splenocytes were fused with myeloma cells P3X63Ag8.653 cells (American Type Culture Collection CRL 1580) using PEG and following standard protocols and plated into 96-well plates at approximately 50,000 myeloma cells/well using standard techniques to maximize clonality of the resulting colonies. Parental hybridomas were selected using selection medium supplemented with AH (Azaserine+Hypoxanthine).

ELISA assays: After 12-14 days of culture, supernatants were collected and subjected to primary screening by ELISA with 96 well plates coated with human and sometimes cynomolgous monkey CD96 extracellular domain. 96-well MAXISORP® flat bottom plates (Thermo Fisher Scientific, Waltham, MA; catalogue number 439454) were coated overnight at 4° C. with 50 µl/well of protein at a concentration of 1 µg/mL or 0.5 µg/mL in coating buffer (0.05 M sodium bicarbonate buffer, pH 9.6 or phosphate buffered saline, PBS). After removing the coating solution, unspecific binding was blocked by addition of 200 µL of assay/blocking solution containing 1% bovine serum albumin (BSA) in phosphate buffered saline (PBS) pH 7.4 (ELISA diluent) and incubation at room temperature for one hour with agitation or overnight at 4° C. without agitation. Plates were then washed three times with 300 µL of PBS, 0.05% TWEEN®-20 (wash buffer). 100 µL of culture supernatant from individual hybridoma clones (or purified antibodies at the indicated concentration) was added to individual wells followed by incubation at room temperature for one hour with agitation. Plates were washed three times with wash buffer, then 50 µL/well of goat anti-mouse IgG Fc HRP (Bethyl Laboratories, Montgomery, TX, USA; catalogue number A90-131P) at 1:3000 dilution or goat anti-mouse IgG (H+L) HRP (Jackson ImmunoResearch, Inc., West Grove PA, USA; catalogue number 109-035-088) at 1:10000 dilution in ELISA diluent was added. The plate was incubated at room temperature for one hour with agitation, washed six times with wash buffer and developed for 3-10 minutes by addition of 50 µL/well of tetramethylbenzidine (TMB) microwell peroxidase substrate (Scytek Laboratories, Inc., Logan, UT, USA; catalogue number TM1999). Enzymatic color development was stopped by acidification with 50 µL/well of 2N $H_2SO_4$ (Sigma-Aldrich Corporation, St. Louis, MO, USA; catalogue number 258105). Plates were analyzed with a SpectraMax i3X plate reader (Molecular Devices LLC, San Jose, CA, USA) at 450 nm.

The parental hybridoma hits identified from the primary screen were expanded to 24-well plates and a confirmatory ELISA was run following the primary screen protocol except that reduced coating antigen density of 0.1 µg/mL was sometimes used, to further confirm and screen for strong anti-hu/anti-cy CD96 binders.

Receptor blocking assay of hybridoma hits: The supernatants of the hybridoma hits identified in the primary screen were also tested for their ability to block human CD155 and CD96 biochemical binding. 96-well MAXISORP® flat bottom plates (Thermo Fisher Scientific, Waltham, MA; Cat #439454) were coated overnight at 4° C. with 1 µg/mL goat anti-human Fc (Thermo Fisher Scientific, Waltham, MA; Cat #PA1-85606) in 50 µL/well in coating buffer (100 mM sodium bicarbonate, pH 9.4, in PBS). After removing the coating solution, unspecific binding was blocked by PBS containing 5% normal mouse serum (blocking buffer) and incubation at room temperature for one hour. Plates were then washed five times with 300 µL of PBS with 0.05% TWEEN®-20 (wash buffer) and added 500 ng/mL human CD155-hFc in 50 µg/well in PBS containing 1% BSA and 0.02% TWEEN®-20 (assay buffer) at room temperature for one hour. During blocking period, 50 ul/well of 100 nM or 50 nM hu-CD96-his and hybridoma supernatant of 50 ul/well in assay buffer were incubated at room temperature for one hour in Nunc F plate (Thermo Fisher Scientific, Waltham, MA; Cat #269620). Then antigen-antibody mix solution 80 ul/well was transferred into antigen coated wells at room temperature for one hour. Plates were washed five times with wash buffer, then 50 µL/well mouse anti-His-HRP (Thermo Fisher Scientific, Waltham, MA; Cat #A16090) in assay buffer was added at room temperature for one hour with agitation, washed five times with wash buffer and developed for 3-10 minutes with 50 µL/well of tetramethylbenzidine (TMB) microwell peroxidase substrate (VWR/Avantor, Radnor, PA, USA; Cat #95059-156). Enzymatic color development was stopped with 50 µL/well of TMB stop solution (VWR/Avantor, Radnor, PA, USA; Cat #95059-200). Plates were analyzed with a SpectraMax i3X plate reader (Molecular Devices LLC, San Jose, CA, USA) at 450 nm. Parental hybridomas with the desired human and cy-CD96 binding as well as ability to block CD155 and CD96 binding were prioritized for subcloning and further characterization. Subcloning was carried out with limited dilution and visual inspection was performed to ensure clonality. Hybridoma subclones were screened with the same binding and blocking assays and selected positive hits were cryopreserved.

Purification of hybridoma antibodies: Subclones were confirmed by primary screen antigen binding ELISA. Positive clones were scaled-up to 30 mL cultures in serum free medium and the antibodies were purified as follows. Supernatant media were clarified by centrifugation at 300 g for 10 min to remove cells and by filtration with 0.22 micron filter. Clarified supernatant media was mixed with POROS Mab-Capture A resin (Thermo Fisher Scientific, Waltham, MA) equilibrated with PBS buffer and incubated with gentle rotation for 1.5 h at room temperature. After incubation, the slurry was loaded into a column and the resin was washed with 20 column volumes of PBS buffer containing 0.5 M NaCl then eluted with 3 column volumes of 0.1 M acetic acid, 0.15 M NaCl. The eluent was quickly neutralized to pH5.2 with 1 M MOPS, pH7.0 and buffer exchanged to PBS buffer with PD-10 column (GE Healthcare, Chicago, IL, USA).

CD96 binding of purified hybridoma antibodies: The hu-CD96 and cy-CD96 antigen binding ELISA was performed on the purified hybridoma antibodies. Briefly, 96-well MAXISORP® flat bottom plates (Thermo Fisher Scientific, Waltham, MA; Cat #439454) were coated overnight at 4° C. with 0.5 µg/mL of hu-CD96D1 D3-hFc and cynomolgus monkey CD96D1 D3-hFc in PBS. After removing the coating solution, unspecific binding was blocked by PBS containing 1% bovine serum albumin (blocking buffer) and incubation at room temperature for one hour. Plates were then washed three times with PBS and 0.05% TWEEN®-20 (wash buffer). Serial dilution of purified antibodies in PBS containing 0.5% BSA and 0.05% Tween 20 (ELISA buffer) was added to individual wells followed by incubation at room temperature for one hour with agitation. Plates were washed three times with wash buffer, then 100 µL/well of anti-mouse IgG-HRP (Thermo Fisher Scientific, Waltham, MA; Cat #626520) in ELISA buffer was added. The plate was incubated at room temperature for one hour with agitation, washed six times with wash buffer and developed for 3-10 minutes by addition of 50 µL/well of tetramethylbenzidine (TMB) microwell peroxidase substrate (VWR/Avantor, Radnor, PA, USA; Cat #95059-156). Enzymatic color development was stopped with 50 µL/well of TMB stop solution (VWR/Avantor, Radnor, PA, USA; Cat #95059-200). Plates were analyzed with a SpectraMax i3X plate reader (Molecular Devices LLC, San Jose, CA, USA) at 450 nm. The CD96 binding $EC_{50}$ values are summarized in Table 3 (below).

TABLE 3

Antigen binding ELISA for anti-CD96 purified hybridoma antibodies

| Hybridoma | hu-CD96 Binding $EC_{50}$ (nM) | cy-CD96 Binding $EC_{50}$ (nM) |
|---|---|---|
| 12F8 | 0.25 | ~10 |
| 10H5 | 0.05 | >100 |
| 1G8 | 0.072 | No binding |
| 16D9 | 0.05 | No binding |
| 9H4 | 0.24 | No binding |
| 7E5 | 0.06 | 0.53 |
| 10G1 | 0.03 | 0.2 |
| NK92.39 | 0.98 | No binding |
| 14D3 | 0.2 | 0.6 |

CD155 receptor blocking of purified hybridoma antibodies: Human CD155 blocking ELISA was performed on purified hybridoma antibodies following the same protocol as described for CD96 (above), except that serial dilution of purified antibodies 50 µL/well (starting at 1 µM, 1:5 dilution) in assay buffer was added into the reaction. The blocking $IC_{50}$ value represents the antibody concentration that inhibited 50% of hu-CD96 binding to coated human CD155 and is summarized in Table 4 (below).

TABLE 4

Human CD155 Blocking ELISA for purified hybridoma antibodies

| Hybridoma | Blocking ELISA $IC_{50}$ (nM) |
|---|---|
| 12F8 | 0.95 |
| 10H5 | 0.958 |
| 1G8 | 0.883 |
| 16D9 | 1.063 |
| 9H4 | 2.23 |
| 7E5 | 2.15 |
| 10G1 | 2.59 |
| NK92.39 | 2.57 |
| 14D3 | No blocking |

As shown by the results in Tables 3 and 4 above, 14D3 is an antibody that binds hu-CD96 well but does not block the CD155 and CD96 interaction. Also, as is shown in Example 4 below, 14D3 does not bind the CD96 D1 domain. It is included herein as an example of CD96 binder, but non-blocker control antibody.

Sequencing of Purified Hybridoma Antibodies

Monoclonal anti-CD96 hybridoma hits were grown to a density of $1-3\times10^5$ in standard hybridoma medium (DMEM/F12, 10% FBS, 1% Glutamax, 1% pen/strep) for 7-10 days in a T75 flask with >80% viability. 1-3 million cells from cultures were pelleted in a 15 mL falcon tube at 300 g for 5 min. Pelleted cells were washed by resuspending cells in 5 mL ice cold PBS. PBS was removed and cells were resuspended in 1 mL of TRIZOL reagent (Life Technologies, Carlsbad, CA, USA). The lysate was passed through a 1 mL syringe with a 20G1 gauge needle (BD 305175) 20 times to ensure lysis of the cells. TRIZOL/cell suspension was immediately frozen on dry ice and stored at −80° C. until processing. Total RNA was isolated from the lysate using Direct-zol RNA Miniprep Plus kit (Zymo Research, Irvine, CA, USA) and 5 µg of total RNA was used to generate 5'-RACE-ready hybridoma cDNA using SMARTer RACE 5' kit (Takara Bio, Japan).

To amplify heavy chain and light chain specific gene fragments from the cDNA, the following mouse variable region primers were used:

(i) $V_H$ region specific primers:
(SEQ ID NO: 476)
TCTTGTCCACCTTGGTGCTGCTGGCCGG,
and
(SEQ ID NO: 477)
TTTGTCCACCGTGGTGCTGCTGGCTGGT;

-continued (ii) V<sub>kappa</sub> region specific primer:

(SEQ ID NO: 478)
GATCAGTCCAACTGTTCAGGACGCC;
and (iii) V<sub>lambda</sub> region specific primers:

(SEQ ID NO: 479)
ACACTCAGCACGGGACAAACTCTTCTCCACAGT, (SEQ ID NO: 480)
ACACTCTGCAGGAGACAGACTCTTTTCCACAGT,
and (SEQ ID NO: 481)
ACACTCAGCACGGGACAAACTCTTCTCCACATG.

The region-specific primers were used in conjunction with universal primer provided in the kit in 5'-RACE PCR reactions. PCR products were purified and cloned into pRACE using an In-Fusion cloning kit (Takara Bio, Japan) and both strands were sequenced using Sanger sequencing with M13 forward and M13 reverse primers. The variable domain sequences of anti-CD96 hybridomas are summarized in Table 2 and provided in the attached Sequence Listing.

The variable sequences of the antibodies of clone 12F8.12B5 (also referred to herein as "12F8") and clone 10G1.3G8 (also referred to herein as "10G1") were used to recombinantly produce mouse human chimeric antibodies. Human IgG1 Fc with a N297G mutation was used to engineer these chimeric antibodies. The N297G mutation removes FcgR binding and the effector function of the antibody. Effector-less function of the anti-hu-CD96 antibodies can be critical for anti-tumor efficacy in binding to CD96 expressed on cytotoxic T cells and NK cells. The chimeric 12F8 and chimeric 10G1 antibodies were tested in CD96 ELISA binding assay and showed very similar properties as purified hybridoma antibodies, thereby further validating the HVR sequences.

Based on their superior properties in the above-described assays, the purified anti-hu-CD96 antibodies derived from hybridoma 12F8 and 10G1 were selected for humanization and further affinity maturation as described in the Examples below.

Example 3: Preparation of Humanized Versions of 12F8 and 10G1

This example illustrates the preparation of humanized versions of the murine anti-hu-CD96 derived from the hybridomas 12F8 and 10G1.

Humanization of Murine Anti-Hu-CD96 "mAb1"

As shown by the sequence alignments depicted in FIG. 1, the light chain variable region ($V_L$) and heavy chain variable region ($V_H$) sequences of murine antibody 12F8 were aligned against human germline antibody sequences, and the human germline kappa light chain (Gene ID—V gene: IGKV1-9*01, J gene: IGKJ2*01) and the human germline heavy chain (Gene ID—V gene: IGHV1-46*01, J gene: IGHJ4*03) were identified as the closest human frameworks.

HVRs of murine 12F8 light chain and heavy chain were grafted into the identified closest human frameworks respectively to generate the humanized antibody clone (also referred to herein as "mAb1"). In the process of humanization, six different versions of the mAb1 heavy chain were generated (versions mAb1.v1-mAb1.v5 and mAb1.v7), where different mouse framework residues were retained with the goal to minimize mouse residues while maintaining hu-CD96 binding. The variable domain amino acid sequences of the humanized antibodies, mAb1.v1-mAb1.v5 and mAb1.v7, are summarized in Table 2 and the attached Sequence Listing.

Humanization of Murine Anti-Hu-CD96 "10G1"

As shown by the sequence alignments depicted in FIG. 2, the light chain variable region ($V_L$) and heavy chain variable region ($V_H$) sequences of murine antibody from hybridoma 10G1 (also referred to as "10G1") were aligned against human germline antibody sequences, and the human germline kappa light chain (Gene ID—V gene: IGKV6D-21*02, J gene: IGKJ4*02) and the human germline heavy chain (Gene ID—V gene: IGHV7-4-1*02, J gene: IGHJ4*03) were identified as the closest human frameworks.

HVRs of murine 10G1 light chain and heavy chain were grafted into the identified closest human frameworks respectively to generate humanized antibody clone (also referred to as "h10G1"). In this process, positions 24-34, 50-56, and 89-97 of murine 10G1 $V_L$ were grafted to the human kappa light chain framework acceptor, and positions 31-35, 50-65, and 95-102 of murine 10G1 $V_H$ were grafted to the human heavy chain framework acceptor.

Position 4 in light chain framework region 1 (FW-L1), position 43 in light chain framework region 2 (FW-L2), position 58 in light chain framework region 3 (FW-L3), position 2 in heavy chain framework region 1 (FW-H1), position 28 in heavy chain framework region 1 (FW-H1) and position 91 in heavy chain framework region 3 (FW-H3) of murine 10G1 were also grafted into the human kappa light chain and heavy chain framework acceptors as those positions were found to be part of VH-VL interacting interface or the framework residues acting as "Vernier" zone, which may adjust HVR structure and fine-tune to fit to antigen; Foote et al., 1992).

The variable domain sequences of the humanized antibody, h10G1 is summarized in Table 2 and the attached Sequence Listing.

Generation of Recombinant IgG Versions of mAb1.v7 and h10G1

The heavy and light chain variable domain of mAb1.v7 and h10G1 were synthesized and cloned into pRK plasmid. The expression of recombinant mAb1.v7 and humanized 10G1 IgGs were performed using Expi293F expression system (Life Technologies, Carlsbad, CA, USA) in accordance with the instruction provided. The ratio of the plasmids for the heavy chain and the light chain was kept at 1 to 1 for the transfection reaction and the transfected cells were cultured for 6 days before harvest.

Recombinant IgG molecules were purified with the following protocols. Supernatant media were clarified by centrifugation at 300 g for 10 min to remove cells and by filtration with 0.22 μm filter. Clarified supernatant media were mixed with POROS MabCapture A resin (Thermo Fisher Scientific, Waltham, MA, USA) equilibrated with PBS buffer and incubated with gentle rotation for 1.5 h at room temperature. After incubation, the slurry was loaded into a column and the resin was washed with 20 column volumes of PBS buffer containing 0.5 M NaCl then eluted with 3 column volumes of 0.1 M acetic acid, 0.15 M NaCl. The pH of the eluent was quickly adjusted to pH 5.2 with 1 M MOPS, pH 7.0 and buffer exchanged into to PBS buffer with PD-10 column (GE Healthcare).

Non-Specific Binding Assessment of mAb1.v7 and h10G1 IgG

Non-specific binding of mAb1.v7 and humanized 10G1 IgGs were assessed using baculovirus ELISA (see e.g., Hotzel et al., 2012). Briefly, baculovirus particles were coated on 96-well Maxisorp plates at a 2.5% suspension in 50 mM sodium carbonate buffer pH 9.6 at 4° C. for overnight. The plates were then blocked in PBS with 0.5% BSA (blocking buffer) at room temperature for one hour. Serial dilution of mAb1.v7 and h10G1 IgGs in PBS were added to the plates for an hour and plate was washed with PBS six times. Bound antibodies were detected with goat anti-human IgG conjugated to horseradish peroxidase (Jackson ImmunoResearch) in PBS. The plate was incubated at room temperature for one hour with agitation, washed six times with PBS and developed for 3-10 minutes by addition of 50 µL/well of tetramethylbenzidine (TMB) microwell peroxidase substrate (VWR, Cat #95059-156). Enzymatic color development was stopped with 50 µL/well of TMB stop solution (VWR, Cat #95059-200). Plates were analyzed with a SpectraMax i3X plate reader (Molecular Devices) at 450 nm and compared to reference antibodies. Both mAb1.v7 and h10G1 IgGs showed no detectable BV ELISA signal, indicating absence of non-specific binding to baculovirus particles.

Binding Affinities of Recombinant mAb1.v7 and h10G1

SPR measurement with a BIACORE™ 8K instrument was performed to determine the monovalent binding affinity of mAb1.v7 and h10G1 IgG to hu-CD96, cy-CD96, and mo-CD96. Briefly, antibodies were diluted at 0.5 µg/mL in HBS-P buffer (0.01 M HEPES pH 7.4, 0.15 M NaCl, 0.005% Surfactant P20) and applied to the Protein A chip at 30 µL/min flow rate for 60 s in flow cell 2 (FC2). Then 3-fold serial dilutions of hu-CD96, cy-CD96, or mo-CD96 in HBS-P buffer (0.01 M HEPES pH 7.4, 0.15 M NaCl, 0.005% surfactant P20) from (0.4 nM) to high (100 nM) were injected (flow rate: 30 µL/min) at 25° C. to both flow cell 1 (FC1) and flow cell 2 (FC2). The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$ and summarized in Table 5.

TABLE 5

Binding affinity of mAb1.v7, h10G1 and NK92.39 to CD96 antigens

| IgG | hu-CD96 $K_D$ (nM) | cy-CD96 $K_D$ (nM) | mo-CD96 $K_D$ (nM) |
|---|---|---|---|
| mAb1.v7 | 4.49 | ~1000 | ~386 |
| h10G1 | 1.17 | 0.74 | No binding |
| NK92.39[1] | 14.3 | No binding | No binding |

[1]NK92.39 is a commercially available antibody (Biolegend catalog # 338405) that was previously described (Fuchs et al., 2004).

Example 4: Epitope Mapping of mAb1.v7 and h10G1

Epitope Binning

The CD155-blocking anti-CD96 antibodies described here were determined by epitope binning to recognize 3 distinct epitopes on CD96. mAb1.v7 and h10G1 were determined to bind distinct but overlapping CD155-blocking epitopes on CD96. Antibodies 1G8, 10H5, 16D9 and NK92.39 share an epitope bin with 10G1, while 9H4 binds an epitope on CD96 that overlaps with that of h10G1 but not with that of mAb1.v7.

Epitope binning experiments were performed on a OctetRed96 by capturing antibody 1 on anti-Fc Octet sensors (ForteBio), binding CD96D1 D3, and subsequently probing with antibody 2. If antibody 2 was capable of binding antibody 1-bound CD96D1 D3 then the two antibodies were assigned to different bins. If antibody 2 was unable to bind antibody 1-bound CD96D1 D3 then the two antibodies were assigned to the same epitope bin. Table 6 shows the epitope binning results.

TABLE 6

Epitope binning of anti-CD96 antibodies

| Antibody | mAb1.v7 | 9H4 | Nk92.39 | h10G1 | 1G8 | 7E5 | 14D3 | PBST |
|---|---|---|---|---|---|---|---|---|
| mAb1.v7 | − | + | − | − | − | + | + | − |
| 9H4 | + | − | − | − | − | + | + | − |
| Nk92.39 | − | − | − | − | − | + | + | − |
| h10G1 | − | − | − | − | − | + | + | − |
| 1G8 | − | − | − | − | − | + | + | − |
| 7E5 | + | + | + | + | + | − | + | − |
| 14D3 | + | + | + | + | + | + | − | − |

Domain Binding Site Mapping mAb1.v7 and h10G1 were determined to bind the D1 domain of CD96. Epitope mapping experiments were performed on an OctetRed96 by capturing the antibodies on anti-Fc Octet sensors (ForteBio) and testing their binding to recombinant huCD96D1-Fc and huCD96D1D3. Both mAb1.v7 and h10G1, but not antibody 14D3, bound to CD96D1 and CD96D1D3 equally well, demonstrating that CD96D1 is sufficient for binding of these antibodies to full-length CD96.

Example 5: Affinity Maturation of Humanized Anti-CD96 Antibody mAb1.v7

This example illustrates phage library construction and panning techniques used for affinity maturation of the humanized anti-hu-CD96 antibody mAb1.v7 for improved binding to hu-CD96 and cy-CD96.

NNK Library Construction and Panning

To further improve the affinity of anti-CD96 antibody clone mAb1.v7, phage libraries were constructed from variant mAb1.v7 in Fab-amber format for monovalent Fab phage display with heavy chain HVR residues (i.e., HVR-H1, HVR-H2, and HVR-H3) randomized using the NNK degenerate codon that encodes for all 20 amino acids with 32 codons (see e.g., Brenner et al., 1992). Libraries were designed to allow one NNK mutation in each of the heavy chain HVRs. Synthesized mutagenesis oligonucleotides were then used to construct heavy chain libraries using Kunkel mutagenesis (see e.g., Kunkel et al., 1987). The resultant library DNA was electroporated into E. coli XL1 cells, yielding approximately $4 \times 10^9$ transformants. Phage libraries were incubated in SUPERBLOCK™ PBS buffer (Pierce) and 0.05% TWEEN® 20 for 30 min and then applied on hu-CD96 and cy-CD96 coated plates for first round panning. In the subsequent two to three rounds, phage libraries were incubated with decreasing concentration of biotinylated hu-CD96 or cy-CD96 antigen with 1000x non-biotinylated human or cy-CD96 as competitor in solution to increase the selection stringency. The eluted phage was infected with log-phase XL-1 and plated on LB carbenicillin plate at 37° C. overnight for further affinity screening Affinity Screening of mAb1.v7 Phage Variants Single spot phage competition ELISA was used to screen for phage affinity screening. 192 colonies from most stringent selections (biotinylated 0.1 nM of hu-CD96 or cy-CD96 with 1000× non-biotinylated human or cy-CD96) were grown in 400 µL 2YT with 4 µL helper phage M13KO7 overnight at 37° C. with shaking. After spinning down the pellet, the phage supernatant was diluted 1:1 with 2 nM hu-CD96, 20 nM cy-CD96 and ELISA buffer (0.5% BSA and 0.05% TWEEN®20 in PBS) in total 100 4 and incubated for two hours at room temperature with agitation. The 80 4 of mixture was transferred to hu-CD96 coated plate for 15 min to capture unbound phage. The plate was washed with wash buffer (0.05% TWEEN®20 in PBS), and HRP-conjugated anti-M13 antibody (Sino biological, Cat #11973-MM05-H-50) was added in ELISA buffer for 30 min. The plates were washed with wash buffer and developed tetramethylbenzidine (TMB) microwell peroxidase substrate (VWR, Cat #95059-156). Enzymatic color development was stopped using TMB stop solution (VWR, Cat #95059-200). Plates were analyzed with a SpectraMax i3X plate reader (Molecular Devices). The % inhibition was calculated by the $OD_{450}$ of wells with hu-CD96/cy-CD96 competitor divided by $OD_{450}$ of wells with buffer alone. The lower % inhibition indicated higher phage $IC_{50}$ against hu-CD96 or cy-CD96.

Selected top inhibition % phage variants from single spot competition were purified from culture supernatants. The optimal phage concentration was incubated with serially-diluted hu-CD96 or cy-CD96 in ELISA buffer in NUNC F plate for two hours. The 80 4 of the mixture was transferred to hu-CD96 coated wells for 15 min to capture unbound phage. The plate was washed with wash buffer (0.05% TWEEN®20 in PBS), and HRP-conjugated anti-M13 antibody (Sino biological, Cat #11973-MM05-H-50) was added in ELISA buffer for 30 min. The plates were washed and developed as described above. The absorbance at 450 nm was plotted as a function of antigen concentration in solution to determine phage $IC_{50}$. This was used as an affinity estimate for the Fab clone displayed on the surface of the phage. Phage plasmids (phagemids) were sequenced using $V_H$ specific primers and the variant sequences within the HVRs of 16 selected top mAb1.v7 phage variants are summarized in Table 7 (below).

TABLE 7

Variant HVR sequences of mAb1.v7 affinity improved phage variants

| Fab | HVR-H1<br>30 31 32 33 34 35 | HVR-H2<br>50 51 52 52A 53 54 55 56 57 58 59 60 61 | HVR-H3<br>93 94 95 96 97 98 99 100 100A 100B 101 102 |
|---|---|---|---|
| mAb1.v7    | T N N W M H | M I H P N S G I T N I N E | R S D G T Y E G Y F D Y |
| mAb1.v7.2  | T N N W R H | M I H F N S G I T N I N E | R S D G V Y E G Y F D Y |
| mAb1.v7.6  | T N R W M H | M I H V N S G I T N I N E | R S D G L Y E G Y F D Y |
| mAb1.v7.8  | T N N W D H | M I H P L S G I T N I N E | R S D G V Y E G Y F D Y |
| mAb1.v7.9  | T N N W R H | M I H M N S G I T N I N E | R S D G V Y E G Y F D Y |
| mAb1.v7.10 | T N N W R H | M I H P L S G I T N I N E | R S D G V Y E G Y F D Y |
| mAb1.v7.11 | T N N F M H | M I H P N S G G T N I N E | R S D E T Y E G Y F D Y |
| mAb1.v7.14 | V N N W M H | M I H P N S G I T N T N E | R S D G I Y E G Y F D Y |
| mAb1.v7.15 | T N N W D H | M I H P M S G I T N I N E | R S D G F Y E G Y F D Y |
| mAb1.v7.16 | T N N W R H | M I H P N S G I T N I N E | R S D G V Y E G Y F D Y |
| mAb1.v7.19 | T N S W M H | M I H P N S G I T N R N E | R S D G I Y E G Y F D Y |
| mAb1.v7.21 | T N Y W M H | M I H P N S G I T N M N E | R S D G V Y E G Y F D Y |
| mAb1.v7.24 | T N N W G H | M I H R N S G I T N I N E | R S D G I Y E G Y F D Y |
| mAb1.v7.48 | T N R W M H | M I H H N S G I T N I N E | R S D G V Y E G Y F D Y |
| mAb1.v7.50 | T N N W S H | M I H R N S G I T N I N E | R S D G V Y E G Y F D Y |

TABLE 7-continued

Variant HVR sequences of mAb1.v7 affinity improved phage variants

| Fab | HVR-H1<br>30 31 32 33<br>34 35 | HVR-H2<br>50 51 52 52A 53 54 55 56<br>57 58 59 60 61 | HVR-H3<br>93 94 95 96 97 98 99 100<br>100A 100B 101 102 |
|---|---|---|---|
| mAb1.v7.59 | T N N W N H | M I H P N S G I T A I N E | R L D G T Y E G Y F D Y |
| mAb1.v7.70 | T N R W M H | M I H A N S G I T N I N E | R S D G V Y E G Y F D Y |

The phage $IC_{50}$ values determined for the 16 selected Fab variants of Table 7 are summarized in Table 8 (below).

TABLE 8

Phage $IC_{50}$ values of mAb1.v7 affinity improved phage variants

| | Phage IC50 (nM) | |
|---|---|---|
| Clone | hCD96 | CyCD96 |
| mAb1.v7 | 0.5 | ~300 |
| mAb1.v7.2 | 0.08 | 1.8 |
| mAb1.v7.6 | 0.16 | 0.15 |
| mAb1.v7.8 | 0.17 | 0.45 |
| mAb1.v7.9 | 0.11 | 0.37 |
| mAb1.v7.10 | 0.19 | 0.76 |
| mAb1.v7.11 | 0.23 | 0.24 |
| mAb1.v7.14 | 0.1 | 1 |
| mAb1.v7.15 | 0.19 | 1.85 |
| mAb1.v7.16 | 0.1 | 1.6 |
| mAb1.v7.19 | 0.23 | 0.84 |
| mAb1.v7.21 | 0.15 | 0.91 |
| mAb1.v7.24 | 0.2 | 0.6 |
| mAb1.v7.48 | 0.1 | 0.3 |
| mAb1.v7.50 | 0.1 | 0.9 |
| mAb1.v7.59 | 0.1 | 1.6 |
| mAb1.v7.70 | 0.14 | 0.4 |

Generation of mAb1.v7 Affinity Improved Fab Variants

The 16 top phage variants of mAb1.v7 shown in Table 7 were synthesized for cloning into a mammalian Fab expression construct containing an 8×His tag to generate Fab proteins. Plasmids encoding the heavy or light chain were transfected into Expi293F cells (Thermo Fisher Scientific) for 20-30 mL expression using a 1:1 ratio of HC:LC. Fabs were purified with a HisPur Ni-NTA column by diluting supernatant 1.5x with 1x phosphate-buffered saline pH 7.2 ("PBS"), adding 10 mM imidazole, and binding to resin in batch mode for 2 hours. Resin was flowed over a column and washed with 20 CV PBS+20 mM imidazole and eluted with 5 CV PBS+250 mM imidazole. Samples were buffer exchanged to PBS using a PD10 column (GE Healthcare).

Affinity Measurement of mAb1.v7 Affinity Improved Fab Variants by BLI Analysis

The binding affinity of the generated Fab variants of mAb1.v7 for hu-CD96 and cy-CD96 was determined by OCTET (Pall ForteBio) Bio-Layer Interferometry (BLI) binding analysis. The biotinylated hu-CD96 or biotinylated cy-CD96 was diluted to a final concentration 10 µg/mL in experimental buffer (PBS buffer with 0.01% Tween-20) and immobilized on the Streptavidin Capture (SA) biosensors (Pall ForteBio). Three-fold serial dilutions of the mAb1.v7 Fab variants starting at 1 µM as analytes were diluted in the experimental buffer (PBS buffer with 0.01% Tween-20). The biosensors were equilibrated in experimental buffer at 30° C. for ten minutes prior to starting the experiment. The kinetics experiment was performed with the following steps, where the step name, solution and time are listed: Baseline (buffer—60 seconds), Loading (biotinylated antigen—200 seconds), Baseline 2 (buffer—minimum 120 seconds), Association (analyte—200-300 seconds) and Dissociation (buffer—1000 seconds). The resulting BLI signal from analyte association and dissociation from the immobilized antibody was analyzed using the Octet Data Analysis software (Pall ForteBio). First a reference subtraction was performed on all recorded traces using the reference well (biosensor that underwent same steps as experimental wells but no analyte for the Association step) and then all the traces were aligned to the beginning of the Association step. The entirety of the Association and Dissociation steps were used in a Global fit (minimum of four analyte concentration traces) in a 1:1 binding model to calculate the $K_D$ values for the 16 selected individual mAb1.v7 Fab variants as summarized in Table 9 (below).

TABLE 9

OCTET $K_D$ results for mAb1.v7 affinity improved phage variants

| | Octet KD (nM) | |
|---|---|---|
| Fab | hCD96 | CyCD96 |
| mAb1.v7 | 76 | >1000 |
| mAb1.v7.2 | 3.75 | 39.1 |
| mAb1.v7.6 | 28.4 | 284 |
| mAb1.v7.8 | 27 | 104 |
| mAb1.v7.9 | ~0.1 | 129 |
| mAb1.v7.10 | 2.71 | 117 |
| mAb1.v7.11 | 156 | 175 |
| mAb1.v7.14 | ~0.1 | 530 |
| mAb1.v7.15 | 3 | 160 |
| mAb1.v7.16 | 1.4 | 97.9 |
| mAb1.v7.19 | 0.63 | 261 |
| mAb1.v7.21 | 0.31 | 118 |
| mAb1.v7.24 | 0.31 | 118 |
| mAb1.v7.48 | ~0.1 | 68 |
| mAb1.v7.50 | 4.16 | 183 |
| mAb1.v7.59 | ~0.1 | 271 |
| mAb1.v7.70 | ~0.1 | 52.6 |

Affinity Measurement of mAb1.v7 Affinity Improved Fab Variants by BIACORE

To determine the binding kinetics of a subset of 5 selected affinity improved Fab variants of mAb1.v7 for binding to hu-CD96 and cy-CD96, SPR measurement with a BIACORE® 8K instrument was performed. Briefly, hu-CD96 Fc and cy-CD96 Fc were diluted at 10 µg/mL in HBS-P buffer (0.01 M HEPES pH 7.4, 0.15 M NaCl, 0.005% Surfactant P20) and applied to the Protein A chip at 30 µL/min flow rate for 60 s in flow cell 2 (FC2). Then flow 3-fold serial dilutions of mAb1.v7 Fab variants in HBS-P buffer (0.01 M HEPES pH 7.4, 0.15 M NaCl, 0.005% surfactant P20) from (0.4 nM) to high (1000 nM) were injected (flow rate: 30 µL/min) at 25° C. to both flow cell 1 (FC1) and flow cell 2 (FC2). The sensorgram was recorded and subject to reference and buffer subtraction before evaluating by BIA- CORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) was calculated as the ratio of $k_{off}/k_{on}$, and the values determined for the mAb1.v7 and the 5 Fab variants are summarized in Table 10 (below).

cells carrying phagemids from the initial phage library (unsorted libraries) and from the second and third rounds of solution selection (sorted libraries). Purified DNA was used as the template to generate amplicons of $V_H$ regions using Illumina 16s library preparation protocol. Sequencing adapters and dual-index barcodes were added using Illumina Nextera XT Index Kit. In preparation for sequencing on

TABLE 10

Binding affinity ($K_D$) and CD155 blocking $IC_{50}$ values for selected top mAb1.v7 Fab variants to hu-CD96 and cy-CD96

| Fab | Biacore_hCD96 | | | Biacore_Cy CD96 | | | CD155 blocking IC50 (nM) | |
|---|---|---|---|---|---|---|---|---|
| | Kon (1/Ms) | Koff (1/s) | KD (nM) | Kon (1/Ms) | Koff (1/s) | KD(nM) | hCD96 | CyCD96 |
| mAb1.v7 | 1.83E+04 | 8.17E−04 | 44.6 | 1.15E+03 | 2.57E−02 | ~1000 | 0.74 | ~300 |
| mAb1.v7.2 | 1.58E+04 | 1.06E−05 | 0.67 | 2.60E+04 | 2.40E−04 | 9.24 | 0.7 | 2.17 |
| mAb1.v7.9 | 1.39E+04 | 7.02E−05 | 5.05 | 3.64E+04 | 8.02E−04 | 22 | 0.42 | 3.18 |
| mAb1.v7.16 | 7.38E+03 | 2.81E−06 | 0.38 | 1.04E+04 | 9.72E−04 | 94 | 0.8 | 1.42 |
| mAb1.v7.48 | 1.59E+04 | 1.26E−05 | 0.795 | 3.66E+04 | 3.28E−04 | 8.9 | 0.42 | 4.8 |
| mAb1.v7.70 | 1.59E+04 | 2.74E−05 | 1.73 | 3.72E+04 | 1.89E−04 | 5 | 0.8 | 2 |

CD155 Receptor Blocking Activity of Affinity Improved Fab Variants of mAb1.v7

The selected 5 affinity matured Fab variants of mAb1.v7 Fab were assayed for blocking of human CD155 (hu-CD155) receptor by ELISA as follows. Briefly, 96-well MAXISORP® flat bottom plates (Thermofisher, Cat #439454) were coated overnight at 4° C. with 2 µg/mL goat anti-mouse Fc (Thermofisher, Cat #31168) in PBS. After removing the coating solution, unspecific binding was blocked with PBS containing 1% bovine serum albumin (BSA) and incubation at room temperature for one hour. Plates were then washed five times in PBS with 0.05% TWEEN®-20 (wash buffer) and added 1/mL hu-CD155-mFc in PBS for 1 hour in room temperature. During blocking period, 50 µL/well of 4 nM biotinylated hu-CD96 or 40 nM biotinylated cy-CD96 with serial dilution of the Fab variants 50 µL/well (starting at 2 µM, 1:3 dilution) for two hours at room temperature with PBS containing 0.5% BSA and 0.05% Tween 20 (ELISA buffer) in NUNC F plate (Thermofisher, Cat #269620). Then transferred the antigen-antibody mix solution 80 µL/well into hu-CD155-mFc coated wells at room temperature for 15 min. Plates were then washed with wash buffer to which was added 50 µL/well Streptavidin poly-HRP (Thermofisher, Cat #21140) diluted 1:5000 in ELISA buffer at room temperature for one hour with agitation. The plates were washed with wash buffer and developed for 3-10 minutes by addition of 50 µL/well of tetramethylbenzidine (TMB) microwell peroxidase substrate (VWR, Cat #95059-156). Enzymatic color development was stopped with 50 µL/well of TMB stop solution (VWR, Cat #95059-200). Plates were analyzed with a SpectraMax i3X plate reader (Molecular Devices) at 450 nm. The blocking $IC_{50}$ represents the concentration of the Fab that inhibits 50% of biotinylated hu-CD96 or biotinylated cy-CD96 binding to the coated hu-CD155-mFc. The blocking $IC_{50}$ values for the mAbv1.7 and the 5 selected affinity matured Fab variants (mAb1.v7.2, mAb1.v7.9, mAb1.v7.16, mAb1.v7.48, mAb1.v7.70) are summarized in Table 10 (above).

Sequencing of mAb1.v7 Affinity Maturation Libraries

In order to further improve affinity and mitigate oxidation liability risks, next-generation sequencing (NGS) of the mAb1.v7 affinity maturation libraries was performed. Phagemid double stranded DNA was isolated from E. coli XL-1

Illumina MiSeq, adapter-ligated amplicons were subjected to standard Illumina library denaturing and sample loading protocol using MiSeq Reagent Kit v3 (600 cycles). Paired-end sequencing was performed to cover the entire length of the amplicon with insert size of 200 bp to 300 bp.

Paired-end sequencing data were first assembled using paired-end assembler PANDAseq (see e.g., Masella et al., 2012) to obtain complete amplicons. Quality control (QC) was then performed on identified amplicons, where each amplicon was checked for no insertion or deletion of sequences and no stop codons, each HVR sequence was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Koenig et al., 2015). The HVR-H region mutations identified by NGS as resulting in improved binding to hu-CD96 and cy-CD96 are summarized in Table 11.

TABLE 11 mAb1.v7 HVR-H mutations with high affinity binding to hu-CD96 and cy-CD96

HVR-H1

T30A, T30D, T30E, T30G, T30H, T30K, T30N, T30Q, T30R, T30S, T30V, T30W, T30Y
N32A, N32F, N32G, N32H, N32M, N32R, N32S, N32V, N32Y
W33F
M34A, M34E, M34F, M34L, M34N, M34Q, M34R, M34S, M34T, M34V, M34W

HVR-H2

M50F
I51L, I51M, I51V
P52aA, P52aD, P52aE, P52aF, P52aG, P52aH, P52aI, P52aK, P52aL, P52aM, P52aN, P52aQ, P52aR, P52aS, P52aT, P52aV, P52aW
N53A, N53D, N53E, N53F, N53G, N53H, N53I, N53K, N53L, N53M, N53Q, N53R, N53S, N53T, N53V, N53W, N53Y
S54A, S54G, S54T, S54V
G55A, G55S

TABLE 11-continued mAb1.v7 HVR-H mutations with high affinity
binding to hu-CD

TABLE 12-continued

Variant HVR sequences and OCTET binding affinities of mAb1.v7 Fab variants mAb1.v7.NGS1-mAb1.v7.NGS9

| Fab | Octet KD (nM) | |
|---|---|---|
| | hu-CD96 | cy-CD96 |
| mAb1.v7 | 76 | ~1000 |
| mAb1.v7.NGS1 | 49 | 271 |
| mAb1.v7.NGS2 | 63 | ~100 |
| mAb1.v7.NGS3 | 0.1 | ~1000 |
| mAb1.v7.NGS4 | 31.5 | 739 |
| mAb1.v7.NGS5 | 43.6 | 85 |
| mAb1.v7.NGS6 | 5.32 | 289 |
| mAb1.v7.NGS7 | 5.61 | 383 |
| mAb1.v7.NGS8 | 0.1 | 93 |
| mAb1.v7.NGS9 | 0.1 | 82 |

According to the OCTET binding analysis in Table 12, the mAb1.v7. NGS8 and mAb1.v7.NGS9 Fab variants showed the highest binding affinity to hu-CD96 and cy-CD96.

In order to mitigate the oxidation risk based on the presence of Met residue at position 50 of HVR-H2, further Fab variants, mAb1.v7.NGS10 and mAb1.v7.NGS11 were generated with an M50F substitution of mAb1.v7.NGS8 and mAb1.v7.NGS9, respectively, as shown by sequences in Table 13 (below).

TABLE 13

| | Variant HVR sequences of mAb1.v7 NGS8-NGS11 | | |
|---|---|---|---|
| Fab | HVR-H1<br>30 31 32 33<br>34 35 | HVR-H2<br>50 51 52 52A 53 54 55 56<br>57 58 59 60 61 | HVR-H3<br>93 94 95 96 97 98 99 100<br>100A 100B 101 102 |
| mAb1.v7 | T N N W M H | M I H P N S G I T N I N E | R S D G T Y E G Y F D Y |
| mAb1.v7.NGS8 | T N N F M H | M I H A N S G I T N I N E | R S D G I Y E G Y F D Y |
| mAb1.v7.NGS9 | T N N F M H | M I H A N S G I T N I N E | R S D G V Y E G Y F D Y |
| mAb1.v7.NGS10 | T N N F M H | F I H A N S G I T N I N E | R S D G I Y E G Y F D Y |
| mAb1.v7.NGS11 | T N N F M H | F I H A N S G I T N I N E | R S D G V Y E G Y F D Y | hu-CD96 and cy-CD96 binding affinities and CD155 blocking activities of mAb1.v7 NGS8-NGS11 Fabs were determined and are summarized in Table 14 (below).

TABLE 14 hu-CD96 and cy-CD96 binding affinities and CD155 blocking activities of mAb1.v7 NGS8-NGS11 Fabs

| | Biacore_hCD96 | | | Biacore_Cy CD96 | | | CD155 blocking IC50 (nM) | |
|---|---|---|---|---|---|---|---|---|
| Fab | Kon (1/Ms) | Koff (1/s) | KD (nM) | Kon (1/Ms) | Koff (1/s) | KD(nM) | hCD96 | CyCD96 |
| mAb1.v7 | 1.83E+04 | 8.17E-04 | 44.6 | 1.15E+03 | 2.57E-02 | >1000 | 0.74 | ~300 |
| mAb1.v7.NGS8 | 1.67E+04 | 2.53E-05 | 1.8 | 2.65E+04 | 3.83E-04 | 14.5 | 0.2 | 0.92 |
| mAb1.v7.NGS9 | 1.42E+04 | 8.32E-05 | 5.85 | 2.48E+04 | 4.14E-04 | 16.7 | 0.78 | 0.73 |
| mAb1.v7.NGS10 | 1.21E+04 | 2.60E-05 | 2.1 | 1.14E+04 | 3.43E-04 | 30 | 0.54 | 0.84 |
| mAb1.v7.NGS11 | 1.05E+04 | 2.75E-05 | 2.62 | 1.12E+04 | 2.15E-04 | 19.1 | 0.59 | 0.95 |

The four lead mAb1.v7 variants NGS8, NGS9, NGS10, and NGS11, were reformatted into pRK mammalian expression IgG vectors, and recombinant IgGs were expressed and purified as described in Example 2.

Example 6: Affinity Maturation of Humanized Anti-CD96 Antibody h10G1

This example illustrates phage library construction and panning techniques used for affinity maturation of the humanized anti-hu-CD96 antibody h10G1 for improved binding to hu-CD96 and cy-CD96.

NNK Library Construction and Panning

To further improve the affinity of anti-CD96 antibody clone h10G1, phage libraries were constructed from h10G1 in Fab-amber format for monovalent Fab phage display with light chain HVR residues (i.e., HVR-L1, HVR-L2 and HVR-L3) and heavy chain HVR residues (i.e., HVR-H1, HVR-H2, and HVR-H3) randomized using the NNK degenerate codon that encodes for all 20 amino acids with 32 codons (see e.g., Brenner et al., 1992). Libraries were designed to allow one NNK mutation in each of the six HVRs. Synthesized mutagenesis oligonucleotides were then used to construct phage libraries using Kunkel mutagenesis (see e.g., Kunkel et al., 1987). The resultant library DNA was electroporated into *E. coli* XL1 cells, yielding approximately 4×10$^9$ transformants. Phage libraries were incubated in SUPERBLOCK™ PBS buffer (Pierce) and 0.05% TWEEN® 20 for 30 min and then applied on hu-CD96 and cy-CD96 coated plates for first round panning. In the subsequent two to three rounds, phage libraries were incubated with decreasing concentration of biotinylated hu-CD96 or cy-CD96 antigen with 1000x non-biotinylated human or cy-CD96 as competitor in solution to increase the selection stringency. The eluted phage was infected with log-phase XL-1 and plated on LB carbenicillin plate at 37° C. overnight for further affinity screening Sequencing of h10G1 Affinity Maturation Libraries In order to further improve affinity and mitigate oxidation liability risks, next-generation sequencing (NGS) of the h10G1 affinity maturation libraries was performed. Phagemid double stranded DNA was isolated from *E. coli* XL-1 cells carrying phagemids from the initial phage library (unsorted libraries) and from the second and third rounds of solution selection (sorted libraries). Purified DNA was used as the template to generate amplicons of $V_L$ and $V_H$ regions using Illumina 16s library preparation protocol. Sequencing adapters and dual-index barcodes were added using Illumina Nextera XT Index Kit. In preparation for sequencing on Illumina MiSeq, adapter-ligated amplicons were subjected to standard Illumina library denaturing and sample loading protocol using MiSeq Reagent Kit v3 (600 cycles). Paired-end sequencing was performed to cover the entire length of the amplicon with insert size of 200 bp to 300 bp.

Paired-end sequencing data were first assembled using paired-end assembler PANDAseq (see e.g., Masella et al., 2012) to obtain complete amplicons. Quality control (QC) was then performed on identified amplicons, where each amplicon was checked for no insertion or deletion of sequences and no stop codons, each HVR sequence was allowed to carry only up to one NNK mutation and no non-NNK mutation. Position weight matrices were generated by calculating the frequency of all mutations of every randomized position. Enrichment ratios for each mutation were calculated by dividing the frequency of a given mutation at a given position in the sorted sample with the frequency of the very same mutation in the unsorted sample, as described previously (Koenig et al., 2015). The HVR-L and H region mutations of h10G1 identified by NGS as resulting in improved binding to hu-CD96 and cy-CD96 are summarized in Table 15 (below).

TABLE 15

HVR-L and HVR-H mutations of h10G1 with high affinity binding to hu-CD96 and cy-CD96

HVR-L1

D28A, D28E, D28G, D28H, D28K, D28N, D28P, D28Q, D28S, D28T
Y30F
R31K, R31Q
L33I, L33M, L33V

HVR-L2

S52E
D53E, D53K, D53Q
S54H, S54L, S54R, S54V
I55V

CDR-L3

L89G, L89M, L89Q
S93A, S93E, S93Q, S93V
Y96F

HVR-H1

T30A, T30D, T30E, T30G, T30H, T30K, T30M, T30N, T30Q, T30R, T30S
T31D, T31E, T31G, T31H, T31N, T31Q, T31S
Y32F, Y32M, Y32Q,
M34I, M34L, M34V

HVR-H2

D53E
S54T

HVR-H3

N95M
N100bF, N100bH, N100bY

Example 7: In Vitro Assays of Anti-CD96 Antibodies

This example illustrates cell-based assays used to characterize the functional activity of the anti-CD96 antibodies described in the previous Examples.

Binding Affinity Determination

To determine the binding affinity to hu-CD96 and cy-CD96 at 37° C. of the recombinant anti-CD96 IgGs, SPR measurement with a BIACORE™ 8K instrument was performed. Briefly, a 1:4 dilution of Biotin CAPture Reagent (GE Healthcare) into HBS-EP buffer (0.01 M HEPES pH 7.4, 0.15 M NaCl, 3 mM EDTA, 0.005% Surfactant P20) was applied to the chip at 2 µL/min flow rate. For the kinetics measurements, 20 nM biotinylated hu-CD96-Fc and cy-CD96-Fc was captured at 10 µL/min to achieve ~50 response units in the second flow cell (FC2). FC1 was kept as a reference. Next, 4-fold serial dilutions of IgG in HBS-P buffer (0.01 M HEPES pH 7.4, 0.15 M NaCl, 0.005% surfactant P20) from low (3.125 nM) to high (200 nM) concentration were injected (flow rate: 10 µL/min) at 37° C. The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) value was calculated as the ratio of $k_{off}/k_{on}$. The BIACORE® determined binding affinity values are summarized in Table 16 (below).

TABLE 16

Binding affinity of anti-CD96 IgGs binding to hu-CD96 and cy-CD96

| Antibody | hu-CD96 @ 37° C. | | | cy-CD96 @ 37° C. | | |
|---|---|---|---|---|---|---|
| | On-rate $k_{on}$ (1/Ms) | Off-rate $k_{off}$ (1/s) | $K_D$ (nM) | On-rate $k_{on}$ (1/Ms) | Off-rate $k_{off}$ (1/s) | $K_D$ (nM) |
| mAb1.v7.NGS8 | $1.29 \times 10^5$ | $1.99 \times 10^{-5}$ | 0.15 | $4.15 \times 10^5$ | $6.06 \times 10^{-4}$ | 1.46 |
| mAb1.v7.NGS9 | $2.66 \times 10^5$ | $5.42 \times 10^{-5}$ | 0.2 | $2.55 \times 10^5$ | $7.34 \times 10^{-4}$ | 2.88 |
| mAb1.v7.NGS10 | $1.44 \times 10^5$ | $1.84 \times 10^{-6}$ | 0.01 | $7.67 \times 10^5$ | $3.74 \times 10^{-4}$ | 0.49 |
| mAb1.v7.NGS11 | $1.73 \times 10^5$ | $1.38 \times 10^{-5}$ | 0.08 | $3.38 \times 10^5$ | $5.13 \times 10^{-4}$ | 1.52 |
| h10G1 | $6.12 \times 10^5$ | $3.93 \times 10^{-4}$ | 0.64 | $6.99 \times 10^6$ | $7.89 \times 10^{-3}$ | 1.13 |
| NK92.39 | $8.44 \times 10^4$ | $1.2 \times 10^{-3}$ | 14.2 | no binding | no binding | no binding |

Binding to Hu-CD96 Isoforms 1 and 2 Expressed on Cells

Only isoform 2 of hu-CD96 was used in the above described in vitro binding affinity experiments. To examine binding of anti-CD96 antibodies to the two distinct isoforms of hu-CD96 expressed on cells, we used HEK293T or CHO cells transiently or stably expressing hu-CD96 and FACS analysis. Only isoform 2 of hu-CD96 was used in the above described in vitro binding affinity experiments. In this experiment, both isoform 1 and isoform 2 of hu-CD96 were tested.

Isoform 1 of hu-CD96 (Origene, catalog #RC213845) was transiently expressed in HEK293T cells following standard lipofectamine or Fugene transfection protocol. CD96-expressing 293 Ts were incubated with antibodies for 20 minutes at 4° C. Cells were washed, and binding was detected by incubation with anti-mouse IgG-FITC (Biolegend, catalog #406001) for 20 minutes at 4° C. Cell binding was analyzed by flow cytometry with a CytoFLEX (Beckman Coulter). Binding curves were calculated as a percentage of cells positive for bound antibody.

As shown by the results in Table 17 (below), the anti-CD96 antibodies, mAb1.v7, 10G1, 7E5, and 9H4 bind to HEK293T-CD96 (iso1) cells dose-dependently and potently. Control antibody muIgG1 did not show any binding above background.

TABLE 17

Anti-CD96 binding to HEK293T-CD96 (isoform 1) cell binding (% positive)

| Antibody (nM) | mAb1.v7 | 10G1 | 7E5 | 9H4 | muIgG1 |
|---|---|---|---|---|---|
| 50 | 61.0 | 56.1 | 52.1 | 57.8 | 0.75 |
| 10 | 48.8 | 53.4 | 47.4 | 48.4 | 0.48 |
| 2 | 27.3 | 48.1 | 37.1 | 28.5 | 0.49 |
| 0.4 | 12.2 | 34.6 | 20.4 | 13.9 | 0.49 |
| 0.08 | 0.8 | 16.5 | 8.5 | 1.5 | 0.41 |
| 0.016 | 0.5 | 4.4 | 1.0 | 0.5 | 0.41 |
| $EC_{50}$ (nM) | 2.6 | 0.24 | 0.71 | 2.1 | |

Isoform 2 of hu-CD96 (DNA construct: Origene, catalog #RC221005) was expressed on a single-cell-clone-derived CHO stable cell line. Binding of the anti-CD96 antibodies to the CHO cells were determined as described above with isoform 1 of hu-CD96.

As shown in Table 18 (below), the anti-CD96 antibodies mAb1.v7, 10G1, 7E5, 9H4, 14D3, and 1G8 bind to the isoform 2 of CD96 expressed on CHO cells dose-dependently and potently. By comparison, NK92.39 (Fuchs et al., 2004; Biolegend catalog #338405) bound the cells with slightly higher $EC_{50}$ and a lower maximal level of binding. The control antibody muIgG1 did not show any binding above background.

TABLE 18

CHO-CD96 (isoform 2) cell binding (% positive)

| Antibody (nM) | mAb1.v7 | 10G1 | 7E5 | 9H4 | 14D3 | 1G8 | NK92.39 | muIgG1 |
|---|---|---|---|---|---|---|---|---|
| 50 | 44.1 | 39.8 | 58.9 | 46.2 | 42.1 | 34.8 | 22.0 | 0.42 |
| 10 | 44.8 | 39.2 | 56.1 | 46.1 | 44.4 | 35.3 | 21.5 | 0.18 |
| 2 | 42.4 | 34.9 | 53.3 | 44.2 | 38.1 | 26.2 | 15.8 | 0.27 |
| 0.4 | 17.7 | 25.0 | 44.1 | 24.1 | 24.1 | 7.1 | 4.0 | 0.14 |
| 0.08 | 1.4 | 9.4 | 24.6 | 3.1 | 6.4 | 0.2 | 0.2 | 0.11 |
| 0.016 | 0.4 | 0.4 | 3.6 | 0.3 | 0.3 | 0.0 | 0.1 | 0.06 |
| 0.0032 | 0.5 | 0.1 | 0.1 | 0.3 | 0.1 | 0.1 | 0.1 | 0.03 |
| $EC_{50}$ (nM) | 0.52 | 0.23 | 0.11 | 0.38 | 0.33 | 1.04 | 1.15 | |

Binding to Human and Cynomolgus Monkey PBMCs

The ability of the anti-CD96 antibodies to bind primary immune cells from human and cynomolgus monkey with lower level of receptor expression was measured. Human PBMCs (StemCell Technologies, catalog #70025) and cynomolgus monkey PBMCs (Primate Biologicals, catalog #CM-MC) were incubated with human TruStain FcX (Biolegend, catalog #422302) for 10 minutes at 4° C., followed by incubation with an anti-CD96 antibody for 20 minutes at 4° C. Cells were washed and the anti-CD96 antibody binding was detected by incubation with anti-mouse IgG-PE (Thermo Fisher, catalog #M30204) or anti-human IgG (Fab) 2-PE (Thermo Fisher, catalog #H10104) for 20 minutes at 4° C. Cells were washed, and immune subtypes were labeled with anti-CD3 (BD, catalog #557705), anti-CD4 (Biolegend, catalog #317424) and anti-CD8 (BD, catalog #557760) for 20 minutes at 4° C. Cell binding was analyzed by flow cytometry with a CytoFLEX (Beckman Coulter). Binding curves were calculated as a percentage of cells positive for bound antibody in the cell type of interest.

As shown in Table 19 (below), the anti-CD96 antibodies mAb1.v7.NGS8, mAb1.v7.NGS9, mAb1.v7.NGS10, mAb1.v7.NGS11, and h10G1 bound to primary human and cynomolgus monkey PBMC immune cells dose-dependently and potently. In comparison, the NK92.39 antibody (Fuchs et al., 2004; Biolegend catalog #338405) only bound to human PBMC but not to cynomolgus monkey PBMC. This is consistent with NK92.39's lack of binding to cy-CD96D1 D3 protein as shown in biochemical binding measurements. The negative control antibodies hu-IgG1 and mu-IgG1 did not show any binding above background.

TABLE 19

Human PBMC and Cynomolgus Monkey PBMC cell binding

| Antibody (nM) | mAb1.v7.NGS8 | mAb1.v7.NGS9 | mAb1.v7.NGS10 | mAb1.v7.NGS11 | h10G1 | NK92.39 | Hu-IgG1 | Mu-IgG1 |
|---|---|---|---|---|---|---|---|---|
| Human PBMC cell binding (% positive) | | | | | | | | |
| 80 | 97.8 | 97.8 | 97.7 | 97.2 | 88.7 | 91.9 | 3.10 | 2.34 |
| 16 | 96.2 | 97.1 | 97.1 | 96.7 | 81.4 | 94.3 | 4.61 | 2.05 |
| 3.2 | 92.3 | 95.1 | 93.8 | 94.2 | 64.4 | 76.7 | 4.67 | 1.42 |
| 0.64 | 89.3 | 90.8 | 88.8 | 89.7 | 53.5 | 27.4 | 4.04 | 1.50 |
| 0.128 | 64.2 | 64.7 | 66.7 | 61.1 | 39.1 | 2.0 | 3.98 | 1.09 |
| 0.0256 | 22.0 | 22.5 | 16.9 | 11.6 | 14.6 | 0.9 | 5.50 | 1.48 |
| 0.00512 | 8.6 | 8.2 | 6.1 | 5.4 | 5.4 | 1.3 | 5.29 | 0.98 |
| $EC_{50}$ (nM) | 0.072 | 0.071 | 0.069 | 0.083 | 0.28 | 1.22 | | |
| Cynomolgus Monkey PBMC cell binding (% positive) | | | | | | | | |
| 80 | 74.5 | 73.8 | 75.2 | 81.9 | 68.3 | 4.9 | 2.36 | 1.90 |
| 16 | 77.2 | 76.1 | 78.5 | 80.8 | 66.1 | 5.4 | 0.64 | 1.77 |
| 3.2 | 75.5 | 77.9 | 76.7 | 78.4 | 58.1 | 5.2 | 1.15 | 0.95 |
| 0.64 | 70.7 | 71.0 | 73.1 | 74.3 | 51.2 | 4.7 | 0.59 | 1.07 |
| 0.128 | 45.3 | 49.4 | 64.6 | 63.5 | 38.2 | 5.2 | 0.31 | 0.83 |
| 0.0256 | 11.6 | 19.7 | 37.2 | 41.0 | 16.8 | 5.0 | 0.57 | 1.00 |
| 0.00512 | 5.1 | 7.1 | 9.5 | 10.4 | 7.4 | 4.5 | 0.41 | 0.76 |
| $EC_{50}$ (nM) | 0.097 | 0.073 | 0.024 | 0.025 | 0.12 | 1.1 | | |

Binding to Hu-CD96-CHO Cells and Blocking of CD155-Fc Binding

CHO cells stably expressing isoform 2 of hu-CD96 (Origene, catalog #RC221005) were incubated with anti-CD96 antibodies for 20 minutes at 4° C. The cells were washed, and then incubated with 10 nM human CD155-Fc-FLAG for 30 minutes at 4° C. Cells were washed, and then human CD155-Fc-FLAG binding was detected by incubation with anti-FLAG-APC (Columbia Biosciences, catalog #D3-1718-1MG) for 20 minutes at 4° C. Cell binding was analyzed by flow cytometry with a CytoFLEX (Beckman Coulter). CD155 binding is represented as median fluorescence intensity (MedFI).

As shown in Table 20 (below), the anti-CD96 antibodies, mAb1.v7.NGS8, mAb1.v7.NGS9, mAb1.v7.NGS10, mAb1.v7.NGS11, and h10G1 inhibited soluble hu-CD155 binding to CD96-expressing CHO cells dose-dependently and potently. The antibody NK92.39 (Fuchs et al., 2004; Biolegend catalog #338405) inhibited receptor binding similarly. The negative control antibodies, hu-IgG1 and mu-IgG1 did not show any inhibition.

TABLE 20

Human CD155-Fc binding to CD96-CHOs (MedFI)

| Antibody (nM) | mAb1.v7.NGS8 | mAb1.v7.NGS9 | mAb1.v7.NGS10 | mAb1.v7.NGS11 | h10G1 | NK92.39 | Hu-IgG1 | Mu-IgG1 |
|---|---|---|---|---|---|---|---|---|
| 100 | 4181 | 4145 | 5113 | 4206 | 5120 | 5053 | 51722 | 75952 |
| 20 | 4287 | 4256 | 4936 | 4460 | 4857 | 5039 | 57317 | 71606 |
| 4 | 4958 | 6098 | 4936 | 4864 | 4857 | 5039 | 63058 | 71606 |
| 0.8 | 23616 | 32194 | 23615 | 23650 | 5871 | 40338 | 58268 | 66575 |
| 0.16 | 52891 | 54650 | 54073 | 51858 | 21243 | 62592 | 59441 | 64380 |
| 0.032 | 47801 | 53011 | 57740 | 57672 | 52051 | 69262 | 52821 | 65374 |
| 0.0064 | 49207 | 56593 | 55923 | 63569 | 65668 | 64104 | 47697 | 64347 |
| $IC_{50}$ (nM) | 0.76 | 0.91 | 0.57 | 0.46 | 0.06 | 0.91 | | |

Primary Human NK Cell Assay

Functional activity of the anti-CD96 antibodies was tested on primary human natural killer (NK) cells. Primary human peripheral blood NK cells (StemCell Technologies, catalog #70036) were incubated with antibodies in complete media containing 100 µg/mL recombinant human IL-12 (VWR, catalog #10773-012) and 50 ng/mL recombinant human IL-18 (VWR, catalog #75791-086) in round bottom plates coated with 0.25 µg per well of CD155-huFc for 5 hours at 37° C. IFNγ in the supernatant was determined by ELISA (Thermo Fisher, catalog #88-7316-86).

As shown in Table 21 (below), the anti-CD96 antibodies, mAb1.v7.NGS10 and h10G1 increased IFNγ secretion from NK cells dose-dependently and potently. NK92.39 (Fuchs et al., 2004; Biolegend catalog #338405) also enhanced IFNγ secretion but the effect was weaker and less potent (61% of maximal efficacy of h10G1).

TABLE 21

Human NK cell IFNγ secretion (fold over background, n = 5/condition)

| Antibody (nM) | mAb1.v7.NGS10 | h10G1 | hu-IgG1 | NK92.39 | mu-IgG1 |
|---|---|---|---|---|---|
| 250 | 1.87 | 1.87 | 1.12 | 1.62 | 1.05 |
| 50 | 2.05 | 2.21 | 1.04 | 1.68 | 0.96 |
| 10 | 1.94 | 2.19 | 1.03 | 1.39 | 0.91 |
| 2 | 2.12 | 2.08 | 1.07 | 1.27 | 1.14 |
| 0.4 | 1.81 | 1.96 | 1.23 | 0.69 | 1.00 |
| 0.08 | 1.36 | 1.38 | 1.51 | 1.38 | |
| 0.016 | 1.24 | 1.13 | 1.01 | | |
| 0.0032 | 1.00 | 1.00 | 1.33 | | |
| $EC_{50}$ (nM) | 0.084 | 0.112 | | 5.53 | |

Primary Human NK Cell Assay in the Presence of Anti-CD226

Functional activity of the anti-CD96 antibodies in triggering IFNγ secretion was also measured in the presence of the antagonistic anti-CD226 antibody DX-11 (Abcam catalog #ab33397). Primary human peripheral blood NK cells were incubated with indicated anti-CD96 antibodies, control isotype antibodies, or anti-CD226 antibody (DX-11) in complete media containing 100 µg/ml recombinant human IL-12 and 50 ng/ml recombinant human IL-18 in plates coated with 0.25 µg per well of CD155-Fc for 5 hours at 37° C. IFNγ concentration in the supernatant was determined by ELISA. Each condition was tested in 5 biological replicates. As shown in FIG. 3, the IFNγ secretion triggered by the anti-CD96 antibodies mAb1.v7.NGS8 and h10G1 was completely elimination by the presence of the antagonistic anti-CD226 antibody DX-11. The results of this experiment thus demonstrate that the effect of the IFNγ stimulatory effect of the anti-CD96 antibodies is CD226-dependent.

Primary Human CD4+ T Cell Assay

Figure 4A:
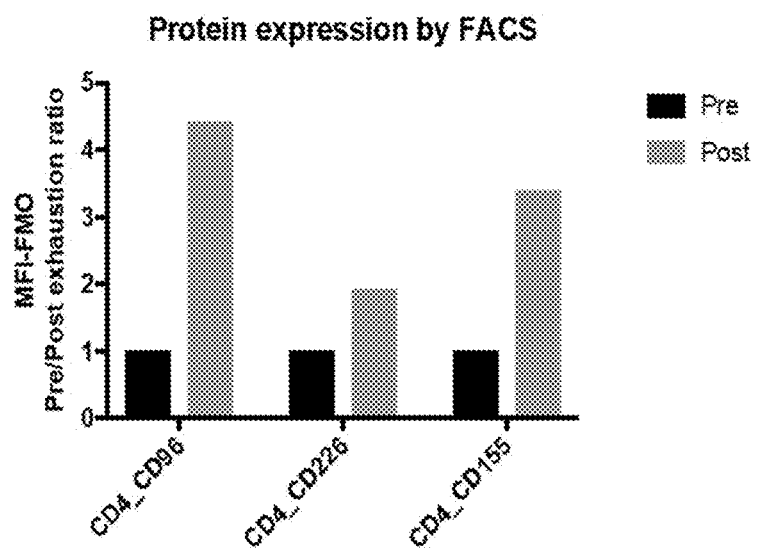
FIG. 4A and FIG. 4B depict plots of the activity of the anti-CD96 antibodies in primary human CD4+ T cells upon treatment with IL-2 and PHA as described in Example 7.
Figure 4B:
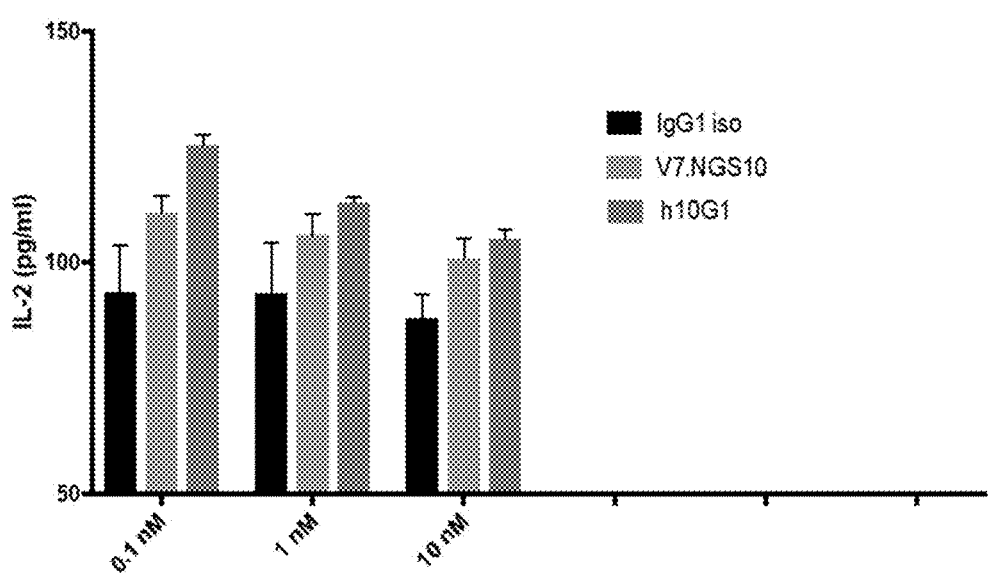

Functional activity of the anti-CD96 antibodies was also tested on primary human CD4+ T cells that were chronically stimulated in vitro for 7 days with 4 ng/ml IL-2 and 2 ug/ml PHA. (A) Treated cells were stained with fluorochrome-conjugated anti-CD96 (clone 6F9), anti-CD226 (clone 11A8), anti-CD155 (clone 2H7CD155), isotype control Abs and live/dead staining dye. Surface expression level were analyzed by flow cytometry with a CytoFLEX (Beckman Coulter). As shown in FIG. 4A, surface expression levels of CD96, CD226, and CD155 were upregulated with IL2 and PHA treatment. CD96 level was upregulated 4.4-fold. (B) These chronically stimulated CD4+ T cells were incubated with anti-CD96 antibodies in complete media for 5 hours at 37° C. in plates previously coated with 10 µg/ml of anti-CD3 (UCHT1) and 10 µg/ml of CD155-huFc. Secreted IL-2 in media was measured by ELISA (Invitrogen Cat #88-7025-88). As shown in FIG. 4B, IL2 secretion was increased by addition of anti-CD96 antibodies mAb1.v7.NGS10 and h10G1 at concentrations as low as 0.1 nM. This effect was seen in at least 3 different donors. Dose titration of mAb1.v7.NGS10 demonstrated an $EC_{50}$ of 53 µM for mAb1.v7.NGS10 (data not shown).

Primary Human PBMC Assay

Figure 5A:
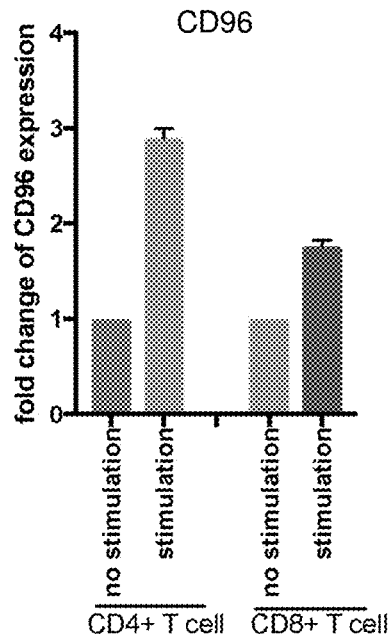
FIG. 5A, FIG. 5B, and FIG. 5C depict plots of the effect of the anti-CD96 antibodies in primary human peripheral blood mononuclear cells (PBMCs) upon anti-CD3 and anti-CD28 treatment as described in Example 7.
Figure 5B:
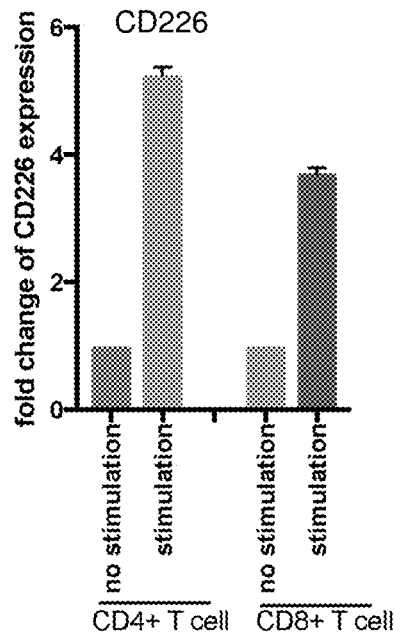
Figure 5C:
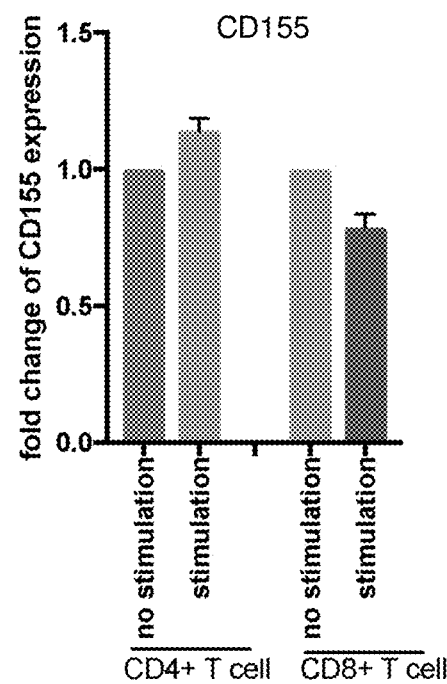

Functional activity of the anti-CD96 antibodies was also tested on primary human peripheral blood mononuclear cells (PBMCs). $2\times10^5$/well human PBMCs were plated in 96-well round-bottom plate. 10 µg/ml mAb1.v7.NGS10 or h10G1 or huIgG1(E−) isotype control Abs were added for 30 min. The cells were then stimulated with 0.1 µg/ml anti-CD3 Ab and 1 µg/ml anti-CD28 Ab for three days. (A) Cells were stained with fluorochrome-conjugated anti-CD3 (OKT3), anti-CD4 (OKT4), anti-CD8 (SK1), anti-CD96 (6F9), anti-CD226 (11A8), anti-CD155 (2H7CD155), isotype control Abs (MOPC21) and live/dead staining dye. Surface expression levels were analyzed by flow cytometry with a CytoFLEX (Beckman Coulter). As shown in FIG. 5A and FIG. 5B surface expression levels of CD96 and CD226 were upregulated with anti-CD3 and anti-CD28 treatment. However, as shown in FIG. 5C, CD155 level was not dramatically changed.

Figure 6:
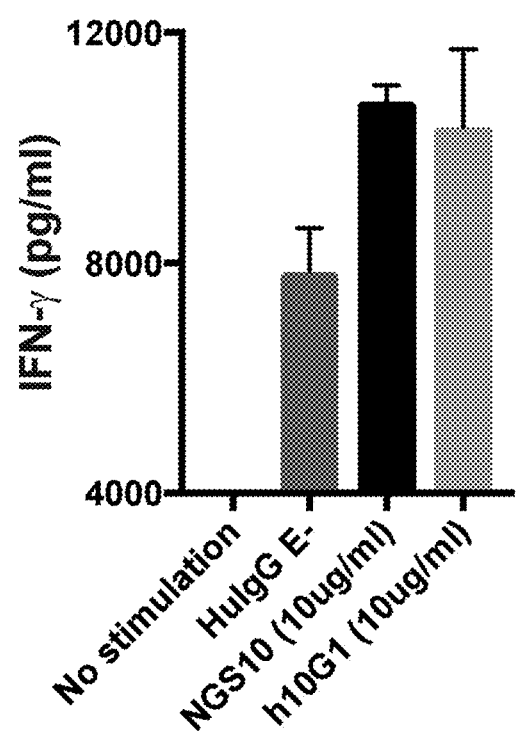
FIG. 6 depicts plots of IFNγ secretion from PBMCs upon addition of anti-CD96 antibodies mAb1.v7.NGS10 and h10G1 as described in Example 7.

IFNγ secretion into the supernatant also was analyzed by ELISA (Invitrogen Cat #88-7316-88). As shown in FIG. 6, IFNγ secretion was increased by addition of anti-CD96 antibodies mAb1.v7.NGS10 and h10G1, and this effect was seen in at least 3 different donors. Dose titration of h10G1 demonstrated an $EC_{50}$ of 23 µM (data not shown).

Example 8: In Vivo Tumor Models to Evaluate Activity of Anti-CD96 Antibodies

This example illustrates in vivo tumor model studies of the functional activity of a surrogate anti-mo-CD96 antibody 3.3.

A. Validation of Surrogate Anti-Mo-CD96 Antibody 3.3 (Antigen Binding, Blocking)

Purified anti-mo-CD96 from clone 3.3 (hereinafter "3.3 antibody") was obtained from BioLegend (Part #93137). IgG was coupled to amine-reactive OCTET sensors (ForteBio) at 20 mg/mL in sodium acetate pH 5.0 using EDC/NHS chemistry according to the manufacturer's protocol. Recombinant mo-CD96 ectodomain (M1-M536, ThermoFisher) was diluted into PBS containing 0.02% v/v Tween 20 and evaluated for binding to mAb2-coated sensors at concentrations of 200 nM, 50 nM, 12.5 nM, 3.125 nM and 0.78 nM. The resulting sensograms were fit with a 1:1 binding model to yield a $K_D$ of 0.75 nM.

The 3.3 antibody was also tested for its ability to bind mo-CD96 expressed on cells and block binding to soluble mouse CD155 protein. CHO cells stably expressing mo-CD96 (Origene, catalog #MR209314) were incubated with the 3.3 antibody for 20 minutes at 4° C. Cells were washed, and then incubated with 10 nM mouse CD155-huFc for 30 minutes at 4° C. Cells were washed, and then CD155-huFc binding was detected by incubation with anti-human IgG-APC (Biolegend, catalog #409306) for 20 minutes at 4° C. Cell binding was analyzed by flow cytometry with a Cyto-FLEX (Beckman Coulter). Antibody 3.3 inhibited mouse CD155 binding with an $IC_{50}$ of 4.8 nM.

The quality of all of the antibodies used for in vivo experiments were checked using HPLC-SEC, A280, and mass-spec (intact reduced, non-reduced). In addition, endotoxin level was determined and acceptable criteria is set at <0.5 EU/mg.

B. Subcutaneous Tumor Models—EMT6 and B16F10

A summary of the subcutaneous tumor model studies is shown in Table 22 (below).

TABLE 22

Summary of in vivo subcutaneous tumor study protocol

| Model | Strain (Vendor) | Cell number | Tumor Volume at randomization | Dosing |
|---|---|---|---|---|
| EMT6 | Balb/cAnHsd (Envigo) | $4 \times 10^5$ | 75-120 mm³ (on Day 11) | 10 mg/kg of each antibody on days 11, 14, 18, 21, 25, 28, 32 |
| B16F10 | C57BL/6J (Jackson Labs) | $5 \times 10^4$ | 48-104 mm³ (on Day 12) | 10 mg/kg of each antibody on days 12, 15, 19, 22, 26, 29, 33 |

Reagents: InVivoPlus Rat IgG2a Isotype control (3.38 mg/ml, Clone: 2A3, Catalog #BP0089, Lot #627416N1) was obtained from BioXcell. ULTRA-LEAF™ Purified Rat IgG1 Isotype control (3.3 mg/ml, Clone: RTK2071, Lot #6252227) was obtained from BioLegend. InVivoPlus anti-mouse PD-1 (3.1 mg/ml, Clone: RMP1-14, Catalog #: BP0146, Lot #66541751) was obtained from BioXcell. ULTRA-LEAF™ Purified anti-mo-CD96 (3.3 mg/ml, Clone: 3.3, Part #93137, Lot #6252222) was obtained from BioLegend.

Animals and husbandry: Female mice (7-9 weeks of age) were used in the studies. The animals were fed irradiated Harlan 2918.15 Rodent Diet and water ad libitum. Animals were ear tagged for identification purposes and shaved on the left dorsal flank area in preparation of cell implantation. Animals were housed in Innovive disposable ventilated caging with corn cob bedding at 60 complete air changes per hour. The environment was controlled to a temperature range of 70°±2° F. and a humidity range of 30-70%. All procedures carried out in this experiment were conducted by skilled personnel in compliance with all the laws, regulations and guidelines of the National Institutes of Health (NIH) and with the approval of Explora Bio Labs' Animal Care and Use Committee (San Diego, CA).

Cell preparation and implantation: EMT6 and B16F10 cells were obtained from ATCC. EMT6 cells were cultured and expanded in Waymouth's MB 752/1 Medium with 2 mM L-glutamine, 15% fetal bovine serum (FBS), and 1% 100× Penicillin/Streptomycin (PS). B16F10 cells were cultured and expanded in Dulbecco's Modified Eagles Medium (DMEM) with 10% fetal bovine serum (FBS), and 1% 100× Penicillin/Streptomycin (PS). The growth environment was maintained in an incubator with a 5% $CO_2$ atmosphere at 37° C. When expansion was complete, the cells (passage 3) were trypsinized using a 0.25% trypsin-EDTA solution. The cells were then washed and counted. Pre-implantation cell viability was 92%-94%. The cells were placed in a 1:1 solution of Dulbecco's Phosphate Buffered Saline (DPBS) and Matrigel (BD Biosciences, Catalog #354234) Test animals were sterilized at the implantation site with an alcohol prep pad and were implanted subcutaneously on Day 0 in 0.1 mL using a 25-gauge needle and 1 mL syringe. $4 \times 10^5$ EMT6 cells were implanted in Balb/c mice.

Measurements and antibody treatment: Tumors were allowed to grow and were then randomized into study groups. Equal distribution of tumor volumes was ensured by using the matched distribution method in StudyLog Study Director version 3.1.399.8. Mice were distributed to ensure that the mean body weights for all groups were within 10% of the overall mean tumor burden for the study population. Mice received twice weekly i.p. injections 10 mg/kg of each antibody treatment for 3 weeks and tumor volumes were monitored. Group 1 received IgG2a and IgG1 isotype control antibodies, group 2 received anti-PD1 and IgG1 isotype control antibodies, and group 3 received anti-PD1 and anti-CD96 antibodies.

Assessment of side effects: All animals were observed for clinical signs of distress or toxicity at least once daily. Animals were weighed once per week. If an individual animal showed overt signs of distress or 15% body weight loss, the individual animal was weighed daily. Animals were euthanized if body weight loss was in excess of 20% or other clinical signs that warranted euthanasia. Individual animals were euthanized when their tumor volume reached or exceeded 2000 mm³.

Results—Subcutaneous EMT6 and B16F10 Tumor Studies

Anti-tumor efficacy of anti-CD96 antibody 3.3 was evaluated in the EMT6 subcutaneous syngeneic mouse model. As shown in Table 23 (below), the combination treatment of an anti-PD1 and an anti-CD96 improved animal survival compared to single agent treatment with anti-PD1.

TABLE 23

EMT6 subcutaneous syngeneic mice with tumors <2000 mm³

| Treatment group | Day 32 | Day 38 | Day 56 |
|---|---|---|---|
| Control (Rat IgG2a control + Rat IgG1 control) | 11/15 (73%) | 3/15 (20%) | 0/15 (0%) |
| Anti-PD1 single agent treatment (Rat anti-PD1 + Rat IgG1 control) | 10/15 (66%) | 6/15 (40%) | 1/15 (7%) |
| Anti-PD1 + anti-CD96 combination (Rat anti-PD1 + Rat anti-CD96) | 14/15 (93%) | 11/15 (73%) | 6/15 (40%) |

Figure 7:
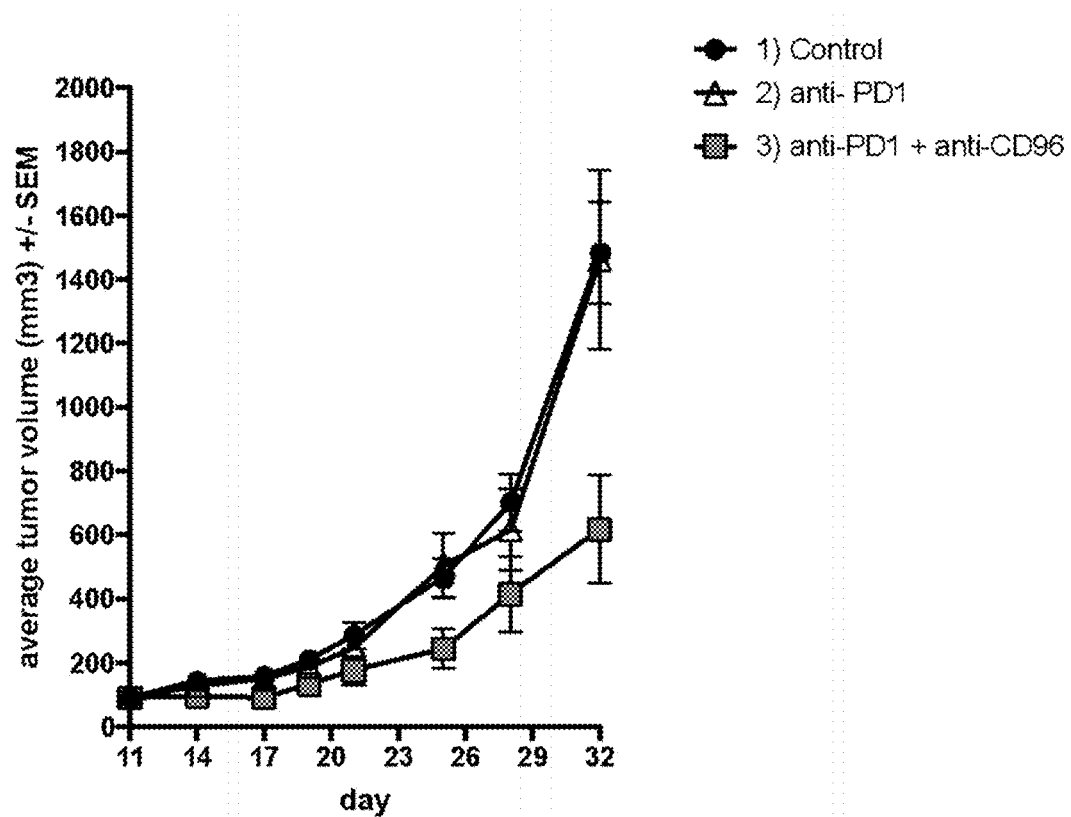
FIG. 7 depicts plots of average tumor volume of EMT6 syngeneic mouse model tumors in mice treated with control (IgG2a and IgG1 isotype control antibodies), anti-CD96 antibody 3.3 alone, or combination of anti-CD96 antibody 3.3 with anti-PD1 antibody RMP1-14.

Further, as shown in FIG. 7, the combination treatment with anti-PD1 and anti-CD96 decreased tumor volume in the EMT6 mouse model compared to single agent treatment with anti-PD1 or isotype control antibodies.

Anti-tumor efficacy of anti-CD96 antibody 3.3 also was evaluated in the B16F10 subcutaneous syngeneic mouse model. As shown in Table 24 (below) the combination treatment of anti-PD1 and anti-CD96 improved animal survival significantly compared to the single-agent treatment with anti-PD1 (p=0.02 for aPD1 v aPD1+aCD96 (Bonferroni adjusted)).

TABLE 24

B16F10 subcutaneous syngeneic mice with tumors <2000 mm³

| Treatment group | Day 26 | Day 31 | Day 35 |
|---|---|---|---|
| Control (Rat IgG2a control + Rat IgG1 control) | 6/15 (40%) | 0/15 (0%) | 0/15 (0%) |
| Anti-PD1 (Rat anti-PD1 + Rat IgG1 control) | 12/15 (66%) | 2/15 (13%) | 0/15 (0%) |
| Anti-PD1 + anti-CD96 (Rat anti-PD1 + Rat anti-CD96) | 14/15 (93%) | 7/15 (46%) | 1/15 (7%) |

Figure 8:
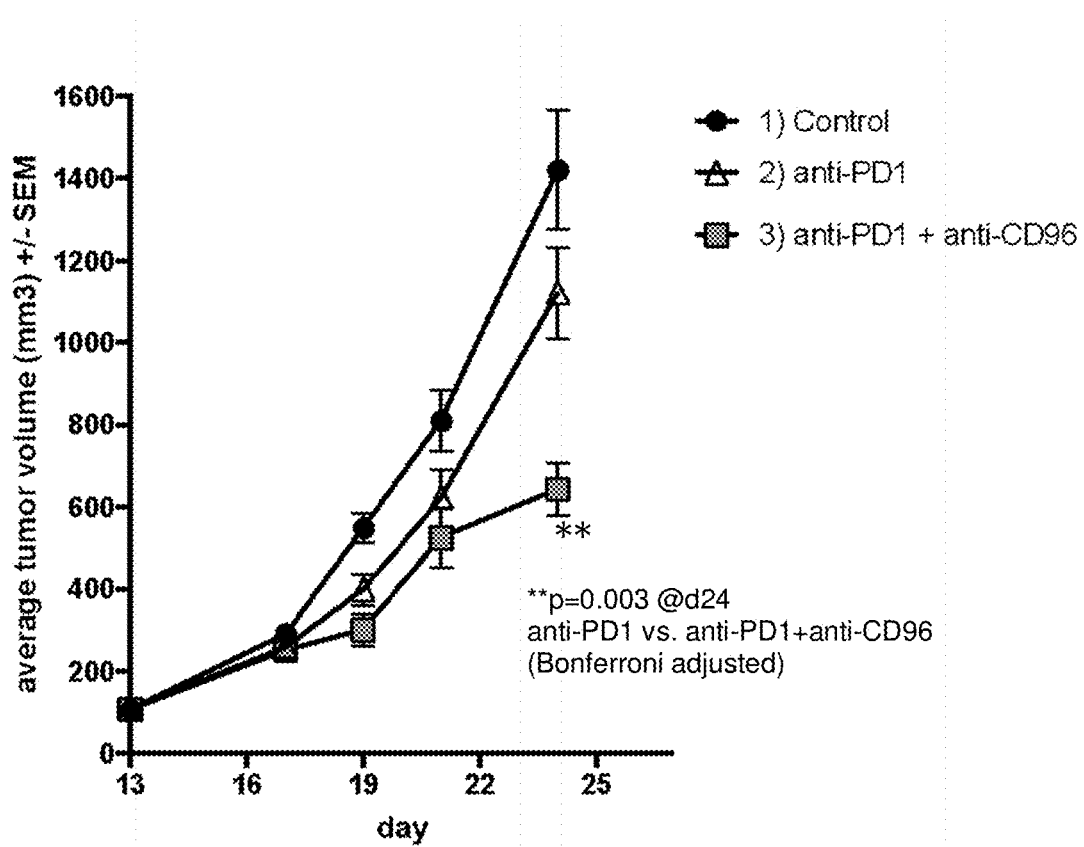
FIG. 8 depicts plots of average tumor volume of B16F10 syngeneic mouse model tumors in mice treated with control (IgG2a and IgG1 isotype control antibodies), anti-CD96 antibody 3.3 alone, or combination of anti-CD96 antibody 3.3 with anti-PD1 antibody RMP1-14.

Further, as shown in FIG. 8, the anti-PD1 and anti-CD96 combination treatment decreased tumor volume significantly in the B16F10 mouse model compared to the anti-PD1 single agent treatment or isotype control antibody treatment.

I.V. Lung Metastasis Model—B16F10

Anti-tumor efficacy of anti-CD96 antibody 3.3 was evaluated in the B16F10 i.v. lung metastasis model. Mice received 250 μg of each antibody via i.p. injection on Day 0 and Day 3 relative to implantation. Further materials and methods of the study are provided below.

Reagents: InVivoPlus Rat IgG2a Isotype control (7.8 mg/ml, Clone: 2A3, Catalog #: BP0089, Lot #627416N1) was obtained from BioXcell. ULTRA-LEAF™ Purified Rat IgG1 Isotype control (1.11 mg/ml, Clone: RTK2071, Part #: 92233, Lot #B231146) was obtained from BioLegend. InVivoPlus anti-mouse PD-1 (6.66 mg/ml, Clone: RMP1-14, Catalog #: BP0146, Lot #61461601) was obtained from BioXcell. InVivoPlus anti-mouse CTLA-4 (6.45 mg/ml, Clone: 9D9, Catalog #: BP0164, Lot #61981651) was obtained from BioXcell. ULTRA-LEAF™ Purified anti-mo-CD96 (2.66 mg/ml, Clone: 3.3, Part #: 93137, Lot #B231145) was obtained from BioLegend.

Animals and husbandry: Female Envigo C57BL/6 mice (C57BL/6NHsd) were used in this study. They were 6-7 weeks old on Day 1 of the experiment. The animals were fed irradiated Harlan 2918.15 Rodent Diet and water ad libitum. Animals were housed in Innovive disposable ventilated caging with corn cob bedding inside Biobubble® Clean Rooms that provide H.E.P.A filtered air into the bubble environment at 100 complete air changes per hour. All treatments and body weight determinations were carried out in the bubble environment. The environment was controlled to a temperature range of 70°±2° F. and a humidity range of 30-70%. All procedures carried out in this experiment were conducted in compliance with all the laws, regulations and guidelines of the National Institutes of Health (NIH) and with the approval of Molecular Imaging, Inc.'s Animal Care and Use Committee. Molecular Imaging, Inc. is an AAALAC accredited facility.

Cell preparation and implantation: B16F10 cells were obtained from ATCC and grown in Dulbecco's Modified Eagle Medium (DMEM) which was supplemented with 10% non-heat-inactivated Fetal Bovine Serum (FBS) and 1% 100× Penicillin/Streptomycin/L-Glutamine (PSG). The growth environment was maintained in an incubator with a 5% CO2 atmosphere at 37° C. When expansion was complete, the cells (passage 10) were trypsinized using 0.25% trypsin-EDTA solution. The pre-implantation cell viability was 95%. Test animals were implanted intravenously, via the lateral tail vein on Day 0 with $2.0\times10^5$ cells in 0.2 mL using a 27-gauge needle and syringe.

Sampling and lung metastasis counting: Whole blood and lungs were sampled from all mice on Day 14 after implantation. All mice were euthanized via over exposure to carbon dioxide. Whole blood was collected via cardiac puncture. Following collection, 60% of the blood collected was added K2EDTA coated Microtainers® and inverted several times to ensure thorough mixing of the blood and EDTA. The same volume (1:1 ratio) of Streck Cell Preservative™ was added to the tube. Lungs were excised, placed in a Petri dish and laid flat. Lungs were photographed on both the dorsal and ventral surfaces and discarded. Lung metastases were counted using Image J software (see e.g., Rasband, W. S., ImageJ, U. S. National Institutes of Health, Bethesda, Maryland, USA; available at: imagej.nih.gov/ij/, 1997-2016). Both ventral and dorsal surfaces were counted. All metastases that were ranging from a light grey to black colors were counted. In case of merged nodules, the best effort was made to distinguish the metastases and count as accurately as possible. If there were too many nodules leading to black regions, the tissue was noted as "Too many to count" (TMTC). Raw counts were then summed (ventral+dorsal surfaces) by animal and averaged by group. All "TMTC" lungs and lung without any metastases to count (0) were excluded from the final average calculation.

Assessment of side-effects: All animals were observed for clinical signs at least once daily. Animals were weighed on each day of treatment. Individual body weights were recorded 3 times weekly. Treatment-related weight loss in excess of 20% is generally considered unacceptably toxic. In this report, a dosage level is described as tolerated if treatment-related weight loss (during and two weeks after treatment) is <20%.

Results—B16F10 i.v. Lung Metastasis Model

Figure 9:
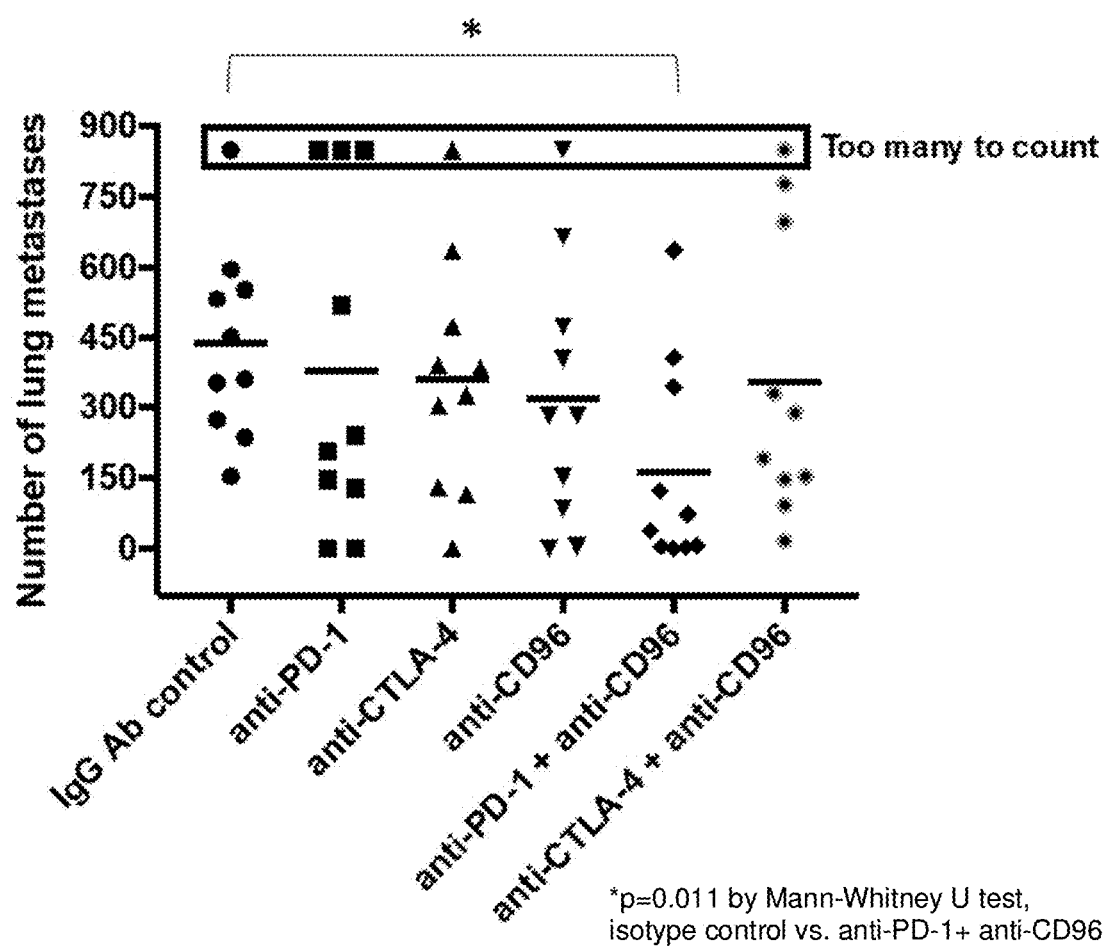
FIG. 9 depicts distributions of the number of metastases counted 14 days after implantation in B16F10 lung metastasis model mice following treatment with an anti-CD96 antibody, an anti-PD1 antibody, an anti-CTLA-4 antibody, each alone, as well as, the anti-CD96 in combination with each of the anti-PD1 antibody, and the anti-CTLA-4 antibody.

As shown in FIG. 9, the anti-PD-1+anti-CD96 combination treatment decreased the number of lung metastases significantly compared to isotype control antibody treatment when evaluated 14 days after implantation (p=0.011 by Mann-Whitney U test, comparing isotype control vs. anti-PD-1+anti-CD96).

Example 9: Design of a Bispecific Anti-CD96 Antibody

A bispecific antibody targeting both CD96 and another antigen target on NK or T cells, such as PD-1, TIGIT, LAG3, PVRIG, or KIR could also be used as an anti-tumor treatment. It is contemplated that a bispecific antibody comprising an anti-CD96 binding component of the present disclosure and another anti-tumor target binding component can be prepared with a common-light-chain manufacturing-friendly approach.

Example 10: Anti-CD96 Antibody Increases IFNγ and IL-2 Secretion from Patient Derived PBMCs Cancer patient PBMC assay: Functional activity of the anti-CD96 antibodies was tested on primary cancer patient PBMCs. Primary cancer patient PBMCs (Discovery Life Sciences) were incubated with antibodies in complete media containing 0.1 μg/mL anti-CD3 Ab (commercially available from Thermo Fisher) and 1 μg/mL anti-CD28 Ab (commercially available from Thermo Fisher) in 384 well plates for 72 hours at 37° C. IFNγ and IL-2 levels in the supernatant were determined by ELISA (kit commercially available from Thermo Fisher).

Figure 10A:
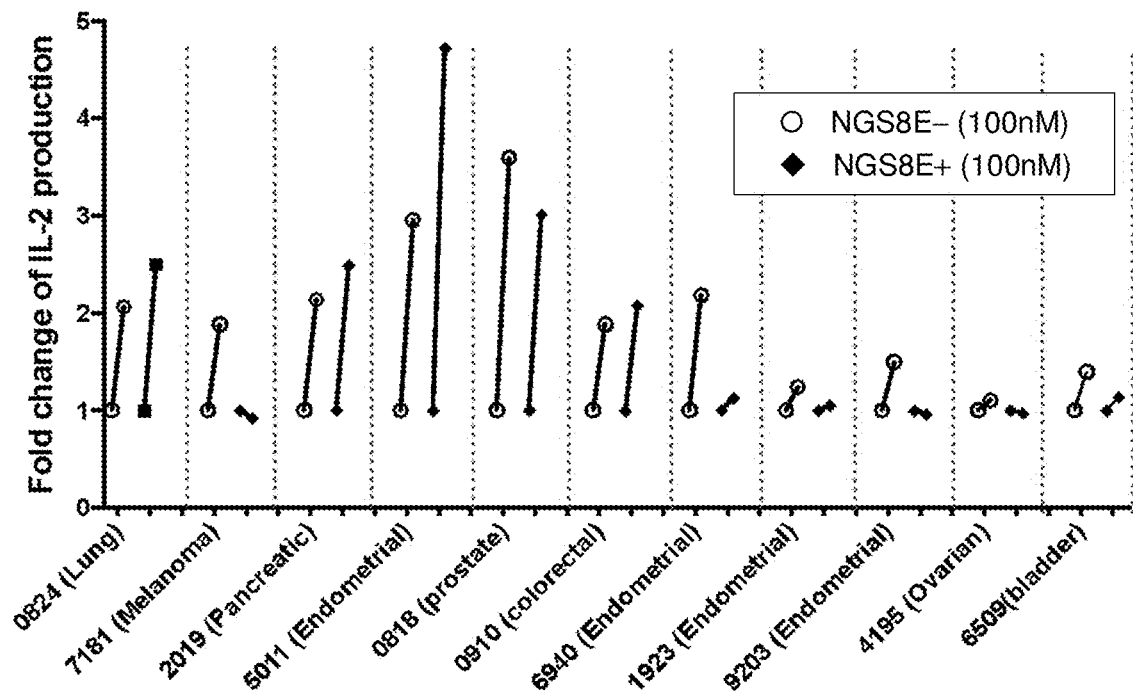
FIG. 10A and FIG. 10B depict the change in cytokine release after treatment of primary PBMC samples from patients with various cancers with anti-CD96 antibody, or an effectorless variant thereof.
Figure 10B:
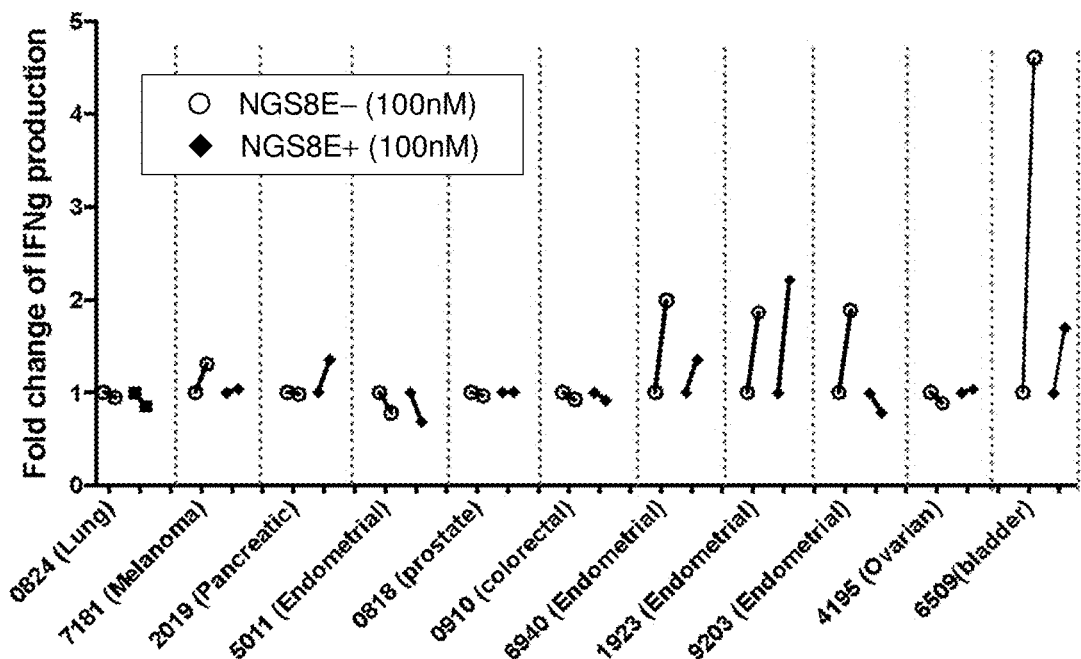

As shown in FIG. 10A, anti-CD96 antibody NGS8 increased PBMC secretion of IL-2 in samples derived from patients having various different cancer types. Specifically, FIG. 10A shows the fold change in IL-2 production, normalized to isotype control, in samples treated with 100 nM of either effector minus NGS8 ("NGS8E−"; human IgG1 with N297G mutation) or effector-containing NGS8 ("NGS8E+"; human IgG1 wildtype Fc). The first (left) marker of each data pair indicates the isotype control and the second (right) marker, linked by a line, indicates the fold-change from isotype control following treatment with the specified antibody. FIG. 10B shows the fold change in IFNγ production, normalized to isotype control, in samples in samples treated with 100 nM of either effector minus NGS8 (NGS8E−) or effector-containing NGS8 (NGS8E+) as assessed in the cancer patient PBMC assay. As above, the first (left) marker of each data pair indicates the isotype control and the second (right) marker, linked by a line, indicates the fold-change from isotype control following treatment with the specified antibody. NGS8E− antibody treatment significantly increased IFNγ production in four of eleven patient PBMC samples. Collectively, FIG. 10A and FIG. 10B demonstrate that treatment with the anti-CD96 antibody stimulates cytokine secretion, resulting in increases in IL-2 and/or IFNγ, in PBMC samples obtained from subjects with various different cancers.

Figure 11A:
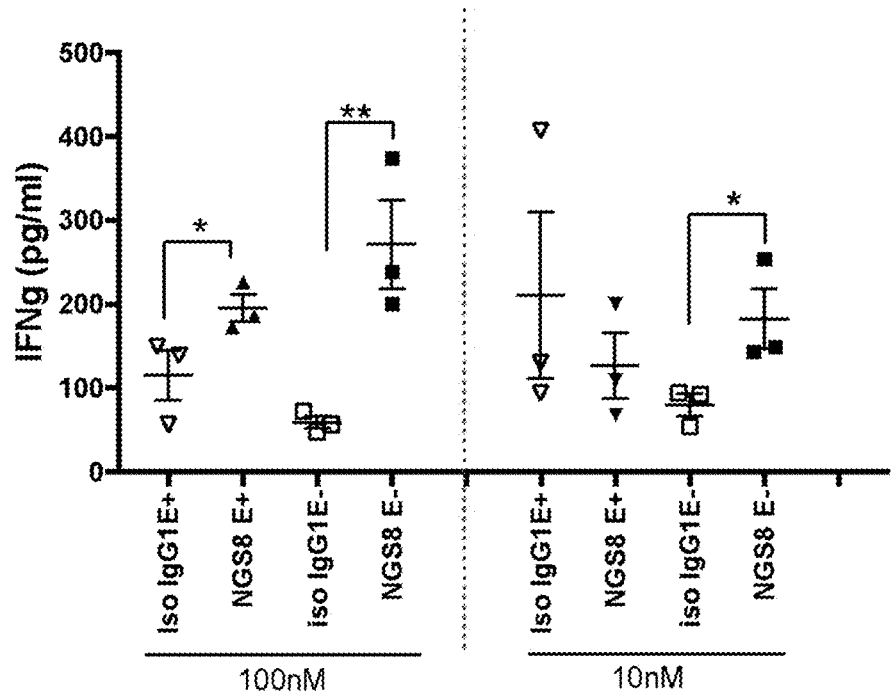
FIG. 11A and FIG. 11B depict the stimulation of cytokine secretion in primary PBMC samples collected from a bladder cancer patient and subsequently treated with anti-CD96 antibody, or an effectorless variant thereof.
Figure 11B:
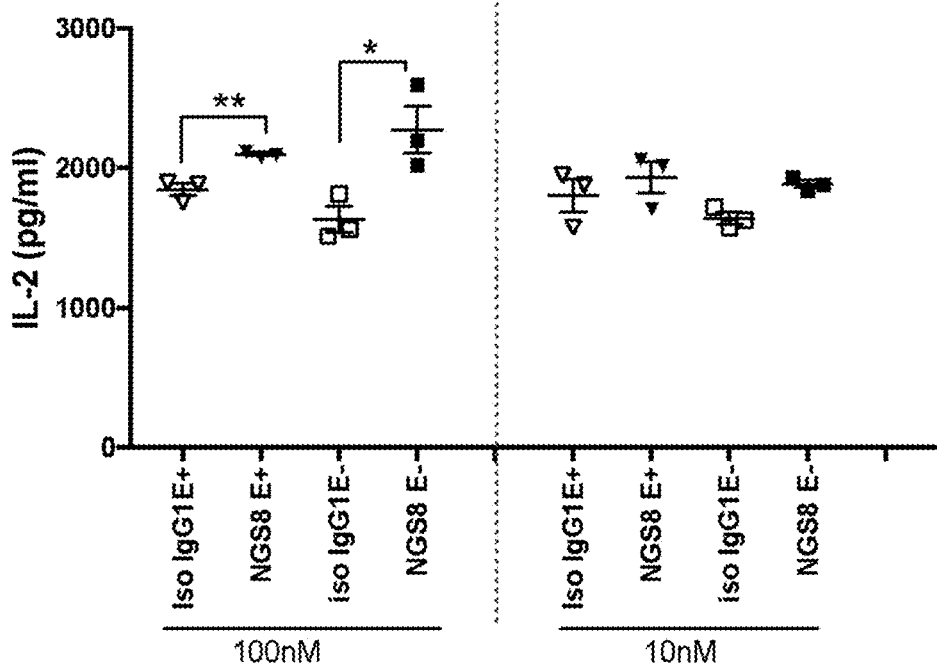

FIG. 11A and FIG. 11B further demonstrate stimulation of cytokine secretion in primary PBMCs collected from a bladder cancer (transitional cell carcinoma, NOS) patient. Specifically, the measured levels of IFNγ ("IFNg"; FIG. 11A) and IL-2 (FIG. 11B) are shown after treatment with 100 nM or 10 nM NGS8E+ or NGS8E−, relative to treatment with corresponding effector-containing (Iso IgG1E+) or effector-minus (Iso IgG1E−) isotype controls. Statistically significant increases (indicated with asterisks) in IFNγ were seen after 100 nM and 10 nM treatments and in IL-2 after the 100 nM treatment. These results further demonstrate the stimulation of cytokine secretion in cancer patient derived PBMCs following treatment with anti-CD96 antibodies described herein.

Example 11: Mapping of Anti-CD96 Antibody Binding Sites Via Site-Directed Mutagenesis Site-directed mutagenesis, mutating hCD96 residues to corresponding cyCD96 residues in the D1 domain, was performed to map the binding sites of anti-CD96 antibodies. The highly homologous human and cynomolgus monkey CD96 amino acid sequences were aligned and the human residues at the indicated positions (see Table 25) were mutated to the corresponding residue in the cyno protein to generate the "human-to-cyno" mutations. Binding to cells transfected to express human-to-cyno mutated forms of CD96 was assessed and the resulting effects on binding of the indicated antibody are shown in the following table.

TABLE 25

Effects on antibody binding of site-directed mutagenesis

| CD96 Residue Position(s) | Human Residue(s) | Cyno Residue(s) | Effect on binding of 9H4 | Effect on binding of mAb1 | Effect on binding of 16D9 or 1G8 |
|---|---|---|---|---|---|
| 49-50 | TV | AK | No effect | Lost binding | Lost binding |
| 53 | F | L | No effect | No effect | No effect |
| 63 | N | D | | No effect | No effect |
| 65 | I | A | | No effect | No effect |
| 70 | V | L | No effect | No effect | No effect |
| 78 | Y | H | Lost binding | No effect | No effect |
| 83 | R | S | | No effect | No effect |
| 93 | E | Q | No effect | No effect | No effect |
| 110 | C | S | | | |
| 121 | V | T | Increased binding | Slightly increased binding | Slightly increased binding |

Example 12: Secondary Binding of NGS8 and 10G1 Antibodies to CD226

In order to assess the generated antibodies for secondary binding to CD226, sequences encoding human CD226 ("hu-CD226") (SEQ ID NO: 482) and cyno CD226 ("cy-CD226") (SEQ ID NO: 483) (see Table 26 and Sequence Listing) were each cloned into pcDNA3.1 expression vector and Expi293 cells were separately transfected with plasmid containing either the hu-CD226 or cy-CD226 coding sequence. Starting concentrations of 1 μM and corresponding 3X serial dilutions of each antibody, NGS8, 10G1, and MABT398 (CD226 positive control, EMD Millipore, Burlington, MA, USA), were prepared for staining. Secondary antibodies employed included goat anti-mouse F(ab)2-PE (Invitrogen, Carlsbad, CA, USA) and goat anti-human F(ab)2-PE (Jackson ImmunoResearch, West Grove, PA, USA).

TABLE 26 encoded CD226 amino acid sequences used in assay:

| | |
|---|---|
| huCD226 (NP_006557.2) | MDYPTLLLALLHVYRALCEEVLWHTSVPFAENMSLECVYPSMGILTQVEWFK IGTQQDSIAIFSPTHGMVIRKPYAERVYFLNSTMASNNMTLFFRNASEDDVG YYSCSLYTYPQGTWQKVIQVVQSDSFEAAVPSNSHIVSEPGKNVTLTCQPQM TWPVQAVRWEKIQPRQIDLLTYCNLVHGRNFTSKFPRQIVSNCSHGRWSVIV IPDVTVSDSGLYRCYLQASAGENETFVMRLTVAEGKTDNQYTLFVAGGTVLL LLFVISITTIIVIFLNRRRRRERRDLFTESWDTQKAPNNYRSPISTSQPTNQ SMDDTREDIYVNYPTFSRRPKTRVDYKDDDDK (SEQ ID NO: 482; signal sequence underlined, flag tag in bold) |
| cyCD226 (XP_005586537.1) | MDYPTLLLALLHVYRALCEEVLWHTSVPFAENMSLECVYPSVGILTQVEWFK IGTEKDSIAIFSPTHGMVIRKPYAERVYFLNSTMASNNMTLFFRNASEDDVG YYSCSLYTYPQGTWQKVIQVVQSDGFEAAVPPNSHIVSEPGKNITLTCQPQM TWPVQEVRWEKVQPHQIDLLTYCDLVHGRNFTSKFPRQIVSNCSHGSWSFIV VPDVTASDSGLYRCHLQASAGENETFVMRLTVAEGQTDNQYTRFVTGGTVLL LLFVISITTIIVIFLNRRRRRERNDLYTESWDTQKAPKNYRSPISANQPTNQ SMDDTREDIYVNYPTFSRRPKTRVDYKDDDDK (SEQ ID NO: 483; signal sequence underlined, flag tag in bold) |

Figure 12A:
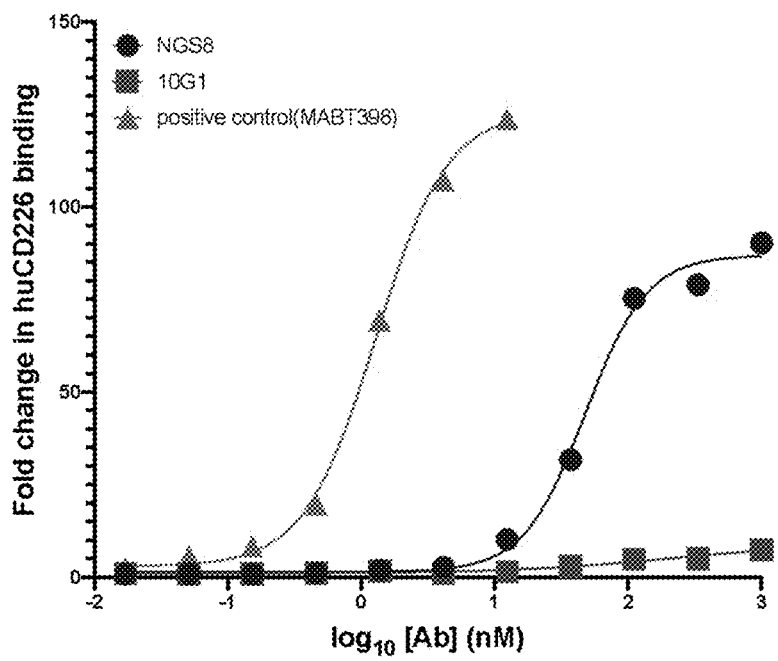
FIG. 12A and FIG. 12B depict the binding of anti-CD96 antibodies to CD226 expressed on cells transfected with CD226-encoding expression constructs.
Figure 12B:
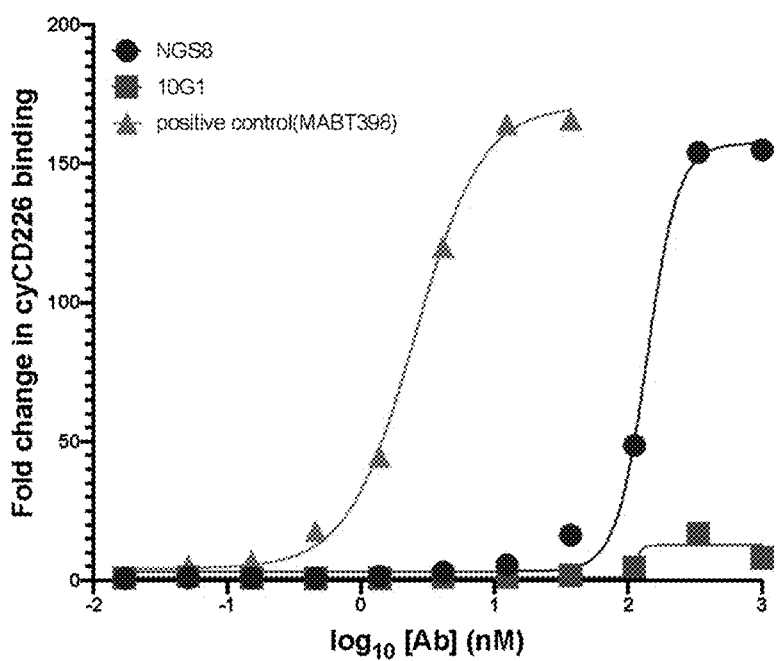

Samples, each containing one million transfected cells, were stained with primary antibody for 1 hr and secondary antibody for 30 min at 4° C. with agitation. Stained cells were washed in FACS buffer (1% BSA in PBS), fixed in 4% freshly prepared paraformaldehyde, and analyzed by flow cytometry. Ten thousand events were collected for each sample and curves, showing the fold change in CD226 binding, were separately plotted for hu-CD226 (FIG. 12A) and cy-CD226 (FIG. 12B) expressing cells. Calculated $EC_{50}$ values are provided in the following table.

TABLE 27

FACS binding of antibodies to hu-CD226 and cy-CD226

| mAb | hu-CD226 EC50(nM) | cy-CD226 EC50(nM) |
|---|---|---|
| NGS8 | 48.13 | 143 |
| 10G1 | 232.1 | N.D. |
| MABT398 | 1.289 | 2.54 |

To determine the binding affinity to hu-CD226 and cy-CD226 of mAb1.v7.NGS8, h10G1, hCD155 and anti-hCD226 antibody DX11 (Abcam, cat #Ab33397), SPR measurement with a BIACORE™ 8K instrument was performed. Briefly, a 1:4 dilution of Biotin CAPture Reagent (GE Healthcare) into HBS-EP buffer (0.01 M HEPES pH 7.4, 0.15 M NaCl, 3 mM EDTA, 0.005% Surfactant P20) was applied to the chip at 2 µL/min flow rate. For the kinetics measurements, 5 µg/ml of biotinylated hu-CD226 His tag (Sino biological, cat #10565-H08H) and cy-CD226 His tag (Arco biosystems, cat #DN1-052H9) was captured at 10 µL/min to achieve ~50 response units in the second flow cell (FC2). FC1 was kept as a reference. Next, 3-fold serial dilutions of IgG in HBS-P buffer (0.01 M HEPES pH 7.4, 0.15 M NaCl, 0.005% surfactant P20) from low (1.3 nM) to high (1000 nM) concentration were injected (flow rate: 30 µL/min) at 25° C. The sensorgram was recorded and subject to reference and buffer subtraction before evaluating by BIACORE® 8K Evaluation Software (version 1.1.1.7442). Association rates ($k_{on}$) and dissociation rates ($k_{off}$) were calculated using a simple one-to-one Langmuir binding model. The equilibrium dissociation constant ($K_D$) value was calculated as the ratio of $k_{off}/k_{on}$. Steady state fitting analysis, using manufacturer's instrument settings (Biacore, Inc., Uppsala, Sweden), was used in some instances due to fast association/dissociation rate. The BIACORE® determined binding affinity values are summarized in Table 28.

TABLE 28

Binding affinity of IgGs or receptor binding to hu-CD226 and cy-CD226

| IgG | hu-CD226 $K_D$ (nM) | cy-CD226 $K_D$ (nM) |
|---|---|---|
| mAb1.v7.NGS8 | 631* | 84.8* |
| h10G1 | No binding | No binding |
| hCD155 | 161* | 67.5* |
| DX11 | 6.9 | 0.02 |

*steady state fitting

The above demonstrates that NGS8 binds to both hu-CD226 and cy-CD226, with SPR measured affinities in the 1 µM to 50 nM range. Thus, in addition to binding CD96 with at least nanomolar and even subnanomolar affinities, in some embodiments, anti-CD96 antibodies of the present disclosure also have demonstrated secondary affinity, e.g., of 700 nM or less, for CD226 which, like CD96, interacts with CD155 expressed on another cell.

Notwithstanding the appended claims, the disclosure set forth herein is also defined by the following clauses, which may be beneficial alone or in combination, with one or more other causes or embodiments. Without limiting the foregoing description, certain non-limiting clauses of the disclosure numbered as below are provided, wherein each of the individually numbered clauses may be used or combined with any of the preceding or following clauses. Thus, this is intended to provide support for all such combinations and is not necessarily limited to specific combinations explicitly provided below:

1. An anti-CD96 antibody comprising: (i) a first light chain hypervariable region (HVR-L1), a second light chain hypervariable region (HVR-L2), and a third light chain hypervariable region (HVR-L3), and/or (ii) a first heavy chain hypervariable region (HVR-H1), a second heavy chain hypervariable region (HVR-H2), and a third heavy chain hypervariable region (HVR-H3); wherein:

(a) HVR-L1 comprises an amino acid sequence selected from KASQNVGTAIV (SEQ ID NO: 13), KSSQSLLDSDGKTYLN (SEQ ID NO: 17), RVSQDISFWLS (SEQ ID NO: 21), RASSNVKYMY (SEQ ID NO: 25), KASQSVTFADTGLMH (SEQ ID NO: 29), RSSTGAVTTSNYAN (SEQ ID NO: 33), RASQDIYRNLH (SEQ ID NO: 37), or RASQXIXXNXH (SEQ ID NO: 308), wherein X at position 5 is D, A, E, G, H, K, N, P, Q, S, or T; X at position 7 is Y, or F; X at position 8 is R, K, or Q; X at position 10 is L, I, M, or V;

(b) HVR-L2 comprises an amino acid sequence selected from SASTRYT (SEQ ID NO: 14), LVSKLDS (SEQ ID NO: 18), KASNLHT (SEQ ID NO: 22), YTSNLAS (SEQ ID NO: 26), RASNLEV (SEQ ID NO: 30), GTNNRAP (SEQ ID NO: 34), HASDSIS (SEQ ID NO: 38), or HAXXXXS (SEQ ID NO: 325), wherein X at position 3 is S, or E; X at position 4 is D, E, K, or Q; X at position 5 is S, H, L, R, or V; X at position 6 is I, or V;

(c) HVR-L3 comprises an amino acid sequence selected from QQYSSSPLT (SEQ ID NO: 15), LQATHSPQT (SEQ ID NO: 19), LQSQSYPYT (SEQ ID NO: 23), QQFTSSPLT (SEQ ID NO: 27), QQSREYPWT (SEQ ID NO: 31), SLWYGSHWV (SEQ ID NO: 35), LQGYSMPYT (SEQ ID NO: 39), or XQGYXMPXT (SEQ ID NO: 335), wherein X at position 1 is L, G, M, or Q; X at position 5 is S, A, E, Q, or V; X at position 8 is Y, or F;

(d) HVR-H1 comprises an amino acid sequence selected from TNNWMH (SEQ ID NO: 41), GYGVT (SEQ ID NO: 45), TDYYIN (SEQ ID NO: 49), NDYYIN(SEQ ID NO: 53), SDYYMY (SEQ ID NO: 57), TNYGIH (SEQ ID NO: 61), TTYGMS (SEQ ID NO: 65), XNXXXH (SEQ ID NO: 72), wherein X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W, or XXXGXS (SEQ ID NO: 344), wherein X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V;

(e) HVR-H2 comprises an amino acid sequence selected from MIHPNSGITNINE (SEQ ID NO: 42), EIYPGTVITYYNA (SEQ ID NO: 46), WIFPGTEGIYYNE (SEQ ID NO: 50), WIFPGRIITYYNE (SEQ ID NO: 54), AISDDGTYTYYPD (SEQ ID NO: 58), IIWAGG- STNYNSA (SEQ ID NO: 62), WINTDSGVPTYAD (SEQ ID NO: 66), XXHXXXXXXXXXNX (SEQ ID NO: 107), wherein X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y, or WINTXXGVPTYAD (SEQ ID NO: 369), wherein X at position 5 is D, or E; X at position 6 is S, or T;

(f) HVR-H3 comprises an amino acid sequence selected from RSDGTYEGYFDY (SEQ ID NO: 43), ARGLGRAMDY (SEQ ID NO: 47), AREGDYRYYSPLGY (SEQ ID NO: 51), ARGVGEGFDY (SEQ ID NO: 55), AKAGSYDYFDV (SEQ ID NO: 59), ARVSMMGFAY (SEQ ID NO: 63), ARNIYYGWGNFDY (SEQ ID NO: 67), RXDXXXXXY (SEQ ID NO: 203), wherein X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T, or ARXIYYGWGXFDY (SEQ ID NO: 372), wherein X at position 3 is N, or M; X at position 10 is N, F, H, or Y.

2. The antibody of clause 1, wherein: (a) HVR-L1 comprises the amino acid sequence of KASQNVGTAIV (SEQ ID NO: 13); (b) HVR-L2 comprises the amino acid sequence of SASTRYT (SEQ ID NO: 14); (c) HVR-L3 comprises the amino acid sequence of QQYSSSPLT (SEQ ID NO: 15).

3. The antibody of any one of clauses 1-2, wherein:
(a) HVR-H1 comprises the amino acid sequence of XNXXXH (SEQ ID NO: 72), wherein X at position 1 is T, A, D, E, G, H, K, N, Q, R, S, V, W, or Y; X at position 3 is N, A, F, G, H, M, R, S, V, or Y; X at position 4 is W, or F; X at position 5 is M, A, D, E, F, G, L, N, Q, R, S, T, V, or W;
(b) HVR-H2 comprises the amino acid sequence of XXHXXXXXXXXXNX (SEQ ID NO: 107), wherein X at position 1 is M or F; X at position 2 is I, L, M, or V; X at position 4 is P, A, D, E, F, G, H, I, K, L, M, N, Q, R, S, T, V, or W; X at position 5 is N, A, D, E, F, G, H, I, K, L, M, Q, R, S, T, V, W, or Y; X at position 6 is S, A, G, T, or V; X at position 7 is G, A, or S; X at position 8 is I, A, or V; X at position 9 is T, A, D, E, G, H, I, K, L, M, N, Q, R, S, V, W, or Y; X at position 10 is N, A, M, or S; X at position 11 is I, F, G, H, K, L, M, N, Q, R, S, T, V, W, or Y; X at position 13 is E, A, D, G, H, K, L, M, N, P, Q, R, S, T, V, W, or Y;
(c) HVR-H3 comprises the amino acid sequence of RXDXXXXXY (SEQ ID NO: 203), wherein X at position 2 is S, A, F, G, I, L, M, N, R, T, V, W, or Y; X at position 4 is G, or W; X at position 5 is T, D, E, F, H, I, K, L, M, N, Q, V, W, or Y; X at position 6 is Y, D, F, H, N, R, or W; X at position 7 is E, D, G, H, K, M, N, Q, R, V, or Y; X at position 8 is G, K, R, S, or T.

4. The antibody of any one of clauses 1-3, wherein: (a) HVR-H1 comprises an amino acid sequence selected from SEQ ID NOs: 41, 73-106; (b) HVR-H2 comprises an amino acid sequence selected from SEQ ID NOs: 42, 108-202; (c) HVR-H3 comprises an amino acid sequence selected from SEQ ID NOs: 43, 204-249.

5. The antibody of any one of clauses 1-4, wherein: (a) HVR-L1 comprises the amino acid sequence of SEQ ID NO: 13; (b) HVR-L2 comprises the amino acid sequence of SEQ ID NO: 14; (c) HVR-L3 comprises the amino acid sequence of SEQ ID NO: 15; (d) HVR-H1 comprises an amino acid sequence selected from SEQ ID NOs: 41, 73-106; (e) HVR-H2 comprises an amino acid sequence selected from SEQ ID NOs: 42, 108-202; (f) HVR-H3 comprises an amino acid sequence selected from SEQ ID NOs: 43, 204-249.

6. The antibody of any one of clauses 1-5, wherein: (a) HVR-L1 comprises the amino acid sequence of SEQ ID NO: 13; (b) HVR-L2 comprises the amino acid sequence of SEQ ID NO: 14; (c) HVR-L3 comprises the amino acid sequence of SEQ ID NO: 15; (d) HVR-H1 comprises an amino acid sequence selected from SEQ ID NOs: 41, 83, 91, 92, 94, 95, 102; (e) HVR-H2 comprises an amino acid sequence selected from SEQ ID NOs: 42, 108, 112, 113, 116, 118, 122, 125, 138, 178, 181, 190, 197; (f) HVR-H3 comprises an amino acid sequence selected from SEQ ID NOs: 43, 208, 219, 221, 223, 227.

7. The antibody of any one of clauses 1-6, wherein: (a) HVR-L1 comprises the amino acid sequence of SEQ ID NO: 13; (b) HVR-L2 comprises the amino acid sequence of SEQ ID NO: 14; (c) HVR-L3 comprises the amino acid sequence of SEQ ID NO: 15; (d) HVR-H1 comprises an amino acid sequence selected from SEQ ID NOs: 41, or 95; (e) HVR-H2 comprises an amino acid sequence selected from SEQ ID NOs: 42, 108, 112, 113, 190, or 197; (f) HVR-H3 comprises an amino acid sequence selected from SEQ ID NOs: 43, 221, or 227.

8. The antibody of clause 1, wherein:
(a) HVR-L1 comprises the amino acid sequence of RASQXIXXNXH (SEQ ID NO: 308), wherein X at position 5 is D, A, E, G, H, K, N, P, Q, S, or T; X at position 7 is Y, or F; X at position 8 is R, K, or Q; X at position 10 is L, I, M, or V;
(b) HVR-L2 comprises the amino acid sequence of HAXXXXS (SEQ ID NO: 325), wherein X at position 3 is S, or E; X at position 4 is D, E, K, or Q; X at position 5 is S, H, L, R, or V; X at position 6 is I, or V;
(c) HVR-L3 comprises the amino acid sequence of XQGYXMPXT (SEQ ID NO: 335), wherein X at position 1 is L, G, M, or Q; X at position 5 is S, A, E, Q, or V; X at position 8 is Y, or F.

9. The antibody of any one of clauses 1 or 8, wherein: (a) HVR-L1 comprises an amino acid sequence selected from SEQ ID NOs: 37, 309-324; (b) HVR-L2 comprises an amino acid sequence selected from SEQ ID NOs: 38, 326-334; (c) HVR-L3 comprises an amino acid sequence selected from SEQ ID NOs: 39, 336-343.

10. The antibody of any one of clauses 1, or 8-9, wherein:
(a) HVR-H1 comprises the amino acid sequence of or XXXGXS (SEQ ID NO: 344), wherein X at position 1 is T, A, D, E, G, H, K, M, N, Q, R, or S; X at position 2 is T, D, E, G, H, N, Q, or S; X at position 3 is Y, F, M, or Q; X at position 5 is M, I, L, or V;
(b) HVR-H2 comprises the amino acid sequence of WINTXXGVPTYAD (SEQ ID NO: 369), wherein X at position 5 is D, or E; X at position 6 is S, or T;
(c) HVR-H3 comprises the amino acid sequence of XIYYGWGXFDY (SEQ ID NO: 372), wherein X at position 1 is N, or M; X at position 8 is N, F, H, or Y.

11. The antibody of any one of clauses 1, 8-10, wherein: (a) HVR-H1 comprises an amino acid sequence selected from SEQ ID NOs: 65, 345-368; (b) HVR-H2 comprises an amino acid sequence selected from SEQ ID NOs: 66, 370-371; (c) HVR-H3 comprises an amino acid sequence selected from SEQ ID NOs: 67, 373-376.

12. The antibody of any one of clauses 1, 8-11, wherein: (a) HVR-L1 comprises the amino acid sequence of SEQ ID NO: 37, 309-324; (b) HVR-L2 comprises the amino acid sequence of SEQ ID NO: 38, 326-334; (c) HVR-L3 comprises the amino acid sequence of SEQ ID NO: 39, 336-343; (d) HVR-H1 comprises an amino acid sequence selected from SEQ ID NOs: 65, 345-368; (e) HVR-H2 comprises an amino acid sequence selected from SEQ ID NOs: 66, 370-371; (f) HVR-H3 comprises an amino acid sequence selected from SEQ ID NOs: 67, 373-376.

13. The antibody of any one of clauses 1-12, wherein the antibody comprises: a first light chain framework region (FR-L1) comprising an amino acid sequence of SEQ ID NO: 276; a second light chain framework region (FR-L2) comprising an amino acid sequence of SEQ ID NO: 277; a third light chain framework region (FR-L3) comprising an amino acid sequence of SEQ ID NO: 278; and a fourth light chain framework region (FR-L4) comprising an amino acid sequence of SEQ ID NO: 279.

14. The antibody of any one of clauses 1-13, wherein the antibody comprises: a first heavy chain framework region (FR-H1) comprising an amino acid sequence of SEQ ID NO: 292; a second heavy chain framework region (FR-H2) comprising an amino acid sequence of SEQ ID NO: 293; a third heavy chain framework region (FR-H3) comprising an amino acid sequence of SEQ ID NO: 294; and a fourth heavy chain framework region (FR-H4) comprising an amino acid sequence of SEQ ID NO: 295.

15. The antibody of any one of clauses 1-12, wherein the antibody comprises: a first light chain framework region (FR-L1) comprising an amino acid sequence of SEQ ID NO: 280; a second light chain framework region (FR-L2) comprising an amino acid sequence of SEQ ID NO: 281; a third light chain framework region (FR-L3) comprising an amino acid sequence of SEQ ID NO: 282; and a fourth light chain framework region (FR-L4) comprising an amino acid sequence of SEQ ID NO: 283;

16. The antibody of any one of clauses 1-12, or 15 wherein the antibody comprises: a first heavy chain framework region (FR-H1) comprising an amino acid sequence of SEQ ID NO: 300; a second heavy chain framework region (FR-H2) comprising an amino acid sequence of SEQ ID NO: 301; a third heavy chain framework region (FR-H3) comprising an amino acid sequence of SEQ ID NO: 302; and a fourth heavy chain framework region (FR-H4) comprising an amino acid of SEQ ID NO: 303.

17. The antibody of any one of clauses 1-12, wherein the antibody comprises: a first light chain framework region (FR-L1) comprising an amino acid sequence of SEQ ID NO: 284; a second light chain framework region (FR-L2) comprising an amino acid sequence of SEQ ID NO: 285; a third light chain framework region (FR-L3) comprising an amino acid sequence of SEQ ID NO: 286; and a fourth light chain framework region (FR-L4) comprising an amino acid sequence of SEQ ID NO: 287.

18. The antibody of any one of clauses 1-12, or 17, wherein the antibody comprises: a first heavy chain framework region (FR-H1) comprising an amino acid sequence of SEQ ID NO: 296; a second heavy chain framework region (FR-H2) comprising an amino acid sequence of SEQ ID NO: 297; a third heavy chain framework region (FR-H3) comprising an amino acid sequence of SEQ ID NO: 298; and a fourth heavy chain framework region (FR-H4) comprising an amino acid sequence of SEQ ID NO: 299.

19. The antibody of any one of clauses 1-12, wherein the antibody comprises: a first light chain framework region (FR-L1) comprising an amino acid sequence of SEQ ID NO: 288; a second light chain framework region (FR-L2) comprising an amino acid sequence of SEQ ID NO: 289; a third light chain framework region (FR-L3) comprising an amino acid sequence of SEQ ID NO: 290; and a fourth light chain framework region (FR-L4) comprising an amino acid sequence of SEQ ID NO: 291;

20. The antibody of any one of clauses 1-12, or 19 wherein the antibody comprises: a first heavy chain framework region (FR-H1) comprising an amino acid sequence of SEQ ID NO: 304; a second heavy chain framework region (FR-H2) comprising an amino acid sequence of SEQ ID NO: 305; a third heavy chain framework region (FR-H3) comprising an amino acid sequence of SEQ ID NO: 306; and a fourth heavy chain framework region (FR-H4) comprising an amino acid of SEQ ID NO: 307.

21. The antibody of any one of clauses 1-20, wherein the antibody comprises a light chain variable domain ($V_L$) amino acid sequence having at least 90% identity to a sequence selected from SEQ ID NO: 12, 16, 20, 24, 28, 32, or 36; and/or a heavy chain variable domain ($V_H$) amino acid sequence having at least 90% identity to a sequence selected from SEQ ID NO: 40, 44, 48, 52, 56, 60, or 64.

22. The antibody of clause 21, wherein the antibody comprises a light chain variable domain ($V_L$) amino acid sequence having at least 90% identity to SEQ ID NO: 12, and/or a heavy chain variable domain ($V_H$) amino acid sequence having at least 90% identity to SEQ ID NO: 40.

23. The antibody of clause 21, wherein the antibody comprises a light chain variable domain ($V_L$) amino acid sequence having at least 90% identity to SEQ ID NO: 36, and/or a heavy chain variable domain ($V_H$) amino acid sequence having at least 90% identity to SEQ ID NO: 64.

24. The antibody of any one of clauses 1-20, wherein the antibody comprises a light chain (LC) amino acid sequence having at least 90% identity to a sequence selected from SEQ ID NO: 440, 441, 442, 443, 444, 445, or 446; and/or a heavy chain (HC) amino acid sequence having at least 90% identity to a sequence selected from SEQ ID NO: 447, 448, 449, 450, 451, 452, 453, 484, 485, 486, 487, 488, 489, or 490.

25. The antibody of clause 24, wherein the antibody comprises a light chain (LC) amino acid sequence having at least 90% identity to SEQ ID NO: 440; and/or a heavy chain (HC) amino acid sequence having at least 90% identity to SEQ ID NO: 447, or 484.

26. The antibody of clause 24, wherein the antibody comprises a light chain (LC) amino acid sequence having at least 90% identity to SEQ ID NO: 446; and/or a heavy chain (HC) amino acid sequence having at least 90% identity to SEQ ID NO: 453, or 490.

27. The antibody of any one of clauses 1-6, wherein the antibody comprises a light chain variable domain ($V_L$) amino acid sequence having at least 90% identity to SEQ ID NO: 68, and/or a heavy chain variable domain ($V_H$) amino acid sequence having at least 90% identity to a sequence selected from SEQ ID NO: 69, 250, 251, 252, 253, 254, 255, 256, 257, 258, 259, 260, 261, 262, 263, 264, 265, 266, 267, 268, 269, 270, 271, 272, 273, 274, 275, 460, 461, 462, 463, or 464.

28. The antibody of clause 27, wherein the antibody comprises a light chain variable domain ($V_L$) amino acid sequence of SEQ ID NO: 68.

29. The antibody of any one of clauses 27 or 28, wherein the antibody comprises a heavy chain variable domain ($V_H$) amino acid sequence selected from SEQ ID NO: 69, 250, 251, 252, 253, 254, 255, 256, 257, 258, 259, 260, 261, 262, 263, 264, 265, 266, 267, 268, 269, 270, 271, 272, 273, 274, or 275.

30. The antibody of clause 27, wherein the antibody comprises:

31. the light chain variable domain ($V_L$) amino acid sequence of SEQ ID NO: 68, and the heavy chain variable domain ($V_H$) amino acid sequence of SEQ ID NO: 69;

32. the light chain variable domain ($V_L$) amino acid sequence of SEQ ID NO: 68, and the heavy chain variable domain ($V_H$) amino acid sequence of SEQ ID NO: 250;

33. the light chain variable domain ($V_L$) amino acid sequence of SEQ ID NO: 68, and the heavy chain variable domain ($V_H$) amino acid sequence of SEQ ID NO: 251;

34. the light chain variable domain ($V_L$) amino acid sequence of SEQ ID NO: 68, and the heavy chain variable domain ($V_H$) amino acid sequence of SEQ ID NO: 252;

35. the light chain variable domain ($V_L$) amino acid sequence of SEQ ID NO: 68, and the heavy chain variable domain ($V_H$) amino acid sequence of SEQ ID NO: 253;

36. the light chain variable domain ($V_L$) amino acid sequence of SEQ ID NO: 68, and the heavy chain variable domain ($V_H$) amino acid sequence of SEQ ID NO: 254;

37. the light chain variable domain ($V_L$) amino acid sequence of SEQ ID NO: 68, and the heavy chain variable domain ($V_H$) amino acid sequence of SEQ ID NO: 255;

38. the light chain variable domain ($V_L$) amino acid sequence of SEQ ID NO: 68, and the heavy chain variable domain ($V_H$) amino acid sequence of SEQ ID NO: 256;

39. the light chain variable domain ($V_L$) amino acid sequence of SEQ ID NO: 68, and the heavy chain variable domain ($V_H$) amino acid sequence of SEQ ID NO: 257;

40. the light chain variable domain ($V_L$) amino acid sequence of SEQ ID NO: 68, and the heavy chain variable domain ($V_H$) amino acid sequence of SEQ ID NO: 258;

41. the light chain variable domain ($V_L$) amino acid sequence of SEQ ID NO: 68, and the heavy chain variable domain ($V_H$) amino acid sequence of SEQ ID NO: 259;

42. the light chain variable domain ($V_L$) amino acid sequence of SEQ ID NO: 68, and the heavy chain variable domain ($V_H$) amino acid sequence of SEQ ID NO: 260;

43. the light chain variable domain ($V_L$) amino acid sequence of SEQ ID NO: 68, and the heavy chain variable domain ($V_H$) amino acid sequence of SEQ ID NO: 261;

44. the light chain variable domain ($V_L$) amino acid sequence of SEQ ID NO: 68, and the heavy chain variable domain ($V_H$) amino acid sequence of SEQ ID NO: 262;

45. the light chain variable domain ($V_L$) amino acid sequence of SEQ ID NO: 68, and the heavy chain variable domain ($V_H$) amino acid sequence of SEQ ID NO: 263;

46. the light chain variable domain ($V_L$) amino acid sequence of SEQ ID NO: 68, and the heavy chain variable domain ($V_H$) amino acid sequence of SEQ ID NO: 264;

47. the light chain variable domain ($V_L$) amino acid sequence of SEQ ID NO: 68, and the heavy chain variable domain ($V_H$) amino acid sequence of SEQ ID NO: 265;

48. the light chain variable domain ($V_L$) amino acid sequence of SEQ ID NO: 68, and the heavy chain variable domain ($V_H$) amino acid sequence of SEQ ID NO: 266;

49. the light chain variable domain ($V_L$) amino acid sequence of SEQ ID NO: 68, and the heavy chain variable domain ($V_H$) amino acid sequence of SEQ ID NO: 267;

50. the light chain variable domain ($V_L$) amino acid sequence of SEQ ID NO: 68, and the heavy chain variable domain ($V_H$) amino acid sequence of SEQ ID NO: 268;

51. the light chain variable domain ($V_L$) amino acid sequence of SEQ ID NO: 68, and the heavy chain variable domain ($V_H$) amino acid sequence of SEQ ID NO: 269;

52. the light chain variable domain ($V_L$) amino acid sequence of SEQ ID NO: 68, and the heavy chain variable domain ($V_H$) amino acid sequence of SEQ ID NO: 270;

53. the light chain variable domain ($V_L$) amino acid sequence of SEQ ID NO: 68, and the heavy chain variable domain ($V_H$) amino acid sequence of SEQ ID NO: 271;

54. the light chain variable domain ($V_L$) amino acid sequence of SEQ ID NO: 68, and the heavy chain variable domain ($V_H$) amino acid sequence of SEQ ID NO: 272;

55. the light chain variable domain ($V_L$) amino acid sequence of SEQ ID NO: 68, and the heavy chain variable domain ($V_H$) amino acid sequence of SEQ ID NO: 273;

56. the light chain variable domain ($V_L$) amino acid sequence of SEQ ID NO: 68, and the heavy chain variable domain ($V_H$) amino acid sequence of SEQ ID NO: 274; or 57. the light chain variable domain ($V_L$) amino acid sequence of SEQ ID NO: 68, and the heavy chain variable domain ($V_H$) amino acid sequence of SEQ ID NO: 275.

58. The antibody of any one of clauses 1-6, wherein the antibody comprises a light chain (LC) amino acid sequence having at least 90% identity to SEQ ID NO: 454, and/or a heavy chain (HC) amino acid sequence having at least 90% identity to a sequence selected from SEQ ID NO: 455, 456, 457, 458, 459, 465, 466, 467, 468, 469, 491, 492, 493, 494, 495, 496, 497, 498, 499, or 500.

59. The antibody of clause 31, wherein the antibody comprises:

60. the light chain (LC) amino acid sequence of SEQ ID NO: 454, and the heavy chain (HC) amino acid sequence of SEQ ID NO: 455;

61. the light chain (LC) amino acid sequence of SEQ ID NO: 454, and the heavy chain (HC) amino acid sequence of SEQ ID NO: 456;

62. the light chain (LC) amino acid sequence of SEQ ID NO: 454, and the heavy chain (HC) amino acid sequence of SEQ ID NO: 457;

63. the light chain (LC) amino acid sequence of SEQ ID NO: 454, and the heavy chain (HC) amino acid sequence of SEQ ID NO: 458;

64. the light chain (LC) amino acid sequence of SEQ ID NO: 454, and the heavy chain (HC) amino acid sequence of SEQ ID NO: 459;

65. the light chain (LC) amino acid sequence of SEQ ID NO: 454, and the heavy chain (HC) amino acid sequence of SEQ ID NO: 491;

66. the light chain (LC) amino acid sequence of SEQ ID NO: 454, and the heavy chain (HC) amino acid sequence of SEQ ID NO: 492;

67. the light chain (LC) amino acid sequence of SEQ ID NO: 454, and the heavy chain (HC) amino acid sequence of SEQ ID NO: 493;

68. the light chain (LC) amino acid sequence of SEQ ID NO: 454, and the heavy chain (HC) amino acid sequence of SEQ ID NO: 494; or 69. the light chain (LC) amino acid sequence of SEQ ID NO: 454, and the heavy chain (HC) amino acid sequence of SEQ ID NO: 495.

70. The antibody of any one of clauses 1, 7-12, wherein the antibody comprises a light chain variable domain ($V_L$) amino acid sequence having at least 90% identity to a sequence selected from SEQ ID NO: 70, and 373-409;

and/or a heavy chain variable domain (V$_H$) amino acid sequence having at least 90% identity to a sequence selected from SEQ ID NO: 71, and 410-439.

71. The antibody of clause 33, wherein the antibody comprises a light chain variable domain (V$_L$) amino acid sequence selected from SEQ ID NO: 70, and 377-409.

72. The antibody of any one of clauses 33 or 34, wherein the antibody comprises a heavy chain variable domain (V$_H$) amino acid sequence selected from SEQ ID NO: 71, and 410-439.

73. The antibody of any one of clauses 1, 7-12, wherein the antibody comprises a light chain (LC) amino acid sequence having at least 90% identity to SEQ ID NO: 470; and/or a heavy chain (HC) amino acid sequence having at least 90% identity to SEQ ID NO: 471 or 501.

74. The antibody of clause 36, wherein the antibody comprises:

75. the light chain (LC) amino acid sequence of SEQ ID NO: 470, and the heavy chain (HC) amino acid sequence of SEQ ID NO: 471 or 501.

76. An anti-CD96 antibody comprising:

77. a first light chain hypervariable region (HVR-L1) of SEQ ID NO: 13, a second light chain hypervariable region (HVR-L2) of SEQ ID NO: 14, and a third light chain hypervariable region (HVR-L3) of SEQ ID NO: 15; and/or a first heavy chain hypervariable region (HVR-H1) of SEQ ID NO: 72, a second heavy chain hypervariable region (HVR-H2) of SEQ ID NO: 107, and a third heavy chain hypervariable region (HVR-H3) of SEQ ID NO: 203; or 78. a first light chain hypervariable region (HVR-L1) of SEQ ID NO: 308, a second light chain hypervariable region (HVR-L2) of SEQ ID NO: 325, a third light chain hypervariable region (HVR-L3) of SEQ ID NO: 335, and/or a first heavy chain hypervariable region (HVR-H1) of SEQ ID NO: 344, a second heavy chain hypervariable region (HVR-H2) of SEQ ID NO: 369, and a third heavy chain hypervariable region (HVR-H3) of SEQ ID NO: 372.

79. An anti-CD96 antibody comprising:

80. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 43;

81. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 42, and a third heavy chain hypervariable region (HVR-H3) of SEQ ID NO: 43;

82. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 108, and a third heavy chain hypervariable region (HVR-H3) of SEQ ID NO: 43;

83. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 112, and a third heavy chain hypervariable region (HVR-H3) of SEQ ID NO: 43;

84. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 190, and a third heavy chain hypervariable region (HVR-H3) of SEQ ID NO: 43;

85. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 197, and a third heavy chain hypervariable region (HVR-H3) of SEQ ID NO: 43;

86. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 221;

87. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 227;

88. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 221;

89. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 112, and a third heavy chain hypervariable region (HVR-H3) of SEQ ID NO: 227;

90. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 221;

91. a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 95, a second heavy chain hypervariable region (HVR-H2) of SEQ ID NO: 113, and a third heavy chain hypervariable region (HVR-H3) of SEQ ID NO: 227; or 92. a first light chain hypervariable region (HVR-L1) of SEQ ID NO: 37, a second light chain hypervariable region (HVR-L2) of SEQ ID NO: 38, a third light chain hypervariable region (HVR-L3) of SEQ ID NO: 39; and/or a first heavy chain hypervariable region (HVR-H1) of SEQ ID NO: 65, a second heavy chain hypervariable region (HVR-H2) of SEQ ID NO: 66, and a third heavy chain hypervariable region (HVR-H3) of SEQ ID NO: 67.

93. An anti-CD96 antibody comprising:

94. a light chain variable domain ($V_L$) amino acid sequence of SEQ ID NO: 68; and/or a heavy chain variable domain ($V_H$) amino acid sequence of SEQ ID NO: 69;

95. a light chain variable domain ($V_L$) amino acid sequence of SEQ ID NO: 68; and/or a heavy chain variable domain ($V_H$) amino acid sequence of SEQ ID NO: 250;

96. a light chain variable domain ($V_L$) amino acid sequence of SEQ ID NO: 68; and/or a heavy chain variable domain ($V_H$) amino acid sequence of SEQ ID NO: 251;

97. a light chain variable domain ($V_L$) amino acid sequence of SEQ ID NO: 68; and/or a heavy chain variable domain ($V_H$) amino acid sequence of SEQ ID NO: 252;

98. a light chain variable domain ($V_L$) amino acid sequence of SEQ ID NO: 68; and/or a heavy chain variable domain ($V_H$) amino acid sequence of SEQ ID NO: 253;

99. a light chain variable domain ($V_L$) amino acid sequence of SEQ ID NO: 68; and/or a heavy chain variable domain ($V_H$) amino acid sequence of SEQ ID NO: 254;

100. a light chain variable domain ($V_L$) amino acid sequence of SEQ ID NO: 68; and/or a heavy chain variable domain ($V_H$) amino acid sequence of SEQ ID NO: 255;

101. a light chain variable domain ($V_L$) amino acid sequence of SEQ ID NO: 68; and/or a heavy chain variable domain ($V_H$) amino acid sequence of SEQ ID NO: 256;

102. a light chain variable domain ($V_L$) amino acid sequence of SEQ ID NO: 68; and/or a heavy chain variable domain ($V_H$) amino acid sequence of SEQ ID NO: 257;

103. a light chain variable domain ($V_L$) amino acid sequence of SEQ ID NO: 68; and/or a heavy chain variable domain ($V_H$) amino acid sequence of SEQ ID NO: 258;

104. a light chain variable domain ($V_L$) amino acid sequence of SEQ ID NO: 68; and/or a heavy chain variable domain ($V_H$) amino acid sequence of SEQ ID NO: 259;

105. a light chain variable domain ($V_L$) amino acid sequence of SEQ ID NO: 68; and/or a heavy chain variable domain ($V_H$) amino acid sequence of SEQ ID NO: 260;

106. a light chain variable domain ($V_L$) amino acid sequence of SEQ ID NO: 68; and/or a heavy chain variable domain ($V_H$) amino acid sequence of SEQ ID NO: 261;

107. a light chain variable domain ($V_L$) amino acid sequence of SEQ ID NO: 68; and/or a heavy chain variable domain ($V_H$) amino acid sequence of SEQ ID NO: 262;

108. a light chain variable domain ($V_L$) amino acid sequence of SEQ ID NO: 68; and/or a heavy chain variable domain ($V_H$) amino acid sequence of SEQ ID NO: 263;

109. a light chain variable domain ($V_L$) amino acid sequence of SEQ ID NO: 68; and/or a heavy chain variable domain ($V_H$) amino acid sequence of SEQ ID NO: 264;

110. a light chain variable domain ($V_L$) amino acid sequence of SEQ ID NO: 68; and/or a heavy chain variable domain ($V_H$) amino acid sequence of SEQ ID NO: 265;

111. a light chain variable domain ($V_L$) amino acid sequence of SEQ ID NO: 68; and/or a heavy chain variable domain ($V_H$) amino acid sequence of SEQ ID NO: 266;

112. a light chain variable domain ($V_L$) amino acid sequence of SEQ ID NO: 68; and/or a heavy chain variable domain ($V_H$) amino acid sequence of SEQ ID NO: 267;

113. a light chain variable domain ($V_L$) amino acid sequence of SEQ ID NO: 68; and/or a heavy chain variable domain ($V_H$) amino acid sequence of SEQ ID NO: 268;

114. a light chain variable domain ($V_L$) amino acid sequence of SEQ ID NO: 68; and/or a heavy chain variable domain ($V_H$) amino acid sequence of SEQ ID NO: 269;

115. a light chain variable domain ($V_L$) amino acid sequence of SEQ ID NO: 68; and/or a heavy chain variable domain ($V_H$) amino acid sequence of SEQ ID NO: 270;

116. a light chain variable domain ($V_L$) amino acid sequence of SEQ ID NO: 68; and/or a heavy chain variable domain ($V_H$) amino acid sequence of SEQ ID NO: 271;

117. a light chain variable domain ($V_L$) amino acid sequence of SEQ ID NO: 68; and/or a heavy chain variable domain ($V_H$) amino acid sequence of SEQ ID NO: 272;

118. a light chain variable domain ($V_L$) amino acid sequence of SEQ ID NO: 68; and/or a heavy chain variable domain ($V_H$) amino acid sequence of SEQ ID NO: 273;

119. a light chain variable domain ($V_L$) amino acid sequence of SEQ ID NO: 68; and/or a heavy chain variable domain ($V_H$) amino acid sequence of SEQ ID NO: 274;

120. a light chain variable domain ($V_L$) amino acid sequence of SEQ ID NO: 68; and/or a heavy chain variable domain ($V_H$) amino acid sequence of SEQ ID NO: 275;

121. a light chain variable domain ($V_L$) amino acid sequence of SEQ ID NO: 70; and/or a heavy chain variable domain ($V_H$) amino acid sequence of SEQ ID NO: 71.

122. An anti-CD96 antibody comprising:

123. a light chain (LC) amino acid sequence of SEQ ID NO: 440; and/or a heavy chain (HC) amino acid sequence of SEQ ID NO: 447;

124. a light chain (LC) amino acid sequence of SEQ ID NO: 441; and/or a heavy chain (HC) amino acid sequence of SEQ ID NO: 448;

125. a light chain (LC) amino acid sequence of SEQ ID NO: 442; and/or a heavy chain (HC) amino acid sequence of SEQ ID NO: 449;

126. a light chain (LC) amino acid sequence of SEQ ID NO: 443; and/or a heavy chain (HC) amino acid sequence of SEQ ID NO: 450;

127. a light chain (LC) amino acid sequence of SEQ ID NO: 444; and/or a heavy chain (HC) amino acid sequence of SEQ ID NO: 451;

128. a light chain (LC) amino acid sequence of SEQ ID NO: 445; and a heavy chain (HC) amino acid sequence of SEQ ID NO: 452;

129. a light chain (LC) amino acid sequence of SEQ ID NO: 446; and/or a heavy chain (HC) amino acid sequence of SEQ ID NO: 453;

130. a light chain (LC) amino acid sequence of SEQ ID NO: 454; and/or a heavy chain (HC) amino acid sequence of SEQ ID NO: 455;

131. a light chain (LC) amino acid sequence of SEQ ID NO: 454; and/or a heavy chain (HC) amino acid sequence of SEQ ID NO: 456;

132. a light chain (LC) amino acid sequence of SEQ ID NO: 454; and/or a heavy chain (HC) amino acid sequence of SEQ ID NO: 457;

133. a light chain (LC) amino acid sequence of SEQ ID NO: 454; and/or a heavy chain (HC) amino acid sequence of SEQ ID NO: 458;

134. a light chain (LC) amino acid sequence of SEQ ID NO: 454; and/or a heavy chain (HC) amino acid sequence of SEQ ID NO: 459;

135. a light chain (LC) amino acid sequence of SEQ ID NO: 470; and/or a heavy chain (HC) amino acid sequence of SEQ ID NO: 471;

136. a light chain (LC) amino acid sequence of SEQ ID NO: 454; and/or a heavy chain (HC) amino acid sequence of SEQ ID NO: 491;
137. a light chain (LC) amino acid sequence of SEQ ID NO: 454; and/or a heavy chain (HC) amino acid sequence of SEQ ID NO: 492;
138. a light chain (LC) amino acid sequence of SEQ ID NO: 454; and/or a heavy chain (HC) amino acid sequence of SEQ ID NO: 493;
139. a light chain (LC) amino acid sequence of SEQ ID NO: 454; and/or a heavy chain (HC) amino acid sequence of SEQ ID NO: 494;
140. a light chain (LC) amino acid sequence of SEQ ID NO: 454; and/or a heavy chain (HC) amino acid sequence of SEQ ID NO: 495; or
141. a light chain (LC) amino acid sequence of SEQ ID NO: 470; and/or a heavy chain (HC) amino acid sequence of SEQ ID NO: 501;
142. The antibody of any one of clauses 1-41, wherein the antibody binds to human CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a hu-CD96 polypeptide of SEQ ID NO: 4.
143. The antibody of any one of clauses 1-42, wherein the antibody binds to cynomolgus monkey CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a cy-CD96 polypeptide of SEQ ID NO: 7.
144. The antibody of any one of clauses 1-43, wherein the antibody binds to human CD96 and to cynomolgus monkey CD96 with a binding affinity of $1 \times 10^{-8}$ M or less, $1 \times 10^{-9}$ M or less, $1 \times 10^{-10}$ M or less, or $1 \times 10^{-11}$ M or less; optionally, wherein the binding affinity is measured by equilibrium dissociation constant ($K_D$) to a hu-CD96 polypeptide of SEQ ID NO: 4 and a cy-CD96 polypeptide of SEQ ID NO: 7.
145. The antibody of any one of clauses 1-44, wherein the antibody binds to human CD96 isoform 1 expressed on a cell with an antibody $EC_{50}$ concentration of 5 nM or less, 1 nM or less, or 0.1 nM or less; optionally, wherein the cell is a HEK293T cell.
146. The antibody of any one of clauses 1-45, wherein the antibody binds to human CD96 isoform 2 expressed on a cell with an antibody $EC_{50}$ concentration of 5 nM or less, 1 nM or less, or 0.1 nM or less; optionally, wherein the cell is a CHO cell.
147. The antibody of any one of clauses 1-46, wherein the antibody binds to human PBMCs with an antibody $EC_{50}$ concentration of 5 nM or less, 1 nM or less, or 0.1 nM or less.
148. The antibody of any one of clauses 1-47, wherein the antibody binds to cynomolgus monkey PBMCs with an antibody $EC_{50}$ concentration of 5 nM or less, 1 nM or less, or 0.1 nM or less.
149. The antibody of any one of clauses 1-48, wherein the antibody decreases binding of human CD155 to human CD96 expressed on CHO cells by at least 90%, at least 95%, at least 99%, or 100%; optionally, wherein at a human CD155 concentration of 10 nM the antibody has an $IC_{50}$ of 5 nM or less, 1 nM or less, or 0.1 nM or less.
150. The antibody of any one of clauses 1-49, wherein the antibody increases IFNγ secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less.
151. The antibody of any one of clauses 1-50, wherein the antibody increases IL-2 secretion from human PBMCs by at least 1.8-fold, at least 1.9-fold, at least 2-fold, at least 2.1 fold, or at least 2.20-fold; optionally, wherein the antibody has an $EC_{50}$ concentration of 0.3 nM or less, 0.2 nM or less, or 0.1 nM or less.
152. The antibody of any one of clauses 1-51, wherein the antibody binds to human and/or cynomolgus monkey CD226 expressed on cells, optionally HEK293 cells, with an antibody $EC_{50}$ concentration of 500 nM or less, 300 nM or less, 250 nM or less, 200 nM or less, 150 nM or less, 100 nM or less, or 50 nM or less.
153. The antibody of any one of clauses 1-52, wherein the antibody binds to human CD226 with a binding affinity of 1 μM or less, 900 nM or less, 800 nM or less, 700 nM or less, from 1 μM to 50 nM, or from 800 nM to 200 nM; optionally, wherein the binding affinity is measured by equilibrium dissociation constant ($K_D$) to a huCD226 polypeptide of SEQ ID NO: 482.
154. The antibody of any one of clauses 1-53, wherein the antibody binds to cynomolgus monkey CD226 with a binding affinity of 1 μM or less, 800 nM or less, 500 nM or less, 300 nM or less, 100 nM or less, from 1 μM to 50 nM, from 500 nM to 60 nM, or from 300 nM to 70 nM; optionally, wherein the binding affinity is measured by equilibrium dissociation constant ($K_D$) to a cyCD226 polypeptide of SEQ ID NO: 483.
155. The antibody of any one of clauses 1-54, wherein the antibody specifically binds to one or more amino acid residues within domain 1 of hu-CD96, wherein domain 1 comprises the amino acid sequence of SEQ ID NO: 5; optionally, wherein the one or more amino acid residues comprise T28 and V29 of SEQ ID NO: 5.
156. The antibody of any one of clauses 1-55, wherein the antibody does not bind to amino acid residues within domain 2 and/or domain 3 of human CD96.
157. The antibody of any one of clauses 1-55, wherein the antibody cross-reacts with a cynomolgus monkey CD96 polypeptide of SEQ ID NO: 7.
158. The antibody of any one of clauses 1-57, wherein the antibody is a monoclonal antibody.
159. The antibody of any one of clauses 1-58, wherein the antibody is a recombinant antibody.
160. The antibody of any one of clauses 1-59, wherein the antibody is a chimeric antibody.
161. The antibody of any one of clauses 1-60, wherein the antibody is a humanized or human antibody.
162. The antibody of any one of clauses 1-61, wherein the antibody is an antibody fragment, optionally selected from the group consisting of F(ab')$_2$, Fab', Fab, Fv, single domain antibody (VHH), single-arm antibody, and scFv.
163. The antibody of any one of clauses 1-61, wherein the antibody is a full-length antibody of class IgG; optionally, wherein the class IgG antibody has an isotype selected from IgG1, IgG2, IgG3, and IgG4.
164. The antibody of clause 63, wherein the antibody is an Fc region variant; optionally wherein the Fc region variant alters effector function or alters half-life.
165. The antibody of clause 64, wherein the Fc region variant decreases effector function and/or results in an effectorless antibody; optionally, wherein the Fc region variant comprises an amino acid substitution at position 297 resulting in effectorless function.

166. The antibody of any one of clauses 1-65, wherein the antibody is an immunoconjugate; optionally, wherein the immunoconjugate comprises a therapeutic agent for treatment of CD96-mediated condition or disease; optionally, wherein the therapeutic agent is a chemotherapeutic agent or cytotoxic agent for the treatment of cancer.
167. The antibody of any one of clauses 1-66, wherein the antibody is a multispecific antibody, optionally a bispecific antibody.
168. The antibody of clause 67, wherein the antibody is a bispecific antibody comprising a specificity for an antigen selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA; optionally, wherein the antigen is selected from PD1, TIGIT, LAG3, PVRIG, KIR, TIM-3, and CRTAM.
169. The antibody of any one of clauses 1-69, wherein the antibody is a synthetic antibody comprising the CDRs grafted onto a scaffold other than an immunoglobulin scaffold or immunoglobulin framework, optionally a scaffold selected from an alternative protein scaffold, and an artificial polymer scaffold.
170. An anti-CD96 antibody that specifically binds to the same epitope as the antibody of any one of clauses 1-69.
171. An anti-CD96 antibody, wherein the antibody specifically binds to one or more amino acid residues within domain 1 of human CD96, wherein domain 1 comprises the amino acid sequence of SEQ ID NO: 5; optionally, wherein the one or more amino acid residues within domain 1 of human CD96 comprise residues 28 and 29 of SEQ ID NO: 5 corresponding to residues 49 and 50 of human CD96 of SEQ ID NO: 2.
172. An isolated polynucleotide encoding the antibody of any one of clauses 1-71.
173. The polynucleotide of clause 72, further comprising a nucleotide sequence encoding a signal peptide (SP).
174. The polynucleotide of clause 72, wherein the polynucleotide encodes a light chain and a heavy chain.
175. The polynucleotide of clause 72, wherein the polynucleotide comprises a polynucleotide sequence comprising one or more codons selected for optimal expression of the antibody in a mammalian cell.
176. The polynucleotide of clause 72, wherein the polynucleotide sequence comprises one or more codons selected for optimal expression of the antibody in a Chinese Hamster Ovary (CHO) cell.
177. A vector comprising a polynucleotide of any one of clauses 72-76.
178. An isolated host cell comprising the vector of clause 77.
179. A host cell comprising a polynucleotide of any one of clauses 72-76.
180. An isolated host cell that expresses the antibody of any one of clauses 1-71.
181. The host cell of clause 80, wherein the host cell is selected from a Chinese hamster ovary (CHO) cell, a myeloma cell (e.g., Y0, NS0, Sp2/0), a monkey kidney cell (COS7), a human embryonic kidney line (293), a baby hamster kidney cell (BHK), a mouse Sertoli cell (e.g., TM4), an African green monkey kidney cell (VERO-76), a human cervical carcinoma cell (HELA), a canine kidney cell, a human lung cell (W138), a human liver cell (Hep G2), a mouse mammary tumor cell, a TRI cell, an MRC 5 cell, and a FS4 cell.
182. A method of producing an antibody comprising culturing the host cell of any one of clauses 78-81 so that an antibody is produced.
183. A hybridoma that produces an antibody of any one of clauses 1-71.
184. A pharmaceutical composition comprising an anti-CD96 antibody of any one of clauses 1-71 and a pharmaceutically acceptable carrier.
185. The pharmaceutical composition of clause 84, wherein the anti-CD96 antibody is the sole active agent of the composition.
186. The pharmaceutical composition of clause 84, wherein the composition comprises an additional active agent.
187. The pharmaceutical composition of clause 86, wherein the additional active agent is a chemotherapeutic agent.
188. The pharmaceutical composition of clause 86, wherein the additional active agent is an antibody comprising a specificity for an immune checkpoint molecule.
189. The pharmaceutical composition of clause 88, wherein the immune checkpoint molecule is selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA; optionally, wherein the immune checkpoint molecule is selected from PD1, TIGIT, LAG3, PVRIG, KIR, TIM-3, and CRTAM.
190. The pharmaceutical composition of clause 86, wherein the additional active agent is an antibody comprising a specificity for PD1; optionally, wherein the antibody comprising a specificity for PD1 is selected from dostarlimab, pembrolizumab, nivolumab, and pidilizumab.
191. A method of treating a CD96 mediated disease in a subject, comprising administering to the subject a therapeutically effective amount of an antibody of any one of clauses 1-71, or administering to the subject a therapeutically effective amount of a pharmaceutical composition of any one of clauses 84-90.
192. A method of treating a disease mediated by binding to CD155 expressed on cells in a subject, the method comprising administering to the subject a therapeutically effective amount of an antibody of any one of clauses 1-71, or administering to the subject a therapeutically effective amount of a pharmaceutical composition of any one of clauses 84-90.
193. A method of treating a disease mediated by CD226 and/or TIGIT in a subject, the method comprising administering to the subject a therapeutically effective amount of an antibody of any one of clauses 1-71, or administering to the subject a therapeutically effective amount of a pharmaceutical composition of any one of clauses 84-90.
194. A method of treating cancer in a subject, the method comprising administering to the subject a therapeutically effective amount of an antibody of any one of clauses 1-71, or administering to the subject a therapeutically effective amount of a pharmaceutical composition of any one of clauses 84-90; optionally, wherein the cancer is selected from adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer.

195. The method of any one of clauses 91-94, wherein the antibody is a bispecific antibody comprising a specificity for an antigen selected from PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R, CD73, CD83, CD39, TRAIL, CD226, and VISTA; optionally, wherein the antigen is selected from PD-1, TIGIT, LAG3, PVRIG, KIR, TIM-3, and CRTAM.

196. The method of any one of clauses 91-95, wherein the method comprises co-administering to the subject a therapeutically effective amount of an antibody comprising a specificity for PD1; optionally, wherein the antibody comprising a specificity for PD1 is selected from dostarlimab, pembrolizumab, nivolumab, and pidilizumab.

197. A method of treating a pathogenic infection in a subject, the method comprising administering to the subject a therapeutically amount of an antibody of any one of clauses 1-71, or administering to the subject a therapeutically effective amount of a pharmaceutical composition of any one of clauses 84-90; optionally, wherein the pathogenic infection is selected from: *Acinetobacter baumannii. Acinetobacter lwoffii*, *Acinetobacter* spp. (incl. MDR), *Actinomycetes, Adenovirus, Aeromonas* spp., *Alcaligenes faecalis, Alcaligenes* spp./*Achromobacter* spp., *Alcaligenes xylosoxidans* (incl. ESBL/MRGN), Arbovirus, *Aspergillus* spp., Astrovirus. *Bacillus anthracis, Bacillus cereus, Bacillus subtilis, Bacteroides fragilis, Bartonella quintana. Bordetella pertussis, Borrelia burgdorferi, Borrelia recurrentis, Brevundimonas diminuta, Brevundimonas vesicularis, Brucella* spp., *Burkholderia cepacia* (incl. MDR), *Burkholderia mallei, Burkholderia pseudomallei. Campylobacter jejuni/coli, Candida albicans, Candida krusei. Candida parapsilosis*, Chikungunya virus (CHIKV), *Chlamydia pneumoniae. Chlamydia psittaci, Chlamydia trachomatis. Citrobacter* spp., *Clostridium botulinum, Clostridium difficile, Clostridium perfringens, Clostridium letani*, Coronavirus (incl. SARS- and MERS-CoV), *Corynebacterium diphtheriae, Corynebacterium pseudotuberculosis, Corynebacterium* spp., *Corynebacterium ulcerans. Coxiella burnetii*, Coxsackievirus, Crimean-Congo haemorrhagic fever virus, *Cryptococcus neoformans, Cryptosporidium hominis, Cryptosporidium parvum, Cyclospora cayetanensis*, Cytomegalovirus (CMV), Dengue virus, Ebola virus, Echovirus, *Entamoeba histolytica, Enterobacter aerogenes, Enterobacter cloacae* (incl. ESBL/MRGN), *Enterococcus faecalis* (incl. VRE), *Enterococcus faecium* (incl. VRE), *Enterococcus hirae, Epidermophyton* spp., Epstein-Barr virus (EBV), *Escherichia coli* (incl. EHEC, EPEC, ETEC, EIEC, EAEC, ESBL/MRGN, DAEC), Foot-and-mouth disease virus (FMDV), *Francisella tularensis, Giardia lamblia, Haemophilus influenzae*, Hantavirus, *Helicobacter pylori*, Helminths (Worms), Hepatitis A virus (HAV), Hepatitis B virus (HBV), Hepatitis C virus (HCV), Hepatitis D virus, Hepatitis E virus, Herpes simplex virus (HSV), *Histoplasma capsulatum*, Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, *Klebsiella granulomatis, Klebsiella oxytoca* (incl. ESBL/MRGN), *Klebsiella pneumoniae* MDR (incl. ESBL/MRGN), Lassa virus, *Leclercia adecarboxylata, Legionella pneumophila, Leishmania* spp., *Leptospira interrogans, Leuconostoc pseudomesenteroides, Listeria monocytogenes*, Marburg virus, Measles virus. *Micrococcus luteus. Microsporum* spp., Molluscipoxvirus, *Morganella* spp., Mumps virus, *Mycobacterium chimaera* Myco, *Mycobacterium leprae* Myco, *Mycobacterium tuberculosis* (incl. MDR), *Mycoplasma genitalium, Mycoplasma pneumoniae, Neisseria meningitidis, Neisseria gonorrhoeae*, Norovirus, *Orientia tsutsugamushi, Pantoea agglomerans*, Parainfluenza virus, Parvovirus, *Pediculus humanus capitis, Pediculus humanus corporis, Plasmodium* spp., *Pneumocystis jiroveci*, Poliovirus, Polyomavirus, *Proteus mirabilis* (incl. ESBL/MRGN), *Proteus vulgaris, Providencia rettgeri, Providencia stuartii, Pseudomonas aeruginosa. Pseudomonas* spp., Rabies virus, *Ralstonia* spp., Respiratory syncytial virus (RSV), Rhinovirus, *Rickettsia prowazekii, Rickettsia typhi, Roseomonas gilardii*, Rotavirus, Rubella virus, *Salmonella enteritidis, Salmonella paratyphi, Salmonella* spp., *Salmonella typhimurium, Sarcoptes scabiei* (Itch mite), Sapovirus, *Serratia marcescens* (incl. ESBL/MRGN), *Shigella sonnei, Sphingomonas species, Staphylococcus aureus* (incl. MRSA, VRSA), *Staphylococcus capitis, Staphylococcus epidermidis* (incl. MRSE), *Staphylococcus haemolyticus, Staphylococcus hominis. Staphylococcus lugdunensis, Staphylococcus saprophyticus, Stenotrophomonas maltophilia, Streptococcus pneumoniae, Streptococcus pyogenes* (incl. PRSP), *Streptococcus* spp., TBE virus, *Toxoplasma gondii, Treponema pallidum, Trichinella spiralis, Trichomonas vaginalis, Trichophyton* spp., *Trichosporon* spp., *Trypanosoma brucei* gambiense, *Trypanosoma brucei* rhodesiense, *Trypanosoma cruzi*, Vaccinia virus, Varicella zoster virus (VSV), Variola virus, *Vibrio cholerae*, West Nile virus (WNV), Yellow fever virus, *Yersinia enterocolitica, Yersinia pestis, Yersinia pseudotuberculosis*, Zika virus, and the like.

198. A method of treating a viral infection in a subject, the method comprising administering to the subject a therapeutically amount of an antibody of any one of clauses 1-71, or administering to the subject a therapeutically effective amount of a pharmaceutical composition of any one of clauses 84-90; optionally, wherein the viral infection is selected from: Adenovirus, Arbovirus, Astrovirus, Chikungunya virus (CHIKV), Coronavirus (incl. SARS- and MERS-CoV), Crimean-Congo haemorrhagic fever virus, Cytomegalovirus (CMV), Dengue virus, Ebola virus, Echovirus, Epstein-Barr virus (EBV), Foot-and-mouth disease virus (FMDV), Hantavirus, Hepatitis A virus (HAV), Hepatitis B virus (HBV), Hepatitis C virus (HCV), Hepatitis D virus, Hepatitis E virus, Herpes simplex virus (HSV), Human enterovirus 71, Human herpesvirus 6 (HHV-6), Human herpesvirus 7 (HHV-7), Human herpesvirus 8 (HHV-8), Human immunodeficiency virus (HIV), Human metapneumovirus, Human papillomavirus (HPV), Influenza virus, Marburg virus, Measles virus, Mumps virus, Norovirus, Parainfluenza virus, Parvovirus. Poliovirus. Polyomavirus, Rabies virus, Respiratory syncytial virus (RSV), Rhinovirus, Rotavirus, Rubella virus, Sapovirus, TBE virus, Vaccinia virus, Varicella zoster virus (VSV), Variola virus, West Nile virus (WNV), Yellow fever virus, and Zika virus.

199. An anti-CD96 antibody that competes with antibody Nk92.39 for binding to an epitope of human CD96 and has a binding affinity of $1 \times 10^{-8}$ M or less; optionally, wherein the binding affinity to human CD96 is measured by equilibrium dissociation constant ($K_D$) to a hu-CD96 polypeptide of SEQ ID NO: 4; optionally, wherein the antibody binds to human and/or cynomolgus monkey CD226 with a binding affinity of 50 nM to 1 µM; optionally wherein the binding affinity to human and/or cynomolgus monkey CD226 is measured by $K_D$ to a hu-CD226 polypeptide of SEQ ID NO: 482 and/or a cy-CD226 polypeptide of SEQ ID NO:483.

200. The antibody of clause 99, wherein the antibody comprises:
a first light chain hypervariable region (HVR-L1) of SEQ ID NO: 13, a second light chain hypervariable region (HVR-L2) of SEQ ID NO: 14, a third light chain hypervariable region (HVR-L3) of SEQ ID NO: 15; and/or a first heavy chain hypervariable region (HVR-H1) of SEQ ID NO: 41, a second heavy chain hypervariable region (HVR-H2) of SEQ ID NO: 42, and a third heavy chain hypervariable region (HVR-H3) of SEQ ID NO: 43;
a first light chain hypervariable region (HVR-L1) of SEQ ID NO: 17, a second light chain hypervariable region (HVR-L2) of SEQ ID NO: 18, a third light chain hypervariable region (HVR-L3) of SEQ ID NO: 19; and/or a first heavy chain hypervariable region (HVR-H1) of SEQ ID NO: 45, a second heavy chain hypervariable region (HVR-H2) of SEQ ID NO: 46, and a third heavy chain hypervariable region (HVR-H3) of SEQ ID NO: 47;
a first light chain hypervariable region (HVR-L1) of SEQ ID NO: 21, a second light chain hypervariable region (HVR-L2) of SEQ ID NO: 22, a third light chain hypervariable region (HVR-L3) of SEQ ID NO: 23; and/or a first heavy chain hypervariable region (HVR-H1) of SEQ ID NO: 49, a second heavy chain hypervariable region (HVR-H2) of SEQ ID NO: 50, and a third heavy chain hypervariable region (HVR-H3) of SEQ ID NO: 51;
a first light chain hypervariable region (HVR-L1) of SEQ ID NO: 25, a second light chain hypervariable region (HVR-L2) of SEQ ID NO: 26, a third light chain hypervariable region (HVR-L3) of SEQ ID NO: 27; and/or a first heavy chain hypervariable region (HVR-H1) of SEQ ID NO: 53, a second heavy chain hypervariable region (HVR-H2) of SEQ ID NO: 54, and a third heavy chain hypervariable region (HVR-H3) of SEQ ID NO: 55;
a first light chain hypervariable region (HVR-L1) of SEQ ID NO: 29, a second light chain hypervariable region (HVR-L2) of SEQ ID NO: 30, a third light chain hypervariable region (HVR-L3) of SEQ ID NO: 31; and/or a first heavy chain hypervariable region (HVR-H1) of SEQ ID NO: 57, a second heavy chain hypervariable region (HVR-H2) of SEQ ID NO: 58, and a third heavy chain hypervariable region (HVR-H3) of SEQ ID NO: 59; or
a first light chain hypervariable region (HVR-L1) of SEQ ID NO: 37, a second light chain hypervariable region (HVR-L2) of SEQ ID NO: 38, a third light chain hypervariable region (HVR-L3) of SEQ ID NO: 39; and/or a first heavy chain hypervariable region (HVR-H1) of SEQ ID NO: 65, a second heavy chain hypervariable region (HVR-H2) of SEQ ID NO: 66, and a third heavy chain hypervariable region (HVR-H3) of SEQ ID NO: 67.

201. The antibody of any one of clauses 99-100, wherein the antibody comprises:
a light chain variable domain ($V_L$) amino acid sequence having at least 90% identity to SEQ ID NO: 12; and/or a heavy chain variable domain ($V_H$) amino acid sequence having at least 90% identity to SEQ ID NO: 40;
a light chain variable domain ($V_L$) amino acid sequence having at least 90% identity to SEQ ID NO: 16; and/or a heavy chain variable domain ($V_H$) amino acid sequence having at least 90% identity to SEQ ID NO: 44;
a light chain variable domain ($V_L$) amino acid sequence having at least 90% identity to SEQ ID NO: 20; and/or a heavy chain variable domain ($V_H$) amino acid sequence having at least 90% identity to SEQ ID NO: 48;
a light chain variable domain ($V_L$) amino acid sequence having at least 90% identity to SEQ ID NO: 24; and/or a heavy chain variable domain ($V_H$) amino acid sequence having at least 90% identity to SEQ ID NO: 52;
a light chain variable domain ($V_L$) amino acid sequence having at least 90% identity to SEQ ID NO: 28; and/or a heavy chain variable domain ($V_H$) amino acid sequence having at least 90% identity to SEQ ID NO: 56;
a light chain variable domain ($V_L$) amino acid sequence having at least 90% identity to SEQ ID NO: 36; and/or a heavy chain variable domain ($V_H$) amino acid sequence having at least 90% identity to SEQ ID NO: 64;
a light chain variable domain ($V_L$) amino acid sequence having at least 90% identity to SEQ ID NO: 68; and/or a heavy chain variable domain ($V_H$) amino acid sequence having at least 90% identity to an amino acid sequence selected from SEQ ID NO: 69, 250-275, or 460-464; or
a light chain variable domain ($V_L$) amino acid sequence having at least 90% identity to SEQ ID NO: 70; and/or a heavy chain variable domain ($V_H$) amino acid sequence having at least 90% identity to SEQ ID NO: 71.

202. The antibody of any one of clauses 99-101, wherein the antibody comprises:
a light chain (LC) amino acid sequence of SEQ ID NO: 440; and/or a heavy chain (HC) amino acid sequence of SEQ ID NO: 447 or 484;
a light chain (LC) amino acid sequence of SEQ ID NO: 441; and/or a heavy chain (HC) amino acid sequence of SEQ ID NO: 448 or 485;
a light chain (LC) amino acid sequence of SEQ ID NO: 442; and/or a heavy chain (HC) amino acid sequence of SEQ ID NO: 449 or 486;
a light chain (LC) amino acid sequence of SEQ ID NO: 443; and/or a heavy chain (HC) amino acid sequence of SEQ ID NO: 450 or 487;
a light chain (LC) amino acid sequence of SEQ ID NO: 444; and/or a heavy chain (HC) amino acid sequence of SEQ ID NO: 451 or 488;
a light chain (LC) amino acid sequence of SEQ ID NO: 446; and/or a heavy chain (HC) amino acid sequence of SEQ ID NO: 453 or 490;
a light chain (LC) amino acid sequence of SEQ ID NO: 454; and/or a heavy chain (HC) amino acid sequence selected from SEQ ID NO: 455-459, and 491-495; or
a light chain (LC) amino acid sequence of SEQ ID NO: 470; and/or a heavy chain (HC) amino acid sequence of SEQ ID NO: 471 or 501.

203. The antibody of any one of clauses 1-71 for use as a medicament; optionally, for use in the treatment of a cancer or a pathogenic infection.

While the foregoing disclosure of the present invention has been described in some detail by way of example and illustration for purposes of clarity and understanding, this disclosure including the examples, descriptions, and embodiments described herein are for illustrative purposes, are intended to be exemplary, and should not be construed as limiting the present disclosure. It will be clear to one skilled in the art that various modifications or changes to the examples, descriptions, and embodiments described herein can be made and are to be included within the spirit and purview of this disclosure and the appended claims. Further, one of skill in the art will recognize a number of equivalent methods and procedure to those described herein. All such equivalents are to be understood to be within the scope of the present disclosure and are covered by the appended claims.

Additional embodiments of the invention are set forth in the following claims.

The disclosures of all publications, patent applications, patents, or other documents mentioned herein are expressly incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including specified terms, will control.

BIBLIOGRAPHY

1. Foote et al., (1992) "Antibody framework residues affecting the conformation of the hypervariable loops" J. Mol. Biol. 224: 487-499
2. Hotzel et al., (2012) "A strategy for risk mitigation of antibodies with fast clearance" mAbs 4(6): 753-760
3. Brenner et al., (1992) "Encoded combinatorial chemistry" Proc. Natl. Acad. Sci. USA 89(12): 5381-5383
4. Kunkel et al., (1987) "Rapid and efficient site-specific mutagenesis without phenotypic selection" Methods Enzymol. 154: 367-382
5. Masella et al., (2012) "PANDAseq: paired-end assembler for illumine sequences" BMC Bioinformatics 13:31
6. Koenig et al., (2015) "Mutational landscape of antibody variable domains reveals a switch modulating the interdomain conformational dynamics and antigen binding" J. Biol. Chem. 290(36): 21773-21786
7. Meyer et al., (2009) "CD96 interaction with CD155 via its first Ig-like domain is modulated by alternative splicing or mutations in distal Ig-like domains." J. Biol. Chem. 284:2235-44
8. Fuchs et al., (2004) "Cutting edge: CD96 (tactile) promotes NK cell-target cell adhesion by interacting with the poliovirus receptor (CD155)." J. Immunol. 172:3994-8.

What is claimed is:

1. A method of treating a CD96 mediated disease in a subject, the method comprising administering to the subject a therapeutically effective amount of a pharmaceutical composition comprising an anti-CD96 antibody and a pharmaceutically acceptable carrier, wherein the anti-CD96 antibody comprises: (i) a first light chain hypervariable region (HVR-L1), a second light chain hypervariable region (HVR-L2), and a third light chain hypervariable region (HVR-L3), and (ii) a first heavy chain hypervariable region (HVR-H1), a second heavy chain hypervariable region (HVR-H2), and a third heavy chain hypervariable region (HVR-H3); wherein:

a) HVR-L1 comprises SEQ ID NO: 13, HVR-L2 comprises SEQ ID NO: 14, HVR-L3 comprises SEQ ID NO: 15, HVR-H1 comprises SEQ ID NO: 41, HVR-H2 comprises SEQ ID NO: 42, and HVR-H3 comprises SEQ ID NO: 43;

b) HVR-L1 comprises SEQ ID NO: 13, HVR-L2 comprises SEQ ID NO: 14, HVR-L3 comprises SEQ ID NO: 15, HVR-H1 comprises SEQ ID NO: 95, HVR-H2 comprises SEQ ID NO: 42, and HVR-H3 comprises SEQ ID NO: 43;

c) HVR-L1 comprises SEQ ID NO: 13, HVR-L2 comprises SEQ ID NO: 14, HVR-L3 comprises SEQ ID NO: 15, HVR-H1 comprises SEQ ID NO: 41, HVR-H2 comprises SEQ ID NO: 112, and HVR-H3 comprises SEQ ID NO: 43;

d) HVR-L1 comprises SEQ ID NO: 13, HVR-L2 comprises SEQ ID NO: 14, HVR-L3 comprises SEQ ID NO: 15, HVR-H1 comprises SEQ ID NO: 41, HVR-H2 comprises SEQ ID NO: 42, and HVR-H3 comprises SEQ ID NO: 221;

e) HVR-L1 comprises SEQ ID NO: 37, HVR-L2 comprises SEQ ID NO: 38, HVR-L3 comprises SEQ ID NO: 39, HVR-H1 comprises SEQ ID NO: 65, HVR-H2 comprises SEQ ID NO: 66, and HVR-H3 comprises SEQ ID NO: 67; or f) HVR-L1 comprises SEQ ID NO: 13, HVR-L2 comprises SEQ ID NO: 14, HVR-L3 comprises SEQ ID NO: 15, HVR-H1 comprises SEQ ID NO: 95, HVR-H2 comprises SEQ ID NO: 112, and HVR-H3 comprises SEQ ID NO: 221.

2. The method of claim 1, wherein the anti-CD96 antibody comprises a light chain variable domain (VL) amino acid sequence having at least 90% identity to SEQ ID NO: 68, and a heavy chain variable domain (VH) amino acid sequence having at least 90% identity to SEQ ID NO: 272.

3. The method of claim 2, wherein the anti-CD96 antibody comprises: the light chain variable domain (VL) amino acid sequence of SEQ ID NO: 68, and the heavy chain variable domain (VH) amino acid sequence of SEQ ID NO: 272.

4. The method of claim 1, wherein the anti-CD96 antibody comprises a light chain (LC) amino acid sequence having at least 90% identity to SEQ ID NO: 454, and a heavy chain (HC) amino acid sequence having at least 90% identity to SEQ ID NO: 492.

5. The method of claim 4, wherein the anti-CD96 antibody comprises: the light chain (LC) amino acid sequence of SEQ ID NO: 454, and the heavy chain (HC) amino acid sequence of SEQ ID NO: 492.

6. The method of claim 1, wherein the anti-CD96 antibody is characterized by at least one of the following properties:

a) binds to human CD96 with a binding affinity of $1\times10^{-8}$ M or less;

b) binds to cynomolgus monkey CD96 with a binding affinity of $1\times10^{-8}$ M or less;

c) binds to human CD96 isoform 1 expressed on a cell with an antibody $EC_{50}$ concentration of 5 nM or less;

d) binds to human CD96 isoform 2 expressed on a cell with an antibody $EC_{50}$ concentration of 5 nM or less;

e) binds to cynomolgus monkey PBMCs with an antibody $EC_{50}$ concentration of 5 nM or less, 1 nM or less, or 0.1 nM or less;

f) decreases binding of human CD155 to human CD96 expressed on CHO cells by at least 90%;

g) increases IFNγ secretion from human PBMCs by at least 1.8-fold;

h) increases IL-2 secretion from human PBMCs by at least 1.8-fold;

i) binds to human and/or cynomolgus monkey CD226 expressed on cells;

j) binds to human CD226 with a binding affinity of 1 μM or less, 900 nM or less, 800 nM or less, 700 nM or less, from 1 μM to 50 nM, or from 800 nM to 200 nM; optionally, wherein the binding affinity is measured by equilibrium dissociation constant ($K_D$) to a hu-CD226 polypeptide of SEQ ID NO: 482; and k) binds to cynomolgus monkey CD226 with a binding affinity of 1 μM or less, 800 nM or less.

7. The method of claim 1, wherein the anti-CD96 antibody binds to human CD96 with a binding affinity of $1\times10^{-8}$ M or less, $1\times10^{-9}$ M or less, $1\times10^{-10}$ M or less, or $1\times10^{-11}$ M or less and wherein the binding affinity is measured by equilibrium dissociation constant ($K_D$) to a hu-CD96 polypeptide of SEQ ID NO: 4.

8. The method of claim 1, wherein the anti-CD96 antibody binds to cynomolgus monkey CD96 with a binding affinity of $1\times10^{-8}$ M or less, $1\times10^{-9}$ M or less, $1\times10^{-10}$ M or less, or $1\times10^{-11}$ M or less and wherein the binding affinity is measured by equilibrium dissociation constant ($K_D$) to a cy-CD96 polypeptide of SEQ ID NO: 7.

9. The method of claim 1, wherein the anti-CD96 antibody binds to human CD96 isoform 1 expressed on a cell with an anti-CD96 antibody $EC_{50}$ concentration of 5 nM or less, 1 nM or less, or 0.1 nM or less and wherein the cell is a HEK293T cell.

10. The method of claim 1, wherein the anti-CD96 antibody binds to human CD96 isoform 2 expressed on a cell with an antibody EC$_{50}$ concentration of 5 nM or less, 1 nM or less, or 0.1 nM or less and wherein the cell is a CHO cell.

11. The method of claim 1, wherein the anti-CD96 antibody decreases binding of human CD155 to human CD96 expressed on CHO cells by at least 90%, at least 95%, at least 99%, or 100% and wherein at a human CD155 concentration of 10 nM the anti-CD96 antibody has an IC$_{50}$ of 5 nM or less, 1 nM or less, or 0.1 nM or less.

12. The method of claim 1, wherein the anti-CD96 antibody increases IFNγ secretion from human PBMCs by at least 1.8-fold, at least 1.9-fold, at least 2-fold, at least 2.1-fold, or at least 2.20-fold and wherein the anti-CD96 antibody has an EC50 concentration of 0.3 nM or less, 0.2 nM or less, or 0.1 nM or less.

13. The method of claim 1, wherein the anti-CD96 antibody increases IL-2 secretion from human PBMCs by at least 1.8-fold, at least 1.9-fold, at least 2-fold, at least 2.1-fold, or at least 2.20-fold and wherein the anti-CD96 antibody has an EC$_{50}$ concentration of 0.3 nM or less, 0.2 nM or less, or 0.1 nM or less.

14. The method of claim 1, wherein the anti-CD96 antibody binds to human or cynomolgus monkey CD226 expressed on HEK293 cells, with an anti-CD96 antibody EC$_{50}$ concentration of 500 nM or less, 300 nM or less, 250 nM or less, 200 nM or less, 150 nM or less, 100 nM or less, or 50 nM or less.

15. The method of claim 1, wherein the anti-CD96 antibody binds to human CD226 with a binding affinity of 1 µM or less, 900 nM or less, 800 nM or less, 700 nM or less, from 1 µM to 50 nM, or from 800 nM to 200 nM; and wherein the binding affinity is measured by equilibrium dissociation constant (K$_D$) to a hu-CD226 polypeptide of SEQ ID NO: 482.

16. The method of claim 1, wherein the anti-CD96 antibody binds to cynomolgus monkey CD226 with a binding affinity of 1 µM or less, 800 nM or less, 500 nM or less, 300 nM or less, 100 nM or less, from 1 µM to 50 nM, from 500 nM to 60 nM, or from 300 nM to 70 nM; and wherein the binding affinity is measured by equilibrium dissociation constant (K$_D$) to a cyCD226 polypeptide of SEQ ID NO: 483.

17. The method of claim 1, wherein the anti-CD96 antibody specifically binds to one or more amino acid residues within domain 1 of hu-CD96, wherein domain 1 comprises the amino acid sequence of SEQ ID NO: 5.

18. The method of claim 1, wherein the CD96 mediated disease is a viral infection or cancer.

19. The method of claim 18, wherein the viral infection is selected from is selected from the group consisting of Cytomegalovirus (CMV), Epstein Barr Virus (EBV), Herpes Simplex Virus (HSV), Human Immunodeficiency Virus (HIV), Human Papilloma Virus (HPV), and Varicella Zoster Virus (VSV).

20. The method of claim 18, wherein the cancer is selected from the group consisting of adrenal gland cancer, bladder cancer, brain cancer, breast cancer, cervical cancer, colorectal cancer, EGJ adenocarcinoma, esophageal cancer, gall bladder cancer, gastric cancer, head and neck cancer, heart cancer, hepatocellular carcinoma, kidney cancer, liver cancer, melanoma, mesothelioma, non-small cell lung cancer, ovarian cancer, pancreatic cancer, prostate cancer, spleen cancer, small cell lung cancer, testicular cancer, thyroid cancer, and uterine cancer; in some embodiments, the cancer is selected from lung cancer, skin cancer (e.g., melanoma), pancreatic cancer, endometrial cancer, prostate cancer, colorectal cancer, ovarian cancer, and bladder cancer.

21. The method of claim 1, wherein the composition comprises a therapeutically effective amount of the anti-CD96 antibody.

22. The method of claim 1, wherein the pharmaceutical composition further comprises a chemotherapeutic agent or a second antibody comprising a specificity for an immune checkpoint molecule.

23. The method of claim 22, wherein the immune checkpoint molecule is selected from the group consisting of: PD1, TIGIT, LAG3, PVRIG, KIR, TIM-3, CRTAM, CTLA-4, BTLA, CD244, CD160, LIGHT, GITR, 4-1BB, OX40, CD27, TMIGD2, ICOS, CD40, CD47, SIRPa, NKG2D, NKG2A, TNFRSF25, CD33, CEA, Epcam, GPC3, CD200, CD200R1, CD73, CD83, CD39, TRAIL, CD226, and VISTA.

24. The method of claim 1, wherein the anti-CD96 antibody is the sole active agent of the composition.

* * * * *

SEQUENCE LISTING

```
Sequence total quantity: 501
SEQ ID NO: 1            moltype = AA  length = 585
FEATURE                 Location/Qualifiers
source                  1..585
                        mol_type = protein
                        organism = Homo sapiens
SEQUENCE: 1
MEKKWKYCAV YYIIQIHFVK GVWEKTVNTE ENVYATLGSD VNLTCQTQTV GFFVQMQWSK   60
VTNKIDLIAV YHPQYGFYCA YGRPCESLVT FTETPENGSK WTLHLRNMSC SVSGRYECML  120
VLYPEGIQTK IYNLLIQTHV TADEWNSNHT IEIEINQTLE IPCFQNSSSK ISSEFTYAWS  180
VENSSTDSWV LLSKGIKEDN GTQETLISQN HLISNSTLLK DRVKLGTDYR LHLSPVQIFD  240
DGRKFSCHIR VGPNKILRSS TTVKVFAKPE IPVIVENNST DVLVERRFTC LLKNVFPKAN  300
ITWFIDGSFL HDEKEGIYIT NEERKGKDGF LELKSVLTRV HSNKPAQSDN LTIWCMALSP  360
VPGNKVWNIS SEKITFLLGS EISSTDPPLS VTESTLDTQP SPASSVSPAR YPATSSVTLV  420
DVSALRPNTT PQPSNSSMTT RGFNYPWTSS GTDTKKSVSR IPSETYSSSP SGAGSTLHDN  480
VFTSTARAFS EVPTTANGST KTNHVHITGI VVNKPKDGMS WPVIVAALLF CCMILFGLGV  540
RKWCQYQKEI MERPPPFKPP PPPIKYTCIQ EPNESDLPYH EMETL                 585

SEQ ID NO: 2            moltype = AA  length = 569
FEATURE                 Location/Qualifiers
source                  1..569
                        mol_type = protein
                        organism = Homo sapiens
SEQUENCE: 2
MEKKWKYCAV YYIIQIHFVK GVWEKTVNTE ENVYATLGSD VNLTCQTQTV GFFVQMQWSK   60
VTNKIDLIAV YHPQYGFYCA YGRPCESLVT FTETPENGSK WTLHLRNMSC SVSGRYECML  120
VLYPEGIQTK IYNLLIQTHV TADEWNSNHT IEIEINQTLE IPCFQNSSSK ISSEFTYAWS  180
VEDNGTQETL ISQNHLISNS TLLKDRVKLG TDYRLHLSPV QIFDDGRKFS CHIRVGPNKI  240
LRSSTTVKVF AKPEIPVIVE NNSTDVLVER RFTCLLKNVF PKANITWFID GSFLHDEKEG  300
IYITNEERKG KDGFLELKSV LTRVHSNKPA QSDNLTIWCM ALSPVPGNKV WNISSEKITF  360
LLGSEISSTD PPLSVTESTL DTQPSPASSV SPARYPATSS VTLVDVSALR PNTTPQPSNS  420
SMTTRGFNYP WTSSGTDTKK SVSRIPSETY SSSPSGAGST LHDNVFTSTA RAFSEVPTTA  480
NGSTKTNHVH ITGIVVNKPK DGMSWPVIVA ALLFCCMILF GLGVRKWCQY QKEIMERPPP  540
FKPPPPPIKY TCIQEPNESD LPYHEMETL                                   569

SEQ ID NO: 3            moltype = DNA  length = 1710
FEATURE                 Location/Qualifiers
source                  1..1710
                        mol_type = genomic DNA
                        organism = Homo sapiens
SEQUENCE: 3
atggagaaaa aatggaaata ctgtgctgtc tattacatca tccagataca ttttgtcaag   60
ggagtttggg aaaaaacagt caacacagaa gaaaatgttt atgctacact tggctctgat  120
gtcaacctga cctgccaaac acagacagta ggcttcttcg tgcagatgca atggtccaag  180
gtcaccaata agatagacct gattgctgtc tatcatcccc aatacggctt ctactgtgcc  240
```

```
tatgggagac cctgtgagtc acttgtgact ttcacagaaa ctcctgagaa tgggtcaaaa    300
tggactctgc acttaaggaa tatgtcttgt tcagtcagtg gaaggtacga gtgtatgctt    360
gttctgtatc cagagggcat tcagactaaa atctacaacc ttctcattca gacacacgtt    420
acagcagatg aatggaacag caaccatacg atagaaatag ataaatca gactctgaa    480
ataccatgct ttcaaaatag ctcctcaaaa atttcatctg agttcaccta tgcatggtcg    540
gtggaggata atggaactca ggaaacactt atctcccaaa atcacctcat cagcaattcc    600
acattactta agatagagt caagcttggt acagactaca gactccacct ctctccagtc    660
caaatcttcg atgatgggcg gaagttctct tgccacatta gagtcggtcc taacaaaatc    720
ttgaggagct ccaccacagt caaggttttt gctaaaccag aaatccctgt gattgtggaa    780
aataactcca cggatgtctt ggtagagaga agatttacct gcttactaaa gaatgtattt    840
cccaaagcaa atatcacatg gtttatagat ggaagtttc ttcatgatga aaaagaagga    900
atatatatta ctaatgaaga gagaaaaggc aagatggat ttttggaact gaagtctgtt    960
ttaacaaggg tacatagtaa taaaccagcc aatcagaca acttgaccat tggtgtatg   1020
gctctgtctc cagtcccagg aaataaagtg tggaacatct catcagaaaa gatcacttt    1080
ctcttaggtt ctgaaatttc ctcaacagac cctccactga gtgttacaga atctaccctt    1140
gacacccaac cttctccagc cagcagtgta tctcctgcaa gatatccagc tacatcttca    1200
gtgacccttg tagatgtgag tgccttgagg ccaaacacca ctcctcaacc cagcaattcc    1260
agtatgacta cccgaggctt caactatccc tggacctcca gtgggacaga taccaaaaaa    1320
tcagtttcac ggatacctag tgaaacatac agttcatccc cctcaggtgc aggctcaaca    1380
cttcatgaca atgtctttac cagcacagcc agagcatttt cagaagtccc cacaactgcc    1440
aatggatcta cgaaaactaa tcacgtccat atcactggta ttgtggtcaa taagcccaaa    1500
gatggaaatgt cctggccagt gattgtagca gctttactct tttgctgcat gatattgttt    1560
ggtcttggag tgagaaaatg gtgtcagtac caaaagaaa taatgaaag acctccacct    1620
ttcaagccac caccacctcc catcaagtac acttgcattc aagagcccaa cgaaagtgat    1680
ctgccttatc atgagatgga gaccctctag                                    1710

SEQ ID NO: 4            moltype = AA   length = 479
FEATURE                 Location/Qualifiers
REGION                  1..479
                        note = Synthetic polypeptide
source                  1..479
                        mol_type = protein
                        organism = synthetic construct
SEQUENCE: 4
VWEKTVNTEE NVYATLGSDV NLTCQTQTVG FFVQMQWSKV TNKIDLIAVY HPQYGFYCAY     60
GRPCESLVTF TETPENGSKW TLHLRNMSCS VSGRYECMLV LYPEGIQTKI YNLLIQTHVT    120
ADEWNSNHTI EIEINQTLEI PCFQNSSSKI SSEFTYAWSV EDNGTQETLI SQNHLISNST    180
LLKDRVKLGT DYRLHLSPVQ IFDDRKFSC HIRVGPNKIL RSSTTVKVFA KPEIPVIVEN    240
NSTDVLVERR FTCLLKNVFP KANITWFIDG SFLHDEKEGI YITNEERKGK DGFLELKSVL    300
TRVHSNKPAQ SDNLTIWCMA LSPVPGNKVW NISSEKITFL LGSEISSTDP PLSVTESTLD    360
TQPSPASSVS PARYPATSSV TLVDVSALRP NTTPQPSNSS MTTRGFNYPW TSSGTDTKKS    420
VSRIPSETYS SSPSGAGSTL HDNVFTSTAR AFSEVPTTAN GSTKTNHVHI TGIVVNKPK    479

SEQ ID NO: 5            moltype = AA   length = 116
FEATURE                 Location/Qualifiers
REGION                  1..116
                        note = Synthetic polypeptide
source                  1..116
                        mol_type = protein
                        organism = synthetic construct
SEQUENCE: 5
VWEKTVNTEE NVYATLGSDV NLTCQTQTVG FFVQMQWSKV TNKIDLIAVY HPQYGFYCAY     60
GRPCESLVTF TETPENGSKW TLHLRNMSCS VSGRYECMLV LYPEGIQTKI YNLLIQ        116

SEQ ID NO: 6            moltype = AA   length = 338
FEATURE                 Location/Qualifiers
REGION                  1..338
                        note = Synthetic polypeptide
source                  1..338
                        mol_type = protein
                        organism = synthetic construct
SEQUENCE: 6
VWEKTVNTEE NVYATLGSDV NLTCQTQTVG FFVQMQWSKV TNKIDLIAVY HPQYGFYCAY     60
GRPCESLVTF TETPENGSKW TLHLRNMSCS VSGRYECMLV LYPEGIQTKI YNLLIQTHVT    120
ADEWNSNHTI EIEINQTLEI PCFQNSSSKI SSEFTYAWSV EDNGTQETLI SQNHLISNST    180
LLKDRVKLGT DYRLHLSPVQ IFDDRKFSC HIRVGPNKIL RSSTTVKVFA KPEIPVIVEN    240
NSTDVLVERR FTCLLKNVFP KANITWFIDG SFLHDEKEGI YITNEERKGK DGFLELKSVL    300
TRVHSNKPAQ SDNLTIWCMA LSPVPGNKVW NISSEKIT                            338

SEQ ID NO: 7            moltype = AA   length = 479
FEATURE                 Location/Qualifiers
REGION                  1..479
                        note = Synthetic polypeptide
source                  1..479
                        mol_type = protein
                        organism = synthetic construct
SEQUENCE: 7
VWGKPFNTEE NIYATLGSDV NLTCQTQAKG FLVQMQWSKV TDKADLIALY HPQYGFHCAY     60
GSPCESLVTF TQTPENGSKW TLHLRNMSSS VSGRYECMLT LYPEGMQTKI YNLLIQTHVT    120
```

```
PDEWKSNHTI EIEINQTLEI PCFQNSSSEI SSEFTYAWLV EDNGTQQTLI SQDHLISSST    180
LLKDRVKVGI DYRLHLSPVQ IFDDGRKFSC HIRVGPDKIL RSSTTIKVFA KPEIPMIVEN    240
NSTDVLVERT FTCLLKNVFP KANIIWFIDG SFLHDEKEGI YITNEERKGK DGFLELKSVL    300
TRVHSDKPAQ SDNLTIWCMA LSPVPGNKVW NISSEKITFL LGSEMSTTDL PPSVTESTLD    360
TQPSPASSVS PTRYPATSSV TLADVSALRP NTTPQSSSSS VTTQDFNYPW TSSGTDAKKS    420
FSQIPSETYS SSPSGAGSTL HDNVFTSTTR ALSEVPTTAN GSTKTNHVHI TGIVVSKPK    479

SEQ ID NO: 8            moltype = AA  length = 338
FEATURE                 Location/Qualifiers
REGION                  1..338
                        note = Synthetic polypeptide
source                  1..338
                        mol_type = protein
                        organism = synthetic construct
SEQUENCE: 8
VWGKPFNTEE NIYATLGSDV NLTCQTQAKG FLVQMQWSKV TDKADLIALY HPQYGFHCAY     60
GSPCESLVTF TQTPENGSKW TLHLRNMSSS VSGRYECMLT LYPEGMQTKI YNLLIQTHVT    120
PDEWKSNHTI EIEINQTLEI PCFQNSSSEI SSEFTYAWLV EDNGTQQTLI SQDHLISSST    180
LLKDRVKVGI DYRLHLSPVQ IFDDGRKFSC HIRVGPDKIL RSSTTIKVFA KPEIPMIVEN    240
NSTDVLVERT FTCLLKNVFP KANIIWFIDG SFLHDEKEGI YITNEERKGK DGFLELKSVL    300
TRVHSDKPAQ SDNLTIWCMA LSPVPGNKVW NISSEKIT                           338

SEQ ID NO: 9            moltype = AA  length = 338
FEATURE                 Location/Qualifiers
REGION                  1..338
                        note = Synthetic polypeptide
source                  1..338
                        mol_type = protein
                        organism = synthetic construct
SEQUENCE: 9
VWGKPLNTEE NIYATLGSDV NLTCQTQAKG FLVQMQWSKV TDKADLIALY HPQYGFHCAY     60
GSPCESLVTF TQTPENGSKW TLHLRNMSSS VSGRYECMLT LYPEGMQTKI YNLLIQTHVT    120
PDEWKSNHTI EIEINQTLEI PCFQNSSSEI SSEFTYAWLV EDNGTQQTLI SQDHLISSST    180
LLKDRVKVGT DYRLHLSPVQ IFDDGRKFSC HIRVGPDKIL RSSTTIKVFA KPEIPMIVEN    240
NSTDVLVERI FTCLLTNVFP KANIIWFIDG SFLHDEKEGI YITNEERKGK DGFLELKSVL    300
TRVHSDKPAQ SDNLTIWCMA LSPVPGNKVW NISSEKIT                           338

SEQ ID NO: 10           moltype = AA  length = 323
FEATURE                 Location/Qualifiers
REGION                  1..323
                        note = Synthetic polypeptide
source                  1..323
                        mol_type = protein
                        organism = synthetic construct
SEQUENCE: 10
WPPPGTGDVV VQAPTQVPGF LGDSVTLPCY LQVPNMEVTH VSQLTWARHG ESGSMAVFHQ     60
TQGPSYSESK RLEFVAARLG AELRNASLRM FGLRVEDEGN YTCLFVTFPQ GSRSVDIWLR    120
VLAKPQNTAE VQKVQLTGEP VPMARCVSTG GRPPAQITWH SDLGGMPNTS QVPGFLSGTV    180
TVTSLWILVP SSQVDGKNVT CKVEHESFEK PQLLTVNLTV YPPPEVSISG YDNNWYLGQN    240
EATLTCDARS NPEPTGYNWS TTMGPLPPFA VAQGAQLLIR PVDKPINTTL ICNVTNALGA    300
RQAELTVQVK EGPPSEHSGM SRN                                           323

SEQ ID NO: 11           moltype = AA  length = 317
FEATURE                 Location/Qualifiers
REGION                  1..317
                        note = Synthetic polypeptide
source                  1..317
                        mol_type = protein
                        organism = synthetic construct
SEQUENCE: 11
DIRVLVPYNS TGVLGGSTTL HCSLTSNENV TITQITWMKK DSGGSHALVA VFHPKKGPNI     60
KEPERVKFLA AQQDLRNASL AISNLSVEDE GIYECQIATF PRGSRSTNAW LKVQARPKNT    120
AEALEPSPTL ILQDVAKCIS ANGHPPGRIS WPSNVNGSHR EMKEPGSQPG TTTVTSYLSM    180
VPSRQADGKN ITCTVEHESL QELDQLLVTL SQPYPPENVS ISGYDGNWYV GLTNLTLTCE    240
AHSKPAPDMA GYNWSTTTGD FPNSVKRQGN MLLISTVEDG LNNTVIVCEV TNALGSGQGQ    300
VHIIVKEKPE NMQQNTR                                                  317

SEQ ID NO: 12           moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 12
DIVMTQSQKF MSTSVGDRVS VTCKASQNVG TAIVWYQKKP GQSPKTLIYS ASTRYTGVPD     60
RFTGSGSGTD FTLTISNVQS EDLAEYFCQQ YSSSPLTFGS GTKLEIK                 107

SEQ ID NO: 13           moltype = AA  length = 11
```

```
FEATURE            Location/Qualifiers
REGION             1..11
                   note = Synthetic polypeptide
source             1..11
                   mol_type = protein
                   organism = synthetic construct
SEQUENCE: 13
KASQNVGTAI V                                                              11

SEQ ID NO: 14      moltype = AA  length = 7
FEATURE            Location/Qualifiers
REGION             1..7
                   note = Synthetic polypeptide
source             1..7
                   mol_type = protein
                   organism = synthetic construct
SEQUENCE: 14
SASTRYT                                                                    7

SEQ ID NO: 15      moltype = AA  length = 9
FEATURE            Location/Qualifiers
REGION             1..9
                   note = Synthetic polypeptide
source             1..9
                   mol_type = protein
                   organism = synthetic construct
SEQUENCE: 15
QQYSSSPLT                                                                  9

SEQ ID NO: 16      moltype = AA  length = 112
FEATURE            Location/Qualifiers
REGION             1..112
                   note = Synthetic polypeptide
source             1..112
                   mol_type = protein
                   organism = synthetic construct
SEQUENCE: 16
DVVMTQTPLT LSVTLGHPAS ISCKSSQSLL DSDGKTYLNW LLQRPGESPK LLIYLVSKLD          60
SGVPDRFTGS GSGTDFTLKI SRVEAEDLGV YYCLQATHSP QTFGGGTKLE IK                 112

SEQ ID NO: 17      moltype = AA  length = 16
FEATURE            Location/Qualifiers
REGION             1..16
                   note = Synthetic polypeptide
source             1..16
                   mol_type = protein
                   organism = synthetic construct
SEQUENCE: 17
KSSQSLLDSD GKTYLN                                                         16

SEQ ID NO: 18      moltype = AA  length = 7
FEATURE            Location/Qualifiers
REGION             1..7
                   note = Synthetic polypeptide
source             1..7
                   mol_type = protein
                   organism = synthetic construct
SEQUENCE: 18
LVSKLDS                                                                    7

SEQ ID NO: 19      moltype = AA  length = 9
FEATURE            Location/Qualifiers
REGION             1..9
                   note = Synthetic polypeptide
source             1..9
                   mol_type = protein
                   organism = synthetic construct
SEQUENCE: 19
LQATHSPQT                                                                  9

SEQ ID NO: 20      moltype = AA  length = 107
FEATURE            Location/Qualifiers
REGION             1..107
                   note = Synthetic polypeptide
source             1..107
                   mol_type = protein
                   organism = synthetic construct
SEQUENCE: 20
DIQMNQSPSS LSASLGDTIT ITCRVSQDIS FWLSWYQQKP GNIPKLLIYK ASNLHTGVPP          60
```

```
RFSGSGSGTD FTLTISSLQP EDIAAYYCLQ SQSYPYTFGG GTKLEIK                  107

SEQ ID NO: 21           moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 21
RVSQDISFWL S                                                         11

SEQ ID NO: 22           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 22
KASNLHT                                                              7

SEQ ID NO: 23           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 23
LQSQSYPYT                                                            9

SEQ ID NO: 24           moltype = AA   length = 106
FEATURE                 Location/Qualifiers
REGION                  1..106
                        note = Synthetic polypeptide
source                  1..106
                        mol_type = protein
                        organism = synthetic construct
SEQUENCE: 24
ENVLTQSPAI MSATLGEKVT MNCRASSNVK YMYWYQQKSG VSPKLWIYYT SNLASGVPTR    60
FSGSGSGTSY SLTISSVEAE DAATYYCQQF TSSPLTFGAG TKLELK                   106

SEQ ID NO: 25           moltype = AA   length = 10
FEATURE                 Location/Qualifiers
REGION                  1..10
                        note = Synthetic polypeptide
source                  1..10
                        mol_type = protein
                        organism = synthetic construct
SEQUENCE: 25
RASSNVKYMY                                                           10

SEQ ID NO: 26           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 26
YTSNLAS                                                              7

SEQ ID NO: 27           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 27
QQFTSSPLT                                                            9

SEQ ID NO: 28           moltype = AA   length = 111
FEATURE                 Location/Qualifiers
REGION                  1..111
                        note = Synthetic polypeptide
source                  1..111
                        mol_type = protein
```

```
                              organism = synthetic construct
SEQUENCE: 28
DIVLTQSPAS LAVSLGQRAI ISCKASQSVT FADTGLMHWY QQKPGQQPKL LIYRASNLEV    60
GVPTRFSGSG SGTDFTLNIH PVEEEDVATY YCQQSREYPW TFGGGTKLEI K            111

SEQ ID NO: 29           moltype = AA   length = 15
FEATURE                 Location/Qualifiers
REGION                  1..15
                        note = Synthetic polypeptide
source                  1..15
                        mol_type = protein
                        organism = synthetic construct
SEQUENCE: 29
KASQSVTFAD TGLMH                                                     15

SEQ ID NO: 30           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 30
RASNLEV                                                              7

SEQ ID NO: 31           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 31
QQSREYPWT                                                            9

SEQ ID NO: 32           moltype = AA   length = 109
FEATURE                 Location/Qualifiers
REGION                  1..109
                        note = Synthetic polypeptide
source                  1..109
                        mol_type = protein
                        organism = synthetic construct
SEQUENCE: 32
QAVVTQESAL TTSPGETVTL TCRSSTGAVT TSNYANWVQE KPDHLFTGLI GGTNNRAPGV    60
PARFSGSLIG DKAALTITGA QTEDEAIYFC SLWYGSHWVF GGGTKLTVL                109

SEQ ID NO: 33           moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 33
RSSTGAVTTS NYAN                                                      14

SEQ ID NO: 34           moltype = AA   length = 7
FEATURE                 Location/Qualifiers
REGION                  1..7
                        note = Synthetic polypeptide
source                  1..7
                        mol_type = protein
                        organism = synthetic construct
SEQUENCE: 34
GTNNRAP                                                              7

SEQ ID NO: 35           moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 35
SLWYGSHWV                                                            9

SEQ ID NO: 36           moltype = AA   length = 107
FEATURE                 Location/Qualifiers
REGION                  1..107
```

```
                          note = Synthetic polypeptide
source                    1..107
                          mol_type = protein
                          organism = synthetic construct
SEQUENCE: 36
DILMTQSPTT LSVTPGETVS LSCRASQDIY RNLHWYQQKS QGTPRLLIKH ASDSISGIPS    60
RFTGSGSGTD FTLSINSVKP EDEGIYYCLQ GYSMPYTFGG GTKLEIK                 107

SEQ ID NO: 37             moltype = AA   length = 11
FEATURE                   Location/Qualifiers
REGION                    1..11
                          note = Synthetic polypeptide
source                    1..11
                          mol_type = protein
                          organism = synthetic construct
SEQUENCE: 37
RASQDIYRNL H                                                         11

SEQ ID NO: 38             moltype = AA   length = 7
FEATURE                   Location/Qualifiers
REGION                    1..7
                          note = Synthetic polypeptide
source                    1..7
                          mol_type = protein
                          organism = synthetic construct
SEQUENCE: 38
HASDSIS                                                               7

SEQ ID NO: 39             moltype = AA   length = 9
FEATURE                   Location/Qualifiers
REGION                    1..9
                          note = Synthetic polypeptide
source                    1..9
                          mol_type = protein
                          organism = synthetic construct
SEQUENCE: 39
LQGYSMPYT                                                             9

SEQ ID NO: 40             moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 40
QVQLQQPGAE LVTPGASVKL SCKASGFTFT NNWMHWVKQR PGQGLEWIGM IHPNSGITNI    60
NEKFKNKATV TVDKSSSTVY IQLSSLTSED SAVYYCRSDG TYEGYFDYWG QGTPLTVSS    119

SEQ ID NO: 41             moltype = AA   length = 6
FEATURE                   Location/Qualifiers
REGION                    1..6
                          note = Synthetic polypeptide
source                    1..6
                          mol_type = protein
                          organism = synthetic construct
SEQUENCE: 41
TNNWMH                                                                6

SEQ ID NO: 42             moltype = AA   length = 13
FEATURE                   Location/Qualifiers
REGION                    1..13
                          note = Synthetic polypeptide
source                    1..13
                          mol_type = protein
                          organism = synthetic construct
SEQUENCE: 42
MIHPNSGITN INE                                                       13

SEQ ID NO: 43             moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 43
RSDGTYEGYF DY                                                        12
```

| | | |
|---|---|---|
| SEQ ID NO: 44<br>FEATURE<br>REGION<br><br>source | moltype = AA   length = 117<br>Location/Qualifiers<br>1..117<br>note = Synthetic polypeptide<br>1..117<br>mol_type = protein<br>organism = synthetic construct | |
| SEQUENCE: 44<br>QVQLQQSGAD LARPGASIKL SCKASGYTFT GYGVTWVKQS TGQGLDWIGE IYPGTVITYY<br>NAKFKGKATL TADKSSSTAY MELRSLTSED SAVYFCARGL GRAMDYWGQG TSVTVSS | | 60<br>117 |
| SEQ ID NO: 45<br>FEATURE<br>REGION<br><br>source | moltype = AA   length = 6<br>Location/Qualifiers<br>1..6<br>note = Synthetic polypeptide<br>1..6<br>mol_type = protein<br>organism = synthetic construct | |
| SEQUENCE: 45<br>TGYGVT | | 6 |
| SEQ ID NO: 46<br>FEATURE<br>REGION<br><br>source | moltype = AA   length = 13<br>Location/Qualifiers<br>1..13<br>note = Synthetic polypeptide<br>1..13<br>mol_type = protein<br>organism = synthetic construct | |
| SEQUENCE: 46<br>EIYPGTVITY YNA | | 13 |
| SEQ ID NO: 47<br>FEATURE<br>REGION<br><br>source | moltype = AA   length = 10<br>Location/Qualifiers<br>1..10<br>note = Synthetic polypeptide<br>1..10<br>mol_type = protein<br>organism = synthetic construct | |
| SEQUENCE: 47<br>ARGLGRAMDY | | 10 |
| SEQ ID NO: 48<br>FEATURE<br>REGION<br><br>source | moltype = AA   length = 121<br>Location/Qualifiers<br>1..121<br>note = Synthetic polypeptide<br>1..121<br>mol_type = protein<br>organism = synthetic construct | |
| SEQUENCE: 48<br>QVQLQQSGPE LLKPGASVKI SCKASGYTFT DYYINWVKQR PGQGLEWIGW IFPGTEGIYY<br>NEKFKGKATL TVDKSSTTAY MLLSSLTSED SAVYFCAREG DYRYYSPLGY WGQGTLVTVS<br>A | | 60<br>120<br>121 |
| SEQ ID NO: 49<br>FEATURE<br>REGION<br><br>source | moltype = AA   length = 6<br>Location/Qualifiers<br>1..6<br>note = Synthetic polypeptide<br>1..6<br>mol_type = protein<br>organism = synthetic construct | |
| SEQUENCE: 49<br>TDYYIN | | 6 |
| SEQ ID NO: 50<br>FEATURE<br>REGION<br><br>source | moltype = AA   length = 13<br>Location/Qualifiers<br>1..13<br>note = Synthetic polypeptide<br>1..13<br>mol_type = protein<br>organism = synthetic construct | |
| SEQUENCE: 50<br>WIFPGTEGIY YNE | | 13 |
| SEQ ID NO: 51<br>FEATURE<br>REGION<br><br>source | moltype = AA   length = 14<br>Location/Qualifiers<br>1..14<br>note = Synthetic polypeptide<br>1..14<br>mol_type = protein | |

```
                                         organism = synthetic construct
SEQUENCE: 51
AREGDYRYYS PLGY                                                                14

SEQ ID NO: 52            moltype = AA   length = 117
FEATURE                  Location/Qualifiers
REGION                   1..117
                         note = Synthetic polypeptide
source                   1..117
                         mol_type = protein
                         organism = synthetic construct
SEQUENCE: 52
QVQLQQSGPE LVKPGASVKI SCKASGYNFN DYYINWVNQR PGQGLEWIGW IFPGRIITYY    60
NEKFKGKATL TVDTSSNTAY MLLSSLTSED SAVYFCARGV GEGFDYWGQG TTLTVSS      117

SEQ ID NO: 53            moltype = AA   length = 6
FEATURE                  Location/Qualifiers
REGION                   1..6
                         note = Synthetic polypeptide
source                   1..6
                         mol_type = protein
                         organism = synthetic construct
SEQUENCE: 53
NDYYIN                                                                          6

SEQ ID NO: 54            moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 54
WIFPGRIITY YNE                                                                 13

SEQ ID NO: 55            moltype = AA   length = 10
FEATURE                  Location/Qualifiers
REGION                   1..10
                         note = Synthetic polypeptide
source                   1..10
                         mol_type = protein
                         organism = synthetic construct
SEQUENCE: 55
ARGVGEGFDY                                                                     10

SEQ ID NO: 56            moltype = AA   length = 118
FEATURE                  Location/Qualifiers
REGION                   1..118
                         note = Synthetic polypeptide
source                   1..118
                         mol_type = protein
                         organism = synthetic construct
SEQUENCE: 56
EVQLLETGGG LVKSGGSLKL SCAASGFTFS DYYMYWVRQT PEKRLEWVAA ISDDGTYTYY   60
PDSVKGRFTI SRDNANNYLY LQMSSLKSED TAIYYCAKAG SYDYFDVWGA GTTVTVSS    118

SEQ ID NO: 57            moltype = AA   length = 6
FEATURE                  Location/Qualifiers
REGION                   1..6
                         note = Synthetic polypeptide
source                   1..6
                         mol_type = protein
                         organism = synthetic construct
SEQUENCE: 57
SDYYMY                                                                          6

SEQ ID NO: 58            moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 58
AISDDGTYTY YPD                                                                 13

SEQ ID NO: 59            moltype = AA   length = 11
FEATURE                  Location/Qualifiers
REGION                   1..11
```

```
                        note = Synthetic polypeptide
source                  1..11
                        mol_type = protein
                        organism = synthetic construct
SEQUENCE: 59
AKAGSYDYFD V                                                                11

SEQ ID NO: 60           moltype = AA  length = 116
FEATURE                 Location/Qualifiers
REGION                  1..116
                        note = Synthetic polypeptide
source                  1..116
                        mol_type = protein
                        organism = synthetic construct
SEQUENCE: 60
QVQLKESGPG LVAPSQSLSI ICTVSGFSLT NYGIHWIRQP PGKGLEWLGI IWAGGSTNYN      60
SALMSRLTIS KDNSKSQVFL KMNSLQTNDT AIYYCARVSM MGFAYWGQGT LVTVSA         116

SEQ ID NO: 61           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 61
TNYGIH                                                                       6

SEQ ID NO: 62           moltype = AA  length = 12
FEATURE                 Location/Qualifiers
REGION                  1..12
                        note = Synthetic polypeptide
source                  1..12
                        mol_type = protein
                        organism = synthetic construct
SEQUENCE: 62
IIWAGGSTNY NS                                                               12

SEQ ID NO: 63           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 63
ARVSMMGFAY                                                                  10

SEQ ID NO: 64           moltype = AA  length = 120
FEATURE                 Location/Qualifiers
REGION                  1..120
                        note = Synthetic polypeptide
source                  1..120
                        mol_type = protein
                        organism = synthetic construct
SEQUENCE: 64
QIQLVQSGPE LKKPGETVKI SCKASGYPFT TYGMSWVKQA PGKGLKWMGW INTDSGVPTY      60
ADDFKGRFAF SLETSANTAY LQINSLKNED AATYFCARNI YYGWGNFDYW GQGTILTVSS     120

SEQ ID NO: 65           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 65
TTYGMS                                                                       6

SEQ ID NO: 66           moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 66
WINTDSGVPT YAD                                                              13
```

```
SEQ ID NO: 67              moltype = AA   length = 13
FEATURE                    Location/Qualifiers
REGION                     1..13
                           note = Synthetic polypeptide
source                     1..13
                           mol_type = protein
                           organism = synthetic construct
SEQUENCE: 67
ARNIYYGWGN FDY                                                              13

SEQ ID NO: 68              moltype = AA   length = 107
FEATURE                    Location/Qualifiers
REGION                     1..107
                           note = Synthetic polypeptide
source                     1..107
                           mol_type = protein
                           organism = synthetic construct
SEQUENCE: 68
DIQLTQSPSS LSASVGDRVT ITCKASQNVG TAIVWYQQKP GKAPKVLIYS ASTRYTGVPS            60
RFSGSGSGTD FTLTISSLQP EDFATYYCQQ YSSSPLTFGQ GTKVEIK                         107

SEQ ID NO: 69              moltype = AA   length = 119
FEATURE                    Location/Qualifiers
REGION                     1..119
                           note = Synthetic polypeptide
source                     1..119
                           mol_type = protein
                           organism = synthetic construct
SEQUENCE: 69
EVQLVQSGAE VKKPGASVKV SCKASGFTFT NNWMHWVRQA PGQGLEWIGM IHPNSGITNI            60
NEKFKNRVTM TTDTSTSTAY MELRSLRSED TAVYYCRSDG TYEGYFDYWG QGTLVTVSS            119

SEQ ID NO: 70              moltype = AA   length = 107
FEATURE                    Location/Qualifiers
REGION                     1..107
                           note = Synthetic polypeptide
source                     1..107
                           mol_type = protein
                           organism = synthetic construct
SEQUENCE: 70
EIVMTQSPDF QSVTPKEKVT ITCRASQDIY RNLHWYQQKP DQTPKLLIKH ASDSISGIPS            60
RFSGSGSGTD FTLTINSLEA EDAAAYYCLQ GYSMPYTFGG GTKVEIK                         107

SEQ ID NO: 71              moltype = AA   length = 120
FEATURE                    Location/Qualifiers
REGION                     1..120
                           note = Synthetic polypeptide
source                     1..120
                           mol_type = protein
                           organism = synthetic construct
SEQUENCE: 71
EIQLVQSGSE LKKPGASVKV SCKASGYPFT TYGMSWVRQA PGQGLEWMGW INTDSGVPTY            60
ADDFKGRFVF SLDTSVSTAY LQISSLKAED TAVYFCARNI YYGWGNFDYW GQGTLVTVSS           120

SEQ ID NO: 72              moltype =      length =
SEQUENCE: 72
000

SEQ ID NO: 73              moltype = AA   length = 6
FEATURE                    Location/Qualifiers
REGION                     1..6
                           note = Synthetic polypeptide
source                     1..6
                           mol_type = protein
                           organism = synthetic construct
SEQUENCE: 73
ANNWMH                                                                       6

SEQ ID NO: 74              moltype = AA   length = 6
FEATURE                    Location/Qualifiers
REGION                     1..6
                           note = Synthetic polypeptide
source                     1..6
                           mol_type = protein
                           organism = synthetic construct
SEQUENCE: 74
DNNWMH                                                                       6

SEQ ID NO: 75              moltype = AA   length = 6
```

```
FEATURE                 Location/Qualifiers
REGION                  1..6
                        note = Synthetic polypeptide
source                  1..6
                        mol_type = protein
                        organism = synthetic construct
SEQUENCE: 75
ENNWMH                                                                      6

SEQ ID NO: 76           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 76
GNNWMH                                                                      6

SEQ ID NO: 77           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 77
HNNWMH                                                                      6

SEQ ID NO: 78           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 78
KNNWMH                                                                      6

SEQ ID NO: 79           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 79
NNNWMH                                                                      6

SEQ ID NO: 80           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 80
QNNWMH                                                                      6

SEQ ID NO: 81           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 81
RNNWMH                                                                      6

SEQ ID NO: 82           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 82
SNNWMH                                                                      6
```

```
SEQ ID NO: 83                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 83
VNNWMH                                                                      6

SEQ ID NO: 84                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 84
WNNWMH                                                                      6

SEQ ID NO: 85                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 85
YNNWMH                                                                      6

SEQ ID NO: 86                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 86
TNAWMH                                                                      6

SEQ ID NO: 87                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 87
TNFWMH                                                                      6

SEQ ID NO: 88                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 88
TNGWMH                                                                      6

SEQ ID NO: 89                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 89
TNHWMH                                                                      6

SEQ ID NO: 90                  moltype = AA  length = 6
FEATURE                        Location/Qualifiers
REGION                         1..6
                               note = Synthetic polypeptide
source                         1..6
                               mol_type = protein
                               organism = synthetic construct
SEQUENCE: 90
TNMWMH                                                                      6
```

```
SEQ ID NO: 91           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 91
TNRWMH                                                                      6

SEQ ID NO: 92           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 92
TNSWMH                                                                      6

SEQ ID NO: 93           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 93
TNVWMH                                                                      6

SEQ ID NO: 94           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 94
TNYWMH                                                                      6

SEQ ID NO: 95           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 95
TNNFMH                                                                      6

SEQ ID NO: 96           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 96
TNNWAH                                                                      6

SEQ ID NO: 97           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 97
TNNWEH                                                                      6

SEQ ID NO: 98           moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 98
```

```
TNNWFH                                                                                  6

SEQ ID NO: 99            moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 99
TNNWLH                                                                                  6

SEQ ID NO: 100           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 100
TNNWNH                                                                                  6

SEQ ID NO: 101           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 101
TNNWQH                                                                                  6

SEQ ID NO: 102           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 102
TNNWRH                                                                                  6

SEQ ID NO: 103           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 103
TNNWSH                                                                                  6

SEQ ID NO: 104           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 104
TNNWTH                                                                                  6

SEQ ID NO: 105           moltype = AA  length = 6
FEATURE                  Location/Qualifiers
REGION                   1..6
                         note = Synthetic polypeptide
source                   1..6
                         mol_type = protein
                         organism = synthetic construct
SEQUENCE: 105
TNNWVH                                                                                  6

SEQ ID NO: 106           moltype = AA  length = 6
FEATURE                  Location/Qualifiers
REGION                   1..6
                         note = Synthetic polypeptide
source                   1..6
                         mol_type = protein
                         organism = synthetic construct
```

| | | |
|---|---|---|
| SEQUENCE: 106 | | |
| TNNWWH | | 6 |
| | | |
| SEQ ID NO: 107 | moltype =    length = | |
| SEQUENCE: 107 | | |
| 000 | | |
| | | |
| SEQ ID NO: 108 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 108 | | |
| FIHPNSGITN INE | | 13 |
| | | |
| SEQ ID NO: 109 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 109 | | |
| MLHPNSGITN INE | | 13 |
| | | |
| SEQ ID NO: 110 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 110 | | |
| MMHPNSGITN INE | | 13 |
| | | |
| SEQ ID NO: 111 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 111 | | |
| MVHPNSGITN INE | | 13 |
| | | |
| SEQ ID NO: 112 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 112 | | |
| MIHANSGITN INE | | 13 |
| | | |
| SEQ ID NO: 113 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 113 | | |
| FIHANSGITN INE | | 13 |
| | | |
| SEQ ID NO: 114 | moltype = AA   length = 13 | |
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 114 | | |
| MIHDNSGITN INE | | 13 |
| | | |
| SEQ ID NO: 115 | moltype = AA   length = 13 | |
| FEATURE | Location/Qualifiers | |

```
REGION                  1..13
                        note = Synthetic polypeptide
source                  1..13
                        mol_type = protein
                        organism = synthetic construct
SEQUENCE: 115
MIHENSGITN INE                                                            13

SEQ ID NO: 116          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 116
MIHFNSGITN INE                                                            13

SEQ ID NO: 117          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 117
MIHGNSGITN INE                                                            13

SEQ ID NO: 118          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 118
MIHHNSGITN INE                                                            13

SEQ ID NO: 119          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 119
MIHINSGITN INE                                                            13

SEQ ID NO: 120          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 120
MIHKNSGITN INE                                                            13

SEQ ID NO: 121          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 121
MIHLNSGITN INE                                                            13

SEQ ID NO: 122          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 122
MIHMNSGITN INE                                                            13

SEQ ID NO: 123          moltype = AA  length = 13
```

```
FEATURE            Location/Qualifiers
REGION             1..13
                   note = Synthetic polypeptide
source             1..13
                   mol_type = protein
                   organism = synthetic construct
SEQUENCE: 123
MIHNNSGITN INE                                                             13

SEQ ID NO: 124     moltype = AA  length = 13
FEATURE            Location/Qualifiers
REGION             1..13
                   note = Synthetic polypeptide
source             1..13
                   mol_type = protein
                   organism = synthetic construct
SEQUENCE: 124
MIHQNSGITN INE                                                             13

SEQ ID NO: 125     moltype = AA  length = 13
FEATURE            Location/Qualifiers
REGION             1..13
                   note = Synthetic polypeptide
source             1..13
                   mol_type = protein
                   organism = synthetic construct
SEQUENCE: 125
MIHRNSGITN INE                                                             13

SEQ ID NO: 126     moltype = AA  length = 13
FEATURE            Location/Qualifiers
REGION             1..13
                   note = Synthetic polypeptide
source             1..13
                   mol_type = protein
                   organism = synthetic construct
SEQUENCE: 126
MIHSNSGITN INE                                                             13

SEQ ID NO: 127     moltype = AA  length = 13
FEATURE            Location/Qualifiers
REGION             1..13
                   note = Synthetic polypeptide
source             1..13
                   mol_type = protein
                   organism = synthetic construct
SEQUENCE: 127
MIHTNSGITN INE                                                             13

SEQ ID NO: 128     moltype = AA  length = 13
FEATURE            Location/Qualifiers
REGION             1..13
                   note = Synthetic polypeptide
source             1..13
                   mol_type = protein
                   organism = synthetic construct
SEQUENCE: 128
MIHVNSGITN INE                                                             13

SEQ ID NO: 129     moltype = AA  length = 13
FEATURE            Location/Qualifiers
REGION             1..13
                   note = Synthetic polypeptide
source             1..13
                   mol_type = protein
                   organism = synthetic construct
SEQUENCE: 129
MIHWNSGITN INE                                                             13

SEQ ID NO: 130     moltype = AA  length = 13
FEATURE            Location/Qualifiers
REGION             1..13
                   note = Synthetic polypeptide
source             1..13
                   mol_type = protein
                   organism = synthetic construct
SEQUENCE: 130
MIHPASGITN INE                                                             13
```

```
SEQ ID NO: 131          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 131
MIHPDSGITN INE                                                              13

SEQ ID NO: 132          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 132
MIHPESGITN INE                                                              13

SEQ ID NO: 133          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 133
MIHPFSGITN INE                                                              13

SEQ ID NO: 134          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 134
MIHPGSGITN INE                                                              13

SEQ ID NO: 135          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 135
MIHPHSGITN INE                                                              13

SEQ ID NO: 136          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 136
MIHPISGITN INE                                                              13

SEQ ID NO: 137          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 137
MIHPKSGITN INE                                                              13

SEQ ID NO: 138          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 138
MIHPLSGITN INE                                                              13
```

```
SEQ ID NO: 139          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 139
MIHPMSGITN INE                                                               13

SEQ ID NO: 140          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 140
MIHPQSGITN INE                                                               13

SEQ ID NO: 141          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 141
MIHPRSGITN INE                                                               13

SEQ ID NO: 142          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 142
MIHPSSGITN INE                                                               13

SEQ ID NO: 143          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 143
MIHPTSGITN INE                                                               13

SEQ ID NO: 144          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 144
MIHPVSGITN INE                                                               13

SEQ ID NO: 145          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 145
MIHPWSGITN INE                                                               13

SEQ ID NO: 146          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 146
```

MIHPYSGITN INE 13

SEQ ID NO: 147    moltype = AA  length = 13
FEATURE           Location/Qualifiers
REGION            1..13
                  note = Synthetic polypeptide
source            1..13
                  mol_type = protein
                  organism = synthetic construct
SEQUENCE: 147
MIHPNAGITN INE 13

SEQ ID NO: 148    moltype = AA  length = 13
FEATURE           Location/Qualifiers
REGION            1..13
                  note = Synthetic polypeptide
source            1..13
                  mol_type = protein
                  organism = synthetic construct
SEQUENCE: 148
MIHPNGGITN INE 13

SEQ ID NO: 149    moltype = AA  length = 13
FEATURE           Location/Qualifiers
REGION            1..13
                  note = Synthetic polypeptide
source            1..13
                  mol_type = protein
                  organism = synthetic construct
SEQUENCE: 149
MIHPNTGITN INE 13

SEQ ID NO: 150    moltype = AA  length = 13
FEATURE           Location/Qualifiers
REGION            1..13
                  note = Synthetic polypeptide
source            1..13
                  mol_type = protein
                  organism = synthetic construct
SEQUENCE: 150
MIHPNVGITN INE 13

SEQ ID NO: 151    moltype = AA  length = 13
FEATURE           Location/Qualifiers
REGION            1..13
                  note = Synthetic polypeptide
source            1..13
                  mol_type = protein
                  organism = synthetic construct
SEQUENCE: 151
MIHPNSAITN INE 13

SEQ ID NO: 152    moltype = AA  length = 13
FEATURE           Location/Qualifiers
REGION            1..13
                  note = Synthetic polypeptide
source            1..13
                  mol_type = protein
                  organism = synthetic construct
SEQUENCE: 152
MIHPNSSITN INE 13

SEQ ID NO: 153    moltype = AA  length = 13
FEATURE           Location/Qualifiers
REGION            1..13
                  note = Synthetic polypeptide
source            1..13
                  mol_type = protein
                  organism = synthetic construct
SEQUENCE: 153
MIHPNSGATN INE 13

SEQ ID NO: 154    moltype = AA  length = 13
FEATURE           Location/Qualifiers
REGION            1..13
                  note = Synthetic polypeptide
source            1..13
                  mol_type = protein
                  organism = synthetic construct

```
SEQUENCE: 154
MIHPNSGVTN INE                                                          13

SEQ ID NO: 155           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 155
MIHPNSGIAN INE                                                          13

SEQ ID NO: 156           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 156
MIHPNSGIDN INE                                                          13

SEQ ID NO: 157           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 157
MIHPNSGIEN INE                                                          13

SEQ ID NO: 158           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 158
MIHPNSGIGN INE                                                          13

SEQ ID NO: 159           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 159
MIHPNSGIHN INE                                                          13

SEQ ID NO: 160           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 160
MIHPNSGIIN INE                                                          13

SEQ ID NO: 161           moltype = AA  length = 13
FEATURE                  Location/Qualifiers
REGION                   1..13
                         note = Synthetic polypeptide
source                   1..13
                         mol_type = protein
                         organism = synthetic construct
SEQUENCE: 161
MIHPNSGIKN INE                                                          13

SEQ ID NO: 162           moltype = AA  length = 13
FEATURE                  Location/Qualifiers
REGION                   1..13
                         note = Synthetic polypeptide
source                   1..13
                         mol_type = protein
```

```
                    organism = synthetic construct
SEQUENCE: 162
MIHPNSGILN INE                                                    13

SEQ ID NO: 163      moltype = AA  length = 13
FEATURE             Location/Qualifiers
REGION              1..13
                    note = Synthetic polypeptide
source              1..13
                    mol_type = protein
                    organism = synthetic construct
SEQUENCE: 163
MIHPNSGIMN INE                                                    13

SEQ ID NO: 164      moltype = AA  length = 13
FEATURE             Location/Qualifiers
REGION              1..13
                    note = Synthetic polypeptide
source              1..13
                    mol_type = protein
                    organism = synthetic construct
SEQUENCE: 164
MIHPNSGINN INE                                                    13

SEQ ID NO: 165      moltype = AA  length = 13
FEATURE             Location/Qualifiers
REGION              1..13
                    note = Synthetic polypeptide
source              1..13
                    mol_type = protein
                    organism = synthetic construct
SEQUENCE: 165
MIHPNSGIQN INE                                                    13

SEQ ID NO: 166      moltype = AA  length = 13
FEATURE             Location/Qualifiers
REGION              1..13
                    note = Synthetic polypeptide
source              1..13
                    mol_type = protein
                    organism = synthetic construct
SEQUENCE: 166
MIHPNSGIRN INE                                                    13

SEQ ID NO: 167      moltype = AA  length = 13
FEATURE             Location/Qualifiers
REGION              1..13
                    note = Synthetic polypeptide
source              1..13
                    mol_type = protein
                    organism = synthetic construct
SEQUENCE: 167
MIHPNSGISN INE                                                    13

SEQ ID NO: 168      moltype = AA  length = 13
FEATURE             Location/Qualifiers
REGION              1..13
                    note = Synthetic polypeptide
source              1..13
                    mol_type = protein
                    organism = synthetic construct
SEQUENCE: 168
MIHPNSGIVN INE                                                    13

SEQ ID NO: 169      moltype = AA  length = 13
FEATURE             Location/Qualifiers
REGION              1..13
                    note = Synthetic polypeptide
source              1..13
                    mol_type = protein
                    organism = synthetic construct
SEQUENCE: 169
MIHPNSGIWN INE                                                    13

SEQ ID NO: 170      moltype = AA  length = 13
FEATURE             Location/Qualifiers
REGION              1..13
                    note = Synthetic polypeptide
source              1..13
```

```
                        mol_type = protein
                        organism = synthetic construct
SEQUENCE: 170
MIHPNSGIYN INE                                                          13

SEQ ID NO: 171          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 171
MIHPNSGITM INE                                                          13

SEQ ID NO: 172          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 172
MIHPNSGITS INE                                                          13

SEQ ID NO: 173          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 173
MIHPNSGITN FNE                                                          13

SEQ ID NO: 174          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 174
MIHPNSGITN GNE                                                          13

SEQ ID NO: 175          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 175
MIHPNSGITN HNE                                                          13

SEQ ID NO: 176          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 176
MIHPNSGITN KNE                                                          13

SEQ ID NO: 177          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 177
MIHPNSGITN LNE                                                          13

SEQ ID NO: 178          moltype = AA  length = 13
FEATURE                 Location/Qualifiers
REGION                  1..13
                        note = Synthetic polypeptide
```

```
                      -continued source                1..13
                      mol_type = protein
                      organism = synthetic construct
SEQUENCE: 178
MIHPNSGITN MNE                                                      13

SEQ ID NO: 179        moltype = AA  length = 13
FEATURE               Location/Qualifiers
REGION                1..13
                      note = Synthetic polypeptide
source                1..13
                      mol_type = protein
                      organism = synthetic construct
SEQUENCE: 179
MIHPNSGITN NNE                                                      13

SEQ ID NO: 180        moltype = AA  length = 13
FEATURE               Location/Qualifiers
REGION                1..13
                      note = Synthetic polypeptide
source                1..13
                      mol_type = protein
                      organism = synthetic construct
SEQUENCE: 180
MIHPNSGITN QNE                                                      13

SEQ ID NO: 181        moltype = AA  length = 13
FEATURE               Location/Qualifiers
REGION                1..13
                      note = Synthetic polypeptide
source                1..13
                      mol_type = protein
                      organism = synthetic construct
SEQUENCE: 181
MIHPNSGITN RNE                                                      13

SEQ ID NO: 182        moltype = AA  length = 13
FEATURE               Location/Qualifiers
REGION                1..13
                      note = Synthetic polypeptide
source                1..13
                      mol_type = protein
                      organism = synthetic construct
SEQUENCE: 182
MIHPNSGITN SNE                                                      13

SEQ ID NO: 183        moltype = AA  length = 13
FEATURE               Location/Qualifiers
REGION                1..13
                      note = Synthetic polypeptide
source                1..13
                      mol_type = protein
                      organism = synthetic construct
SEQUENCE: 183
MIHPNSGITN TNE                                                      13

SEQ ID NO: 184        moltype = AA  length = 13
FEATURE               Location/Qualifiers
REGION                1..13
                      note = Synthetic polypeptide
source                1..13
                      mol_type = protein
                      organism = synthetic construct
SEQUENCE: 184
MIHPNSGITN VNE                                                      13

SEQ ID NO: 185        moltype = AA  length = 13
FEATURE               Location/Qualifiers
REGION                1..13
                      note = Synthetic polypeptide
source                1..13
                      mol_type = protein
                      organism = synthetic construct
SEQUENCE: 185
MIHPNSGITN WNE                                                      13

SEQ ID NO: 186        moltype = AA  length = 13
FEATURE               Location/Qualifiers
REGION                1..13
```

```
                        note = Synthetic polypeptide
source                  1..13
                        mol_type = protein
                        organism = synthetic construct
SEQUENCE: 186
MIHPNSGITN YNE                                                          13

SEQ ID NO: 187          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 187
MIHPNSGITN INA                                                          13

SEQ ID NO: 188          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 188
MIHPNSGITN IND                                                          13

SEQ ID NO: 189          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 189
MIHPNSGITN ING                                                          13

SEQ ID NO: 190          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 190
MIHPNSGITN INH                                                          13

SEQ ID NO: 191          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 191
MIHPNSGITN INK                                                          13

SEQ ID NO: 192          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 192
MIHPNSGITN INL                                                          13

SEQ ID NO: 193          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 193
MIHPNSGITN INM                                                          13

SEQ ID NO: 194          moltype = AA   length = 13
FEATURE                 Location/Qualifiers
```

```
REGION                   1..13
                         note = Synthetic polypeptide
source                   1..13
                         mol_type = protein
                         organism = synthetic construct
SEQUENCE: 194
MIHPNSGITN INN                                                          13

SEQ ID NO: 195           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 195
MIHPNSGITN INP                                                          13

SEQ ID NO: 196           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 196
MIHPNSGITN INQ                                                          13

SEQ ID NO: 197           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 197
MIHPNSGITN INR                                                          13

SEQ ID NO: 198           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 198
MIHPNSGITN INS                                                          13

SEQ ID NO: 199           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 199
MIHPNSGITN INT                                                          13

SEQ ID NO: 200           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 200
MIHPNSGITN INV                                                          13

SEQ ID NO: 201           moltype = AA   length = 13
FEATURE                  Location/Qualifiers
REGION                   1..13
                         note = Synthetic polypeptide
source                   1..13
                         mol_type = protein
                         organism = synthetic construct
SEQUENCE: 201
MIHPNSGITN INW                                                          13

SEQ ID NO: 202           moltype = AA   length = 13
```

| | | |
|---|---|---|
| FEATURE | Location/Qualifiers | |
| REGION | 1..13 | |
| | note = Synthetic polypeptide | |
| source | 1..13 | |
| | mol_type = protein | |
| | organism = synthetic construct | |
| SEQUENCE: 202 | | |
| MIHPNSGITN INY | | 13 |
| | | |
| SEQ ID NO: 203 | moltype = AA   length = 12 | |
| FEATURE | Location/Qualifiers | |
| REGION | 1..12 | |
| | note = Synthetic polypeptide | |
| VARIANT | 2 | |
| | note = X at 2 is S, A, F, G, I, L, M, N, R, T, V, W, or Y. | |
| VARIANT | 4 | |
| | note = X at 4 is G or W. | |
| VARIANT | 5 | |
| | note = X at 5 is T, D, E, F, H, I, K, L, M, N, Q, V, W, or Y. | |
| VARIANT | 6 | |
| | note = X at 6 is Y, D, F, H, N, R, or W. | |
| VARIANT | 7 | |
| | note = X at 7 is E, D, G, H, K, M, N, Q, R, V, or Y. | |
| VARIANT | 8 | |
| | note = X at 8 is G, K, R, S, or T. | |
| source | 1..12 | |
| | mol_type = protein | |
| | organism = synthetic construct | |
| SEQUENCE: 203 | | |
| RXDXXXXYF DY | | 12 |
| | | |
| SEQ ID NO: 204 | moltype = AA   length = 12 | |
| FEATURE | Location/Qualifiers | |
| REGION | 1..12 | |
| | note = Synthetic polypeptide | |
| source | 1..12 | |
| | mol_type = protein | |
| | organism = synthetic construct | |
| SEQUENCE: 204 | | |
| RADGTYEGYF DY | | 12 |
| | | |
| SEQ ID NO: 205 | moltype = AA   length = 12 | |
| FEATURE | Location/Qualifiers | |
| REGION | 1..12 | |
| | note = Synthetic polypeptide | |
| source | 1..12 | |
| | mol_type = protein | |
| | organism = synthetic construct | |
| SEQUENCE: 205 | | |
| RFDGTYEGYF DY | | 12 |
| | | |
| SEQ ID NO: 206 | moltype = AA   length = 12 | |
| FEATURE | Location/Qualifiers | |
| REGION | 1..12 | |
| | note = Synthetic polypeptide | |
| source | 1..12 | |
| | mol_type = protein | |
| | organism = synthetic construct | |
| SEQUENCE: 206 | | |
| RGDGTYEGYF DY | | 12 |
| | | |
| SEQ ID NO: 207 | moltype = AA   length = 12 | |
| FEATURE | Location/Qualifiers | |
| REGION | 1..12 | |
| | note = Synthetic polypeptide | |
| source | 1..12 | |
| | mol_type = protein | |
| | organism = synthetic construct | |
| SEQUENCE: 207 | | |
| RIDGTYEGYF DY | | 12 |
| | | |
| SEQ ID NO: 208 | moltype = AA   length = 12 | |
| FEATURE | Location/Qualifiers | |
| REGION | 1..12 | |
| | note = Synthetic polypeptide | |
| source | 1..12 | |
| | mol_type = protein | |
| | organism = synthetic construct | |

```
SEQUENCE: 208
RLDGTYEGYF DY                                                              12

SEQ ID NO: 209         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 209
RMDGTYEGYF DY                                                              12

SEQ ID NO: 210         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 210
RNDGTYEGYF DY                                                              12

SEQ ID NO: 211         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 211
RRDGTYEGYF DY                                                              12

SEQ ID NO: 212         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 212
RTDGTYEGYF DY                                                              12

SEQ ID NO: 213         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 213
RVDGTYEGYF DY                                                              12

SEQ ID NO: 214         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 214
RWDGTYEGYF DY                                                              12

SEQ ID NO: 215         moltype = AA  length = 12
FEATURE                Location/Qualifiers
REGION                 1..12
                       note = Synthetic polypeptide
source                 1..12
                       mol_type = protein
                       organism = synthetic construct
SEQUENCE: 215
RYDGTYEGYF DY                                                              12

SEQ ID NO: 216         moltype = AA  length = 12
FEATURE                Location/Qualifiers
REGION                 1..12
                       note = Synthetic polypeptide
source                 1..12
                       mol_type = protein
```

```
                        organism = synthetic construct
SEQUENCE: 216
RSDWTYEGYF DY                                                                    12

SEQ ID NO: 217          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 217
RSDGDYEGYF DY                                                                    12

SEQ ID NO: 218          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 218
RSDGEYEGYF DY                                                                    12

SEQ ID NO: 219          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 219
RSDGFYEGYF DY                                                                    12

SEQ ID NO: 220          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 220
RSDGHYEGYF DY                                                                    12

SEQ ID NO: 221          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 221
RSDGIYEGYF DY                                                                    12

SEQ ID NO: 222          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 222
RSDGKYEGYF DY                                                                    12

SEQ ID NO: 223          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 223
RSDGLYEGYF DY                                                                    12

SEQ ID NO: 224          moltype = AA   length = 12
FEATURE                 Location/Qualifiers
REGION                  1..12
                        note = Synthetic polypeptide
source                  1..12
```

```
                        mol_type = protein
                        organism = synthetic construct
SEQUENCE: 224
RSDGMYEGYF DY                                                              12

SEQ ID NO: 225          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 225
RSDGNYEGYF DY                                                              12

SEQ ID NO: 226          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 226
RSDGQYEGYF DY                                                              12

SEQ ID NO: 227          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 227
RSDGVYEGYF DY                                                              12

SEQ ID NO: 228          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 228
RSDGWYEGYF DY                                                              12

SEQ ID NO: 229          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 229
RSDGYYEGYF DY                                                              12

SEQ ID NO: 230          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 230
RSDGTDEGYF DY                                                              12

SEQ ID NO: 231          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 231
RSDGTFEGYF DY                                                              12

SEQ ID NO: 232          moltype = AA   length = 12
FEATURE                 Location/Qualifiers
REGION                  1..12
                        note = Synthetic polypeptide
```

```
source                    1..12
                          mol_type = protein
                          organism = synthetic construct
SEQUENCE: 232
RSDGTHEGYF DY                                                             12

SEQ ID NO: 233            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 233
RSDGTNEGYF DY                                                             12

SEQ ID NO: 234            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 234
RSDGTREGYF DY                                                             12

SEQ ID NO: 235            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 235
RSDGTWEGYF DY                                                             12

SEQ ID NO: 236            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 236
RSDGTYDGYF DY                                                             12

SEQ ID NO: 237            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 237
RSDGTYGGYF DY                                                             12

SEQ ID NO: 238            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 238
RSDGTYHGYF DY                                                             12

SEQ ID NO: 239            moltype = AA   length = 12
FEATURE                   Location/Qualifiers
REGION                    1..12
                          note = Synthetic polypeptide
source                    1..12
                          mol_type = protein
                          organism = synthetic construct
SEQUENCE: 239
RSDGTYKGYF DY                                                             12

SEQ ID NO: 240            moltype = AA   length = 12
FEATURE                   Location/Qualifiers
REGION                    1..12
```

```
                        note = Synthetic polypeptide
source                  1..12
                        mol_type = protein
                        organism = synthetic construct
SEQUENCE: 240
RSDGTYMGYF DY                                                          12

SEQ ID NO: 241          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 241
RSDGTYNGYF DY                                                          12

SEQ ID NO: 242          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 242
RSDGTYQGYF DY                                                          12

SEQ ID NO: 243          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 243
RSDGTYRGYF DY                                                          12

SEQ ID NO: 244          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 244
RSDGTYVGYF DY                                                          12

SEQ ID NO: 245          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 245
RSDGTYYGYF DY                                                          12

SEQ ID NO: 246          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 246
RSDGTYEKYF DY                                                          12

SEQ ID NO: 247          moltype = AA   length = 12
FEATURE                 Location/Qualifiers
REGION                  1..12
                        note = Synthetic polypeptide
source                  1..12
                        mol_type = protein
                        organism = synthetic construct
SEQUENCE: 247
RSDGTYERYF DY                                                          12

SEQ ID NO: 248          moltype = AA   length = 12
FEATURE                 Location/Qualifiers
```

```
REGION                   1..12
                         note = Synthetic polypeptide
source                   1..12
                         mol_type = protein
                         organism = synthetic construct
SEQUENCE: 248
RSDGTYESYF DY                                                            12

SEQ ID NO: 249           moltype = AA  length = 12
FEATURE                  Location/Qualifiers
REGION                   1..12
                         note = Synthetic polypeptide
source                   1..12
                         mol_type = protein
                         organism = synthetic construct
SEQUENCE: 249
RSDGTYETYF DY                                                            12

SEQ ID NO: 250           moltype = AA  length = 119
FEATURE                  Location/Qualifiers
REGION                   1..119
                         note = Synthetic polypeptide
source                   1..119
                         mol_type = protein
                         organism = synthetic construct
SEQUENCE: 250
EVQLVQSGAE VKKPGASVKV SCKASGFTFT NNWRHWVRQA PGQGLEWIGM IHFNSGITNI         60
NEKFKNRVTM TTDTSTSTAY MELRSLRSED TAVYYCRSDG VYEGYFDYWG QGTLVTVSS         119

SEQ ID NO: 251           moltype = AA  length = 119
FEATURE                  Location/Qualifiers
REGION                   1..119
                         note = Synthetic polypeptide
source                   1..119
                         mol_type = protein
                         organism = synthetic construct
SEQUENCE: 251
EVQLVQSGAE VKKPGASVKV SCKASGFTFT NRWMHWVRQA PGQGLEWIGM IHVNSGITNI         60
NEKFKNRVTM TTDTSTSTAY MELRSLRSED TAVYYCRSDG LYEGYFDYWG QGTLVTVSS         119

SEQ ID NO: 252           moltype = AA  length = 119
FEATURE                  Location/Qualifiers
REGION                   1..119
                         note = Synthetic polypeptide
source                   1..119
                         mol_type = protein
                         organism = synthetic construct
SEQUENCE: 252
EVQLVQSGAE VKKPGASVKV SCKASGFTFT NNWDHWVRQA PGQGLEWIGM IHPLSGITNI         60
NEKFKNRVTM TTDTSTSTAY MELRSLRSED TAVYYCRSDG VYEGYFDYWG QGTLVTVSS         119

SEQ ID NO: 253           moltype = AA  length = 119
FEATURE                  Location/Qualifiers
REGION                   1..119
                         note = Synthetic polypeptide
source                   1..119
                         mol_type = protein
                         organism = synthetic construct
SEQUENCE: 253
EVQLVQSGAE VKKPGASVKV SCKASGFTFT NNWRHWVRQA PGQGLEWIGM IHMNSGITNI         60
NEKFKNRVTM TTDTSTSTAY MELRSLRSED TAVYYCRSDG VYEGYFDYWG QGTLVTVSS         119

SEQ ID NO: 254           moltype = AA  length = 119
FEATURE                  Location/Qualifiers
REGION                   1..119
                         note = Synthetic polypeptide
source                   1..119
                         mol_type = protein
                         organism = synthetic construct
SEQUENCE: 254
EVQLVQSGAE VKKPGASVKV SCKASGFTFT NNWRHWVRQA PGQGLEWIGM IHPLSGITNI         60
NEKFKNRVTM TTDTSTSTAY MELRSLRSED TAVYYCRSDG VYEGYFDYWG QGTLVTVSS         119

SEQ ID NO: 255           moltype = AA  length = 119
FEATURE                  Location/Qualifiers
REGION                   1..119
                         note = Synthetic polypeptide
source                   1..119
                         mol_type = protein
```

```
                          organism = synthetic construct
SEQUENCE: 255
EVQLVQSGAE VKKPGASVKV SCKASGFTFV NNWMHWVRQA PGQGLEWIGM IHPNSGITNT       60
NEKFKNRVTM TTDTSTSTAY MELRSLRSED TAVYYCRSDG IYEGYFDYWG QGTLVTVSS       119

SEQ ID NO: 256            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 256
EVQLVQSGAE VKKPGASVKV SCKASGFTFT NNWDHWVRQA PGQGLEWIGM IHPMSGITNI       60
NEKFKNRVTM TTDTSTSTAY MELRSLRSED TAVYYCRSDG FYEGYFDYWG QGTLVTVSS       119

SEQ ID NO: 257            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 257
EVQLVQSGAE VKKPGASVKV SCKASGFTFT NNWRHWVRQA PGQGLEWIGM IHPNSGITNI       60
NEKFKNRVTM TTDTSTSTAY MELRSLRSED TAVYYCRSDG VYEGYFDYWG QGTLVTVSS       119

SEQ ID NO: 258            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 258
EVQLVQSGAE VKKPGASVKV SCKASGFTFT NSWMHWVRQA PGQGLEWIGM IHPNSGITNR       60
NEKFKNRVTM TTDTSTSTAY MELRSLRSED TAVYYCRSDG IYEGYFDYWG QGTLVTVSS       119

SEQ ID NO: 259            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 259
EVQLVQSGAE VKKPGASVKV SCKASGFTFT NYWMHWVRQA PGQGLEWIGM IHPNSGITNM       60
NEKFKNRVTM TTDTSTSTAY MELRSLRSED TAVYYCRSDG VYEGYFDYWG QGTLVTVSS       119

SEQ ID NO: 260            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 260
EVQLVQSGAE VKKPGASVKV SCKASGFTFT NNWGHWVRQA PGQGLEWIGM IHRNSGITNI       60
NEKFKNRVTM TTDTSTSTAY MELRSLRSED TAVYYCRSDG IYEGYFDYWG QGTLVTVSS       119

SEQ ID NO: 261            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 261
EVQLVQSGAE VKKPGASVKV SCKASGFTFT NRWMHWVRQA PGQGLEWIGM IHHNSGITNI       60
NEKFKNRVTM TTDTSTSTAY MELRSLRSED TAVYYCRSDG VYEGYFDYWG QGTLVTVSS       119

SEQ ID NO: 262            moltype = AA   length = 119
FEATURE                   Location/Qualifiers
REGION                    1..119
                          note = Synthetic polypeptide
source                    1..119
                          mol_type = protein
                          organism = synthetic construct
SEQUENCE: 262
```

```
EVQLVQSGAE VKKPGASVKV SCKASGFTFT NNWSHWVRQA PGQGLEWIGM IHRNSGITNI    60
NEKFKNRVTM TTDTSTSTAY MELRSLRSED TAVYYCRSDG VYEGYFDYWG QGTLVTVSS    119

SEQ ID NO: 263          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 263
EVQLVQSGAE VKKPGASVKV SCKASGFTFT NNWNHWVRQA PGQGLEWIGM IHPNSGITAI    60
NEKFKNRVTM TTDTSTSTAY MELRSLRSED TAVYYCRLDG TYEGYFDYWG QGTLVTVSS    119

SEQ ID NO: 264          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 264
EVQLVQSGAE VKKPGASVKV SCKASGFTFT NRWMHWVRQA PGQGLEWIGM IHANSGITNI    60
NEKFKNRVTM TTDTSTSTAY MELRSLRSED TAVYYCRSDG VYEGYFDYWG QGTLVTVSS    119

SEQ ID NO: 265          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 265
EVQLVQSGAE VKKPGASVKV SCKASGFTFT NNFMHWVRQA PGQGLEWIGM IHPNSGITNI    60
NEKFKNRVTM TTDTSTSTAY MELRSLRSED TAVYYCRSDG TYEGYFDYWG QGTLVTVSS    119

SEQ ID NO: 266          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 266
EVQLVQSGAE VKKPGASVKV SCKASGFTFT NNWMHWVRQA PGQGLEWIGF IHPNSGITNI    60
NEKFKNRVTM TTDTSTSTAY MELRSLRSED TAVYYCRSDG TYEGYFDYWG QGTLVTVSS    119

SEQ ID NO: 267          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 267
EVQLVQSGAE VKKPGASVKV SCKASGFTFT NNWMHWVRQA PGQGLEWIGM IHANSGITNI    60
NEKFKNRVTM TTDTSTSTAY MELRSLRSED TAVYYCRSDG TYEGYFDYWG QGTLVTVSS    119

SEQ ID NO: 268          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 268
EVQLVQSGAE VKKPGASVKV SCKASGFTFT NNWMHWVRQA PGQGLEWIGM IHPNSGITNI    60
NHKFKNRVTM TTDTSTSTAY MELRSLRSED TAVYYCRSDG TYEGYFDYWG QGTLVTVSS    119

SEQ ID NO: 269          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 269
EVQLVQSGAE VKKPGASVKV SCKASGFTFT NNWMHWVRQA PGQGLEWIGM IHPNSGITNI    60
NRKFKNRVTM TTDTSTSTAY MELRSLRSED TAVYYCRSDG TYEGYFDYWG QGTLVTVSS    119
```

```
SEQ ID NO: 270          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 270
EVQLVQSGAE VKKPGASVKV SCKASGFTFT NNWMHWVRQA PGQGLEWIGM IHPNSGITNI    60
NEKFKNRVTM TTDTSTSTAY MELRSLRSED TAVYYCRSDG IYEGYFDYWG QGTLVTVSS    119

SEQ ID NO: 271          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 271
EVQLVQSGAE VKKPGASVKV SCKASGFTFT NNWMHWVRQA PGQGLEWIGM IHPNSGITNI    60
NEKFKNRVTM TTDTSTSTAY MELRSLRSED TAVYYCRSDG VYEGYFDYWG QGTLVTVSS    119

SEQ ID NO: 272          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 272
EVQLVQSGAE VKKPGASVKV SCKASGFTFT NNFMHWVRQA PGQGLEWIGM IHANSGITNI    60
NEKFKNRVTM TTDTSTSTAY MELRSLRSED TAVYYCRSDG IYEGYFDYWG QGTLVTVSS    119

SEQ ID NO: 273          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 273
EVQLVQSGAE VKKPGASVKV SCKASGFTFT NNFMHWVRQA PGQGLEWIGM IHANSGITNI    60
NEKFKNRVTM TTDTSTSTAY MELRSLRSED TAVYYCRSDG VYEGYFDYWG QGTLVTVSS    119

SEQ ID NO: 274          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 274
EVQLVQSGAE VKKPGASVKV SCKASGFTFT NNFMHWVRQA PGQGLEWIGF IHANSGITNI    60
NEKFKNRVTM TTDTSTSTAY MELRSLRSED TAVYYCRSDG IYEGYFDYWG QGTLVTVSS    119

SEQ ID NO: 275          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 275
EVQLVQSGAE VKKPGASVKV SCKASGFTFT NNFMHWVRQA PGQGLEWIGF IHANSGITNI    60
NEKFKNRVTM TTDTSTSTAY MELRSLRSED TAVYYCRSDG VYEGYFDYWG QGTLVTVSS    119

SEQ ID NO: 276          moltype = AA  length = 23
FEATURE                 Location/Qualifiers
REGION                  1..23
                        note = Synthetic polypeptide
source                  1..23
                        mol_type = protein
                        organism = synthetic construct
SEQUENCE: 276
DIVMTQSQKF MSTSVGDRVS VTC                                            23

SEQ ID NO: 277          moltype = AA  length = 15
FEATURE                 Location/Qualifiers
```

```
REGION                  1..15
                        note = Synthetic polypeptide
source                  1..15
                        mol_type = protein
                        organism = synthetic construct
SEQUENCE: 277
WYQKKPGQSP KTLIY                                                         15

SEQ ID NO: 278          moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 278
GVPDRFTGSG SGTDFTLTIS NVQSEDLAEY FC                                       32

SEQ ID NO: 279          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 279
FGSGTKLEIK                                                               10

SEQ ID NO: 280          moltype = AA  length = 23
FEATURE                 Location/Qualifiers
REGION                  1..23
                        note = Synthetic polypeptide
source                  1..23
                        mol_type = protein
                        organism = synthetic construct
SEQUENCE: 280
DIQLTQSPSS LSASVGDRVT ITC                                                23

SEQ ID NO: 281          moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 281
WYQQKPGKAP KVLIY                                                         15

SEQ ID NO: 282          moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 282
GVPSRFSGSG SGTDFTLTIS SLQPEDFATY YC                                       32

SEQ ID NO: 283          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 283
FGQGTKVEIK                                                               10

SEQ ID NO: 284          moltype = AA  length = 23
FEATURE                 Location/Qualifiers
REGION                  1..23
                        note = Synthetic polypeptide
source                  1..23
                        mol_type = protein
                        organism = synthetic construct
SEQUENCE: 284
DILMTQSPTT LSVTPGETVS LSC                                                23

SEQ ID NO: 285          moltype = AA  length = 15
```

```
FEATURE                 Location/Qualifiers
REGION                  1..15
                        note = Synthetic polypeptide
source                  1..15
                        mol_type = protein
                        organism = synthetic construct
SEQUENCE: 285
WYQQKSQGTP RLLIK                                                    15

SEQ ID NO: 286          moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 286
GIPSRFTGSG SGTDFTLSIN SVKPEDEGIY YC                                 32

SEQ ID NO: 287          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 287
FGGGTKLEIK                                                          10

SEQ ID NO: 288          moltype = AA  length = 23
FEATURE                 Location/Qualifiers
REGION                  1..23
                        note = Synthetic polypeptide
source                  1..23
                        mol_type = protein
                        organism = synthetic construct
SEQUENCE: 288
EIVMTQSPDF QSVTPKEKVT ITC                                           23

SEQ ID NO: 289          moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 289
WYQQKPDQTP KLLIK                                                    15

SEQ ID NO: 290          moltype = AA  length = 32
FEATURE                 Location/Qualifiers
REGION                  1..32
                        note = Synthetic polypeptide
source                  1..32
                        mol_type = protein
                        organism = synthetic construct
SEQUENCE: 290
GIPSRFSGSG SGTDFTLTIN SLEAEDAAAY YC                                 32

SEQ ID NO: 291          moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 291
FGGGTKVEIK                                                          10

SEQ ID NO: 292          moltype = AA  length = 29
FEATURE                 Location/Qualifiers
REGION                  1..29
                        note = Synthetic polypeptide
source                  1..29
                        mol_type = protein
                        organism = synthetic construct
SEQUENCE: 292
QVQLQQPGAE LVTPGASVKL SCKASGFTF                                     29
```

```
SEQ ID NO: 293           moltype = AA  length = 14
FEATURE                  Location/Qualifiers
REGION                   1..14
                         note = Synthetic polypeptide
source                   1..14
                         mol_type = protein
                         organism = synthetic construct
SEQUENCE: 293
WVKQRPGQGL EWIG                                                          14

SEQ ID NO: 294           moltype = AA  length = 34
FEATURE                  Location/Qualifiers
REGION                   1..34
                         note = Synthetic polypeptide
source                   1..34
                         mol_type = protein
                         organism = synthetic construct
SEQUENCE: 294
KFKNKATVTV DKSSSTVYIQ LSSLTSEDSA VYYC                                    34

SEQ ID NO: 295           moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 295
WGQGTPLTVS S                                                             11

SEQ ID NO: 296           moltype = AA  length = 29
FEATURE                  Location/Qualifiers
REGION                   1..29
                         note = Synthetic polypeptide
source                   1..29
                         mol_type = protein
                         organism = synthetic construct
SEQUENCE: 296
QIQLVQSGPE LKKPGETVKI SCKASGYPF                                          29

SEQ ID NO: 297           moltype = AA  length = 14
FEATURE                  Location/Qualifiers
REGION                   1..14
                         note = Synthetic polypeptide
source                   1..14
                         mol_type = protein
                         organism = synthetic construct
SEQUENCE: 297
WVKQAPGKGL KWMG                                                          14

SEQ ID NO: 298           moltype = AA  length = 34
FEATURE                  Location/Qualifiers
REGION                   1..34
                         note = Synthetic polypeptide
source                   1..34
                         mol_type = protein
                         organism = synthetic construct
SEQUENCE: 298
DFKGRFAFSL ETSANTAYLQ INSLKNEDAA TYFC                                    34

SEQ ID NO: 299           moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 299
WGQGTILTVS S                                                             11

SEQ ID NO: 300           moltype = AA  length = 29
FEATURE                  Location/Qualifiers
REGION                   1..29
                         note = Synthetic polypeptide
source                   1..29
                         mol_type = protein
                         organism = synthetic construct
SEQUENCE: 300
EVQLVQSGAE VKKPGASVKV SCKASGFTF                                          29
```

```
SEQ ID NO: 301          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 301
WVRQAPGQGL EWIG                                                           14

SEQ ID NO: 302          moltype = AA   length = 34
FEATURE                 Location/Qualifiers
REGION                  1..34
                        note = Synthetic polypeptide
source                  1..34
                        mol_type = protein
                        organism = synthetic construct
SEQUENCE: 302
KFKNRVTMTT DTSTSTAYME LRSLRSEDTA VYYC                                     34

SEQ ID NO: 303          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 303
WGQGTLVTVS S                                                              11

SEQ ID NO: 304          moltype = AA   length = 29
FEATURE                 Location/Qualifiers
REGION                  1..29
                        note = Synthetic polypeptide
source                  1..29
                        mol_type = protein
                        organism = synthetic construct
SEQUENCE: 304
EIQLVQSGSE LKKPGASVKV SCKASGYPF                                           29

SEQ ID NO: 305          moltype = AA   length = 14
FEATURE                 Location/Qualifiers
REGION                  1..14
                        note = Synthetic polypeptide
source                  1..14
                        mol_type = protein
                        organism = synthetic construct
SEQUENCE: 305
WVRQAPGQGL EWMG                                                           14

SEQ ID NO: 306          moltype = AA   length = 34
FEATURE                 Location/Qualifiers
REGION                  1..34
                        note = Synthetic polypeptide
source                  1..34
                        mol_type = protein
                        organism = synthetic construct
SEQUENCE: 306
DFKGRFVFSL DTSVSTAYLQ ISSLKAEDTA VYFC                                     34

SEQ ID NO: 307          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 307
WGQGTLVTVS S                                                              11

SEQ ID NO: 308          moltype = AA   length = 11
FEATURE                 Location/Qualifiers
REGION                  1..11
                        note = Synthetic polypeptide
VARIANT                 5
                        note = X at 5 is D, A, E, G, H, K, N, P, Q, S, or T.
VARIANT                 7
                        note = X at 7 is Y or F.
```

```
VARIANT                     8
                            note = X at 8 is R, K, or Q.
VARIANT                     10
                            note = X at 10 is L, I, M, or V.
source                      1..11
                            mol_type = protein
                            organism = synthetic construct
SEQUENCE: 308
RASQXIXXNX H                                                              11

SEQ ID NO: 309              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 309
RASQAIYRNL H                                                              11

SEQ ID NO: 310              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 310
RASQEIYRNL H                                                              11

SEQ ID NO: 311              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 311
RASQGIYRNL H                                                              11

SEQ ID NO: 312              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 312
RASQHIYRNL H                                                              11

SEQ ID NO: 313              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 313
RASQKIYRNL H                                                              11

SEQ ID NO: 314              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 314
RASQNIYRNL H                                                              11

SEQ ID NO: 315              moltype = AA  length = 11
FEATURE                     Location/Qualifiers
REGION                      1..11
                            note = Synthetic polypeptide
source                      1..11
                            mol_type = protein
                            organism = synthetic construct
SEQUENCE: 315
RASQPIYRNL H                                                              11
```

```
SEQ ID NO: 316          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 316
RASQQIYRNL H                                                                  11

SEQ ID NO: 317          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 317
RASQSIYRNL H                                                                  11

SEQ ID NO: 318          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 318
RASQTIYRNL H                                                                  11

SEQ ID NO: 319          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 319
RASQDIFRNL H                                                                  11

SEQ ID NO: 320          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 320
RASQDIYKNL H                                                                  11

SEQ ID NO: 321          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 321
RASQDIYQNL H                                                                  11

SEQ ID NO: 322          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 322
RASQDIYRNI H                                                                  11

SEQ ID NO: 323          moltype = AA   length = 11
FEATURE                 Location/Qualifiers
REGION                  1..11
                        note = Synthetic polypeptide
source                  1..11
                        mol_type = protein
                        organism = synthetic construct
SEQUENCE: 323
```

```
RASQDIYRNM H                                                                                              11

SEQ ID NO: 324           moltype = AA  length = 11
FEATURE                  Location/Qualifiers
REGION                   1..11
                         note = Synthetic polypeptide
source                   1..11
                         mol_type = protein
                         organism = synthetic construct
SEQUENCE: 324
RASQDIYRNV H                                                                                              11

SEQ ID NO: 325           moltype =   length =
SEQUENCE: 325
000

SEQ ID NO: 326           moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 326
HAEDSIS                                                                                                    7

SEQ ID NO: 327           moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 327
HASESIS                                                                                                    7

SEQ ID NO: 328           moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 328
HASKSIS                                                                                                    7

SEQ ID NO: 329           moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 329
HASQSIS                                                                                                    7

SEQ ID NO: 330           moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 330
HASDHIS                                                                                                    7

SEQ ID NO: 331           moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 331
HASDLIS                                                                                                    7

SEQ ID NO: 332           moltype = AA  length = 7
FEATURE                  Location/Qualifiers
REGION                   1..7
```

```
                           note = Synthetic polypeptide
source                     1..7
                           mol_type = protein
                           organism = synthetic construct
SEQUENCE: 332
HASDRIS                                                                        7

SEQ ID NO: 333             moltype = AA  length = 7
FEATURE                    Location/Qualifiers
REGION                     1..7
                           note = Synthetic polypeptide
source                     1..7
                           mol_type = protein
                           organism = synthetic construct
SEQUENCE: 333
HASDVIS                                                                        7

SEQ ID NO: 334             moltype = AA  length = 7
FEATURE                    Location/Qualifiers
REGION                     1..7
                           note = Synthetic polypeptide
source                     1..7
                           mol_type = protein
                           organism = synthetic construct
SEQUENCE: 334
HASDSVS                                                                        7

SEQ ID NO: 335             moltype = AA  length = 9
FEATURE                    Location/Qualifiers
REGION                     1..9
                           note = Synthetic polypeptide
VARIANT                    1
                           note = X at 1 is L, G, M, or Q.
VARIANT                    5
                           note = X at 5 is S, A, E, Q, or V.
VARIANT                    8
                           note = X at 8 is Y or F.
source                     1..9
                           mol_type = protein
                           organism = synthetic construct
SEQUENCE: 335
XQGYXMPXT                                                                      9

SEQ ID NO: 336             moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 336
GQGYSMPYT                                                                      9

SEQ ID NO: 337             moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 337
MQGYSMPYT                                                                      9

SEQ ID NO: 338             moltype = AA  length = 9
FEATURE                    Location/Qualifiers
REGION                     1..9
                           note = Synthetic polypeptide
source                     1..9
                           mol_type = protein
                           organism = synthetic construct
SEQUENCE: 338
QQGYSMPYT                                                                      9

SEQ ID NO: 339             moltype = AA  length = 9
FEATURE                    Location/Qualifiers
REGION                     1..9
                           note = Synthetic polypeptide
source                     1..9
                           mol_type = protein
```

```
                    organism = synthetic construct
SEQUENCE: 339
LQGYAMPYT                                                                  9

SEQ ID NO: 340          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 340
LQGYEMPYT                                                                  9

SEQ ID NO: 341          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 341
LQGYQMPYT                                                                  9

SEQ ID NO: 342          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 342
LQGYVMPYT                                                                  9

SEQ ID NO: 343          moltype = AA   length = 9
FEATURE                 Location/Qualifiers
REGION                  1..9
                        note = Synthetic polypeptide
source                  1..9
                        mol_type = protein
                        organism = synthetic construct
SEQUENCE: 343
LQGYSMPFT                                                                  9

SEQ ID NO: 344          moltype =     length =
SEQUENCE: 344
000

SEQ ID NO: 345          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 345
ATYGMS                                                                     6

SEQ ID NO: 346          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 346
DTYGMS                                                                     6

SEQ ID NO: 347          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 347
ETYGMS                                                                     6

SEQ ID NO: 348          moltype = AA   length = 6
```

```
FEATURE              Location/Qualifiers
REGION               1..6
                     note = Synthetic polypeptide
source               1..6
                     mol_type = protein
                     organism = synthetic construct
SEQUENCE: 348
GTYGMS                                                                      6

SEQ ID NO: 349       moltype = AA  length = 6
FEATURE              Location/Qualifiers
REGION               1..6
                     note = Synthetic polypeptide
source               1..6
                     mol_type = protein
                     organism = synthetic construct
SEQUENCE: 349
HTYGMS                                                                      6

SEQ ID NO: 350       moltype = AA  length = 6
FEATURE              Location/Qualifiers
REGION               1..6
                     note = Synthetic polypeptide
source               1..6
                     mol_type = protein
                     organism = synthetic construct
SEQUENCE: 350
KTYGMS                                                                      6

SEQ ID NO: 351       moltype = AA  length = 6
FEATURE              Location/Qualifiers
REGION               1..6
                     note = Synthetic polypeptide
source               1..6
                     mol_type = protein
                     organism = synthetic construct
SEQUENCE: 351
MTYGMS                                                                      6

SEQ ID NO: 352       moltype = AA  length = 6
FEATURE              Location/Qualifiers
REGION               1..6
                     note = Synthetic polypeptide
source               1..6
                     mol_type = protein
                     organism = synthetic construct
SEQUENCE: 352
NTYGMS                                                                      6

SEQ ID NO: 353       moltype = AA  length = 6
FEATURE              Location/Qualifiers
REGION               1..6
                     note = Synthetic polypeptide
source               1..6
                     mol_type = protein
                     organism = synthetic construct
SEQUENCE: 353
QTYGMS                                                                      6

SEQ ID NO: 354       moltype = AA  length = 6
FEATURE              Location/Qualifiers
REGION               1..6
                     note = Synthetic polypeptide
source               1..6
                     mol_type = protein
                     organism = synthetic construct
SEQUENCE: 354
RTYGMS                                                                      6

SEQ ID NO: 355       moltype = AA  length = 6
FEATURE              Location/Qualifiers
REGION               1..6
                     note = Synthetic polypeptide
source               1..6
                     mol_type = protein
                     organism = synthetic construct
SEQUENCE: 355
STYGMS                                                                      6
```

-continued

```
SEQ ID NO: 356        moltype = AA  length = 6
FEATURE               Location/Qualifiers
REGION                1..6
                      note = Synthetic polypeptide
source                1..6
                      mol_type = protein
                      organism = synthetic construct
SEQUENCE: 356
TDYGMS                                                                         6

SEQ ID NO: 357        moltype = AA  length = 6
FEATURE               Location/Qualifiers
REGION                1..6
                      note = Synthetic polypeptide
source                1..6
                      mol_type = protein
                      organism = synthetic construct
SEQUENCE: 357
TEYGMS                                                                         6

SEQ ID NO: 358        moltype = AA  length = 6
FEATURE               Location/Qualifiers
REGION                1..6
                      note = Synthetic polypeptide
source                1..6
                      mol_type = protein
                      organism = synthetic construct
SEQUENCE: 358
TGYGMS                                                                         6

SEQ ID NO: 359        moltype = AA  length = 6
FEATURE               Location/Qualifiers
REGION                1..6
                      note = Synthetic polypeptide
source                1..6
                      mol_type = protein
                      organism = synthetic construct
SEQUENCE: 359
THYGMS                                                                         6

SEQ ID NO: 360        moltype = AA  length = 6
FEATURE               Location/Qualifiers
REGION                1..6
                      note = Synthetic polypeptide
source                1..6
                      mol_type = protein
                      organism = synthetic construct
SEQUENCE: 360
TNYGMS                                                                         6

SEQ ID NO: 361        moltype = AA  length = 6
FEATURE               Location/Qualifiers
REGION                1..6
                      note = Synthetic polypeptide
source                1..6
                      mol_type = protein
                      organism = synthetic construct
SEQUENCE: 361
TQYGMS                                                                         6

SEQ ID NO: 362        moltype = AA  length = 6
FEATURE               Location/Qualifiers
REGION                1..6
                      note = Synthetic polypeptide
source                1..6
                      mol_type = protein
                      organism = synthetic construct
SEQUENCE: 362
TSYGMS                                                                         6

SEQ ID NO: 363        moltype = AA  length = 6
FEATURE               Location/Qualifiers
REGION                1..6
                      note = Synthetic polypeptide
source                1..6
                      mol_type = protein
                      organism = synthetic construct
SEQUENCE: 363
TTFGMS                                                                         6
```

```
SEQ ID NO: 364          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 364
TTMGMS                                                                    6

SEQ ID NO: 365          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 365
TTQGMS                                                                    6

SEQ ID NO: 366          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 366
TTYGIS                                                                    6

SEQ ID NO: 367          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 367
TTYGLS                                                                    6

SEQ ID NO: 368          moltype = AA   length = 6
FEATURE                 Location/Qualifiers
REGION                  1..6
                        note = Synthetic polypeptide
source                  1..6
                        mol_type = protein
                        organism = synthetic construct
SEQUENCE: 368
TTYGVS                                                                    6

SEQ ID NO: 369          moltype = AA   length = 13
FEATURE                 Location/Qualifiers
REGION                  1..13
                        note = Synthetic polypeptide
VARIANT                 5
                        note = X at 5 is D or E.
VARIANT                 6
                        note = X at 6 is S or T.
source                  1..13
                        mol_type = protein
                        organism = synthetic construct
SEQUENCE: 369
WINTXXGVPT YAD                                                           13

SEQ ID NO: 370          moltype = AA   length = 13
FEATURE                 Location/Qualifiers
REGION                  1..13
                        note = Synthetic polypeptide
source                  1..13
                        mol_type = protein
                        organism = synthetic construct
SEQUENCE: 370
WINTESGVPT YAD                                                           13

SEQ ID NO: 371          moltype = AA   length = 13
FEATURE                 Location/Qualifiers
REGION                  1..13
                        note = Synthetic polypeptide
```

```
source                  1..13
                        mol_type = protein
                        organism = synthetic construct
SEQUENCE: 371
WINTDTGVPT YAD                                                          13

SEQ ID NO: 372          moltype = AA  length = 13
FEATURE                 Location/Qualifiers
REGION                  1..13
                        note = Synthetic polypeptide
VARIANT                 3
                        note = X at 3 is N or M.
VARIANT                 10
                        note = X at 10 is N, F, H, or Y.
source                  1..13
                        mol_type = protein
                        organism = synthetic construct
SEQUENCE: 372
ARXIYYGWGX FDY                                                          13

SEQ ID NO: 373          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 373
ARMIYYGWGN FDY                                                          13

SEQ ID NO: 374          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 374
ARNIYYGWGF FDY                                                          13

SEQ ID NO: 375          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 375
ARNIYYGWGH FDY                                                          13

SEQ ID NO: 376          moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 376
ARNIYYGWGY FDY                                                          13

SEQ ID NO: 377          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 377
EIVMTQSPDF QSVTPKEKVT ITCRASQAIY RNLHWYQQKP DQTPKLLIKH ASDSISGIPS        60
RFSGSGSGTD FTLTINSLEA EDAAAYYCLQ GYSMPYTFGG GTKVEIK                     107

SEQ ID NO: 378          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 378
```

```
EIVMTQSPDF QSVTPKEKVT ITCRASQEIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 379          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 379
EIVMTQSPDF QSVTPKEKVT ITCRASQGIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 380          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 380
EIVMTQSPDF QSVTPKEKVT ITCRASQHIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 381          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 381
EIVMTQSPDF QSVTPKEKVT ITCRASQKIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 382          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 382
EIVMTQSPDF QSVTPKEKVT ITCRASQNIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 383          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 383
EIVMTQSPDF QSVTPKEKVT ITCRASQPIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 384          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 384
EIVMTQSPDF QSVTPKEKVT ITCRASQQIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 385          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 385
EIVMTQSPDF QSVTPKEKVT ITCRASQSIY RNLHWYQQKP DQTPKLLIKH ASDSISGIPS    60
RFSGSGSGTD FTLTINSLEA EDAAAYYCLQ GYSMPYTFGG GTKVEIK                 107
```

```
SEQ ID NO: 386           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 386
EIVMTQSPDF QSVTPKEKVT ITCRASQTIY RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 387           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 387
EIVMTQSPDF QSVTPKEKVT ITCRASQDIF RNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 388           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 388
EIVMTQSPDF QSVTPKEKVT ITCRASQDIY KNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 389           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 389
EIVMTQSPDF QSVTPKEKVT ITCRASQDIY QNLHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 390           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 390
EIVMTQSPDF QSVTPKEKVT ITCRASQDIY RNIHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 391           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 391
EIVMTQSPDF QSVTPKEKVT ITCRASQDIY RNMHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 392           moltype = AA  length = 107
FEATURE                  Location/Qualifiers
REGION                   1..107
                         note = Synthetic polypeptide
source                   1..107
                         mol_type = protein
                         organism = synthetic construct
SEQUENCE: 392
EIVMTQSPDF QSVTPKEKVT ITCRASQDIY RNVHWYQQKP DQTPKLLIKH ASDSISGIPS    60
RFSGSGSGTD FTLTINSLEA EDAAAYYCLQ GYSMPYTFGG GTKVEIK                 107

SEQ ID NO: 393           moltype = AA  length = 107
```

```
FEATURE               Location/Qualifiers
REGION                1..107
                      note = Synthetic polypeptide
source                1..107
                      mol_type = protein
                      organism = synthetic construct
SEQUENCE: 393
EIVMTQSPDF QSVTPKEKVT ITCRASQDIY RNLHWYQQKP DQTPKLLIKH AEDSISGIPS    60
RFSGSGSGTD FTLTINSLEA EDAAAYYCLQ GYSMPYTFGG GTKVEIK                 107

SEQ ID NO: 394        moltype = AA   length = 107
FEATURE               Location/Qualifiers
REGION                1..107
                      note = Synthetic polypeptide
source                1..107
                      mol_type = protein
                      organism = synthetic construct
SEQUENCE: 394
EIVMTQSPDF QSVTPKEKVT ITCRASQDIY RNLHWYQQKP DQTPKLLIKH ASESISGIPS    60
RFSGSGSGTD FTLTINSLEA EDAAAYYCLQ GYSMPYTFGG GTKVEIK                 107

SEQ ID NO: 395        moltype = AA   length = 107
FEATURE               Location/Qualifiers
REGION                1..107
                      note = Synthetic polypeptide
source                1..107
                      mol_type = protein
                      organism = synthetic construct
SEQUENCE: 395
EIVMTQSPDF QSVTPKEKVT ITCRASQDIY RNLHWYQQKP DQTPKLLIKH ASKSISGIPS    60
RFSGSGSGTD FTLTINSLEA EDAAAYYCLQ GYSMPYTFGG GTKVEIK                 107

SEQ ID NO: 396        moltype = AA   length = 107
FEATURE               Location/Qualifiers
REGION                1..107
                      note = Synthetic polypeptide
source                1..107
                      mol_type = protein
                      organism = synthetic construct
SEQUENCE: 396
EIVMTQSPDF QSVTPKEKVT ITCRASQDIY RNLHWYQQKP DQTPKLLIKH ASQSISGIPS    60
RFSGSGSGTD FTLTINSLEA EDAAAYYCLQ GYSMPYTFGG GTKVEIK                 107

SEQ ID NO: 397        moltype = AA   length = 107
FEATURE               Location/Qualifiers
REGION                1..107
                      note = Synthetic polypeptide
source                1..107
                      mol_type = protein
                      organism = synthetic construct
SEQUENCE: 397
EIVMTQSPDF QSVTPKEKVT ITCRASQDIY RNLHWYQQKP DQTPKLLIKH ASDHISGIPS    60
RFSGSGSGTD FTLTINSLEA EDAAAYYCLQ GYSMPYTFGG GTKVEIK                 107

SEQ ID NO: 398        moltype = AA   length = 107
FEATURE               Location/Qualifiers
REGION                1..107
                      note = Synthetic polypeptide
source                1..107
                      mol_type = protein
                      organism = synthetic construct
SEQUENCE: 398
EIVMTQSPDF QSVTPKEKVT ITCRASQDIY RNLHWYQQKP DQTPKLLIKH ASDLISGIPS    60
RFSGSGSGTD FTLTINSLEA EDAAAYYCLQ GYSMPYTFGG GTKVEIK                 107

SEQ ID NO: 399        moltype = AA   length = 107
FEATURE               Location/Qualifiers
REGION                1..107
                      note = Synthetic polypeptide
source                1..107
                      mol_type = protein
                      organism = synthetic construct
SEQUENCE: 399
EIVMTQSPDF QSVTPKEKVT ITCRASQDIY RNLHWYQQKP DQTPKLLIKH ASDRISGIPS    60
RFSGSGSGTD FTLTINSLEA EDAAAYYCLQ GYSMPYTFGG GTKVEIK                 107

SEQ ID NO: 400        moltype = AA   length = 107
FEATURE               Location/Qualifiers
REGION                1..107
```

```
                        note = Synthetic polypeptide
source                  1..107
                        mol_type = protein
                        organism = synthetic construct
SEQUENCE: 400
EIVMTQSPDF QSVTPKEKVT ITCRASQDIY RNLHWYQQKP DQTPKLLIKH ASDVISGIPS      60
RFSGSGSGTD FTLTINSLEA EDAAAYYCLQ GYSMPYTFGG GTKVEIK                   107

SEQ ID NO: 401          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 401
EIVMTQSPDF QSVTPKEKVT ITCRASQDIY RNLHWYQQKP DQTPKLLIKH ASDSVSGIPS      60
RFSGSGSGTD FTLTINSLEA EDAAAYYCLQ GYSMPYTFGG GTKVEIK                   107

SEQ ID NO: 402          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 402
EIVMTQSPDF QSVTPKEKVT ITCRASQDIY RNLHWYQQKP DQTPKLLIKH ASDSISGIPS      60
RFSGSGSGTD FTLTINSLEA EDAAAYYCGQ GYSMPYTFGG GTKVEIK                   107

SEQ ID NO: 403          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 403
EIVMTQSPDF QSVTPKEKVT ITCRASQDIY RNLHWYQQKP DQTPKLLIKH ASDSISGIPS      60
RFSGSGSGTD FTLTINSLEA EDAAAYYCMQ GYSMPYTFGG GTKVEIK                   107

SEQ ID NO: 404          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 404
EIVMTQSPDF QSVTPKEKVT ITCRASQDIY RNLHWYQQKP DQTPKLLIKH ASDSISGIPS      60
RFSGSGSGTD FTLTINSLEA EDAAAYYCQQ GYSMPYTFGG GTKVEIK                   107

SEQ ID NO: 405          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 405
EIVMTQSPDF QSVTPKEKVT ITCRASQDIY RNLHWYQQKP DQTPKLLIKH ASDSISGIPS      60
RFSGSGSGTD FTLTINSLEA EDAAAYYCLQ GYAMPYTFGG GTKVEIK                   107

SEQ ID NO: 406          moltype = AA  length = 107
FEATURE                 Location/Qualifiers
REGION                  1..107
                        note = Synthetic polypeptide
source                  1..107
                        mol_type = protein
                        organism = synthetic construct
SEQUENCE: 406
EIVMTQSPDF QSVTPKEKVT ITCRASQDIY RNLHWYQQKP DQTPKLLIKH ASDSISGIPS      60
RFSGSGSGTD FTLTINSLEA EDAAAYYCLQ GYEMPYTFGG GTKVEIK                   107

SEQ ID NO: 407          moltype = AA  length = 107
FEATURE                 Location/Qualifiers
REGION                  1..107
                        note = Synthetic polypeptide
source                  1..107
```

```
                           mol_type = protein
                           organism = synthetic construct
SEQUENCE: 407
EIVMTQSPDF QSVTPKEKVT ITCRASQDIY RNLHWYQQKP DQTPKLLIKH ASDSISGIPS    60
RFSGSGSGTD FTLTINSLEA EDAAAYYCLQ GYQMPYTFGG GTKVEIK                 107

SEQ ID NO: 408             moltype = AA   length = 107
FEATURE                    Location/Qualifiers
REGION                     1..107
                           note = Synthetic polypeptide
source                     1..107
                           mol_type = protein
                           organism = synthetic construct
SEQUENCE: 408
EIVMTQSPDF QSVTPKEKVT ITCRASQDIY RNLHWYQQKP DQTPKLLIKH ASDSISGIPS    60
RFSGSGSGTD FTLTINSLEA EDAAAYYCLQ GYVMPYTFGG GTKVEIK                 107

SEQ ID NO: 409             moltype = AA   length = 107
FEATURE                    Location/Qualifiers
REGION                     1..107
                           note = Synthetic polypeptide
source                     1..107
                           mol_type = protein
                           organism = synthetic construct
SEQUENCE: 409
EIVMTQSPDF QSVTPKEKVT ITCRASQDIY RNLHWYQQKP DQTPKLLIKH ASDSISGIPS    60
RFSGSGSGTD FTLTINSLEA EDAAAYYCLQ GYSMPFTFGG GTKVEIK                 107

SEQ ID NO: 410             moltype = AA   length = 120
FEATURE                    Location/Qualifiers
REGION                     1..120
                           note = Synthetic polypeptide
source                     1..120
                           mol_type = protein
                           organism = synthetic construct
SEQUENCE: 410
EIQLVQSGSE LKKPGASVKV SCKASGYPFA TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 411             moltype = AA   length = 120
FEATURE                    Location/Qualifiers
REGION                     1..120
                           note = Synthetic polypeptide
source                     1..120
                           mol_type = protein
                           organism = synthetic construct
SEQUENCE: 411
EIQLVQSGSE LKKPGASVKV SCKASGYPFD TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 412             moltype = AA   length = 120
FEATURE                    Location/Qualifiers
REGION                     1..120
                           note = Synthetic polypeptide
source                     1..120
                           mol_type = protein
                           organism = synthetic construct
SEQUENCE: 412
EIQLVQSGSE LKKPGASVKV SCKASGYPFE TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 413             moltype = AA   length = 120
FEATURE                    Location/Qualifiers
REGION                     1..120
                           note = Synthetic polypeptide
source                     1..120
                           mol_type = protein
                           organism = synthetic construct
SEQUENCE: 413
EIQLVQSGSE LKKPGASVKV SCKASGYPFG TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 414             moltype = AA   length = 120
FEATURE                    Location/Qualifiers
REGION                     1..120
                           note = Synthetic polypeptide
source                     1..120
                           mol_type = protein
                           organism = synthetic construct
```

```
SEQUENCE: 414
EIQLVQSGSE LKKPGASVKV SCKASGYPFH TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 415           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 415
EIQLVQSGSE LKKPGASVKV SCKASGYPFK TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 416           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 416
EIQLVQSGSE LKKPGASVKV SCKASGYPFM TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 417           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 417
EIQLVQSGSE LKKPGASVKV SCKASGYPFN TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 418           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 418
EIQLVQSGSE LKKPGASVKV SCKASGYPFQ TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 419           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 419
EIQLVQSGSE LKKPGASVKV SCKASGYPFR TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 420           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 420
EIQLVQSGSE LKKPGASVKV SCKASGYPFS TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 421           moltype = AA   length = 120
FEATURE                  Location/Qualifiers
REGION                   1..120
                         note = Synthetic polypeptide
source                   1..120
                         mol_type = protein
                         organism = synthetic construct
SEQUENCE: 421
EIQLVQSGSE LKKPGASVKV SCKASGYPFT DYGMSWVRQA PGQGLEWMGW INTDSGVPTY    60
```

```
ADDFKGRFVF SLDTSVSTAY LQISSLKAED TAVYFCARNI YYGWGNFDYW GQGTLVTVSS    120

SEQ ID NO: 422          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 422
EIQLVQSGSE LKKPGASVKV SCKASGYPFT EYGMSWVRQA PGQGLEWMGW INTDSGVPTY     60
ADDFKGRFVF SLDTSVSTAY LQISSLKAED TAVYFCARNI YYGWGNFDYW GQGTLVTVSS    120

SEQ ID NO: 423          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 423
EIQLVQSGSE LKKPGASVKV SCKASGYPFT GYGMSWVRQA PGQGLEWMGW INTDSGVPTY     60
ADDFKGRFVF SLDTSVSTAY LQISSLKAED TAVYFCARNI YYGWGNFDYW GQGTLVTVSS    120

SEQ ID NO: 424          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 424
EIQLVQSGSE LKKPGASVKV SCKASGYPFT HYGMSWVRQA PGQGLEWMGW INTDSGVPTY     60
ADDFKGRFVF SLDTSVSTAY LQISSLKAED TAVYFCARNI YYGWGNFDYW GQGTLVTVSS    120

SEQ ID NO: 425          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 425
EIQLVQSGSE LKKPGASVKV SCKASGYPFT NYGMSWVRQA PGQGLEWMGW INTDSGVPTY     60
ADDFKGRFVF SLDTSVSTAY LQISSLKAED TAVYFCARNI YYGWGNFDYW GQGTLVTVSS    120

SEQ ID NO: 426          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 426
EIQLVQSGSE LKKPGASVKV SCKASGYPFT QYGMSWVRQA PGQGLEWMGW INTDSGVPTY     60
ADDFKGRFVF SLDTSVSTAY LQISSLKAED TAVYFCARNI YYGWGNFDYW GQGTLVTVSS    120

SEQ ID NO: 427          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 427
EIQLVQSGSE LKKPGASVKV SCKASGYPFT SYGMSWVRQA PGQGLEWMGW INTDSGVPTY     60
ADDFKGRFVF SLDTSVSTAY LQISSLKAED TAVYFCARNI YYGWGNFDYW GQGTLVTVSS    120

SEQ ID NO: 428          moltype = AA   length = 120
FEATURE                 Location/Qualifiers
REGION                  1..120
                        note = Synthetic polypeptide
source                  1..120
                        mol_type = protein
                        organism = synthetic construct
SEQUENCE: 428
EIQLVQSGSE LKKPGASVKV SCKASGYPFT TFGMSWVRQA PGQGLEWMGW INTDSGVPTY     60
ADDFKGRFVF SLDTSVSTAY LQISSLKAED TAVYFCARNI YYGWGNFDYW GQGTLVTVSS    120
```

```
SEQ ID NO: 429            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 429
EIQLVQSGSE LKKPGASVKV SCKASGYPFT TMGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 430            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 430
EIQLVQSGSE LKKPGASVKV SCKASGYPFT TQGMSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 431            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 431
EIQLVQSGSE LKKPGASVKV SCKASGYPFT TYGISWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 432            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 432
EIQLVQSGSE LKKPGASVKV SCKASGYPFT TYGLSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 433            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 433
EIQLVQSGSE LKKPGASVKV SCKASGYPFT TYGVSWVRQA PGQGLEWMGW INTDSGVPTY    60
ADDFKGRFVF SLDTSVSTAY LQISSLKAED TAVYFCARNI YYGWGNFDYW GQGTLVTVSS   120

SEQ ID NO: 434            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 434
EIQLVQSGSE LKKPGASVKV SCKASGYPFT TYGMSWVRQA PGQGLEWMGW INTESGVPTY    60
ADDFKGRFVF SLDTSVSTAY LQISSLKAED TAVYFCARNI YYGWGNFDYW GQGTLVTVSS   120

SEQ ID NO: 435            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 435
EIQLVQSGSE LKKPGASVKV SCKASGYPFT TYGMSWVRQA PGQGLEWMGW INTDTGVPTY    60
ADDFKGRFVF SLDTSVSTAY LQISSLKAED TAVYFCARNI YYGWGNFDYW GQGTLVTVSS   120

SEQ ID NO: 436            moltype = AA  length = 120
FEATURE                   Location/Qualifiers
```

```
REGION                    1..120
                          note = Synthetic polypeptide
source                    1..120
                          mol_type = protein
                          organism = synthetic construct
SEQUENCE: 436
EIQLVQSGSE LKKPGASVKV SCKASGYPFT TYGMSWVRQA PGQGLEWMGW INTDSGVPTY    60
ADDFKGRFVF SLDTSVSTAY LQISSLKAED TAVYFCARMI YYGWGNFDYW GQGTLVTVSS   120

SEQ ID NO: 437            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 437
EIQLVQSGSE LKKPGASVKV SCKASGYPFT TYGMSWVRQA PGQGLEWMGW INTDSGVPTY    60
ADDFKGRFVF SLDTSVSTAY LQISSLKAED TAVYFCARNI YYGWGFFDYW GQGTLVTVSS   120

SEQ ID NO: 438            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 438
EIQLVQSGSE LKKPGASVKV SCKASGYPFT TYGMSWVRQA PGQGLEWMGW INTDSGVPTY    60
ADDFKGRFVF SLDTSVSTAY LQISSLKAED TAVYFCARNI YYGWGHFDYW GQGTLVTVSS   120

SEQ ID NO: 439            moltype = AA  length = 120
FEATURE                   Location/Qualifiers
REGION                    1..120
                          note = Synthetic polypeptide
source                    1..120
                          mol_type = protein
                          organism = synthetic construct
SEQUENCE: 439
EIQLVQSGSE LKKPGASVKV SCKASGYPFT TYGMSWVRQA PGQGLEWMGW INTDSGVPTY    60
ADDFKGRFVF SLDTSVSTAY LQISSLKAED TAVYFCARNI YYGWGYFDYW GQGTLVTVSS   120

SEQ ID NO: 440            moltype = AA  length = 213
FEATURE                   Location/Qualifiers
REGION                    1..213
                          note = Synthetic polypeptide
source                    1..213
                          mol_type = protein
                          organism = synthetic construct
SEQUENCE: 440
DIVMTQSQKF MSTSVGDRVS VTCKASQNVG TAIVWYQKKP GQSPKTLIYS ASTRYTGVPD    60
RFTGSGSGTD FTLTISNVQS EDLAEYFCQQ YSSSPLTFGS GTKLEIKGQP KAAPSVTLFP   120
PSSEELQANK ATLVCLISDF YPGAVTVAWK ADSSPVKAGV ETTTPSKQSN NKYAASSYLS   180
LTPEQWKSHK SYSCQVTHEG STVEKTVAPT ECS                                213

SEQ ID NO: 441            moltype = AA  length = 218
FEATURE                   Location/Qualifiers
REGION                    1..218
                          note = Synthetic polypeptide
source                    1..218
                          mol_type = protein
                          organism = synthetic construct
SEQUENCE: 441
DVVMTQTPLT LSVTLGHPAS ISCKSSQSLL DSDGKTYLNW LLQRPGESPK LLIYLVSKLD    60
SGVPDRFTGS GSGTDFTLKI SRVEAEDLGV YYCLQATHSP QTFGGGTKLE IKGQPKAAPS   120
VTLFPPSSEE LQANKATLVC LISDFYPGAV TVAWKADSSP VKAGVETTTP SKQSNNKYAA   180
SSYLSLTPEQ WKSHKSYSCQ VTHEGSTVEK TVAPTECS                           218

SEQ ID NO: 442            moltype = AA  length = 213
FEATURE                   Location/Qualifiers
REGION                    1..213
                          note = Synthetic polypeptide
source                    1..213
                          mol_type = protein
                          organism = synthetic construct
SEQUENCE: 442
DIQMNQSPSS LSASLGDTIT ITCRVSQDIS FWLSWYQQKP GNIPKLLIYK ASNLHTGVPP    60
RFSGSGSGTD FTLTISSLQP EDIAAYYCLQ SQSYPYTFGG GTKLEIKGQP KAAPSVTLFP   120
PSSEELQANK ATLVCLISDF YPGAVTVAWK ADSSPVKAGV ETTTPSKQSN NKYAASSYLS   180
```

```
                                                       -continued
LTPEQWKSHK SYSCQVTHEG STVEKTVAPT ECS                             213

SEQ ID NO: 443          moltype = AA   length = 212
FEATURE                 Location/Qualifiers
REGION                  1..212
                        note = Synthetic polypeptide
source                  1..212
                        mol_type = protein
                        organism = synthetic construct
SEQUENCE: 443
ENVLTQSPAI MSATLGEKVT MNCRASSNVK YMYWYQQKSG VSPKLWIYYT SNLASGVPTR  60
FSGSGSGTSY SLTISSVEAE DAATYYCQQF TSSPLTFGAG TKLELKGQPK AAPSVTLFPP 120
SSEELQANKA TLVCLISDFY PGAVTVAWKA DSSPVKAGVE TTTPSKQSNN KYAASSYLSL 180
TPEQWKSHKS YSCQVTHEGS TVEKTVAPTE CS                              212

SEQ ID NO: 444          moltype = AA   length = 217
FEATURE                 Location/Qualifiers
REGION                  1..217
                        note = Synthetic polypeptide
source                  1..217
                        mol_type = protein
                        organism = synthetic construct
SEQUENCE: 444
DIVLTQSPAS LAVSLGQRAI ISCKASQSVT FADTGLMHWY QQKPGQQPKL LIYRASNLEV  60
GVPTRFSGSG SGTDFTLNIH PVEEEDVATY YCQQSREYPW TFGGGTKLEI KGQPKAAPSV 120
TLFPPSSEEL QANKATLVCL ISDFYPGAVT VAWKADSSPV KAGVETTTPS KQSNNKYAAS 180
SYLSLTPEQW KSHKSYSCQV THEGSTVEKT VAPTECS                         217

SEQ ID NO: 445          moltype = AA   length = 215
FEATURE                 Location/Qualifiers
REGION                  1..215
                        note = Synthetic polypeptide
source                  1..215
                        mol_type = protein
                        organism = synthetic construct
SEQUENCE: 445
QAVVTQESAL TTSPGETVTL TCRSSTGAVT TSNYANWVQE KPDHLFTGLI GGTNNRAPGV  60
PARFSGSGLIG DKAALTITGA QTEDEAIYFC SLWYGSHWVF GGGTKLTVLG QPKAAPSVTL 120
FPPSSEELQA NKATLVCLIS DFYPGAVTVA WKADSSPVKA GVETTTPSKQ SNNKYAASSY 180
LSLTPEQWKS HKSYSCQVTH EGSTVEKTVA PTECS                           215

SEQ ID NO: 446          moltype = AA   length = 213
FEATURE                 Location/Qualifiers
REGION                  1..213
                        note = Synthetic polypeptide
source                  1..213
                        mol_type = protein
                        organism = synthetic construct
SEQUENCE: 446
DILMTQSPTT LSVTPGETVS LSCRASQDIY RNLHWYQQKS QGTPRLLIKH ASDSISGIPS  60
RFTGSGSGTD FTLSINSVKP EDEGIYYCLQ GYSMPYTFGG GTKLEIKGQP KAAPSVTLFP 120
PSSEELQANK ATLVCLISDF YPGAVTVAWK ADSSPVKAGV ETTTPSKQSN NKYAASSYLS 180
LTPEQWKSHK SYSCQVTHEG STVEKTVAPT ECS                             213

SEQ ID NO: 447          moltype = AA   length = 448
FEATURE                 Location/Qualifiers
REGION                  1..448
                        note = Synthetic polypeptide
source                  1..448
                        mol_type = protein
                        organism = synthetic construct
SEQUENCE: 447
QVQLQQPGAE LVTPGASVKL SCKASGFTFT NNWMHWVKQR PGQGLEWIGM IHPNSGITNI  60
NEKFKNKATV TVDKSSSTVY IQLSSLTSED SAVYYCRSDG TYEGYFDYWG QGTPLTVSSA 120
STKGPSVFPL APSSKSTSGG TAALGCLVKD YFPEPVTVSW NSGALTSGVH TFPAVLQSSG 180
LYSLSSVVTV PSSSLGTQTY ICNVNHKPSN TKVDKKVEPK SCDKTHTCPP CPAPELLGGP 240
SVFLFPPKPK DTLMISRTPE VTCVVVDVSH EDPEVKFNWY VDGVEVHNAK TKPREEQYGS 300
TYRVVSVLTV LHQDWLNGKE YKCKVSNKAL PAPIEKTISK AKGQPREPQV YTLPPSRDEL 360
TKNQVSLTCL VKGFYPSDIA VEWESNGQPE NNYKTTPPVL DSDGSFFLYS KLTVDKSRWQ 420
QGNVFSCSVM HEALHNHYTQ KSLSLSPG                                   448

SEQ ID NO: 448          moltype = AA   length = 446
FEATURE                 Location/Qualifiers
REGION                  1..446
                        note = Synthetic polypeptide
source                  1..446
                        mol_type = protein
                        organism = synthetic construct
SEQUENCE: 448
```

```
QVQLQQSGAD LARPGASIKL SCKASGYTFT GYGVTWVKQS TGQGLDWIGE IYPGTVITYY    60
NAKFKGKATL TADKSSSTAY MELRSLTSED SAVYFCARGL GRAMDYWGQG TSVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYGSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                      446

SEQ ID NO: 449          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 449
QVQLQQSGPE LLKPGASVKI SCKASGYTFT DYYINWVKQR PGQGLEWIGW IFPGTEGIYY    60
NEKFKGKATL TVDKSSTTAY MLLSSLTSED SAVYFCAREG DYRYYSPLGY WGQGTLVTVS   120
AASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
GSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                   450

SEQ ID NO: 450          moltype = AA  length = 446
FEATURE                 Location/Qualifiers
REGION                  1..446
                        note = Synthetic polypeptide
source                  1..446
                        mol_type = protein
                        organism = synthetic construct
SEQUENCE: 450
QVQLQQSGPE LVKPGASVKI SCKASGYNFN DYYINWVNQR PGQGLEWIGW IFPGRIITYY    60
NEKFKGKATL TVDTSSNTAY MLLSSLTSED SAVYFCARGV GEGFDYWGQG TTLTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APELLGGPSV   240
FLFPPKPKDT LMISRTPEVT CVVVDVSHED PEVKFNWYVD GVEVHNAKTK PREEQYGSTY   300
RVVSVLTVLH QDWLNGKEYK CKVSNKALPA PIEKTISKAK GQPREPQVYT LPPSRDELTK   360
NQVSLTCLVK GFYPSDIAVE WESNGQPENN YKTTPPVLDS DGSFFLYSKL TVDKSRWQQG   420
NVFSCSVMHE ALHNHYTQKS LSLSPG                                      446

SEQ ID NO: 451          moltype = AA  length = 447
FEATURE                 Location/Qualifiers
REGION                  1..447
                        note = Synthetic polypeptide
source                  1..447
                        mol_type = protein
                        organism = synthetic construct
SEQUENCE: 451
EVQLLETGGG LVKSGGSLKL SCAASGFTFS DYYMWVRQT PEKRLEWVAA ISDDGTYTYY     60
PDSVKGRFTI SRDNANNYLY LQMSSLKSED TAIYYCAKAG SYDYFDVWGA GTTVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYGST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                     447

SEQ ID NO: 452          moltype = AA  length = 445
FEATURE                 Location/Qualifiers
REGION                  1..445
                        note = Synthetic polypeptide
source                  1..445
                        mol_type = protein
                        organism = synthetic construct
SEQUENCE: 452
QVQLKESGPG LVAPSQSLSI ICTVSGFSLT NYGIHWIRQP PGKGLEWLGI IWAGGSTNYN    60
SALMSRLTIS KDNSKSQVFL KMNSLQTNDT AIYYCARVSM MGFAYWGQGT LVTVSAASTK   120
GPSVFPLAPS SKSTSGGTAA LGCLVKDYFP EPVTVSWNSG ALTSGVHTFP AVLQSSGLYS   180
LSSVVTVPSS SLGTQTYICN VNHKPSNTKV DKKVEPKSCD KTHTCPPCPA PELLGGPSVF   240
LFPPKPKDTL MISRTPEVTC VVVDVSHEDP EVKFNWYVDG VEVHNAKTKP REEQYGSTYR   300
VVSVLTVLHQ DWLNGKEYKC KVSNKALPAP IEKTISKAKG QPREPQVYTL PPSRDELTKN   360
QVSLTCLVKG FYPSDIAVEW ESNGQPENNY KTTPPVLDSD GSFFLYSKLT VDKSRWQQGN   420
VFSCSVMHEA LHNHYTQKSL SLSPG                                       445

SEQ ID NO: 453          moltype = AA  length = 449
FEATURE                 Location/Qualifiers
```

```
REGION                  1..449
                        note = Synthetic polypeptide
source                  1..449
                        mol_type = protein
                        organism = synthetic construct
SEQUENCE: 453
QIQLVQSGPE LKKPGETVKI SCKASGYPFT TYGMSWVKQA PGKGLKWMGW INTDSGVPTY    60
ADDFKGRFAF SLETSANTAY LQINSLKNED AATYFCARNI YYGWGNFDYW GQGTILTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYG   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 454          moltype = AA  length = 213
FEATURE                 Location/Qualifiers
REGION                  1..213
                        note = Synthetic polypeptide
source                  1..213
                        mol_type = protein
                        organism = synthetic construct
SEQUENCE: 454
DIQLTQSPSS LSASVGDRVT ITCKASQNVG TAIVWYQQKP GKAPKVLIYS ASTRYTGVPS    60
RFSGSGSGTD FTLTISSLQP EDFATYYCQQ YSSSPLTFGQ GTKVEIKGQP KAAPSVTLFP   120
PSSEELQANK ATLVCLISDF YPGAVTVAWK ADSSPVKAGV ETTTPSKQSN NKYAASSYLS   180
LTPEQWKSHK SYSCQVTHEG STVEKTVAPT ECS                               213

SEQ ID NO: 455          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 455
EVQLVQSGAE VKKPGASVKV SCKASGFTFT NNWMHWVRQA PGQGLEWIGM IHPNSGITNI    60
NEKFKNRVTM TTDTSTSTAY MELRSLRSED TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 456          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 456
EVQLVQSGAE VKKPGASVKV SCKASGFTFT NNFMHWVRQA PGQGLEWIGM IHANSGITNI    60
NEKFKNRVTM TTDTSTSTAY MELRSLRSED TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 457          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 457
EVQLVQSGAE VKKPGASVKV SCKASGFTFT NNFMHWVRQA PGQGLEWIGM IHANSGITNI    60
NEKFKNRVTM TTDTSTSTAY MELRSLRSED TAVYYCRSDG VYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448
```

```
SEQ ID NO: 458          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 458
EVQLVQSGAE VKKPGASVKV SCKASGFTFT NNFMHWVRQA PGQGLEWIGF IHANSGITNI    60
NEKFKNRVTM TTDTSTSTAY MELRSLRSED TAVYYCRSDG IYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 459          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 459
EVQLVQSGAE VKKPGASVKV SCKASGFTFT NNFMHWVRQA PGQGLEWIGF IHANSGITNI    60
NEKFKNRVTM TTDTSTSTAY MELRSLRSED TAVYYCRSDG VYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 460          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 460
QVQLVQSGAE VKKPGASVKV SCKASGFTFT NNWMHWVRQR PGQGLEWIGM IHPNSGITNI    60
NEKFKNRATV TVDKSSSTVY IELRSLRSED TAVYYCRSDG TYEGYFDYWG QGTLVTVSS    119

SEQ ID NO: 461          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 461
QVQLVQSGAE VKKPGASVKV SCKASGFTFT NNWMHWVRQR PGQGLEWIGM IHPNSGITNI    60
NEKFKNRATV TVDKSSSTVY IELRSLRSED TAVYYCRSDG TYEGYFDYWG QGTLVTVSS    119

SEQ ID NO: 462          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 462
QVQLVQSGAE VKKPGASVKV SCKASGFTFT NNWMHWVRQA PGQGLEWVGM IHPNSGITNI    60
NEKFKNRVTM TVDKSTSTVY MELRSLRSDD TAVYYCRSDG TYEGYFDYWG QGTLVTVSS    119

SEQ ID NO: 463          moltype = AA  length = 119
FEATURE                 Location/Qualifiers
REGION                  1..119
                        note = Synthetic polypeptide
source                  1..119
                        mol_type = protein
                        organism = synthetic construct
SEQUENCE: 463
QVQLVQSGAE VKKPGASVKV SCKASGFTFT NNWMHWVRQA PGQGLEWIGM IHPNSGITNI    60
NEKFKNRVTM TTDTSTSTAY MELRSLRSDD TAVYYCRSDG TYEGYFDYWG QGTLVTVSS    119

SEQ ID NO: 464          moltype = AA  length = 119
```

```
FEATURE                 Location/Qualifiers
REGION                  1..119
                        note = Synthetic polypeptide
source                  1..119
                        mol_type = protein
                        organism = synthetic construct
SEQUENCE: 464
QVQLVQSGAE VKKPGASVKV SCKASGFTFT NNWMHWVRQA PGQGLEWIGM IHPNSGITNI    60
NEKFKNRVTM TVDKSTSTVY MELRSLRSDD TAVYYCARDG TYEGYFDYWG QGTLVTVSS    119

SEQ ID NO: 465          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 465
QVQLVQSGAE VKKPGASVKV SCKASGFTFT NNWMHWVRQR PGQGLEWIGM IHPNSGITNI    60
NEKFKNRATV TVDKSSSTVY IELRSLRSED TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 466          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 466
QVQLVQSGAE VKKPGASVKV SCKASGFTFT NNWMHWVRQR PGQGLEWIGM IHPNSGITNI    60
NEKFKNRATV TVDKSSSTVY IELRSLRSED TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 467          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 467
QVQLVQSGAE VKKPGASVKV SCKASGFTFT NNWMHWVRQA PGQGLEWVGM IHPNSGITNI    60
NEKFKNRVTM TVDKSTSTVY MELRSLRSDD TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 468          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 468
QVQLVQSGAE VKKPGASVKV SCKASGFTFT NNWMHWVRQA PGQGLEWIGM IHPNSGITNI    60
NEKFKNRVTM TTDTSTSTAY MELRSLRSDD TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 469          moltype = AA  length = 448
```

```
FEATURE                 Location/Qualifiers
REGION                  1..448
                        note = Synthetic polypeptide
source                  1..448
                        mol_type = protein
                        organism = synthetic construct
SEQUENCE: 469
QVQLVQSGAE VKKPGASVKV SCKASGFTFT NNWMHWVRQA PGQGLEWIGM IHPNSGITNI    60
NEKFKNRVTM TVDKSTSTVY MELRSLRSDD TAVYYCARDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPG                                     448

SEQ ID NO: 470          moltype = AA  length = 213
FEATURE                 Location/Qualifiers
REGION                  1..213
                        note = Synthetic polypeptide
source                  1..213
                        mol_type = protein
                        organism = synthetic construct
SEQUENCE: 470
EIVMTQSPDF QSVTPKEKVT ITCRASQDIY RNLHWYQQKP DQTPKLLIKH ASDSISGIPS    60
RFSGSGSGTD FTLTINSLEA EDAAAYYCLQ GYSMPYTFGG GTKVEIKQSP KAAPSVTLFP   120
PSSEELQANK ATLVCLISDF YPGAVTVAWK ADSSPVKAGV ETTTPSKQSN NKYAASSYLS   180
LTPEQWKSHK SYSCQVTHEG STVEKTVAPT ECS                                213

SEQ ID NO: 471          moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 471
EIQLVQSGSE LKKPGASVKV SCKASGYPFT TYGMSWVRQA PGQGLEWMGW INTDSGVPTY    60
ADDFKGRFVF SLDTSVSTAY LQISSLKAED TAVYFCARNI YYGWGNFDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYG   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPG                                    449

SEQ ID NO: 472          moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 472
TNNWDH                                                               6

SEQ ID NO: 473          moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 473
TNNWGH                                                               6

SEQ ID NO: 474          moltype = AA  length = 17
FEATURE                 Location/Qualifiers
REGION                  1..17
                        note = Synthetic polypeptide
source                  1..17
                        mol_type = protein
                        organism = synthetic construct
SEQUENCE: 474
MIHPNSGITA INEKFKN                                                  17

SEQ ID NO: 475          moltype = AA  length = 256
FEATURE                 Location/Qualifiers
REGION                  1..256
```

```
                        note = Synthetic polypeptide
source                  1..256
                        mol_type = protein
                        organism = synthetic construct
SEQUENCE: 475
GGGGSENLYF QGGGGSEPKS CDKTHTCPPC PAPELLGGPS VFLFPPKPKD TLMISRTPEV    60
TCVVVDVSHE DPEVKFNWYV DGVEVHNAKT KPREEQYNST YRVVSVLTVL HQDWLNGKEY   120
KCKVSNKALP APIEKTISKA KGQPREPQVY TLPPSRDELT KNQVSLTCLV KGFYPSDIAV   180
EWESNGQPEN NYKTTPPVLD SDGSFFLYSK LTVDKSRWQQ GNVFSCSVMH EALHNHYTQK   240
SLSLSPGKDY KDDDDK                                                   256

SEQ ID NO: 476          moltype = DNA  length = 28
FEATURE                 Location/Qualifiers
misc_feature            1..28
                        note = Synthetic polypeptide
source                  1..28
                        mol_type = other DNA
                        organism = synthetic construct
SEQUENCE: 476
tcttgtccac cttggtgctg ctggccgg                                       28

SEQ ID NO: 477          moltype = DNA  length = 28
FEATURE                 Location/Qualifiers
misc_feature            1..28
                        note = Synthetic polypeptide
source                  1..28
                        mol_type = other DNA
                        organism = synthetic construct
SEQUENCE: 477
tttgtccacc gtggtgctgc tggctggt                                       28

SEQ ID NO: 478          moltype = DNA  length = 25
FEATURE                 Location/Qualifiers
misc_feature            1..25
                        note = Synthetic polypeptide
source                  1..25
                        mol_type = other DNA
                        organism = synthetic construct
SEQUENCE: 478
gatcagtcca actgttcagg acgcc                                          25

SEQ ID NO: 479          moltype = DNA  length = 33
FEATURE                 Location/Qualifiers
misc_feature            1..33
                        note = Synthetic polypeptide
source                  1..33
                        mol_type = other DNA
                        organism = synthetic construct
SEQUENCE: 479
acactcagca cgggacaaac tcttctccac agt                                 33

SEQ ID NO: 480          moltype = DNA  length = 33
FEATURE                 Location/Qualifiers
misc_feature            1..33
                        note = Synthetic polypeptide
source                  1..33
                        mol_type = other DNA
                        organism = synthetic construct
SEQUENCE: 480
acactctgca ggagacagac tcttttccac agt                                 33

SEQ ID NO: 481          moltype = DNA  length = 33
FEATURE                 Location/Qualifiers
misc_feature            1..33
                        note = Synthetic polypeptide
source                  1..33
                        mol_type = other DNA
                        organism = synthetic construct
SEQUENCE: 481
acactcagca cgggacaaac tcttctccac atg                                 33

SEQ ID NO: 482          moltype = AA  length = 344
FEATURE                 Location/Qualifiers
source                  1..344
                        mol_type = protein
                        organism = Homo sapiens
SEQUENCE: 482
MDYPTLLLAL LHVYRALCEE VLWHTSVPFA ENMSLECVYP SMGILTQVEW FKIGTQQDSI    60
AIFSPTHGMV IRKPYAERVY FLNSTMASNN MTLFFRNASE DDVGYYSCSL YTYPQGTWQK   120
```

```
VIQVVQSDSF EAAVPSNSHI VSEPGKNVTL TCQPQMTWPV QAVRWEKIQP RQIDLLTYCN    180
LVHGRNFTSK FPRQIVSNCS HGRWSVIVIP DVTVSDSGLY RCYLQASAGE NETFVMRLTV    240
AEGKTDNQYT LFVAGGTVLL LLFVISITTI IVIFLNRRRR RERRDLFTES WDTQKAPNNY    300
RSPISTSQPT NQSMDDTRED IYVNYPTFSR RPKTRVDYKD DDDK                     344

SEQ ID NO: 483          moltype = AA   length = 344
FEATURE                 Location/Qualifiers
source                  1..344
                        mol_type = protein
                        organism = Macaca fascicularis
SEQUENCE: 483
MDYPTLLLAL LHVYRALCEE VLWHTSVPFA ENMSLECVYP SVGILTQVEW FKIGTEKDSI     60
AIFSPTHGMV IRKPYAERVY FLNSTMASNN MTLFFRNASE DDVGYYSCSL YTYPQGTWQK    120
VIQVVQSDGF EAAVPPNSHI VSEPGKNITL TCQPQMTWPV QEVRWEKVQP HQIDLLTYCD    180
LVHGRNFTSK FPRQIVSNCS HGSWSFIVVP DVTASDSGLY RCHLQASAGE NETFVMRLTV    240
AEGQTDNQYT RFVTGGTVLL LLFVISITTI IVIFLNRRRR RERNDLYTES WDTQKAPKNY    300
RSPISANQPT NQSMDDTRED IYVNYPTFSR RPKTRVDYKD DDDK                     344

SEQ ID NO: 484          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 484
QVQLQQPGAE LVTPGASVKL SCKASGFTFT NNWMHWVKQR PGQGLEWIGM IHPNSGITNI     60
NEKFKNKATV TVDKSSSTVY IQLSSLTSED SAVYYCRSDG TYEGYFDYWG QGTPLTVSSA    120
STKGPSVFPL APSSKSTSGG TAALGCLVKD YFPEPVTVSW NSGALTSGVH TFPAVLQSSG    180
LYSLSSVVTV PSSSLGTQTY ICNVNHKPSN TKVDKKVEPK SCDKTHTCPP CPAPELLGGP    240
SVFLFPPKPK DTLMISRTPE VTCVVVDVSH EDPEVKFNWY VDGVEVHNAK TKPREEQYGS    300
TYRVVSVLTV LHQDWLNGKE YKCKVSNKAL PAPIEKTISK AKGQPREPQV YTLPPSRDEL    360
TKNQVSLTCL VKGFYPSDIA VEWESNGQPE NNYKTTPPVL DSDGSFFLYS KLTVDKSRWQ    420
QGNVFSCSVM HEALHNHYTQ KSLSLSPGK                                      449

SEQ ID NO: 485          moltype = AA   length = 447
FEATURE                 Location/Qualifiers
REGION                  1..447
                        note = Synthetic polypeptide
source                  1..447
                        mol_type = protein
                        organism = synthetic construct
SEQUENCE: 485
QVQLQQSGAD LARPGASIKL SCKASGYTFT GYGVTWVKQS TGQGLDWIGE IYPGTVITYY     60
NAKFKGKATL TADKSSSTAY MELRSLTSED SAVYFCARGL GRAMDYWGQG TSVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKKVEPKSC DKTHTCPPCP APELLGGPSV    240
FLFPPKPKDT LMISRTPEVT CVVVDVSHED PEVKFNWYVD GVEVHNAKTK PREEQYGSTY    300
RVVSVLTVLH QDWLNGKEYK CKVSNKALPA PIEKTISKAK GQPREPQVYT LPPSRDELTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                        447

SEQ ID NO: 486          moltype = AA   length = 451
FEATURE                 Location/Qualifiers
REGION                  1..451
                        note = Synthetic polypeptide
source                  1..451
                        mol_type = protein
                        organism = synthetic construct
SEQUENCE: 486
QVQLQQSGPE LLKPGASVKI SCKASGYTFT DYYINWVKQR PGQGLEWIGW IFPGTEGIYY     60
NEKFKGKATL TVDKSSTTAY MLLSSLTSED SAVYFCAREG DYRYYSPLGY WGQGTLVTVS    120
AASTKGPSVF PLAPSSKSTS GGTAALGCLV KDYFPEPVTV SWNSGALTSG VHTFPAVLQS    180
SGLYSLSSVV TVPSSSLGTQ TYICNVNHKP SNTKVDKKVE PKSCDKTHTC PPCPAPELLG    240
GPSVFLFPPK PKDTLMISRT PEVTCVVVDV SHEDPEVKFN WYVDGVEVHN AKTKPREEQY    300
GSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                   451

SEQ ID NO: 487          moltype = AA   length = 447
FEATURE                 Location/Qualifiers
REGION                  1..447
                        note = Synthetic polypeptide
source                  1..447
                        mol_type = protein
                        organism = synthetic construct
SEQUENCE: 487
QVQLQQSGPE LVKPGASVKI SCKASGYNFN DYYINWVNQR PGQGLEWIGW IFPGRIITYY     60
NEKFKGKATL TVDTSSNTAY MLLSSLTSED SAVYFCARGV GEGFDYWGQG TTLTVSSAST    120
```

```
KGPSVFPPLAP SSKSTSGGTA ALGCLVKDYF PEPVTVSWNS GALTSGVHTF PAVLQSSGLY    180
SLSSVVTVPS  SSLGTQTYIC NVNHKPSNTK VDKKVEPKSC DKTHTCPPCP APELLGGPSV    240
FLFPPKPKDT  LMISRTPEVT CVVVDVSHED PEVKFNWYVD GVEVHNAKTK PREEQYGSTY    300
RVVSVLTVLH  QDWLNGKEYK CKVSNKALPA PIEKTISKAK GQPREPQVYT LPPSRDELTK    360
NQVSLTCLVK  GFYPSDIAVE WESNGQPENN YKTTPPVLDS DGSFFLYSKL TVDKSRWQQG    420
NVFSCSVMHE  ALHNHYTQKS LSLSPGK                                        447

SEQ ID NO: 488          moltype = AA  length = 448
FEATURE                 Location/Qualifiers
REGION                  1..448
                        note = Synthetic polypeptide
source                  1..448
                        mol_type = protein
                        organism = synthetic construct
SEQUENCE: 488
EVQLLETGGG  LVKSGGSLKL SCAASGFTFS DYYMYWVRQT PEKRLEWVAA ISDDGTYTYY    60
PDSVKGRFTI  SRDNANNYLY LQMSSLKSED TAIYYCAKAG SYDYFDVWGA GTTVTVSSAS    120
TKGPSVFPLA  PSSKSTSGGT AALGCLVKDY FPEPVTVSWN SGALTSGVHT FPAVLQSSGL    180
YSLSSVVTVP  SSSLGTQTYI CNVNHKPSNT KVDKKVEPKS CDKTHTCPPC PAPELLGGPS    240
VFLFPPKPKD  TLMISRTPEV TCVVVDVSHE DPEVKFNWYV DGVEVHNAKT KPREEQYGST    300
YRVVSVLTVL  HQDWLNGKEY KCKVSNKALP APIEKTISKA KGQPREPQVY TLPPSRDELT    360
KNQVSLTCLV  KGFYPSDIAV EWESNGQPEN NYKTTPPVLD SDGSFFLYSK LTVDKSRWQQ    420
GNVFSCSVMH  EALHNHYTQK SLSLSPGK                                       448

SEQ ID NO: 489          moltype = AA  length = 446
FEATURE                 Location/Qualifiers
REGION                  1..446
                        note = Synthetic polypeptide
source                  1..446
                        mol_type = protein
                        organism = synthetic construct
SEQUENCE: 489
QVQLKESGPG  LVAPSQSLSI ICTVSGFSLT NYGIHWIRQP PGKGLEWLGI IWAGGSTNYN    60
SALMSRLTIS  KDNSKSQVFL KMNSLQTNDT AIYYCARVSM MGFAYWGQGT LVTVSAASTK    120
GPSVFPLAPS  SKSTSGGTAA LGCLVKDYFP EPVTVSWNSG ALTSGVHTFP AVLQSSGLYS    180
LSSVVTVPSS  SLGTQTYICN VNHKPSNTKV DKKVEPKSCD KTHTCPPCPA PELLGGPSVF    240
LFPPKPKDTL  MISRTPEVTC VVVDVSHEDP EVKFNWYVDG VEVHNAKTKP REEQYGSTYR    300
VVSVLTVLHQ  DWLNGKEYKC KVSNKALPAP IEKTISKAKG QPREPQVYTL PPSRDELTKN    360
QVSLTCLVKG  FYPSDIAVEW ESNGQPENNY KTTPPVLDSD GSFFLYSKLT VDKSRWQQGN    420
VFSCSVMHEA  LHNHYTQKSL SLSPGK                                         446

SEQ ID NO: 490          moltype = AA  length = 450
FEATURE                 Location/Qualifiers
REGION                  1..450
                        note = Synthetic polypeptide
source                  1..450
                        mol_type = protein
                        organism = synthetic construct
SEQUENCE: 490
QIQLVQSGPE  LKKPGETVKI SCKASGYPFT TYGMSWVKQA PGKGLKWMGW INTDSGVPTY    60
ADDFKGRFAF  SLETSANTAY LQINSLKNED AATYFCARNI YYGWGNFDYW GQGTILTVSS    120
ASTKGPSVFP  LAPSSKSTSG GTAALGCLVK DYFPEPVTVS WNSGALTSGV HTFPAVLQSS    180
GLYSLSSVVT  VPSSSLGTQT YICNVNHKPS NTKVDKKVEP KSCDKTHTCP PCPAPELLGG    240
PSVFLFPPKP  KDTLMISRTP EVTCVVVDVS HEDPEVKFNW YVDGVEVHNA KTKPREEQYG    300
STYRVVSVLT  VLHQDWLNGK EYKCKVSNKA LPAPIEKTIS KAKGQPREPQ VYTLPPSRDE    360
LTKNQVSLTC  LVKGFYPSDI AVEWESNGQP ENNYKTTPPV LDSDGSFFLY SKLTVDKSRW    420
QQGNVFSCSV  MHEALHNHYT QKSLSLSPGK                                     450

SEQ ID NO: 491          moltype = AA  length = 449
FEATURE                 Location/Qualifiers
REGION                  1..449
                        note = Synthetic polypeptide
source                  1..449
                        mol_type = protein
                        organism = synthetic construct
SEQUENCE: 491
EVQLVQSGAE  VKKPGASVKV SCKASGFTFT NNWMHWVRQA PGQGLEWIGM IHPNSGITNI    60
NEKFKNRVTM  TTDTSTSTAY MELRSLRSED TAVYYCRSDG TYEGYFDYWG QGTLVTVSSA    120
STKGPSVFPL  APSSKSTSGG TAALGCLVKD YFPEPVTVSW NSGALTSGVH TFPAVLQSSG    180
LYSLSSVVTV  PSSSLGTQTY ICNVNHKPSN TKVDKKVEPK SCDKTHTCPP CPAPELLGGP    240
SVFLFPPKPK  DTLMISRTPE VTCVVVDVSH EDPEVKFNWY VDGVEVHNAK TKPREEQYGS    300
TYRVVSVLTV  LHQDWLNGKE YKCKVSNKAL PAPIEKTISK AKGQPREPQV YTLPPSRDEL    360
TKNQVSLTCL  VKGFYPSDIA VEWESNGQPE NNYKTTPPVL DSDGSFFLYS KLTVDKSRWQ    420
QGNVFSCSVM  HEALHNHYTQ KSLSLSPGK                                      449

SEQ ID NO: 492          moltype = AA  length = 449
FEATURE                 Location/Qualifiers
REGION                  1..449
                        note = Synthetic polypeptide
```

```
source                  1..449
                        mol_type = protein
                        organism = synthetic construct
SEQUENCE: 492
EVQLVQSGAE VKKPGASVKV SCKASGFTFT NNFMHWVRQA PGQGLEWIGM IHANSGITNI    60
NEKFKNRVTM TTDTSTSTAY MELRSLRSED TAVYYCRSDG IYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 493          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 493
EVQLVQSGAE VKKPGASVKV SCKASGFTFT NNFMHWVRQA PGQGLEWIGM IHANSGITNI    60
NEKFKNRVTM TTDTSTSTAY MELRSLRSED TAVYYCRSDG VYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 494          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 494
EVQLVQSGAE VKKPGASVKV SCKASGFTFT NNFMHWVRQA PGQGLEWIGF IHANSGITNI    60
NEKFKNRVTM TTDTSTSTAY MELRSLRSED TAVYYCRSDG IYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 495          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 495
EVQLVQSGAE VKKPGASVKV SCKASGFTFT NNFMHWVRQA PGQGLEWIGF IHANSGITNI    60
NEKFKNRVTM TTDTSTSTAY MELRSLRSED TAVYYCRSDG VYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 496          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 496
QVQLVQSGAE VKKPGASVKV SCKASGFTFT NNWMHWVRQR PGQGLEWIGM IHPNSGITNI    60
NEKFKNRATV TVDKSSSTVY IELRSLRSED TAVYYCRSDG TYEGYFDYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYGS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
```

```
QGNVFSCSVM HEALHNHYTQ KSLSLSPGK                                         449

SEQ ID NO: 497          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 497
QVQLVQSGAE VKKPGASVKV SCKASGFTFT NNWMHWVRQR PGQGLEWIGM IHPNSGITNI        60
NEKFKNRATV TVDKSSSTVY IELRSLRSED TAVYYCRSDG TYEGYFDYWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYGS       300
TYRVVSVLTV LHQDWLNGKE YKCKVSNKAL PAPIEKTISK AKGQPREPQV YTLPPSRDEL       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                         449

SEQ ID NO: 498          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 498
QVQLVQSGAE VKKPGASVKV SCKASGFTFT NNWMHWVRQA PGQGLEWVGM IHPNSGITNI        60
NEKFKNRVTM TVDKSTSTVY MELRSLRSDD TAVYYCRSDG TYEGYFDYWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYGS       300
TYRVVSVLTV LHQDWLNGKE YKCKVSNKAL PAPIEKTISK AKGQPREPQV YTLPPSRDEL       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                         449

SEQ ID NO: 499          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 499
QVQLVQSGAE VKKPGASVKV SCKASGFTFT NNWMHWVRQA PGQGLEWIGM IHPNSGITNI        60
NEKFKNRVTM TTDTSTSTAY MELRSLRSDD TAVYYCRSDG TYEGYFDYWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYGS       300
TYRVVSVLTV LHQDWLNGKE YKCKVSNKAL PAPIEKTISK AKGQPREPQV YTLPPSRDEL       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                         449

SEQ ID NO: 500          moltype = AA   length = 449
FEATURE                 Location/Qualifiers
REGION                  1..449
                        note = Synthetic polypeptide
source                  1..449
                        mol_type = protein
                        organism = synthetic construct
SEQUENCE: 500
QVQLVQSGAE VKKPGASVKV SCKASGFTFT NNWMHWVRQA PGQGLEWIGM IHPNSGITNI        60
NEKFKNRVTM TVDKSTSTVY MELRSLRSDD TAVYYCARDG TYEGYFDYWG QGTLVTVSSA       120
STKGPSVFPL APSSKSTSGG TAALGCLVKD YFPEPVTVSW NSGALTSGVH TFPAVLQSSG       180
LYSLSSVVTV PSSSLGTQTY ICNVNHKPSN TKVDKKVEPK SCDKTHTCPP CPAPELLGGP       240
SVFLFPPKPK DTLMISRTPE VTCVVVDVSH EDPEVKFNWY VDGVEVHNAK TKPREEQYGS       300
TYRVVSVLTV LHQDWLNGKE YKCKVSNKAL PAPIEKTISK AKGQPREPQV YTLPPSRDEL       360
TKNQVSLTCL VKGFYPSDIA VEWESNGQPE NNYKTTPPVL DSDGSFFLYS KLTVDKSRWQ       420
QGNVFSCSVM HEALHNHYTQ KSLSLSPGK                                         449

SEQ ID NO: 501          moltype = AA   length = 450
FEATURE                 Location/Qualifiers
REGION                  1..450
                        note = Synthetic polypeptide
source                  1..450
                        mol_type = protein
                        organism = synthetic construct
SEQUENCE: 501
EIQLVQSGSE LKKPGASVKV SCKASGYPFT TYGMSWVRQA PGQGLEWMGW INTDSGVPTY        60
```

-continued

```
ADDFKGRFVF SLDTSVSTAY LQISSLKAED TAVYFCARNI YYGWGNFDYW GQGTLVTVSS 120
ASTKGPSVFP LAPSSKSTSG GTAALGCLVK DYFPEPVTVS WNSGALTSGV HTFPAVLQSS 180
GLYSLSSVVT VPSSSLGTQT YICNVNHKPS NTKVDKKVEP KSCDKTHTCP PCPAPELLGG 240
PSVFLFPPKP KDTLMISRTP EVTCVVVDVS HEDPEVKFNW YVDGVEVHNA KTKPREEQYG 300
STYRVVSVLT VLHQDWLNGK EYKCKVSNKA LPAPIEKTIS KAKGQPREPQ VYTLPPSRDE 360
LTKNQVSLTC LVKGFYPSDI AVEWESNGQP ENNYKTTPPV LDSDGSFFLY SKLTVDKSRW 420
QQGNVFSCSV MHEALHNHYT QKSLSLSPGK                                450
```